US006251588B1

(12) United States Patent
Shannon et al.

(10) Patent No.: US 6,251,588 B1
(45) Date of Patent: *Jun. 26, 2001

(54) METHOD FOR EVALUATING OLIGONUCLEOTIDE PROBE SEQUENCES

(75) Inventors: Karen W. Shannon, Los Gatos; Paul K. Wolber, Los Altos; Glenda C. Delenstarr, Belmont; Peter G. Webb, Menlo Park; Robert H. Kincaid, Half Moon Bay, all of CA (US)

(73) Assignee: Agilent Technologies, Inc., Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 46 days.

(21) Appl. No.: 09/021,701

(22) Filed: Feb. 10, 1998

(51) Int. Cl.[7] .................................................. C12Q 1/68

(52) U.S. Cl. ................... 435/6; 422/67; 364/496; 364/497; 364/498

(58) Field of Search .............................. 435/6, 91.1, 91.2; 364/496, 497, 498; 422/67

(56) References Cited

U.S. PATENT DOCUMENTS

| | | | |
|---|---|---|---|
| 5,081,584 | 1/1992 | Omichiniski et al. | 364/497 |
| 5,512,438 | 4/1996 | Ecker | 435/6 |
| 5,556,749 | 9/1996 | Mitsuhashi et al. | 435/6 |
| 5,582,986 | 12/1996 | Monia et al. | 435/6 |
| 5,593,834 | 1/1997 | Lane et al. | 435/6 |
| 5,670,633 | 9/1997 | Cook et al. | 536/23.1 |

OTHER PUBLICATIONS

Southern et al. "Analysing and comparing nucleic acid sequences by hybridization to arrays of oligonucleotides: evaluation using experimental models" Genomics vol. 13, pp. 1008–1017, 1992.*
Handbook of chemistry and physics. The chemicla Rubber CO. 44th edition pp. 9–10, 1961.*
Kress et al. Journal of biomechanical Engineering, 109 (3), pp. 218–225, 1987.*
D. J. Lockhart, et al., *Nature Biotech.* 14: 1675–1684 (1996); "Expression Monitoring by Hybridization to High–Density Oligonucleotide Arrays".
M. Mitsuhashi, et al., *Nature,* 367: 759–761 (1994); "Olignonucleotide Probe Design: A New Approach".
R. A. Stull, et al., *Nuc. Acids Res.,* 20(13): 3501–3508 (1992); "Predicting Antisense Olignucleotide Inhibitory Efficacy: A Computational Approach Using Histograms and Thermodynamic Indices".

(List continued on next page.)

*Primary Examiner*—Ardin H. Marschel

(57) ABSTRACT

Methods are disclosed for predicting the potential of an oligonucleotide to hybridize to a target nucleotide sequence. A predetermined number of unique oligonucleotides is identified. The unique oligonucleotides are chosen to sample the entire length of a nucleotide sequence that is hybridizable with the target nucleotide sequence. At least one parameter that is independently predictive of the ability of each of the oligonucleotides of the set to hybridize to the target nucleotide sequence is determined and evaluated for each of the above oligonucleotides. A subset of oligonucleotides within the predetermined number of unique oligonucleotides is identified based on the evaluation of the parameter. Oligonucleotides in the subset are identified that are clustered along a region of the nucleotide sequence that is hybridizable to the target nucleotide sequence. The method may be carried out with the aid of a computer.

98 Claims, 8 Drawing Sheets

OTHER PUBLICATIONS

L. Wodicka, et al., *Nature Biotechnology*, 15: 1359–1367 (1997); "Genome–wide Expression Monitoring in *Saccaromyces cerevisiae*".

J. SantaLucia Jr., et al., *Biochemistry*, 35: 3555 (1996); "Improved Nearest–Neighbor Parameter for Predicting DNA Duplex Stability".

N. Sugimoto, et al., *Biochemistry*, 34: 11211 (1995); "Thermodynamic Parameters to Predict Stability of RNA/DNA Hybrid Duplexes".

A. Kunitsyn, et al., *J. of Biomolecular Structure & Dynamics*, 14(2): 239–244 (1996); "Partial Thermodynamic Parameters for Prediction Stability and Washing Behavior of DNA Duplexes Immobilized on Gel Matrix".

H. Chen, et al., *BioTechniques*, 22(6): 1158–1160 (1997); "Computer Program for Calculating the Melting Temperature of Degenerate Oligonucleotides Used in PCR of Hybridization".

N. Eberhardt, *BioTechniques*, 13(6): 914–917 (1992); "A Shell Program for the Design of PCR Primers Using Genetics Computer Group (GCG) Software (7.1) on VAX/VMS™ Systems".

D. Hyndman, et al., *BioTechniques*, 20(6): 1090–1094 (1996); "Software to Determine Optimal Oligonucleotide Sequence Based on Hybridization Simulation Data".

M. Mitsuhashi, et al., *J. of Clinical Laboratory Analysis*, 10(5): 277–284 (1996); "Technical Report: Part 1. Basic Requirements for Designing Optimal Oligonucleotide Probe Sequences".

M. Mitsuhashi, et al., *J. of Clinical Laboratory Analysis*, 10(5): 285–293 (1996); "Technical Report: Part 2. Basic Requirements for Designing Optimal PCR Primers".

M. Mitsuhashi, et al., *J. of Gastroenterology*, 32(2): 282–287 (1997); "Strategy for Designing Specific Antisense Oligonucleotide Sequences".

W. Rychlik, et al., *Nucleic Acids Research*, 17(21): 8543–8551 (1989); "A Computer Program for Choosing Optimal Oligonucleotides for Filter Hybridization, Sequencing and in vitro Amplification of DNA".

J.A. Jaeger, et al., *Proc. Natl. Acad. Sci. USA*, 86: 7706 (1989); "Improved Predictions of Secondary Structures for RNA".

S. F. Altschul, et al., *Nature Genetics*, 6: 119–129 (1994); "Issues in Searching Molecular Sequence Databases".

V. Patzel, et al., *Nature Biotechnology*, 16: 64–68 (1998); "Theorectical Design of Antisense RNA Structures Substantially Improves Annealing Kinetics and Efficacy in Human Cells".

N. Milner, et al., *Nature Biotechnology*, 15: 537–541 (1997); Selecting Effective Antisense Reagents on Combinatorial Oligonucleotide Arrays.

A. Pease, et al., *Proc. Natl. Acad. Sic. USA*, 91: 5022–5026 (1994); "Light–generated Oligonucleotide Arrays for Rapid DNA Sequence Analysis".

Weber, et al., *J. Chem Phys.*, 71(11): 4760–4762 (1979); "Molecular Dynamics Simulation of Polymers. I. Structure".

* cited by examiner

METHOD FOR EVALUATING OLIGONUCLEOTIDE PROBE SEQUENCES

This patent application includes a computer program listing appendix, which contains the source code for the software used in carrying out the examples in accordance with the present invention. The Appendix is contained on one compact disc submitted in duplicate designated as Copy 1 and Copy 2. The Appendix is in a single file that is 292 kB in size and named "computer program listing appendix U.S. Ser. No. 09-021,701". The file was created on Feb. 2, 1998 and is a Microsoft Word document. The material in the Appendix is incorporated herein by reference.

A portion of the present disclosure contains material that is subject to copyright protection. The copyright owner has no objection to the facsimile reproduction by anyone of the patent document or the patent disclosure as it appears in the U.S. Patent and Trademark Office patent files or records, but otherwise reserves all copyright rights whatsoever.

BACKGROUND OF THE INVENTION

1. Field of the Invention

Significant morbidity and mortality are associated with infectious diseases and genetically inherited disorders. More rapid and accurate diagnostic methods are required for better monitoring and treatment of these conditions. Molecular methods using DNA probes, nucleic acid hybridization and in vitro amplification techniques are promising methods offering advantages to conventional methods used for patient diagnoses.

Nucleic acid hybridization has been employed for investigating the identity and establishing the presence of nucleic acids. Hybridization is based on complementary base pairing. When complementary single stranded nucleic acids are incubated together, the complementary base sequences pair to form double-stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the development of methods for their incorporation into DNA and RNA has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. The application of nucleic acid hybridization as a diagnostic tool in clinical medicine is limited due to the cost and effort associated with the development of sufficiently sensitive and specific methods for detecting potentially low concentrations of disease-related DNA or RNA present in the complex mixture of nucleic acid sequences found in patient samples.

One method for detecting specific nucleic acid sequences generally involves immobilization of the target nucleic acid on a solid support such as nitrocellulose paper, cellulose paper, diazotized paper, or a nylon membrane. After the target nucleic acid is fixed on the support, the support is contacted with a suitably labeled probe nucleic acid for about two to forty-eight hours. After the above time period, the solid support is washed several times at a controlled temperature to remove unhybridized probe. The support is then dried and the hybridized material is detected by autoradiography or by spectrometric methods. When very low concentrations must be detected, the above method is slow and labor intensive, and nonisotopic labels that are less readily detected than radio labels are frequently not suitable.

A method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Other methods for amplifying nucleic acids have also been developed. These methods include single primer amplification, ligase chain reaction (LCR), transcription-mediated amplification methods including 3SR and NASBA, and the Q-beta-replicase method. Regardless of the amplification used, the amplified product must be detected.

One method for detecting nucleic acids is to employ nucleic acid probes that have sequences complementary to sequences in the target nucleic acid. A nucleic acid probe may be, or may be capable of being, labeled with a reporter group or may be, or may be capable of becoming, bound to a support. Detection of signal depends upon the nature of the label or reporter group. Usually, the probe is comprised of natural nucleotides such as ribonucleotides and deoxyribonucleotides and their derivatives although unnatural nucleotide mimetics such as peptide nucleic acids and oligomeric nucleoside phosphonates are also used. Commonly, binding of the probes to the target is detected by means of a label incorporated into the probe. Alternatively, the probe may be unlabeled and the target nucleic acid labeled. Binding can be detected by separating the bound probe or target from the free probe or target and detecting the label. In one approach, a sandwich is formed comprised of one probe, which may be labeled, the target and a probe that is or can become bound to a surface. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target, allowing the target to hybridize to a surface-bound probe, washing away the unbound target and detecting the labeled target that remains.

Direct detection of labeled target hybridized to surface-bound probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. One difficulty in the design of oligonucleotide arrays is that oligonucleotides targeted to different regions of the same gene can show large differences in hybridization efficiency, presumably due, at least in part, to the interplay between the secondary structures of the oligonucleotides and their targets and the stability of the final probe/target hybridization product. A method for predicting which oligonucleotides will show detectable hybridization would substantially decrease the number of iterations required for optimal array design and would be particularly useful when the total number of oligonucleotide probes on the array is limited. A method to predict oligonucleotide hybridization efficiency would also streamline the empirical approaches currently used to select potential antisense therapeutics, which are designed to modulate gene expression in vivo by hybridizing to specific messenger RNA (mRNA) molecules and inhibiting their translation into proteins.

While it is well known that the structure of the target nucleic acid affects the affinity of oligonucleotide hybridization, current methods for predicting target structures from the primary sequence fail to predict target regions accessible for oligonucleotide binding. Consequently, selection of oligonucleotides for antisense reagents or oligonucleotide probe arrays has been largely empirical. As most of the target sequence is sequestered by intramolecular base pairing and not accessible for oligonucleotide binding, the process of identifying good oligonucleotides has required large numbers of low efficiency experiments.

The design and implementation of algorithms that effectively predict the ability of oligonucleotides to rapidly and avidly bind to complementary nucleotide sequences has been an important problem in molecular biology since the invention of facile methods for chemical DNA synthesis. The subsequent inventions of the polymerase chain reaction (PCR), antisense inhibition of gene expression and oligonucleotide array methods for performing massively parallel hybridization experiments have made the need for effective predictive algorithms even more critical.

Previous attempts to solve the nucleic acid probe design problem include PCR primer design software applications (e.g., OLIGO®), neural networks, PCR primer design applications that search for sequences that possess minimal ability to cross-hybridize with other targets present in a sample (e.g., HYBsimulator™), and approaches that attempt to predict the efficiency of antisense sequence suppression of mRNA translation from a combination of predicted nucleic acid duplex melting temperature and predicted target strand structure. The methods that predict effective oligonucleotide primers for performing PCR from DNA templates work well for that application where relatively stringent conditions are employed. This is because PCR experimental design greatly simplifies the prediction problem: hybridization is performed at high temperature, at relatively low ionic strength and in the presence of a large molar excess of oligonucleotide. Under these conditions, the oligonucleotide and target secondary structures are relatively unimportant.

Unfortunately, these conditions do not apply to oligonucleotide arrays, which are usually hybridized under relatively non-denaturing conditions, or to antisense suppression of gene expression, which takes place in vivo. Oligonucleotide arrays can contain hundreds of thousands of different sequences and conditions are chosen to allow the oligonucleotide with the lowest melting temperature to hybridize efficiently. These "lowest common denominator" conditions are usually relatively non-denaturing and secondary structure constraints become significant. Accordingly, the above applications require new predictive methods that are capable of estimating the effects of oligonucleotide and target structure on hybridization efficiency. For these reasons, current algorithms for designing PCR primer oligonucleotides fail badly when applied to the problems of oligonucleotide array or antisense oligonucleotide design.

To date, the most effective approach for identifying oligonucleotides with good hybridization efficiency has been an empirical one. Such an approach involves the synthesis of large numbers of oligonucleotide probes for a given target nucleotide sequence. Arrays are formed that include the above oligonucleotide probes. Hybridization experiments are carried out to determine which of the oligonucleotide probes exhibit good hybridization efficiencies. Examples of such an approach are found in D. Lockhart, et al., *Nature Biotech.*, infra, L. Wodicka, et al., *Nature Biotechnology*, infra., and N. Milner et al. *Nature Biotech*, infra. One major drawback to this approach is the vast number of oligonucleotides that must be synthesized in order to achieve a satisfactory result. Typically, about 2%–5% of the test probes synthesized yield acceptable signal levels.

The use of neural networks for oligonucleotide design has also been investigated. Neural networks are easily taught with real data; they therefore afford a general approach to many problems. However, their performance is limited by the "senses" that they are given. An analogy works best here: the human brain is an astoundingly capable neural network, but a blind person cannot be taught to reliably distinguish colors by smell. In addition, a large amount of data is required to adequately teach a neural network to perform its job well. A comprehensive database for either oligonucleotide array design or antisense suppression of gene expression has not been made available. For these reasons, the performance reported to-date of neural network solutions against the probe design problem is mediocre.

Finally, approaches that have attempted to use target nucleic acid folding calculations to predict experimental results inferred to depend upon hybridization efficiency (e.g. antisense suppression of mRNA translation) have so far only demonstrated that the predictions of current nucleic acid folding calculations correlate poorly with observed behavior. The probable reason for this is that the structures predicted by such programs for long sequences are poor predictors of chemical reality; the results of experiments that attempt to confirm the predictions of such calculations support this assessment. Recent improvements to this approach which use predicted RNA structure topology as a predictor of relative RNA/RNA association kinetics have been more successful at forecasting the results of antisense experiments. However, these methods are not computationally efficient, and have so far only been shown to work for targets less than 100 bases long. Such methods are therefore not yet capable of predicting the behavior of full-length mRNA targets, which are typically between 1,000 and 2,000 bases in length.

2. Description of the Related Art

U.S. Pat. No. 5,512,438 (Ecker) discloses the inhibition of RNA expression by forming a pseudo-half knot RNA at the target's RNA secondary structure using antisense oligonucleotides.

Cook, et al., in U.S. Pat. No. 5,670,633 discuss sugar-modified oligonucleotides that detect and modulate gene expression.

Antisense oligonucleotide inhibition of the RAS gene is disclosed in U.S. Pat. No. 5,582,986 (Monia, et al.).

U.S. Pat. No. 5,593,834 (Lane, et al.) discusses a method of preparing DNA sequences with known ligand binding characteristics.

Mitsuhashi, et al., in U.S. Pat. No. 5,556,749 discusses a computerized method for designing optimal DNA probes and an oligonucleotide probe design station.

U.S. Pat. No. 5,081,584 (Omichinski, et al.) discloses a computer-assisted design of anti-peptides based on the amino acid sequence of a target peptide.

A PCR primer design application that searches for sequences that possess minimal ability to cross-hybridize with other targets present in a sample is available as HYBsimulatorm™, version 2.0, AGCT, Inc., 2102 Business Center Drive, Suite 170, Irvine, Calif. 92715 (714) 833-9983.

A PCR primer design software application is available as OLIGO®, version 5.0, National Biosciences, Inc., 3650 Annapolis Lane North, #140, Plymouth, Minn. 55447 (800) 747–4362.

D. J. Lockhart, et al., *Nature Biotech.* 14:1675–1684 (1996) describe a neural network approach to the selection of efficient surface-bound oligonucleotide probes.

M. Mitsuhashi, etal., *Nature*, 367:759–761 (1994) disclose a method for designing specific oligonucleotide probes and primers by modeling the potential cross-hybridization of candidate probes to non-target sequences known to be present in samples.

R. A. Stull, et al., *Nuc. Acids Res.*, 20:3501–3508 (1992) describe a method of predicting the efficacy of antisense oligonucleotides, using predicted target secondary structure and predicted oligonucleotide/target binding free energy as input parameters.

N. Milner, et al., *Nature Biotechnology*, 15:537–541 (1997) compare observed patterns of probe hybridization to those expected from the predicted secondary structure of the nucleic acid target.

L. Wodicka, et al., *Nature Biotechnology*, 15:1359–1367 (1997) describe simple rules for avoiding inefficient and non-specific probes during design and synthesis of oligonucleotides arrays.

J. SantaLucia Jr., et al., *Biochemistry*, 35:3555 (1996) disclose parameters and methods for the calculation of thermodynamic properties of DNA/DNA homoduplexes.

N. Sugimoto, et al., *Biochemistry*, 34:11211 (1995) disclose parameters and methods for the calculation of thermodynamic properties of DNA/RNA heteroduplexes.

J. A. Jaeger, et al., *Proc. Natl. Acad. Sci. USA*, 86:7706 (1989) disclose methods for estimation of the free energy of the most stable intramolecular structure of a single-stranded polynucleotide, by means of a dynamic programming algorithm.

S. F. Altschul, et al., *Nature Genetics*, 6:119–129 (1994) disclose methods for calculating the complexity and information content of amino acid and nucleic acid sequences.

T. A. Weber and E. Helfand, *J. Chem. Phys.*, 71, 4760 (1979) describe approaches for the modeling of polymer structures by molecular dynamics simulations.

V. Patzel and G. Sczakiel, *Nature Biotech.*, 16, 64–68 (1998) disclose methods for estimating rate constants for association of antisense RNA molecules with mRNA targets by examination of predicted antisense RNA secondary structures.

Light-generated oligonucleotide arrays for rapid DNA sequence analysis is described by A. C. Pease, et al., *Proc. Nat. Acad. Sci. USA* (1994) 91:5022–5026.

Mitsuhashi discusses basic requirements for designing optimal oligonucleotide probe sequences in *J. Clinical Laboratory Analysis* (1996) 10:277–284.

Rychlik, et al., discloses a computer program for choosing optimal oligonucleotides for filter hybridization, sequencing and in vitro amplification of DNA in *Nucleic Acids Research* (1989) 17(21):8543–8551.

A strategy for designing specific antisense oligonucleotide sequences is described by Mitsuhashi in *J. Gastroenterol.* (1997) 32:282–287.

Mitsuhashi discusses basic requirements for designing optimal PCR primers in *J. Clinical Laboratory Analysis* (1996) 10:285–293.

Hyndman, et al., disclose software to determine optimal oligonucleotide sequences based on hybridization simulation data in *BioTechniques* (1996) 20(6):1090–1094.

Eberhardt discloses a shell program for the design of PCR primers using genetics computer group (GCG) software (7.1) on VAX/VMS™ systems in *BioTechniques* (1992) 13(6):914–917.

Chen, et al., disclose a computer program for calculating the melting temperature of degenerate oligonucleotides used in PCR or hybridization in *BioTechniques* (1997) 22(6):1158–1160.

Partial thermodynamic parameters for prediction stability and washing behavior of DNA duplexes immobilized on gel matrix is described by Kunitsyn, et al., in *J. Biomolecular Structure & Dynamics*, ISSN 0739-1102 (1996) 14(1):239–244.

SUMMARY OF THE INVENTION

One embodiment of the present invention is a method for predicting the potential of an oligonucleotide to hybridize to a target nucleotide sequence. A predetermined set of unique oligonucleotide sequences is identified. The unique. oligonucleotide sequences are chosen to sample the entire length of a nucleotide sequence that is hybridizable with the target nucleotide sequence. At least one parameter that is predictive of the ability of each of the oligonucleotides specified by the set of sequences to hybridize to the target nucleotide sequence is determined and evaluated for each of the above oligonucleotide sequences. A subset of oligonucleotide sequences within the predetermined set of unique oligonucleotide sequences is identified based on the examination of the parameter values. Finally, oligonucleotide sequences in the subset are identified that are clustered along one or more regions of the nucleotide sequence that is hybridizable to the target nucleotide sequence. The oligonucleotide probes corresponding to the identified sequences find use in polynucleotide assays particularly where the assays involve oligonucleotide arrays. For a discussion of oligonucleotide arrays, see, e.g., U.S. Pat. No. 5,700,637 (E. Southern) and U.S. Pat. No. 5,667,667 (E. Southern), the relevant disclosures of which are incorporated herein by reference.

Another embodiment of the present invention is a method for predicting the potential of an oligonucleotide to hybridize to a complementary target nucleotide sequence. A set of overlapping oligonucleotide sequences is identified based on a nucleotide sequence that is complementary to the target nucleotide sequence. At least two parameters that are independently predictive of the ability of each of the oligonucleotides specified by the oligonucleotide sequences to hybridize to the target nucleotide sequence are determined and evaluated for each of the oligonucleotide sequences. Independence is assured by requiring that the parameters be poorly correlated with respect to one another. A subset of oligonucleotide sequences within the set of oligonucleotide sequences is identified based on the examination of the parameter values. Finally, oligonucleotide sequences in the subset are identified that are clustered along one or more regions of the nucleotide sequence that is complementary to the target nucleotide sequence.

Another embodiment of the present invention is a method for predicting the potential of an oligonucleotide to hybridize to a complementary target nucleotide sequence. A set of overlapping oligonucleotide sequences is obtained based on a nucleotide sequence of length L, complementary to the target nucleotide sequence. The oligonucleotide sequences of the set of overlapping oligonucleotide sequences are of identical length N and spaced one nucleotide apart. The set comprises L–N+1 oligonucleotide sequences. Parameters are determined for each of the oligonucleotide sequences of the set of overlapping oligonucleotide sequences. One parameter is the predicted melting temperature of the duplex of each of the oligonucleotides specified by the oligonucleotide sequences and the target nucleotide sequence, corrected for salt concentration. The other parameter is the predicted free energy of the most stable intramolecular structure of each of the oligonucleotides specified by the oligonucleotide sequences at the temperature of hybridization of the oligonucleotide with the target nucleotide sequence. A subset of oligonucleotide sequences within the set of oligonucleotide sequences is selected based on an examination of the parameter values by establishing cut-off values for each of the parameters. Oligonucleotide sequences in the subset that are clustered along one or more regions of the complementary nucleotide sequence are ranked based on the sizes of the clusters of oligonucleotide sequences. Finally, a subset of the clustered oligonucleotide sequences is selected that statistically samples the clusters of oligonucleotide sequences. The selected sampled subset is used to specify the synthesis of oligonucleotides for experimental evaluation.

Another aspect of the present invention is a computer based method for predicting the potential of an oligonucleotide to hybridize to a target nucleotide sequence. A predetermined number of unique oligonucleotides within a nucleotide sequence that is hybridizable with the target nucleotide sequence is identified under computer control. The oligonucleotides are chosen to sample the entire length of the nucleotide sequence. A value is determined and evaluated under computer control for each of the oligonucleotides for at least one parameter that is independently predictive of the ability of each of the oligonucleotides to hybridize to the target nucleotide sequence. The parameter values are stored. A subset of oligonucleotides within the predetermined number of unique oligonucleotides is identified by examination of the stored parameter values under computer control. Then, oligonucleotides in the subset that are clustered along a region of the nucleotide sequence that is hybridizable to the target nucleotide sequence are identified under computer control.

Another aspect of the present invention is a computer system for conducting a method for predicting the potential of an oligonucleotide to hybridize to a target nucleotide sequence. The system comprises (a) input means for introducing a target nucleotide sequence into the computer system, (b) means for determining a number of unique oligonucleotide sequences that are within a nucleotide sequence that is hybridizable with the target nucleotide sequence where the oligonucleotide sequences are chosen to sample the entire length of the nucleotide sequence, (c) memory means for storing the oligonucleotide sequences, (d) means for controlling the computer system to carry out for each of the oligonucleotide sequences a determination and evaluation of a value for at least one parameter that is independently predictive of the ability of each of the oligonucleotide sequences to hybridize to the target nucleotide sequence, (e) means for storing the parameter values, (f) means for controlling the computer to carry out an identification from the stored parameter values a subset of oligonucleotide sequences within the number of unique oligonucleotide sequences based on the examination of the parameter, (g) means for storing the subset of oligonucleotides, (h) means for controlling the computer to carry out an identification of oligonucleotide sequences in the subset that are clustered along a region of the nucleotide sequence that is hybridizable to the target nucleotide sequence, (i) means for storing the oligonucleotide sequences in the subset, and (j) means for outputting data relating to the oligonucleotide sequences in the subset.

DEFINITIONS

Figure 1:
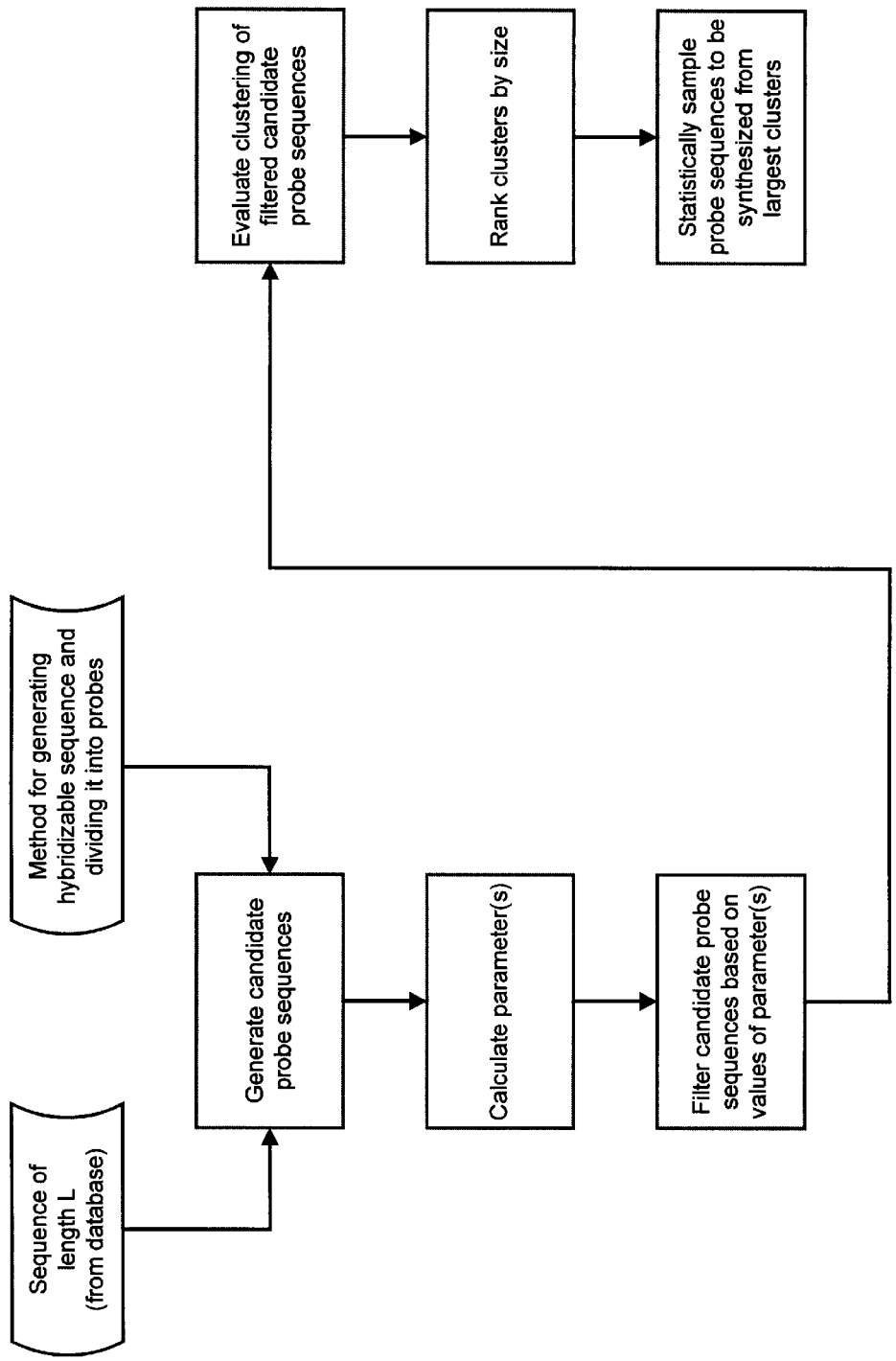
FIG. 1 is a general flow chart depicting the method of the present invention.

Before proceeding further with a description of the specific embodiments of the present invention, a number of terms will be defined.

Nucleic Acids:

Polynucleotide—a compound or composition that is a polymeric nucleotide or nucleic acid polymer. The polynucleotide may be a natural compound or a synthetic compound. In the context of an assay, the polynucleotide is often referred to as a polynucleotide analyte. The polynucleotide can have from about 20 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. It is thus obvious that isolation of a polynucleotide from the natural state often results in fragmentation. The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, dsDNA can be heated at 90–100° C. for a period of about 1 to 10 minutes to produce denatured material.

Target nucleotide sequence—a sequence of nucleotides to be identified, usually existing within a portion or all of a polynucleotide, usually a polynucleotide analyte. The identity of the target nucleotide sequence generally is known to an extent sufficient to allow preparation of various sequences hybridizable with the target nucleotide sequence and of oligonucleotides, such as probes and primers, and other molecules necessary for conducting methods in accordance with the present invention, an amplification of the target polynucleotide, and so forth.

The target sequence usually contains from about 30 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, preferably, 10 to 100 nucleotides, more preferably, 20 to 50 nucleotides, and usually 10 to 30 nucleotides, more preferably, 20 to 30 nucleotides, and desirably about 25 nucleotides in length.

Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol*, 101:20–78.

Other methods of oligonucleotide synthesis include phosphotriester and phosphodiester methods (Narang, et al. (1979) *Meth. Enzymol* 68:90) and synthesis on a support (Beaucage, et al. (1981) *Tetrahedron Letters* 22:1859–1862) as well as phosphoramidite techniques (Caruthers, M. H., et al., "Methods in Enzymology," Vol. 154, pp.287–314 (1988)) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al., *Proc. Nat. Acad. Sci. USA* (1994) 91:5022–5026.

Oligonucleotide probe—an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

Oligonucleotide primer(s)—an oligonucleotide that is usually employed in a chain extension on a polynucleotide template such as in, for example, an amplification of a nucleic acid. The oligonucleotide primer is usually a synthetic nucleotide that is single stranded, containing a sequence at its 3'-end that is capable of hybridizing with a defined sequence of the target polynucleotide. Normally, an oligonucleotide primer has at least 80%, preferably 90%, more preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the oligonucleotide primer will be at least as great as the defined sequence of the target polynucleotide, namely, at least ten nucleotides, preferably at least 15 nucleotides, and generally from about 10 to 200, preferably 20 to 50, nucleotides.

In general, in primer extension, amplification primers hybridize to, and are extended along (chain extended), at least the target nucleotide sequence within the target polynucleotide and, thus, the target sequence acts as a template. The extended primers are chain "extension products." The target sequence usually lies between two defined sequences but need not. In general, the primers hybridize with the defined sequences or with at least a portion of such target polynucleotide, usually at least a ten-nucleotide segment at the 3'-end thereof and preferably at least 15, frequently a 20 to 50 nucleotide segment thereof.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates.

Nucleotide—a base-sugar-phosphate combination that is the monomeric unit of nucleic acid polymers, i.e., DNA and RNA. The term "nucleotide" as used herein includes modified nucleotides as defined below.

DNA—deoxyribonucleic acid.

RNA—ribonucleic acid.

Modified nucleotide—a unit in a nucleic acid polymer that contains a modified base, sugar or phosphate group. The modified nucleotide can be produced by a chemical modification of the nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and the like and also include phosphorothioate, phosphite, ring atom modified derivatives, and so forth.

Nucleoside—is a base-sugar combination or a nucleotide lacking a phosphate moiety.

Nucleotide polymerase—a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, reverse transcriptase, Vent DNA polymerase, Pfu DNA polymerase, Taq DNA polymerase, and the like, or RNA polymerases, such as T3 and T7 RNA polymerases. Polymerase enzymes may be derived from any source such as cells, bacteria such as *E. coli*, plants, animals, virus, thermophilic bacteria, and so forth.

Amplification of nucleic acids or polynucleotides—any method that results in the formation of one or more copies of a nucleic acid or polynucleotide molecule (exponential amplification) or in the formation of one or more copies of only the complement of a nucleic acid or polynucleotide molecule (linear amplification).

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like.

Hybridization efficiency—the productivity of a hybridization reaction, measured as either the absolute or relative yield of oligonucleotide probe/polynucleotide target duplex formed under a given set of conditions in a given amount of time.

Homologous or substantially identical polynucleotides—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G/U or U/G base pairs.

Member of a specific binding pair ("sbp member")—one of two different molecules, having an area on the surface or in a cavity that specifically binds to and is thereby defined as complementary with a particular spatial and polar organization of the other molecule. The members of the specific binding pair are referred to as cognates or as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Oligonucleotide Properties:

Potential of an oligonucleotide to hybridize—the combination of duplex formation rate and duplex dissociation rate that determines the amount of duplex nucleic acid hybrid that will form under a given set of experimental conditions in a given amount of time.

Parameter—a factor that provides information about the hybridization of an oligonucleotide with a target nucleotide sequence. Generally, the factor is one that is predictive of the ability of an oligonucleotide to hybridize with a target nucleotide sequence. Such factors include composition factors, thermodynamic factors, chemosynthetic efficiencies, kinetic factors, and the like.

Parameter predictive of the ability to hybridize—a parameter calculated from a set of oligonucleotide sequences wherein the parameter positively correlates with observed hybridization efficiencies of those sequences. The parameter is, therefore, predictive of the ability of those sequences to hybridize. "Positive correlation" can be rigorously defined in statistical terms. The correlation coefficient $\rho_{x,y}$ of two experimentally measured discreet quantities x and y (N values in each set) is defined as $$\rho_{x,y} = \frac{\text{Covariance}(x, y)}{\sqrt{\text{Variance}(x)\text{Variance}(y)}},$$

where the Covariance (x,y) is defined by $$\text{Covariance}(x, y) = \frac{1}{N}\sum_{j=1}^{N}(x_j - \mu_x)(y_j - \mu_y).$$

The quantities $\mu_x$ and $\mu_y$ are the averages of the quantities x and y, while the variances are simply the squares of the standard deviations (defined below). The correlation coefficient is a dimensionless (unitless) quantity between −1 and 1. A correlation coefficient of 1 or −1 indicates that x and y have a linear relationship with a positive or negative slope, respectively. A correlation coefficient of zero indicates no relationship; for example, two sets of random numbers will yield a correlation coefficient near zero. Intermediate correlation coefficients indicate intermediate degrees of relatedness between two sets of numbers. The correlation coefficient is a good statistical measure of the degree to which one set of numbers predicts a second set of numbers.

Composition factor—a numerical factor based solely on the composition or sequence of an oligonucleotide without involving additional parameters, such as experimentally measured nearest-neighbor thermodynamic parameters. For instance, the fraction (G+C), given by the formula $$f_{GC} = \frac{n_G + n_C}{n_G + n_C + n_A + n_{T \text{ or } U}},$$

where $n_G$, $n_C$, $n_A$ and $n_{T \text{ or } U}$ are the numbers of G, C, A and T (or U) bases in an oligonucleotide, is an example of a composition factor. Examples of composition factors, by way of illustration and not limitation, are mole fraction (G+C), percent (G+C), sequence complexity, sequence information content, frequency of occurrence of specific oligonucleotide sequences in a sequence database and so forth.

Thermodynamic factor—numerical factors that predict the behavior of an oligonucleotide in some process that has reached equilibrium. For instance, the free energy of duplex formation between an oligonucleotide and its complement is a thermodynamic factor. Thermodynamic factors for systems that can be subdivided into constituent parts are often estimated by summing contributions from the constituent parts. Such an approach is used to calculate the thermodynamic properties of oligonucleotides.

Examples of thermodynamic factors, by way of illustration and not limitation, are predicted duplex melting temperature, predicted enthalpy of duplex formation, predicted entropy of duplex formation, free energy of duplex formation, predicted melting temperature of the most stable intramolecular structure of the oligonucleotide or its complement, predicted enthalpy of the most stable intramolecular structure of the oligonucleotide or its complement, predicted entropy of the most stable intramolecular structure of the oligonucleotide or its complement, predicted free energy of the most stable intramolecular structure of the oligonucleotide or its complement, predicted melting temperature of the most stable hairpin structure of the oligonucleotide or its complement, predicted enthalpy of the most stable hairpin structure of the oligonucleotide or its complement, predicted entropy of the most stable hairpin structure of the oligonucleotide or its complement, predicted free energy of the most stable hairpin structure of the oligonucleotide or its complement, thermodynamic partition function for intramolecular structure of the oligonucleotide or its complement and the like.

Chemosynthetic efficiency—oligonucleotides and nucleotide sequences may both be made by sequential polymerization of the constituent nucleotides. However, the individual addition steps are not perfect; they instead proceed with some fractional efficiency that is less than unity. This may vary as a function of position in the sequence. Therefore, what is really produced is a family of molecules that consists of the desired molecule plus many truncated sequences. These "failure sequences" affect the observed efficiency of hybridization between an oligonucleotide and its complementary target. Examples of chemosynthetic efficiency factors, by way of illustration and not limitation, are coupling efficiencies, overall efficiencies of the synthesis of a target nucleotide sequence or an oligonucleotide probe, and so forth.

Kinetic factor—numerical factors that predict the rate at which an oligonucleotide hybridizes to its complementary sequence or the rate at which the hybridized sequence dissociates from its complement are called kinetic factors. Examples of kinetic factors are steric factors calculated via molecular modeling or measured experimentally, rate constants calculated via molecular dynamics simulations, associative rate constants, dissociative rate constants, enthalpies of activation, entropies of activation, free energies of activation, and the like.

Predicted duplex melting temperature—the temperature at which an oligonucleotide mixed with a hybridizable nucleotide sequence is predicted to form a duplex structure (double-helix hybrid) with 50% of the hybridizable sequence. At higher temperatures, the amount of duplex is less than 50%; at lower temperatures, the amount of duplex is greater than 50%. The melting temperature $T_m$ (° C.) is calculated from the enthalpy ($\Delta H$), entropy ($\Delta S$) and C, the concentration of the most abundant duplex component (for hybridization arrays, the soluble hybridization target), using the equation $$T_m = \frac{\Delta H}{\Delta S + R \ln C} - 273.15,$$

where R is the gas constant, 1.987 cal/(mole-° K). For longer sequences (>100 nucleotides), $T_m$ can also be estimated from the mole fraction (G+C), $\chi_{G+C}$, using the equation $$T_m = 81.5 + 41.0 \chi_{G+C}.$$

Melting temperature corrected for salt concentration—polynucleotide duplex melting temperatures are calculated with the assumption that the concentration of sodium ion, Na$^+$, is 1 M. Melting temperatures $T_m$ calculated for duplexes formed at different salt concentrations are corrected via the semi-empirical equation $$T_m([Na^+]) = T_m + 16.6 \log([Na^+]).$$

Predicted enthalpy, entropy and free energy of duplex formation—the enthalpy ($\Delta H$), entropy and free energy ($\Delta G$) are thermodynamic state functions, related by the equation $$\Delta G = \Delta H - T \Delta S,$$

where T is the temperature in °K. In practice, the enthalpy and entropy are predicted via a thermodynamic model of duplex formation (the "nearest neighbor" model which is explained in more detail below), and used to calculate the free energy and melting temperature.

Predicted free energy of the most stable intramolecular structure of an oligonucleotide or its complement—single-stranded DNA and RNA molecules that contain self-complementary sequences can form intramolecular secondary structures. For instance, the oligonucleotide

5'-ACTGGCAATCACAATTGCCAGTAA-3' (SEQ ID NO:1)

can base pair with itself, to form the structure

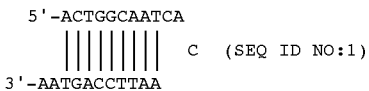

where a vertical line indicates Watson-Crick base pair formation. Many such structures are possible for a given sequence; two are of particular interest. The first is the lowest energy "hairpin" structure (formed by folding a sequence back on itself with a connecting loop at least 3 nucleotides long). The second is the lowest energy structure that can be formed by including more complex topologies, such as "bulge loops" (unpaired duplexes between two regions of base-paired duplex) and cloverleaf structures, where 3 base-paired stretches meet at a triple-junction. A good example of a complex secondary structure is the structure of a tRNA molecule, an example of which, namely, yeast tRNA$^{Ala}$ is shown below.

For either type of structure, a value of the free energy of that structure can be calculated, relative to the unpaired strand, by means of a thermodynamic model similar to that used to calculate the free energy of a base-paired duplex structure. Again, the free energy $\Delta G$ is calculated from the enthalpy $\Delta H$ and the entropy $\Delta S$ at a given absolute temperature T via the equation $$\Delta G = \Delta H - T \Delta S.$$

However, in this case there is the added difficulty that the lowest energy structure must be found. For a simple hairpin structure, this optimization can be performed via a relatively simple search algorithm. For more complex structures (such as a cloverleaf a dynamic programming algorithm, such as that implemented in the program MFOLD, must be used.

Yeast tRNA$^{Ala}$—The RNA sequence includes many non-standard ribonucleotides, such as D (5,6 dihydrouridine), m$^1$G (1-methylguanosine), m$^2$G (N$^2$-dimethylguanosine), ψ (pseudouridine), I (inosine), m$^1$I (1-methylinosine) and T (ribothymidine). Dots (•) mark (non-standard) G=U base pairs. The structure is taken from A. L. Lehninger, et al., *Principles of Biochemistry*, 2$^{nd}$ Ed. (Worth Publishers, New York, N.Y., 1993).

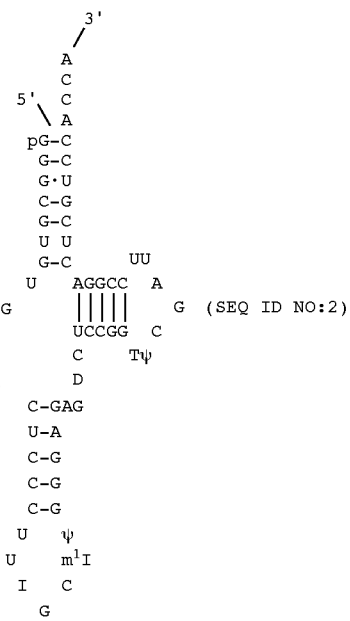

Coupling efficiencies—chemosynthetic efficiencies are called coupling efficiencies when the synthetic scheme involves successive attachment of different monomers to a growing oligomer; a good example is oligonucleotide synthesis via phosphoramidite coupling chemistry.

Algorithmic Operations:

Evaluating a parameter—determination of the numerical value of a numerical descriptor of a property of an oligonucleotide sequence by means of a formula, algorithm or look-up table.

Filter—a mathematical rule or formula that divides a set of numbers into two subsets. Generally, one subset is retained for further analysis while the other is discarded. If the division into two subsets is achieved by testing the numbers against a simple inequality, then the filter is referred to as a "cut-off". In the context of the current invention, an example by way of illustration and not limitation is the statement "The predicted self structure free energy must be greater than or equal to −0.4 kcal/mole," which can be used as a filter for oligonucleotide sequences; this particular filter is also an example of a cut-off.

Filter set—A set of rules or formulae that successively winnow a set of numbers by identifying and discarding subsets that do not meet specific criteria. In the context of the current invention, an example by way of illustration and not limitation is the compound statement "the predicted self structure free energy must be greater than or equal to −0.4 kcal/mole and the predicted RNA/DNA heteroduplex melting temperature must lie between 600° C. and 85° C.," which can be used as a filter set for oligonucleotide sequences.

Examining a parameter—comparing the numerical value of a parameter to some cutoff-value or filter.

Statistical sampling of a cluster—extraction of a subset of oligonucleotides from a cluster of oligonucleotides based upon some statistical measure, such as rank by oligonucleotide starting position in the sequence complementary to the target sequence.

First quartile, median and third quartile—If a set of numbers is ranked by value, then the value that divides the lower ¼ from the upper ¾ of the set is the first quartile, the value that divides the set in half is the median and the value that divides the lower ¾ from the upper ¼ of the set is the third quartile.

Poorly correlated—If it is not possible to perform a "good" prediction, as defined via statistics, of one set of numbers from another set of numbers using a simple linear model, then the two sets of numbers are said to be poorly correlated.

Computer program—a written set of instructions that symbolically instructs an appropriately configured computer to execute an algorithm that will yield desired outputs from some set of inputs. The instructions may be written in one or several standard programming languages, such as C, C++, Visual BASIC, FORTRAN or the like. Alternatively, the instructions may be written by imposing a template onto a general-purpose numerical analysis program, such as a spreadsheet.

Experimental System Components:

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The surface can have any one of a number of shapes, such as strip, plate, disk, rod, particle, including bead, and the like. The support can be hydrophilic or capable of being rendered hydrophilic and includes inorganic powders such as glass, silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of oligonucleotides to a support or surface may be accomplished by well-known techniques, commonly available in the literature. See, for example, A. C. Pease, et al, *Proc. Nat. Acad. Sci. USA*, 91:5022–5026 (1994).

Label—a member of a signal producing system. Usually the label is part of a target nucleotide sequence or an oligonucleotide probe, either being conjugated thereto or otherwise bound thereto or associated therewith. The label is capable of being detected directly or indirectly. Labels include (i) reporter molecules that can be detected directly by virtue of generating a signal, (ii) specific binding pair members that may be detected indirectly by subsequent binding to a cognate that contains a reporter molecule, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used.

The reporter molecule can be isotopic or nonisotopic, usually non-isotopic, and can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label is a member of a signal producing system and can generate a detectable signal either alone or together with other members of the signal producing system. As mentioned above, a reporter molecule can be bound directly to a nucleotide sequence or can become bound thereto by being bound to an sbp member complementary to an sbp member that is bound to a nucleotide sequence. Examples of particular labels or reporter molecules and their detection can be found in U.S. Pat. No. 5,508,178 issued Apr. 16, 1996, at column 11, line 66, to column 14, line 33, the relevant disclosure of which is incorporated herein by reference. When a reporter molecule is not conjugated to a nucleotide sequence, the reporter molecule may be bound to an sbp member complementary to an sbp member that is bound to or part of a nucleotide sequence.

Signal Producing System—the signal producing system may have one or more components, at least one component being the label. The signal producing system generates a signal that relates to the presence or amount of a target polynucleotide in a medium. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Signal-producing systems that may be employed in the present invention are those described more fully in U.S. Pat. No. 5,508,178, the relevant disclosure of which is incorporated herein by reference.

Ancillary Materials—Various ancillary materials will frequently be employed in the methods and assays utilizing oligonucleotide probes designed in accordance with the present invention. For example, buffers and salts will normally be present in an assay medium, as well as stabilizers for the assay medium and the assay components. Frequently, in addition to these additives, proteins may be included, such as albumins, organic solvents such as formamide, quaternary ammonium salts, polycations such as spermine, surfactants, particularly non-ionic surfactants, binding enhancers, e.g., polyalkylene glycols, or the like.

DETAILED DESCRIPTION OF THE INVENTION

The invention is directed to methods or algorithms for predicting oligonucleotides specific for a nucleic acid target where the oligonucleotides exhibit a high potential for hybridization. The algorithm uses parameters of the oligonucleotide and the oligonucleotide/target nucleotide sequence duplex, which can be readily predicted from the primary sequences of the target polynucleotide and candidate oligonucleotides. In the methods of the present invention, oligonucleotides are filtered based on one or more of these parameters, then further filtered based on the sizes of clusters of oligonucleotides along the input polynucleotide sequence. The methods or algorithms of the present invention may be carried out using either relatively simple user-written subroutines or publicly available stand-alone software applications (e.g., dynamic programming algorithm for calculating self-structure free energies of oligonucleotides). The parameter calculations may be orchestrated and the filtering algorithms may be implemented using any of a number of commercially available computer programs as a framework such as, e.g., Microsoft® Excel spreadsheet, Microsoft® Access relational database and the like. The basic steps involved in the present methods involve parsing a sequence that is complementary to a target nucleotide sequence into a set of overlapping oligonucleotide sequences, evaluating one or more parameters for each of the oligonucleotide sequences, said parameter or parameters being predictive of probe hybridization to the target nucleotide sequence, filtering the oligonucleotide sequences based on the values for each parameter, filtering the oligonucleotide sequences based on the length of contiguous sequence elements and ranking the contiguous sequence elements based on their length. We have found that oligonucleotides in the longest contiguous sequence elements generally show the highest hybridization efficiencies.

The present methods are based on our recognition that oligonucleotides showing high hybridization efficiencies tend to form clusters. It is believed that this clustering reflects local regions of the target nucleotide sequence that are unstructured and accessible for oligonucleotide binding. Oligonucleotides that are contiguous along a region of the input nucleic acid sequence are identified. These oligonucleotides are sorted based on the length of the contiguous sequence elements. The sorting approach used in the present invention apparently serves as a surrogate for the calculation of local secondary structure of the target a nucleotide sequence. This is supported by our observation that treatments intended to eliminate long-range nucleic acid structure (e.g., random fragmentation) do not eliminate the differences in hybridization yields across oligonucleotide probe arrays. This implies that major determinants of efficient hybridization are local regions of the target sequence. The identification of contiguous sequence elements is a simple and efficient method for recognizing clusters of such determinants and, thus, for identifying oligonucleotide probes that exhibit high hybridization efficiency for a target nucleotide sequence.

As mentioned above one embodiment of the present invention is a method for predicting the potential of an oligonucleotide to hybridize to a target nucleotide sequence. A predetermined number of unique oligonucleotides is identified. The length of the oligonucleotides may be the same or different. The oligonucleotides are unique in that no two of the oligonucleotides are identical. The unique oligonucleotides are chosen to sample the entire length of a nucleotide sequence that is hybridizable with the target nucleotide sequence. The actual number of oligonucleotides is generally determined by the length of the nucleotide sequence and the desired result. The number of oligonucleotides should be sufficient to achieve a consensus behavior. In other words, the oligonucleotide sequences should be sufficiently numerous that several possible probes overlap or fall within a given region that is expected to yield acceptable hybridization efficiency. Since the location of these regions is not known before hand, the best strategy is to equally space the probe sequences along the sequence that is hybridizable to the target sequence. Since regions of acceptable hybridization efficiency are generally on the order of 20 nucleotides in length, a practical strategy is to space the starting nucleotides of the oligonucleotide sequences no more than five base pairs apart. If computation time needed to calculate the predictive parameters is not an issue, then the best strategy is to space the starting nucleotides one nucleotide apart. An important feature of the present invention is to determine oligonucleotides that are clustered along a region of the nucleotide sequence. The individual predictions made for individual oligonucleotide sequences are not very good. However, we have found that the predictions that are experimentally observed tend to form contiguous clusters, while the spurious predictions tend to be solitary. Thus, the number of oligonucleotides should be sufficient to achieve the desired clustering.

Preferably, a set of overlapping sequences is chosen. To this end, the subsequences are chosen so that there is overlap of at least one nucleotide from one oligonucleotide to the next. More preferably, the overlap is two or more nucleotides. Most preferably, the oligonucleotides are spaced one nucleotide apart and the predetermined number is L−N+1 oligonucleotides where L is the length of the nucleotide sequence and N is the length of the oligonucleotides. In the latter situation, the unique oligonucleotides are of identical length N. Thus, a set of overlapping oligonucleotides is a set of oligonucleotides that are subsequences derived from some master sequence by subdividing that sequence in such a way that each subsequence contains either the start or end of at least one other subsequence in the set.

An example of the above for purposes of illustration and not limitation is presented by the sequence ATGGACTTAG-CATTCG (SEQ ID NO:3), from which the following set of overlapping oligonucleotides can be identified:

ATGGACTTAGCA (SEQ ID NO:4)

TGGACTTAGCAT (SEQ ID NO:5)

GGACTTAGCATT (SEQ ID NO:6)

GACTTAGCATTC (SEQ ID NO:7)

ACTTAGCATTCG (SEQ ID NO:8)

In this example the overlapping oligonucleotides are spaced one nucleotide apart. In other words, there is overlap of all but one nucleotide from one oligonucleotide to the next. In the example above, the original nucleotide sequence is 16 nucleotides long (L=16). The length of each of the overlapping oligonucleotides is 12 nucleotides long (N=12) and there are L−N+1=5 oligonucleotides.

The length of the oligonucleotides may be the same or different and may vary depending on the length of the nucleotide sequence. The length of the oligonucleotides is determined by a practical compromise between the limits of current chemistries for oligonucleotide synthesis and the need for longer oligonucleotides, which exhibit greater binding affinity for the target sequence and are more likely to occur only once in complicated mixtures of polynucleotide targets. Usually, the length of the oligonucleotides is from about 10 to 50 nucleotides, more usually, from about 25 to 35 nucleotides.

In the next step of the method at least one parameter that is independently predictive of the ability of each of the oligonucleotides of the set to hybridize to the target nucleotide sequence is determined and evaluated for each of the above oligonucleotides. Examples of such a parameter, by way of illustration and not limitation, is a parameter selected from the group consisting of composition factors, thermodynamic factors, chemosynthetic efficiencies, kinetic factors and mathematical combinations of these quantities.

The determination of a parameter may be carried out by known methods. For example, melting temperature of the oligonucleotide/target duplex may be determined using the nearest neighbor method and parameters appropriate for the nucleotide acids involved. For DNA/DNA parameters, see J. SantaLucia Jr., et al., (1996) *Biochemistry*, 35:3555. For RNA/DNA parameters, see N. Sugimoto, et al., (1995) *Biochemistry*, 34:11211. Briefly, these methods are based on the observation that the thermodynamics of a nucleic acid duplex can be modeled as the sum of a term arising from the entire duplex and a set of terms arising from overlapping pairs of nucleotides ("nearest neighbor" model). For a discussion of the nearest neighbor see J. SantaLucia Jr., et al., (1996) *Biochemistry*, supra, and N. Sugimoto, et al., (1995) *Biochemistry*, supra. For example, the enthalpy ΔH of the duplex formed by the sequence

ATGGACTTAGCA (SEQ ID NO:4)

and its perfect complement can be approximated by the equation $$\Delta H = H_{init} + H_{AT} + H_{TG} + H_{GG} + H_{GA} + H_{AC} + H_{CT} + H_{TT} + H_{TA} + H_{AG} + H_{GC} + H_{CA}.$$

In the above equation, the term Hinit is the initiation enthalpy for the entire duplex, while the terms $H_{AT}, \ldots, H_{CA}$ are the so-called "nearest neighbor" enthalpies. Similar equations can be written for the entropy, for the corresponding quantities for RNA homoduplexes, or for DNA/RNA heteroduplexes. The free energy can then be calculated from the enthalpy, entropy and absolute temperature, as described previously.

Predicted free energy of the most stable intramolecular structure of an oligonucleotide ($\Delta G_{MFOLD}$) may be determined using the nucleic acid folding algorithm MFOLD and parameters appropriate for the oligonucleotide, e.g., DNA or RNA. For MFOLD, see J. A. Jaeger, et al., (1989), supra. For DNA folding parameters, see J. SantaLucia Jr., et al., (1996), supra. Briefly, these methods operate in two steps. First, a map of all possible compatible intramolecular base pairs is made. Second, the global minimum of the free energy of the various possible base pairing configurations is found, using the nearest neighbor model to estimate the enthalpy and entropy, the user input temperature to complete the calculation of free energy, and a dynamic programming algorithm to find the global minimum. The algorithm is computationally intensive; calculation times scale as the third power of the sequence length.

The following Table 1 summarizes groups of parameters that are independently predictive of the ability of each of the oligonucleotides to hybridize to the target nucleotide sequence together with a reference to methods for their determination. Parameters within a given group are known or expected to be strongly correlated to one another, while parameters in different groups are known or expected to be poorly correlated with one another.

TABLE 1

| Group | Parameter | Source or Reference |
|---|---|---|
| I | duplex enthalpy, ΔH | Santa Lucia et al., 1996; Sugimoto et al., 1995 |
|  | duplex entropy, ΔS | Santa Lucia et al., 1996; Sugimoto et al., 1995 |
|  | duplex free energy, ΔG | ΔG = ΔH − TΔS (see text) |
|  | melting temperature, $T_m$ | (see text) |
|  | mole fraction (or percent) G + C | self-explanatory |
|  | subsequence duplex enthalpy | Santa Lucia et al., 1996; Sugimoto et al., 1995 |
|  | subsequence duplex entropy | Santa Lucia et al., 1996; Sugimoto et al., 1995 |
|  | subsequence duplex free energy | ΔG = ΔH − TΔS (see text) |
|  | subsequence duplex $T_m$ | (see text) |
|  | subsequence duplex mole fraction (or percent) G + C | self-explanatory |
| II | intramolecular enthalpy, $\Delta H_{MFOLD}$ | Jaeger et al., 1989; Santa Lucia et al., 1996 |
|  | intramolecular entropy, $\Delta S_{MFOLD}$ | Jaeger et al., 1989; Santa Lucia et al., 1996 |
|  | intramolecular free energy, $\Delta G_{MFOLD}$ | ΔG = ΔH − TΔS (see text) |
|  | hairpin enthalpy, $\Delta H_{hairpin}$ | Jaeger et al., 1989; Santa Lucia et al., 1996 |
|  | hairpin entropy, $\Delta S_{hairpin}$ | Jaeger et al., 1989; Santa Lucia et al., 1996 |
|  | hairpin free energy, $\Delta G_{hairpin}$ | ΔG = ΔH − TΔS (see text) |
|  | intramolecular partition function, Z | $Z = \sum_{k \, structures} \exp(-\Delta G^{(k)}_{intramolecular} / RT)$ |
| III | sequence complexity | Altschul et al., 1994 |
|  | sequence information content | Altschul et al., 1994 |
| IV | steric factors | molecular modeling or experiment |
|  | molecular dynamic simulation | Weber & Hefland, 1979 |
|  | enthalpy, entropy & free energy of activation | measured experimentally |
|  | association & dissociation rates | Patzel & Sczakiel, 1998 |
| V | oligonucleotide chemosynthetic efficiencies | measured experimentally |
| VI | target synthetic efficiencies | measured experimentally |

In a next step of the present method, a subset of oligonucleotides within the predetermined number of unique oligonucleotides is identified based on the above evaluation of the parameter. A number of mathematical approaches may be followed to sort the oligonucleotides based on a parameter. In one approach a cut-off value is established. The cut-off value is adjustable and can be optimized relative to one or more training data sets. This is done by first establishing some metric for how well a cutoff value is performing; for example, one might use the normalized signal observed for each oligonucleotide in the training set. Once such a metric is established, the cutoff value can be numerically optimized to maximize the value of that metric, using optimization algorithms well known to the art. Alternatively, the cutoff value can be estimated using graphical methods, by graphing the value of the metric as a function of one or more parameters, and then establishing cutoff values that bracket the region of the graph where the chosen metric exceeds some chosen threshold value. In essence, the cut off values are chosen so that the rule set used yields training data that maximizes the inclusion of oligonucleotides that exhibit good hybridization efficiency and minimizes the inclusion of oligonucleotides that exhibit poor hybridization efficiency.

Figure 3:
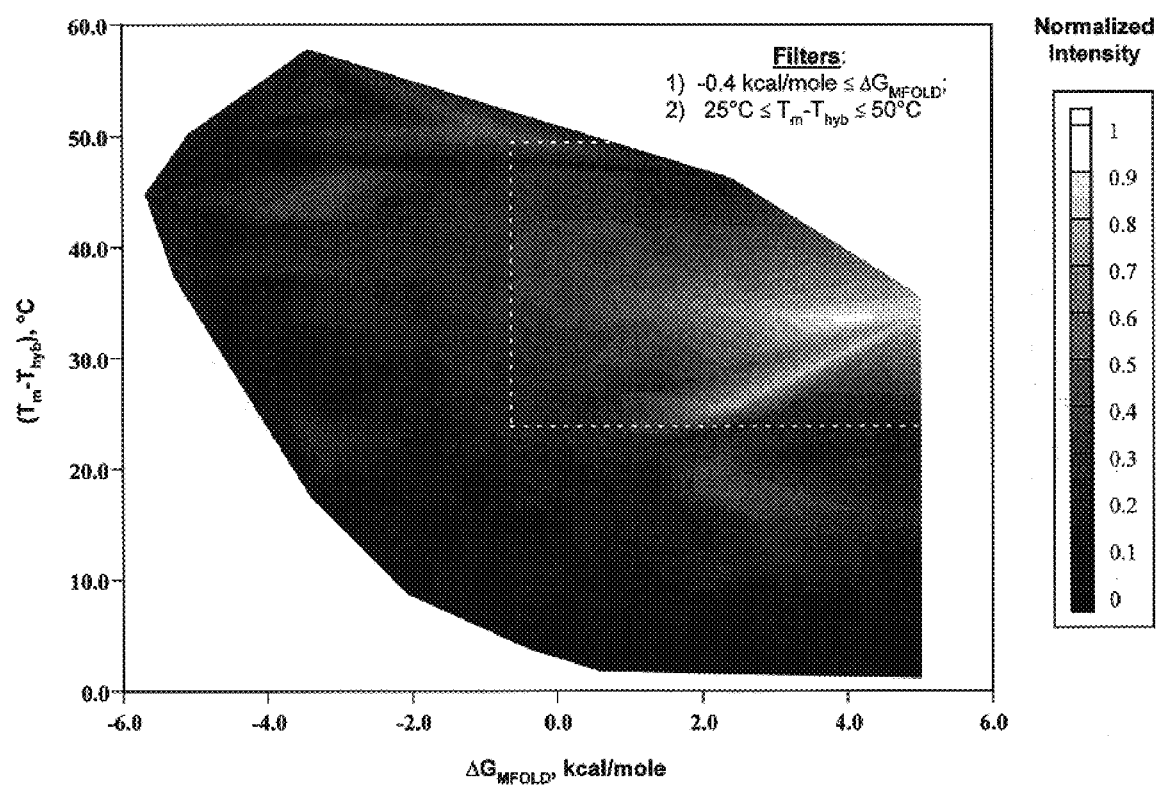
FIG. 3 is a contour plot of normalized hybridization intensity from multiple experiments, as a function of the free energy of the most stable probe intramolecular structure ($\Delta G_{MFOLD}$) and the difference between the predicted RNA/DNA heteroduplex melting temperature ($T_m$) and the temperature of hybridization ($T_{hyb}$).

A preferred approach to performing such a graph-based optimization of filter parameters is shown in FIG. 3. In FIG. 3, hybridization data from several different genes have been used to prepare a contour plot of relative hybridization intensity as a function of DNA/RNA heteroduplex melting temperature and free energy of the most stable intramolecular structure of the probe. Contours are shown only for regions for which there are data; the white space outside of the outermost contour indicates that there are no experimental data for that region. The details of how the data were obtained can be found in Example 1 below. A summary of the sequences and number of data points employed is shown in Table 2 below. The measured hybridization intensities for each data set were normalized prior to construction of the contour plot depicted in FIG. 3 by dividing each observed intensity by the maximum intensity observed for that gene. In addition, differences in hybridization salt concentrations and hybridization temperatures were accounted for by using the salt concentration-corrected values of the melting temperatures and by subtracting the hybridization temperature from each predicted melting temperature, respectively. The filter set determined by examination of FIG. 3 is indicated by both the dotted open box in the figure and by the inequalities above the box.

One way in which such a contour plot may be prepared involves the use of an appropriate software application such as Microsoft® Excel® or the like. For example, the cross-abulation tool may be used in the Microsoft Excel® program. Data is accumulated into rectangular bins that are 0.5 kcal $\Delta G_{MFOLD}$ wide and 2.5° C. $T_m$ wide. In each bin the average values of $\Delta G_{MFOLD}$, $T_m-T_{hyb}$, and the normalized hybridization intensity are calculated. The data is output to the software application DeltaGraph® (Deltapoint, Inc., Monterey, Calif.) and the contour plot is prepared using the tools and instructions provided.

TABLE 2

| Target (GenBank Accession No.) | Target Strand | No. Data Points | $T_{hyb}$ | [Na$^+$] Correction |
|---|---|---|---|---|
| HIV protease-reverse transcriptase (PRT)[a] (M15654) | Sense | 1,022 | 35° C. | −1.4° C. |
| HIV protease-reverse transcriptase (PRT)[a] (M15654) | antisense | 1,041 | 30° C. | −1.4° C. |
| HIV protease-reverse transcriptase (PRT)[b] (M15654) | Sense | 88 | 35° C. | −1.4° C. |
| Human G3PDH (glyceraldehyde-3-dehydrogenase)[b] (X01677) | antisense | 93 | 35° C. | −1.4° C. |

TABLE 2-continued

| Target (GenBank Accession No.) | Target Strand | No. Data Points | $T_{hyb}$ | [Na$^+$] Correction |
|---|---|---|---|---|
| Human p53[b] (X02469) | antisense | 93 | 35° C. | −1.4° C. |
| Rabbit β-globin[c] (K03256) | antisense | 106 | 30° C. | 0° C. |

[a]Data from Affymetrix GeneChip ™ Array
[b]Data from biotinylated probes bound to streptavidin-coated microtiter wells
[c]Literature data: see N. Milner, K. U. Mir & E. M. Southern (1997) Nature Biotech. 15, 537–541.

Once the cut-off value is selected, a subset of oligonucleotides having parameter values greater than or equal to the cut-off value is identified. This refers to the inclusion of oligonucleotides in a subset based on whether the value of a predictive parameter satisfies an inequality.

Examples of identifying a subset of oligonucleotides by establishing cut-off values for predictive parameters are as follows: for melting temperature an inequality might be 60° C.$\leq T_m$; for predicted free energy an inequality, preferably, might be $$\Delta G_{MFOLD} \geq -0.4 \frac{\text{kcal}}{\text{mole}}.$$

In a variation of the above, both a maximum and a minimum cut-off value may be selected. A subset of oligonucleotides is identified whose values fall within the maximum and minimum values, i.e., values greater than or equal to the minimum cut-off value and less than or equal to the maximum cut-off value. An example of this approach for melting temperature might be the inequality $$60° \text{C.} \leq T_m \leq 85° \text{C.}$$

With regard to cut off values for $T_m$ the lower limit is most important, and is preferably $T_m=T_{hyb}$, more preferably, $T_m=T_{hyb}+15°$ C. The upper cutoff is important when the sequence region under consideration is unusually rich in G and C, and is preferably $T_m=T_{hyb}+40°$ C. With regard to $\Delta G_{MFOLD}$ the cutoff value is usually greater than or equal to −1.0 kcal/mole. As mentioned above, the cutoff values preferably are determined from real data through experimental observations.

In another approach the parameter values may be converted into dimensionless numbers. The parameter value is converted into a dimensionless number by determining a dimensionless score for each parameter resulting in a distribution of scores having a mean value of zero and a standard deviation of one. The dimensionless score is a number that is used to rank some object (such as an oligonucleotide) to which that score relates. A score that has no units (i.e., a pure number) is called a dimensionless score.

In one approach the following equations are used for converting the values of said parameters into dimensionless numbers:

$$s_{i,x} = \frac{x_i - \langle x \rangle}{\sigma_{\{x\}}},$$

where $S_{i,x}$ is the dimensionless score derived from parameter x calculated for oligonucleotide i, $x_i$ is the value of parameter x calculated for oligonucleotide i, <x> is the average of parameter x calculated for all of the oligonucleotides under consideration for a given nucleotide sequence target, and $\sigma_{\{x\}}$ is the standard deviation of parameter x calculated for all of the oligonucleotides under consideration for a given nucleotide sequence target, and is given by the equation $$\sigma_{[x]} = \sqrt{\frac{\sum_{j=1}^{M}(x_j - \langle x \rangle)^2}{M-1}},$$

where M is the number of oligonucleotides. The resulting distribution of scores, {S} has a mean value of zero and a standard deviation of one. These properties can be important for a combination of the scores discussed below.

The use of a dimensionless number approach may further include calculating a combination score $S_i$ by evaluating a weighted average of the individual values of the dimensionless scores $s_{i,x}$ by the equation:

$$S_i = \sum_{[x]} q_x s_{i,x},$$

where $q_x$ is the weight assigned to the score derived from parameter x, the individual values of $q_x$ are always greater than zero, and the sum of the weights $q_x$ is unity.

In another variation of the above approach, the method of calculation of the composite parameter is optimized based on the correlation of the individual composite scores to real data, as explained more fully below.

In one approach the calculation of the composite score further involves determining a moving window-averaged combination score $\langle S_i \rangle$ for the ith probe by the equation:

$$\langle S_i \rangle = \frac{1}{w} \sum_{j=i-\frac{w-1}{2}}^{i+\frac{w-1}{2}} S_j, \quad w = \text{an odd integer},$$

where w is the length of the window for averaging (i.e., w nucleotides long), and then applying a cutoff filter to the value of $\langle S_i \rangle$. This procedure results in smoothing (smoothing procedure) by turning each score into a consensus metric for a set of w adjacent oligonucleotide probes. The score, referred to as the "smoothed score," is essentially continuous rather than a few discrete values. The value of the smoothed score is strongly influenced by clustering of scores with high or low values; window averaging therefore provides a measurement of cluster size.

An advantage of the dimensionless score approach to the probe prediction algorithm is that it is easy to objectively optimize. In one approach to training the algorithm, optimization of the weights $q_x$ above may be performed by varying the values of the weights so that the correlation coefficient $\rho_{\{<S_i>\},\{V_i\}}$ between the set of window-averaged combination scores $\{<S_i>\}$ and a set of calibration experimental measurements $\{V_i\}$ is maximized. The correlation coefficient $\rho_{\{<S_i>\},\{V_i\}}$ is calculated from the equation $$\rho_{\{<S_i>\},\{V_i\}} = \left(\frac{1}{M}\right)\frac{\text{Covariance}(\langle S \rangle, V)}{\sigma_{\{<S_i>\}}\sigma_{\{V_i\}}},$$

where M is the number of window averaged, combination dimensionless scores and the number of corresponding measurements, the covariance is as defined earlier (see earlier equations) and $\sigma_{\{<S_i>\}}$ and $\sigma_{\{V_i\}}$ are the standard deviations of $\{<S_i>\}$ and $\{V_i\}$, as defined previously. An example of this approach is shown in Example 2, below.

In another approach the parameter is derived from one or more factors by mathematical transformation of the factors. This involves the calculation of a new predictive parameter from one or more existing predictive parameters, by means of an equation. For instance, the equilibrium constant $K_{open}$ for formation of an oligonucleotide with no intramolecular structure from its structured form can be calculated from the intramolecular structure free energy $\Delta G_{MFOLD}$, using the equation $$K_{open} = \exp\left(\frac{\Delta G_{MFOLD}}{RT}\right).$$

In a next step of the method oligonucleotides in the subset are then identified that are clustered along a region of the nucleotide sequence that is hybridizable to the target nucleotide sequence. For example, consider a set of overlapping oligonucleotides identified by dividing a nucleotide sequence into subsequences. A subset of the oligonucleotides is obtained as described above. In general, this subset is obtained by applying a rule that rejects some members of the set. For the remaining members of the set, namely, the subset, there will be some average number of nucleotides in the nucleotide sequence between the first nucleotides of adjacent remaining subsequences. If, for some sub-region of the nucleotide sequence, the average number of nucleotides in the nucleotide sequence between the first nucleotides of adjacent remaining subsequences is less than the average for the entire nucleotide sequence, then the oligonucleotides are clustered. The smaller the average number of nucleotides between the first nucleotides of adjacent oligonucleotides, the stronger the clustering. The strongest clustering occurs when there are no intervening nucleotides between adjacent starting nucleotides. In this case, the oligonucleotides are said to be contiguous and may be referred to as contiguous sequence elements or "contigs."

Accordingly, in this step oligonucleotides are sorted based on length of contiguous sequence elements. Oligonucleotides in the subset determined above are identified that are contiguous along a region of the input nucleic acid sequence. The length of each contigs that is equal to the number of oligonucleotides in each contigs, namely, oligonucleotides from the above step whose complement begin at positions m+1, m+2, . . . , m+k in the target sequence, form a contig of length k. Contigs can be identified and contig length can be calculated using, for example, a Visual Basic® module that can be incorporated into a Microsoft® Excel workbook.

Cluster size can be defined in several ways:

For contiguous clusters, the size is simply the number of adjacent oligonucleotides in the cluster. Again, this may also be referred to as contiguous sequence elements. The number may also be referred to as "contig length". For example, consider the nucleotide sequence discussed above, namely, ATGGACTTAGCATTCG (SEQ ID NO:3) and the identified set of overlapping oligonucleotides

ATGGACTTAGCA (SEQ ID NO:4)

TGGACTTAGCAT (SEQ ID NO:5)

GGACTTAGCATT (SEQ ID NO:6)

GACTTAGCATTC (SEQ ID NO:7)

ACTTAGCATTCG (SEQ ID NO:8)

Suppose that, after calculation and evaluation of the predictive parameters, four nucleotides remain:

```
ATGGACTTAGCA    (SEQ ID NO:4)   ▌
TGGACTTAGCAT    (SEQ ID NO:5)   ▌   contig
GGACTTAGCATT    (SEQ ID NO:6)   ▌
  ACTTAGCATTCG  (SEQ ID NO:8)   ▌   single
                                    oligonucleotide
```

A "contig" encompassing three of the oligonucleotides of the subset is present together with a single oligonucleotide. The contig length is 3 oligonucleotides.

Alternatively, cluster size at some position in the sequence hybridizable or complementary to the target sequence may be defined as the number of oligonucleotides whose center nucleotides fall inside a region of length M centered about the position in question, divided by M. This definition of clustering allows small gaps in clusters. In the example used above for contiguous clusters, if M was 10, then the cluster size would step through the values 0/10, . . . , 0/10, 1/10, 2/10, 3/10, 3/10, 4/10, 4/10, 4/10, 4/10, 4/10, 3/10, 2/10, 1/10, 1/10, 0/10 as the center of the window of length 10 passed through the cluster. In each fraction, the numerator is the number of oligonucleotide sequences that have satisfied the filter set and whose central nucleotides are within a window 10 nucleotides long, centered about the nucleotide under consideration. The denominator (10) is simply the window length.

Another alternative is to define the size of a cluster at some position in the sequence hybridizable or complementary to the target sequence as the number of oligonucleotide sequences overlapping that position. This definition is equivalent to the last definition with M set equal to the oligonucleotide probe length and omission of the division by M.

Finally, cluster size can be approximated at each position in a nucleotide sequence by dividing the sequence into oligonucleotides, evaluating a numerical score for each oligonucleotide, and then averaging the scores in the neighborhood of each position by means of a moving window average as described above. Window averaging has the effect of reinforcing clusters of high or low values around a particular position, while canceling varying values about that position. The window average, therefore, provides a score that is sensitive to both the hybridization potential of a given oligonucleotide and the hybridization potentials of its neighbors.

In a next step of the present method, the oligonucleotides in the subset are ranked. Generally, this ranking is based on the lengths of the clusters or contigs, sizes of the clusters or values of a window averaged score. Oligonucleotides found in the longest contigs or largest clusters, or possessing the highest window averaged scores usually show the highest hybridization efficiencies. Often, the highest signal intensity within the cluster corresponds to the median oligonucleotide of the cluster. However, the peak signal intensity within the contig can be determined experimentally, by sampling the cluster at its first quartile, midpoint and third quartile, measuring the hybridization efficiencies of the sampled oligonucleotides, interpolating or extrapolating the results, predicting the position of the optimal probe, and then iterating the probe design process.

FIG. 1 shows a diagram of an example of the above-described method by way of illustration and not limitation. Referring to FIG. 1 a target sequence of length L from, e.g., a database, is used to generate a sequence that is hybridizable to the target sequence from which candidate oligonucleotide probe sequences are generated. One or more parameters are calculated for each of the oligonucleotide probe sequences. The candidate oligonucleotide probe sequences are filtered based on the values of the parameters. Clustering of the filtered candidate probe sequences is evaluated and the clusters are ranked by size. Then, the oligonucleotide probes are statistically sampled and synthesized. Further evaluation may be made by evaluating the hybridization of the selected oligonucleotide probes in real hybridization experiments. The above process may be reiterated to further define the selection. In this way only a small fraction of the potential oligonucleotide probe candidates are synthesized and tested. This is in sharp contrast to the known method of synthesizing and testing all or a major portion of potential oligonucleotide probes for a given target sequence.

The methods of the present invention are preferably carried out at least in part with the aid of a computer. For example, an IBM® compatible personal computer (PC) may be utilized. The computer is driven by software specific to the methods described herein.

The preferred computer hardware capable of assisting in the operation of the methods in accordance with the present invention involves a system with at least the following specifications: Pentium® processor or better with a clock speed of at least 100 MHz, at least 32 megabytes of random access memory (RAM) and at least 80 megabytes of virtual memory, running under either the Windows 95 or Windows NT 4.0 operating system (or successor thereof).

As mentioned above, software that may be used to carry out the methods may be either Microsoft Excel or Microsoft Access, suitably extended via user written functions and templates, and linked when necessary to stand-alone programs that calculate specific parameters (e.g., MFOLD for intramolecular thermodynamic parameters). Examples of software programs used in assisting in conducting the present methods may be written, preferably, in Visual BASIC, FORTRAN and C++, as exemplified below in the Examples. It should be understood that the above computer information and the software used herein are by way of example and not limitation. The present methods may be adapted to other computers and software. Other languages that may be used include, for example, PASCAL, PERL or assembly language.

Figure 2:
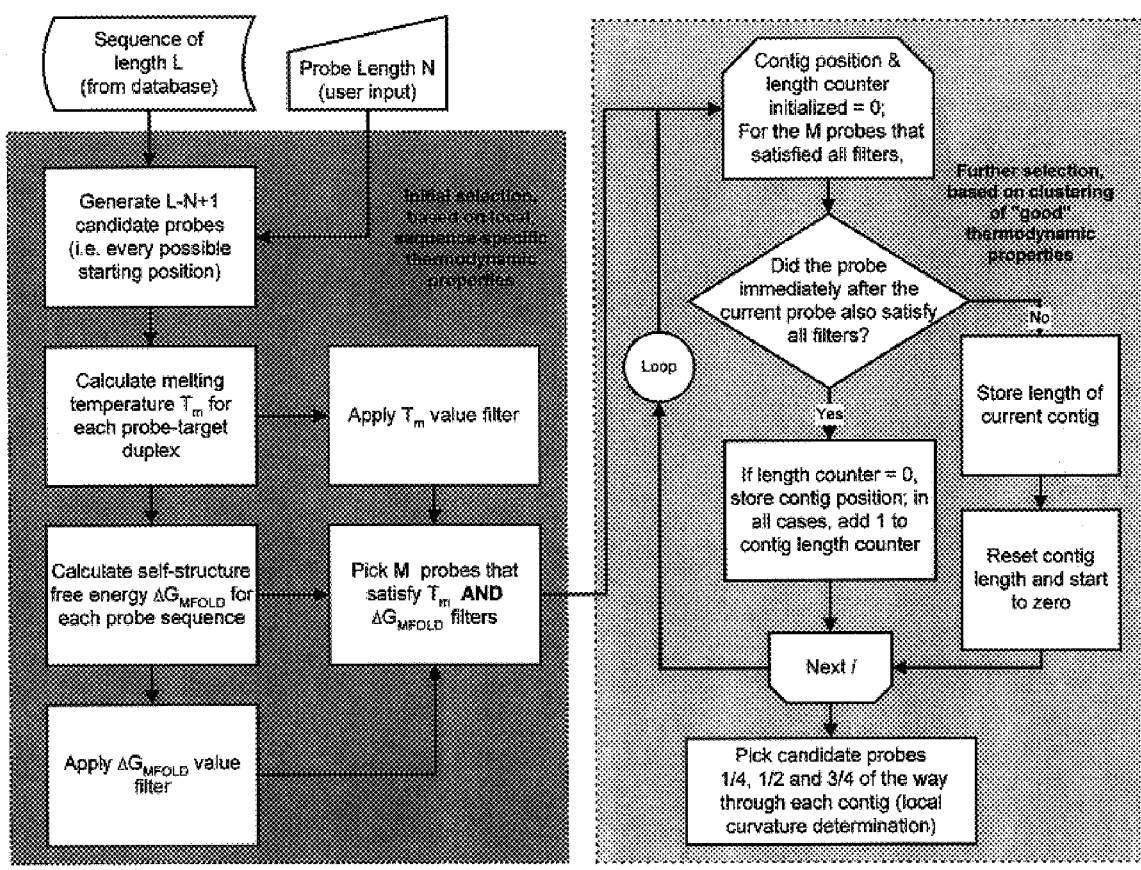
FIG. 2 is a flow chart depicting a preferred embodiment of a method in accordance with the present invention.

FIG. 2 depicts a more specific approach to a method in accordance with the present invention. Referring to FIG. 2, a sequence of length L is obtained from a database such as GenBank, UniGene or a proprietary sequence database. Probe length N is determined by the user based on the requirements for sensitivity and specificity and the limitations of the oligonucleotide synthetic scheme employed. The probe length and sequence length are used to generate L–N+1 candidate oligonucleotide probes, i.e., from every possible starting position. An initial selection is made based on local sequence predicted thermodynamic properties. To this end, melting temperature $T_m$ and the self-structure free energy $\Delta G_{MFOLD}$, are calculated for each of the potential oligonucleotide probe: target nucleotide sequence complexes. Next, M probes that satisfy $T_m$ and $\Delta G_{MFOLD}$ filters are selected. A further selection can be made based on clustering of "good" parameters. Good parameters are parameters that satisfy all of the filters in the filter set. Clustering is defined by any of the methods described previously; in FIG. 2, the "contig length" definition of clustering is used.

For each of the M oligonucleotide sequences that satisfied all filters the question is asked whether the oligonucleotide sequence immediately following the sequence under consideration is also one of the sequences that satisfied all of the filters. If the answer to this question is NO, then one stores the current value of the contig length counter, resets the counter to zero and proceeds to the next oligonucleotide sequence that satisfied all filters. If the answer to the question is YES, then 1 is added to the contig length counter and, if the counter now equals 1 (i.e., this is the first oligonucleotide probe sequence in the contig), the starting position of the oligonucleotide is stored. One then moves to the next oligonucleotide that satisfied all filters, which, in this case, is the same as the next oligonucleotide before the application of the filter set. The process is repeated until all M filtered oligonucleotide sequences have been examined. In this way, a single pass through the set of M filtered oligonucleotide sequences generates the lengths and starting positions of all contigs.

Next, contigs are ranked based on the lengths of their contiguous sequence elements. Longer contig lengths generally correlate with higher hybridization efficiencies. All oligonucleotides of the higher-ranking contigs may be considered, or candidate oligonucleotide probes may be picked. For example, candidate oligonucleotide probes can be picked one quarter, one half and three quarters of the way through each contig. The latter approach provides local curvature determination after experimental determination of hybridization efficiencies, which allows either interpolation or extrapolation of the positions of the next probes to be synthesized in order to close in on the optimal probe in the region. If the contig brackets the actual peak of hybridization efficiency, the process will converge in 2–3 iterations. If the contig lies to one side of the actual peak, the process will converge in 3–4 iterations.

The above illustrative approach is further described with reference to the following DNA nucleotide sequence, which is the complement of the target RNA nucleotide sequence:

GTCCAAAAAGGGTCAGTCTACCTCCCGC-
CATAAAAAACTCATGTTCAAGA (SEQ ID NO:9).

In the first step of the method, the nucleotide sequence is divided into overlapping oligonucleotides that are 25 nucleotides in length. This length is chosen because it is an effective compromise between the need for sensitivity (enhanced by longer oligonucleotides) and the chemosynthetic efficiency of schemes for synthesis of surface-bound arrays of oligonucleotide probes.

Next, the estimated duplex melting temperatures ($T_m$) and self-structure free energies ($\Delta G_{MFOLD}$) are calculated for each oligonucleotide in the set of overlapping oligonucleotides. The values are obtained from a user-written function that calculates DNA/RNA heteroduplex thermodynamic parameters (see N. Sugimoto, et al., *Biochemistry*, 34:11211 (1995)) and a modified version of the program MFOLD that estimates the free energy of the most stable intramolecular structure of a single stranded DNA molecule (see J. A. Jaeger, et al., (1989), supra, respectively. The steps are illustrated below.

| GTCCAAAAAGGGTCAGTCTACCTCCCGCCATAAAAAACTCATGTTCAAGA (target complement sequence) | $T_m$ (° C.) | $\Delta G_{MFOLD}$ | |
|---|---|---|---|
| GTCCAAAAAGGGTCAGTCTACCTCC | 71.77 | -1.20 | SEQ ID NO:10 |
| TCCAAAAAGGGTCAGTCTACCTCCC | 71.99 | -1.20 | SEQ ID NO:11 |
| CCAAAAAGGGTCAGTCTACCTCCCG | 70.78 | -1.20 | SEQ ID NO:12 |
| CAAAAAGGGTCAGTCTACCTCCCGC | 71.23 | -1.20 | SEQ ID NO:13 |
| AAAAAGGGTCAGTCTACCTCCCGCC | 73.07 | -1.20 | SEQ ID NO:14 |
| AAAAGGGTCAGTCTACCTCCCGCCA | 75.68 | -1.20 | SEQ ID NO:15 |
| AAAGGGTCAGTCTACCTCCCGCCAT | 77.53 | -1.20 | SEQ ID NO:16 |
| AAGGGTCAGTCTACCTCCCGCCATA | 79.03 | -1.20 | SEQ ID NO:17 |
| AGGGTCAGTCTACCTCCCGCCATAA | 79.03 | -1.20 | SEQ ID NO:18 |
| GGGTCAGTCTACCTCCCGCCATAAA | 76.85 | -1.20 | SEQ ID NO:19 |
| GGTCAGTCTACCTCCCGCCATAAAA | 73.10 | -0.80 | SEQ ID NO:20 |
| GTCAGTCTACCTCCCGCCATAAAAA | 69.50 | 0.90 | SEQ ID NO:21 |
| TCAGTCTACCTCCCGCCATAAAAAA | 65.60 | 0.90 | SEQ ID NO:22 |
| CAGTCTACCTCCCGCCATAAAAAAC | 64.96 | 0.90 | SEQ ID NO:23 |
| AGTCTACCTCCCGCCATAAAAAACT | 65. | 1.10 | SEQ ID NO:24 |
| GTCTACCTCCCGCCATAAAAAACTC | 66.36 | 2.40 | SEQ ID NO:25 |
| TCTACCTCCCGCCATAAAAAACTCA | 64.97 | 2.90 | SEQ ID NO:26 |
| CTACCTCCCGCCATAAAAAACTCAT | 63.96 | 2.70 | SEQ ID NO:27 |
| TACCTCCCGCCATAAAAAACTCATG | 62.58 | 1.10 | SEQ ID NO:28 |
| ACCTCCCGCCATAAAAAACTCATGT | 65.10 | 0.40 | SEQ ID NO:29 |
| CCTCCCGCCATAAAAAACTCATGTT | 64.96 | 0.10 | SEQ ID NO:30 |
| CTCCCGCCATAAAAAACTCATGTTC | 63.37 | -0.10 | SEQ ID NO:31 |
| TCCCGCCATAAAAAACTCATGTTCA | 62.86 | -0.10 | SEQ ID NO:32 |
| CCCGCCATAAAAAACTCATGTTCAA | 60.47 | -0.10 | SEQ ID NO:33 |
| CCGCCATAAAAAACTCATGTTCAAG | 57.98 | -0.10 | SEQ ID NO:34 |
| CGCCATAAAAAACTCATGTTCAAGA | 56.20 | -0.10 | SEQ ID NO:35 |

Next, the oligonucleotide sequences are filtered on the basis of $T_m$. A high and low cut-off value may be selected, for example, 60° C.$\leq T_m \leq$85° C. Thus, oligonucleotides having $T_m$ values falling within the above range are retained. Those outside the range are discarded, which is indicated below by lining out of those oligonucleotides and parameter values.

```
GTCCAAAAAGGGTCAGTCTACCTCCCGCCATAAAAAACTCATGTTCAAGA   (target complement sequence)

Tₘ(° C.)   ΔG_MFOLD
GTCCAAAAAGGGTCAGTCTACCTCC                             71.77      -1.20
TCCAAAAAGGGTCAGTCTACCTCCC                             71.99      -1.20
 CCAAAAAGGGTCAGTCTACCTCCCG                            70.78      -1.20
  CAAAAAGGGTCAGTCTACCTCCCGC                           71.23      -1.20
   AAAAAGGGTCAGTCTACCTCCCGCC                          73.07      -1.20
    AAAAGGGTCAGTCTACCTCCCGCCA                         75.68      -1.20
     AAAGGGTCAGTCTACCTCCCGCCAT                        77.53      -1.20
      AAGGGTCAGTCTACCTCCCGCCATA                       79.03      -1.20
       AGGGTCAGTCTACCTCCCGCCATAA                      79.03      -1.20
        GGGTCAGTCTACCTCCCGCCATAAA                     76.85      -1.20
         GGTCAGTCTACCTCCCGCCATAAAA                    73.10      -0.80
          GTCAGTCTACCTCCCGCCATAAAAA                   69.50       0.90
           TCAGTCTACCTCCCGCCATAAAAAA                  65.60       0.90
            CAGTCTACCTCCCGCCATAAAAAAC                 64.96       0.90
             AGTCTACCTCCCGCCATAAAAAACT                65.48       1.10
              GTCTACCTCCCGCCATAAAAAACTC               66.36       2.40
               TCTACCTCCCGCCATAAAAAACTCA              64.97       2.90
                CTACCTCCCGCCATAAAAAACTCAT             63.96       2.70
                 TACCTCCCGCCATAAAAAACTCATG            62.58       1.10
                  ACCTCCCGCCATAAAAAACTCATGT           65.10       0.40
                   CCTCCCGCCATAAAAAACTCATGTT          64.96       0.10
                    CTCCCGCCATAAAAAACTCATGTTC         63.37      -0.10
                     TCCCGCCATAAAAAACTCATGTTCA        62.86      -0.10
                      CCCGCCATAAAAAACTCATGTTCAA       60.47      -0.10
                       ~~CCGCCATAAAAAACTCATGTTCAAG~~  ~~57.98~~  -0.10
                        ~~CGCCATAAAAAACTCATGTTCAAGA~~ ~~56.20~~  -0.10
```

Next, the oligonucleotide sequences remaining after the above exercise are iltered on the basis of $\Delta G_{MFOLD}$ and are retained if the value is greater than −0.4. Those oligonucleotides with a $\Delta G_{MFOLD}$ less than −0.4 are discarded, which is indicated below by double lining out of those oligonucleotides and parameter values.

Clusters of retained oligonucleotides are identified and ranked based on cluster size. In this example, a contiguous cluster of 13 retained oligonucleotides is identified by the vertical black bar on the left. Any or all of the oligonucleotides in this cluster may be evaluated experimentally.

```
GTCCAAAAAGGGTCAGTCTACCTCCCGCCATAAAAAACTCATGTTCAAGA   (target complement sequence)

Tₘ(° C.)   ΔG_MFOLD
~~GTCCAAAAAGGGTCAGTCTACCTCC~~                         71.77      ~~-1.20~~
~~TCCAAAAAGGGTCAGTCTACCTCCC~~                         71.99      ~~-1.20~~
 ~~CCAAAAAGGGTCAGTCTACCTCCCG~~                        70.78      ~~-1.20~~
  ~~CAAAAAGGGTCAGTCTACCTCCCGC~~                       71.23      ~~-1.20~~
   ~~AAAAAGGGTCAGTCTACCTCCCGCC~~                      73.07      ~~-1.20~~
    ~~AAAAGGGTCAGTCTACCTCCCGCCA~~                     75.68      ~~-1.20~~
     ~~AAAGGGTCAGTCTACCTCCCGCCAT~~                    77.53      ~~-1.20~~
      ~~AAGGGTCAGTCTACCTCCCGCCATA~~                   79.03      ~~-1.20~~
       ~~AGGGTCAGTCTACCTCCCGCCATAA~~                  79.03      ~~-1.20~~
        ~~GGGTCAGTCTACCTCCCGCCATAAA~~                 76.85      ~~-1.20~~
         GGTCAGTCTACCTCCCGCCATAAAA                    73.10      ~~-0.80~~
          GTCAGTCTACCTCCCGCCATAAAAA                   69.50       0.90
           TCAGTCTACCTCCCGCCATAAAAAA                  65.60       0.90
            CAGTCTACCTCCCGCCATAAAAAAC                 64.96       0.90
             AGTCTACCTCCCGCCATAAAAAACT                65.48       1.10
              GTCTACCTCCCGCCATAAAAAACTC               66.36       2.40
               TCTACCTCCCGCCATAAAAAACTCA              64.97       2.90
                CTACCTCCCGCCATAAAAAACTCAT             63.96       2.70
                 TACCTCCCGCCATAAAAAACTCATG            62.58       1.10
                  ACCTCCCGCCATAAAAAACTCATGT           65.10       0.40
                   CCTCCCGCCATAAAAAACTCATGTT          64.96       0.10
                    CTCCCGCCATAAAAAACTCATGTTC         63.37      -0.10
                     TCCCGCCATAAAAAACTCATGTTCA        62.86      -0.10
                      CCCGCCATAAAAAACTCATGTTCAA       60.47      -0.10
                       ~~CCGCCATAAAAAACTCATGTTCAAG~~  ~~57.98~~  -0.10
                        ~~CGCCATAAAAAACTCATGTTCAAGA~~ ~~56.20~~  -0.10
```

```
GTCCAAAAAGGGTCAGTCTACCTCCCGCCATAAAAAACTCATGTTCAAGA  (target complement sequence)

Tm(° C.)    ΔG_MFOLD
            ~~GTCCAAAAAGGGTCAGTCTACCTCC~~              71.77       ~~-1.20~~
             ~~TCCAAAAAGGGTCAGTCTACCTCCC~~             71.99       ~~-1.20~~
              ~~CCAAAAAGGGTCAGTCTACCTCCCG~~            70.78       ~~-1.20~~
               ~~CAAAAAGGGTCAGTCTACCTCCCGC~~           71.23       ~~-1.20~~
                ~~AAAAAGGGTCAGTCTACCTCCCGCC~~          73.07       ~~-1.20~~
                 ~~AAAAGGGTCAGTCTACCTCCCGCCA~~         75.68       ~~-1.20~~
                  ~~AAAGGGTCAGTCTACCTCCCGCCAT~~        77.53       ~~-1.20~~
                   ~~AAGGGTCAGTCTACCTCCCGCCATA~~       79.03       ~~-1.20~~
                    ~~AGGGTCAGTCTACCTCCCGCCATAA~~      79.03       ~~-1.20~~
                     ~~GGGTCAGTCTACCTCCCGCCATAAA~~     76.85       ~~-1.20~~
                      ~~GGTCAGTCTACCTCCCGCCATAAAA~~    73.10       ~~-0.80~~
                       GTCAGTCTACCTCCCGCCATAAAAA       69.50        0.90
                        TCAGTCTACCTCCCGCCATAAAAAA      65.60        0.90
                         CAGTCTACCTCCCGCCATAAAAAAC     64.96        0.90
                          AGTCTACCTCCCGCCATAAAAAACT    65.48        1.10
                           GTCTACCTCCCGCCATAAAAAACTC   66.36        2.40
                            TCTACCTCCCGCCATAAAAAACTCA  64.97        2.90
                             CTACCTCCCGCCATAAAAAACTCAT 63.96        2.70
                              TACCTCCCGCCATAAAAAACTCATG 62.58       1.10
                               ACCTCCCGCCATAAAAAACTCATGT 65.10      0.40
                                CCTCCCGCCATAAAAAACTCATGTT 64.96     0.10
                                 CTCCCGCCATAAAAAACTCATGTTC 63.37   -0.10
                                  TCCCGCCATAAAAAACTCATGTTCA 62.86  -0.10
                                   CCCGCCATAAAAAACTCATGTTCAA 60.47 -0.10
                                    ~~CCGCCATAAAAAACTCATGTTCAAG~~ ~~57.90~~ -0.10
                                     ~~CGCCATAAAAAACTCATGTTCAAGA~~ ~~56.20~~ -0.10
```

Alternatively, in one approach the oligonucleotides at the first quartile, the median and the third quartile of the cluster may be selected for experimental evaluation, indicated below by bold print.

```
GTCCAAAAAGGGTCAGTCTACCTCCCGCCATAAAAAACTCATGTTCAAGA  (target complement sequence)

Tm(° C.)    ΔG_MFOLD
            ~~GTCCAAAAAGGGTCAGTCTACCTCC~~              71.77       ~~-1.20~~
             ~~TCCAAAAAGGGTCAGTCTACCTCCC~~             71.99       ~~-1.20~~
              ~~CCAAAAAGGGTCAGTCTACCTCCCG~~            70.78       ~~-1.20~~
               ~~CAAAAAGGGTCAGTCTACCTCCCGC~~           71.23       ~~-1.20~~
                ~~AAAAAGGGTCAGTCTACCTCCCGCC~~          73.07       ~~-1.20~~
                 ~~AAAAGGGTCAGTCTACCTCCCGCCA~~         75.68       ~~-1.20~~
                  ~~AAAGGGTCAGTCTACCTCCCGCCAT~~        77.53       ~~-1.20~~
                   ~~AAGGGTCAGTCTACCTCCCGCCATA~~       79.03       ~~-1.20~~
                    ~~AGGGTCAGTCTACCTCCCGCCATAA~~      79.03       ~~-1.20~~
                     ~~GGGTCAGTCTACCTCCCGCCATAAA~~     76.85       ~~-1.20~~
                      ~~GGTCAGTCTACCTCCCGCCATAAAA~~    73.10       ~~-0.80~~
                       GTCAGTCTACCTCCCGCCATAAAAA       69.50        0.90
                        TCAGTCTACCTCCCGCCATAAAAAA      65.60        0.90
                         CAGTCTACCTCCCGCCATAAAAAAC     64.96    0.90
                          AGTCTACCTCCCGCCATAAAAAACT    65.48        1.10
                           GTCTACCTCCCGCCATAAAAAACTC   66.36        2.40
                            TCTACCTCCCGCCATAAAAAACTCA  64.97        2.90
                             CTACCTCCCGCCATAAAAAACTCAT 63.96    2.70
                              TACCTCCCGCCATAAAAAACTCATG 62.58       1.10
                               ACCTCCCGCCATAAAAAACTCATGT 65.10      0.40
                                CCTCCCGCCATAAAAAACTCATGTT 64.96     0.10
                                 CTCCCGCCATAAAAAACTCATGTTC 63.37 -0.10
                                  TCCCGCCATAAAAAACTCATGTTCA 62.86  -0.10
                                   CCCGCCATAAAAAACTCATGTTCAA 60.47 -0.10
                                    ~~CCGCCATAAAAAACTCATGTTCAAG~~ ~~57.90~~ -0.10
                                     ~~CGCCATAAAAAACTCATGTTCAAGA~~ ~~56.20~~ -0.10
```

In one aspect of the present method, at least two parameters are determined wherein the parameters are poorly correlated with respect to one another. The reason for requiring that the different parameters chosen are poorly correlated with one another is that an additional parameter that is strongly correlated to the original parameter brings no additional information to the prediction process. The correlation to the original parameter is a strong indication that both parameters represent the same physical property of the system. Another way of stating this is that correlated parameters are linearly dependent on one another, while poorly correlated parameters are linearly independent of one another. In practice, the absolute value of the correlation coefficient between any two parameters should be less than 0.5, more preferably, less than 0.25, and, most preferably, as close to zero as possible.

In one preferred approach instead of $T_m$, for each oligonucleotide/target nucleotide sequence duplex, the difference between the predicted duplex melting temperature corrected for salt concentration and the temperature of hybridization of each of the oligonucleotides with the target nucleotide sequence is determined.

In one aspect the present method comprises determining two parameters at least one of the parameters being the association free energy between a subsequence within each of the oligonucleotides and its complementary sequence on the target nucleotide sequence, or some similar, strongly correlated parameter. The object of this approach is to identify a particularly stable subsequence of the oligonucleotide that might be capable of acting as a nucleation site for the beginning of the heteroduplex formation between the oligonucleotide and the target nucleotide sequence. Such nucleation is believed to be the rate-limiting step for process of heteroduplex formation.

The subsequence within the oligonucleotide is from about 3 to 9 nucleotides in length, usually, 5 to 7 nucleotides in length. The subsequence is at least three nucleotides from the terminus of the oligonucleotide. For support-bound oligonucleotides the subsequence is at least three nucleotides from the free end of the oligonucleotide, i.e., the end that is not attached to the support. Generally, this free end is the 5' end of the oligonucleotide. When the oligonucleotide is attached to a support, the subsequence is at least three nucleotides from the end of the oligonucleotide that is bound to the surface of the support to which the oligonucleotide is attached. Generally, the 3' end of the oligonucleotide is bound to the support.

The predictive parameter can be, for example, either melting temperature or duplex free energy of the subsequence with the target nucleotide sequence. The subsequence with the maximum (melting temperature) or minimum (free energy) value of one of the above parameters is chosen as the representative subsequence for that oligonucleotide probe. For example, if the oligonucleotide is nucleotides in length and a subsequence of 5 nucleotides is chosen, i.e., a 5-mer, then parameter values are calculated for all 5-mer subsequences of the oligonucleotide that do not include the 2 nucleotides at the free end of the oligonucleotide. Where 5' is the free end of the oligonucleotide with designated nucleotide number 1, the values are calculated for all 5-mer subsequences with starting nucleotides from position number 3 to position number 16. Thus, in this example, parameter values for 14 different subsequences are calculated. The subsequence with the maximum value for the parameter is then assigned as the stability subsequence for the oligonucleotide.

The inclusion of the above determination of a stability subsequence results in the following algorithm for determining the potential of an oligonucleotide to hybridize to a target nucleotide sequence. A predetermined number of unique oligonucleotides are identified within a nucleotide sequence that is hybridizable with said target nucleotide sequence. The oligonucleotides are chosen to sample the entire length of the nucleotide sequence. For each of the oligonucleotides, parameters that are independently predictive of the ability of each of said oligonucleotides to hybridize to said target nucleotide sequence are determined and evaluated. Two parameters that may be used are the thermodynamic parameters of $T_m$ and $\Delta G_{MFOLD}$. These parameters give rise to associated parameter filters. In one approach evaluation of the parameters involves establishing cut-off values as described above. Application of these cut-off values results in the identification of a subset of oligonucleotides for further scrutiny under the algorithm. In accordance with this embodiment of the present invention, there is included a stability subsequence limit in addition to the above. Cutoff values are determined either by means of objective optimization algorithms well known to the art or via graphical estimation methods; both approaches have been described previously in this document. In either case, the optimization of cutoff values involves comparison of predictions to known hybridization efficiency data sets. This process results in objective optimization as it looks at prediction versus experimental results and is otherwise referred to herein as "training the algorithm." The experimental data used to train the algorithm is referred to herein as "training data."

In the present approach filters are assigned to the $T_m$ oligonucleotide probe data. The $T_m$ of each oligonucleotide probe needs to be greater than or equal to the assigned filter ($T_m$ probe limit) to be given a filter score of "1"; otherwise, the filter score is "0". In addition, one can also impose a second filter for this parameter; that is, that the $T_m$ of the oligonucleotide probe also has to be less than a defined upper limit. Filters are also assigned to the $\Delta G_{MFOLD}$ data. The $\Delta A_{GMFOLD}$ of each oligonucleotide probe should be greater than or equal to the assigned filter ($\Delta G_{MFOLD}$ limit) to be given a filter score of "1"; otherwise, the filter score is "0". The filter scores are added. Furthermore, one can also impose a second filter for this parameter; that is, that the $\Delta G_{MFOLD}$ also has to be less than a defined upper limit. In accordance with the above discussion stability subsequences are identified. This leads to another filter. Accordingly, filters are assigned to the stability sequence data. The stability subsequence of each oligonucleotide probe needs to be greater than or equal to the assigned filter limit to be given a filter score of "1"; otherwise, the filter score is "0". In addition, one can also impose a second filter for this parameter; that is, that the stability subsequence also has to be less than a defined upper limit. In all cases, the filter values are determined by objective optimization (algorithmic or graphical) of the predictions of the present method versus training data, as described previously.

On the basis of the above filter sets a subset of oligonucleotides within said predetermined number of unique oligonucleotides is identified. Oligonucleotides in the subset are identified that are clustered along a region of the nucleotide sequence that is hybridizable to the target nucleotide sequence. The resulting number of oligonucleotide probe regions is examined. The above filters may then be loosened or tightened by changing the filter limits to obtain more or fewer clusters of oligonucleotides to match the goal, which is set by the needs of the investigator. For instance, a particular application might require that the investigator design 5 non-overlapping probes that efficiently hybridize to a given target sequence.

As mentioned above, the contigs may be selected on the basis of contig length. In another approach, the scores defined above may be summed for cluster size determination. To this end the probe score of the particular filter set (e.g., $T_m$ probe limit, $\Delta G_{MFOLD}$ limit and stability sequence limit) is calculated for each oligonucleotide probe. The probe score is the sum of the filter scores. Thus, the probe score is 0 if no parameters pass their respective filters. The probe score is 1, 2 or 3 if one, two or three parameters, respectively, pass their filters for that oligonucleotide probe.

This summing is continued for each parameter that is in the current filter set of the algorithm used. For a given algorithm a minimum probe score limit is set. In the current example this limit will be at least 1 and could be 2 or 3 depending on the needs of the investigator, the number of probe clusters required and the results of objective optimizations of algorithm performance against training data. The probe score is compared to this probe score limit. If the probe score of oligonucleotide probe i is greater than or equal to the probe score limit, then oligonucleotide probe i is assigned a score passed value of 1. Next, a window is chosen for the evaluation of clustering (the "cluster window"). This will be the next filter applied. The cluster window ("w") smoothes the score passed values by summing the values in a window w nucleotides long, centered about position i. The resulting sum is called the cluster sum. Usually, the cluster window is an odd integer, usually 7 or 9 nucleotides. The cluster sum values are then filtered, by comparing to a user-set threshold, cluster filter. If cluster sum is greater than or equal to cluster filter, this filter is passed, and the probe is predicted to hybridize efficiently to its target.

This window summing procedure converts the score for the passed value for each oligonucleotide into a consensus metric for a set of w adjacent probes. A "consensus metric" is a measurement that distills a number of values into one consensus value. In this case, the consensus value is calculated by simply summing the individual values. The window summing procedure therefore evaluates a property similar to the contig length metric discussed above. However, the summed score has the advantage of allowing for a few probes within a cluster to have not passed their individual probe score limits. We have found that this allows more observed hybridization peaks to be predicted.

It may be desired in some circumstances to combine the results of multiple algorithm versions. We refer to this operation as "tiling". This may be explained more fully as follows. Tiling generally involves joining together the predicted oligonucleotide probe sets identified by multiple algorithm versions. In the context of the present invention, tiling multiple algorithm versions involves forming the union of multiple sets of predictions. These predictions may arise from different embodiments of the present invention. Alternatively, the different sets of predictions may arise from the same embodiment, but different filter sets. The different filter sets may additionally be restricted to different combinations of parameter values. For instance, one filter set might be used when the predicted duplex melting temperature $T_m$ is greater than or equal to some value, while another might be used when $T_m$ is below that value.

An example of the logical endpoint of tiling multiple filter sets across different regions of the possible combinations of predictive parameters and then forming the union of the resulting predictions is the contour plot shown in FIG. 3, with the associated rule that "the value of the normalized hybridization intensity associated with a particular combination of $(T_m-T_{hyb})$ and $\Delta G_{MFOLD}$ must be greater than or equal to some threshold value." In this case, the contour at the threshold value becomes the filter. This contour and its interior can be thought of as the union of many small rectangular regions ("tiles"), each of which is bracketed by low and high cutoff values for each of the parameters.

The predictions of different algorithm versions can also be combined by forming the intersection of two or more different predictions. The reliability of predictions within such intersection sets is enhanced because such sets are, by definition, insensitive to changes in the details of the predictive algorithm. Intersection is a useful method for reducing the number of predicted probes when a single algorithm version produces too many candidate probes for efficient experimental evaluation.

The most specific oligonucleotide probe set (i.e., the set least likely to include poor probes) will be the intersection set from multiple algorithms. Clusters that have overlapping oligonucleotide probes from multiple algorithms constitute the intersection set of oligonucleotide probes. The oligonucleotide probe that is in the center of an intersection cluster is chosen. This central oligonucleotide probe may have the highest probability of predicting a peak or, in other words, of binding well to the target nucleotide sequence. Oligonucleotide probes on either side of center, which are still within the intersection cluster, may also be selected. The distance of these "side" oligonucleotide probes from the center generally will be shorter or longer depending upon the length of the cluster.

The most sensitive set of oligonucleotide probes (i.e., the set most likely to include at least one good probe) is generally the union set from multiple algorithms. Clusters that are predicted by at least one type of algorithm constitute the union set of oligonucleotide probes. The oligonucleotide probe in the center of a union cluster is chosen. Oligonucleotide probes on either side of center, which are still within the union cluster, usually are also chosen. The distance of these side probes from the center will be shorter or longer depending upon the length of the cluster. In summary, the combination of using the stability subsequence parameter, tiling multiple filter sets, and making union and intersection cluster sets of oligonucleotide probes exhibits very high sensitivity and specificity in predicting oligonucleotide probes that effectively hybridize to a target nucleotide sequence of interest.

Another aspect of the present invention is a computer based method for predicting the potential of an oligonucleotide to hybridize to a target nucleotide sequence. A predetermined number of unique oligonucleotides within a nucleotide sequence that is hybridizable with the target nucleotide sequence is identified under computer control. The oligonucleotides are chosen to sample the entire length of the nucleotide sequence. A value is determined and evaluated under computer control for each of the oligonucleotides for at least one parameter that is independently predictive of the ability of each of the oligonucleotides to hybridize to the target nucleotide sequence. The parameter values are stored. Based on the examination of the stored parameter values, a subset of oligonucleotides within the predetermined number of unique oligonucleotides is identified under computer control. Then, oligonucleotides in the subset that are clustered along a region of the nucleotide sequence that is hybridizable to the target nucleotide sequence are identified under computer control.

A computer program is utilized to carry out the above method steps. The computer program provides for input of a target-hybridizable or target-complementary nucleotide sequence, efficient algorithms for computation of oligonucleotide sequences and their associated predictive parameters, efficient, versatile mechanisms for filtering sets of oligonucleotide sequences based on parameter values, mechanisms for computation of the size of clusters of oligonucleotide sequences that pass multiple filters, and mechanisms for outputting the final predictions of the method of the present invention in a versatile, machine-readable or human-readable form.

Another aspect of the present invention is a computer system for conducting a method for predicting the potential of an oligonucleotide to hybridize to a target nucleotide sequence. An input means for introducing a target nucleotide sequence into the computer system is provided. The input means may permit manual input of the target nucleotide sequence. The input means may also be a database or a standard format file such as GenBank. Also included in the system is means for determining a number of unique oligonucleotide sequences that are within a nucleotide sequence that is hybridizable with the target nucleotide sequence. The oligonucleotide sequences is chosen to sample the entire length of the nucleotide sequence. Suitable means is a computer program or software, which also provides memory means for storing the oligonucleotide sequences. The system also includes means for controlling the computer system to carry out a determination and evaluation for each of the oligonucleotide sequences a value for at least one parameter that is independently predictive of the ability of each of the oligonucleotide sequences to hybridize to the target nucleotide sequence. Suitable means is a computer program or software such as, for example, Microsoft® Excel spreadsheet, Microsoft® Access relational database or the like, which also provides memory means for storing the parameter values. The system further comprises means for controlling the computer to carry out an identification of a subset of oligonucleotide sequences within the number of unique oligonucleotide sequences based on the automated examination of the stored parameter values. Suitable means is a computer program or software, which also allocates memory means for storing the subset of oligonucleotides. The system also includes means for controlling the computer to carry out an identification of oligonucleotide sequences in the subset that are clustered along a region of the nucleotide sequence that is hybridizable to the target nucleotide sequence. Suitable means is a computer program or software, which also allocates memory means for storing the oligonucleotide sequences in the subset. The computer system also includes means for outputting data relating to the oligonucleotide sequences in the subset. Such means may be machine readable or human readable and may be software that communicates with a printer, electronic mail, another computer program, and the like. One particularly attractive feature of the present invention is that the outputting means may communicate directly with software that is part of an oligonucleotide synthesizer. In this way the results of the method of the present invention may be used directly to provide instruction for the synthesis of the desired oligonucleotides.

Another advantage of the present invention is that it may be used to predict efficient hybridization oligonucleotides for each of multiple target sequences. thus, very large arrays may be constructed and tested with minimal synthesis of ligonucleotides.

EXAMPLES

The invention is demonstrated further by the following illustrative examples. Parts and percentages are by weight unless otherwise indicated. Temperatures are in degrees Centigrade (° C.) unless otherwise specified. The following preparations and examples illustrate the invention but are not intended to limit its scope. All reagents used herein were from Amresco, Inc., Solon, Ohio (buffers), Pharmacia Biotech, Piscataway, N.J. (nucleoside triphosphates) or Promega, Madison, Wis. (RNA polymerases) unless indicated otherwise.

Example 1

Synopsis:

Data from labeled RNA target hybridizations to surface-bound DNA probes directed against 4 different gene sequences were compared to the predictions of the preferred version of the prediction algorithm illustrated by the flow chart in FIG. 2. The RNA targets were sequences derived from the human immunodeficiency virus protease-reverse transcriptase region (HIV PRT; sense-strand target polynucleotide), human glyceraldehyde-3-phosphate dehydrogenase gene (G3PDH; antisense-strand target polynucleotide), human tumor suppressor p53 gene (p53; antisense-strand target polynucleotide) and rabbit β-globin gene (β-globin; antisense-strand target polynucleotide). The GenBank accession numbers for the gene sequences, number of data points collected and temperature of hybridization have all been previously listed in Table 2.

Materials and Methods:

Three different experimental systems and two different labeling schemes were used to collect data.

The sequence and hybridization data for β-globin were taken from the literature (see Milner et al., (1997), supra; in this experiment, $^{32}$P-radiolabeled RNA target was used.

The hybridization data for HIV PRT were obtained using an Affymetrix GeneChip™ HIV PRT-sense probe array (i.e. sense strand target polynucleotide) (GeneChip™ HIV PRT 440s, Affymetrix Corporation, Santa Clara, Calif.) as specified by the manufacturer, except that the fluorescein-labeled RNA target was not fragmented prior to hybridization and that hybridization was performed for 24 hours. The concentration of fluorescein-labeled RNA used was 26.3 nM; label density was approximately 18 fluoresceinated uridyl nucleotides per 1 kilobase (kb) RNA transcript. The raw data were collected by scanning the array with a GeneChip™ Scanner 50 (Affymetrix Corporation, Santa Clara, Calif.), as specified by the manufacturer. The raw data were reduced to a feature-averaged ("CEL") file, using the GeneChip™ software supplied with the scanner. Finally, a table of hybridization intensities for perfect-complement 20-mer probes was constructed using the ASCII feature map file supplied with the GeneChip™ software to connect probe sequences to measured hybridization intensities. The resulting data set contained data for every overlapping 20-mer probe to the target sequence.

The data for G3PDH and p53 were measured using 93-feature arrays constructed using commercially available streptavidin-coated microtiter plates (Pierce Chemical Company, Rockford, Ill.). Every tenth possible 25-mer probe complementary to each target was synthesized and 3'-biotinylated by a contract synthesis vendor (Operon, Inc., Alameda, Calif.). The 3'-linked biotin was used to anchor individual probes to microtiter wells, via the well known, strong affinity of streptavidin for biotin. Biotinylated DNA probes were resuspended to a concentration of 10 μM in hybridization buffer (5×sodium chloride-sodium phosphate-disodium ethylenediaminetetraacetate (SSPE), 0.05% Triton X-100, filter-sterilized; 1×SSPE is 150 mM sodium chloride, 10 mM sodium phosphate, 1 mM disodium ethylenediaminetetraacetate (EDTA), pH 7.4). Individual probes were diluted 1:10 in hybridization buffer into specified wells (100 μl total volume per well) of a streptavidin-coated microtiter plate; probes were allowed to bind to the covered plates overnight at 35° C. The other 3 wells of the 96-well microtiter plate were probe-less controls. The coated plates were washed with 3×200 μl of wash buffer (6×SSPE, 0.005% Triton X-100, filter-sterilized). Fluorescein-labeled RNA (100 μl of a 10 nM solution in hybridization buffer) was added to each well. The plates were covered and hybridized at 35° C. for 20–24 hours. The hybridized plates were washed with 3×200 μl of wash buffer. Label was then released in each well by adding 100 μl of 20 μg/ml RNAase I (Sigma Chemical Company, St. Louis, Mo.) in Tris-EDTA (TE) (10 mM Tris(hydroxymethyl)aminomethane (Tris), 1 mM EDTA, pH 8.0, sterile) and incubating at 35° C. for at least 30 minutes. The fluorescence released from the surface of each well was quantitated with a PerSeptive Biosystems Cytofluor II microtiter plate fluorimeter (PerSeptive Biosystems, Inc., Framingham, Mass.) using the manufacturer's recommended excitation and emission filter sets for fluorescein. Each plate hybridization was performed in quadruplicate, and the data for each probe were averaged to obtain the hybridization intensity.

Labeled RNA targets specific for G3PDH and p53 were produced via T7 RNA polymerase transcription of DNA templates in the presence of fluorescein-UTP (Boehringer Mannheim Corporation, Indianapolis, Ind.), using the same method as that outlined by Affymetrix for their GeneChip™ HIV PRT sense probe array. The DNA template for G3PDH was purchased from a commercial source (Clontech, Inc., Palo Alto, Calif.). The DNA template for p53 was obtained by sub-cloning a PCR fragment from an ATCC-derived reference clone (No. 57254) of human p53 into the commercially-available PCR cloning vector pCR2.1-TOPO (Invitrogen, Inc., Carlsbad, Calif.), then linearizing the plasmid at the end of the polycloning site opposite the vector-derived T7 promoter.

Probe predictions were performed using a software application (referred to as "p5") that was built atop Microsoft's Access relational database application, using added Visual Basic modules, the TrueDB Grid Pro 5.0 (Apex Software Corporation, Pittsburgh, Pa.) enhancement to Visual Basic, and a version of the FORTRAN application MFOLD, modified to run in a Windows NT 4.0 environment, as an ActiveX control. The Visual Basic source code for the p5 software application is found in the CD-ROM appendix to this specification. The DNA target sequence complements that were input into p5 for division into potential oligonucleotide probe sequences are listed below:

Parent Sequence Accession No.: K03256
Locus: BUNGLOB.DNA (portion of rabbit β-globin)
Length: 122

```
  1 TTCTTCCACA TTCACCTTGC CCCACAGGGC AGTGACCGCA GACTTCTCCT CACTGGACAG SEQ ID NO:36
 61 ATGCACCATT CTGTCTGTTT TGGGGGATTG CAAGTAAACA CAGTTGTGTC AAAAGCAAGT
121 GT
```

Parent Sequence Accession No.: M15654
Locus: HIV_PRTA.S (HIV PRT antisense; parses into probes specific for sense-strand target)
Length: 1040

```
   1 TGTACTGTCC ATTTATCAGG ATGGAGTTCA TAACCCATCC AAAGGAATGG AGGTTCTTTC SEQ ID NO:37
  61 TGATGTTTTT TGTCTGGTGT GGTAAGTCCC CACCTCAACA GATGTTGTCT CAGCTCCTCT
 121 ATTTTTGTTC TATGCTGCCC TATTTCTAAG TCAGATCCTA CATACAAATC ATCCATGTAT
 181 TGATAGATAA CTATGTCTGG ATTTTGTTTT TTAAAAGGCT CTAAGATTTT TGTCATGCTA
 241 CTTTGGAATA TTGCTGGTGA TCCTTTCCAT CCCTGTGGAA GCACATTGTA CTGATATCTA
 301 ATCCCTGGTG TCTCATTGTT TATACTAGGT ATGGTAAATG CAGTATACTT CCTGAAGTCT
 361 TCATCTAAGG GAACTGAAAA ATATGCATCA CCCACATCCA GTACTGTTAC TGATTTTTTC
 421 TTTTTTAACC CTGCGGGATG TGGTATTCCT AATTGAACTT CCCAGAAGTC TTGAGTTCTC
 481 TTATTAAGTT CTCTGAAATC TACTAATTTT CTCCATTTAG TACTGTCTTT TTTCTTTATG
 541 GCAAATACTG GAGTATTGTA TGGATTCTCA GGCCCAATTT TTGAAATTTT CCCTTCCTTT
 601 TCCATTTCTG TACAAATTTC TACTAATGCT TTTATTTTTT CTTCTGTCAA TGGCCATTGT
 661 TTAACTTTTG GGCCATCCAT TCCTGGCTTT AATTTTACTG GTACAGTCTC AATAGGGCTA
 721 ATGGGAAAAT TTAAAGTGCA ACCAATCTGA GTCAACAGAT TTCTTCCAAT TATGTTGACA
 781 GGTGTAGGTC CTACTAATAC TGTACCTATA GCTTTATGTC CACAGATTTC TATGAGTATC
 841 TGATCATACT GTCTTACTTT GATAAAACCT CCAATTCCCC CTATCATTTT TGGTTTCCAT
 901 CTTCCTGGCA AACTCATTTC TTCTAATACT GTATCATCTG CTCCTGTATC TAATAGAGCT
 961 TCCTTTAGTT GCCCCCCTAT CTTTATTGTG ACGAGGGGTC GTTGCCAAAG AGTGATCTGA
1021 GGGAAGTTAA AGGATACAGT
```

Parent Sequence Accession No.: X01677
Locus: G3PDH (Clontech G3PDH template—parses into probes specific for antisense-strand target)
Length: 999

```
  1 GAAGGTCGGA GTCAACGGAT TTGGTCGTAT TGGGCGCCTG GTCACCAGGG CTGCTTTTAA SEQ ID NO:38

61 CTCTGGTAAA GTGGATATTG TTGCCATCAA TGACCCCTTC ATTGACCTCA ACTACATGGT

121 TTACATGTTC CAATATGATT CCACCCATGG CAAATTCCAT GGCACCGTCA AGGCTGAGAA

181 CGGGAAGCTT GTCATCAATG GAAATCCCAT CACCATCTTC CAGGAGCGAG ATCCCTCCAA

241 AATCAAGTGG GGCGATGCTG GCGCTGAGTA CGTCGTGGAG TCCACTGGCG TCTTCACCAC

301 CATGGAGAAG GCTGGGGCTC ATTTGCAGGG GGGAGCCAAA AGGGTCATCA TCTCTGCCCC

361 CTCTGCTGAT GCCCCCATGT TCGTCATGGG TGTGAACCAT GAGAAGTATG ACAACAGCCT

421 CAAGATCATC AGCAATGCCT CCTGCACCAC CAACTGCTTA GCACCCCTGG CCAAGGTCAT

481 CCATGACAAC TTTGGTATCG TGGAAGGACT CATGACCACA GTCCATGCCA TCACTGCCAC

541 CCAGAAGACT GTGGATGGCC CCTCCGGGAA ACTGTGGCGT GATGGCCGCG GGGCTCTCCA

601 GAACATCATC CCTGCCTCTA CTGGCGCTGC CAAGGCTGTG GGCAAGGTCA TCCCTGAGCT

661 AGACGGGAAG CTCACTGGCA TGGCCTTCCG TGTCCCCACT GCCAACGTGT CAGTGGTGGA

721 CCTGACCTGC CGTCTAGAAA AACCTGCCAA ATATGATGAC ATCAAGAAGG TGGTGAAGCA

781 GGCGTCGGAG GGCCCCCTCA AAGGCATCCT GGGCTACACT GAGCACCAGG TGGTCTCCTC

841 TGACTTCAAC AGCGACACCC ACTCCTCCAC CTTTGACGCT GGGGCTGGCA TTGCCCTCAA

901 CGACCACTTT GTCAAGCTCA TTTCCTGGTA TGACAACGAA TTTGGCTACA GCAACAGGGT

961 GGTGGACCTC ATGGCCCACA TGCTATAGTG AGTCGTATT
```

Parent Sequence Accession No.: X54156
Locus: HSP53PCRa (p53 template—parses into probes specific for antisense-strand target)
Length: 1049

```
  1 GAGGTGCGTG TTTGTGCCTG TCCTGGGAGA GACCGGCGCA CAGAGGAAGA GAATCTCCGC SEQ ID NO:39

61 AAGAAAGGGG AGCCTCACCA CGAGCTGCCC CCAGGGAGCA CTAAGCGAGC ACTGCCCAAC

121 AACACCAGCT CCTCTCCCCA GCCAAAGAAG AAACCACTGG ATGGAGAATA TTTCACCCTT

181 CAGATCCGTG GGCGTGAGCG CTTCGAGATG TTCCGAGAGC TGAATGAGGC CTTGGAACTC

241 AAGGATGCCC AGGCTGGGAA GGAGCCAGGG GGGAGCAGGG CTCACTCCAG CCACCTGAAG

301 TCCAAAAAGG GTCAGTCTAC CTCCCGCCAT AAAAAACTCA TGTTCAAGAC AGAAGGGCCT

361 GACTCAGACT GACATTCTCC ACTTCTTGTT CCCCACTGAC AGCCTCCCTC CCCCATCTCT

421 CCCTCCCCTG CCATTTTGGG TTTTGGGTCT TTGAACCCTT GCTTGCAATA GGTGTGCGTC

481 AGAAGCACCC AGGACTTCCA TTTGCTTTGT CCCGGGGCTC CACTGAACAA GTTGGCCTGC

541 ACTGGTGTTT TGTTGTGGGG AGGAGGATGG GGAGTAGGAC ATACCAGCTT AGATTTTAAG

601 GTTTTTACTG TGAGGGATGT TTGGGAGATG TAAGAAATGT TCTTGCAGTT AAGGGTTAGT

661 TTACAATCAG CCACATTCTA GGTAGGTAGG GGCCCACTTC ACCGTACTAA CCAGGGAAGC

721 TGTCCCTCAT GTTGAATTTT CTCTAACTTC AAGGCCCATA TCTGTGAAAT GCTGGCATTT

781 GCACCTACCT CACAGAGTGC ATTGTGAGGG TTAATGAAAT AATGTACATC TGGCCTTGAA

841 ACCACCTTTT ATTACATGGG GTCTAAAACT TGACCCCCTT GAGGGTGCCT GTTCCCTCTC

901 CCTCTCCCTG TTGGCTGGTG GGTTGGTAGT TTCTACAGTT GGGCAGCTGG TTAGGTAGAG
```

-continued

```
 961 GGAGTTGTCA AGTCTTGCTG GCCCAGCCAA ACCCTGTCTG ACAACCTCTT GGTCGACCTT

1021 AGTACCTAAA AGGAAATCTC ACCCCATCC
```

The sequences indicated above, which are complements of the target sequences, were divided into overlapping oligonucleotide sequences with one nucleotide between starting positions. The oligonucleotide sequence lengths were 17 (rabbit βglobin), 20 (HIV PRT) or 25 (G3PDH; p53). The oligonucleotide sequence lengths were dictated by the probe lengths used in the experiments to which the predictions were compared. The RNA target concentrations used to calculate predicted RNA/DNA duplex melting temperatures were 100 pM (rabbit β-globin), 26.3 nM (HIV PRT) and 10 nM (G3PDH; p53). These were also dictated by experimental conditions for the comparison data. The cut-off filter used for the predicted free energy of the most stable probe sequence intramolecular structure, $\Delta G_{MFOLD}$, was $$\Delta G_{MFOLD} \geq -0.4 \frac{kcal}{mole}.$$

The filter condition used for the predicted RNA/DNA duplex melting temperature was $$25°\,C. \leq T_m + 16.6\,\log([Na^+]) - T_{hyb} \leq 50°\,C.,$$

where $T_m$ is the target concentration-dependent value of the predicted RNA/DNA duplex melting temperature before correction for salt concentration, the term "16.6 log([Na$^+$])" corrects the melting temperature for salt effects, and $T_{hyb}$ is the hybridization temperature. The values of the salt correction term and $T_{hyb}$ have already been listed in Table 2. For convenient use within p5, the above condition was algebraically rearranged into the equivalent form $$25°\,C. -16.6\,\log([Na^+]) + T_{hyb} \leq T_m \leq 50°\,C. -16.6\,\log([Na^+]) + T_{hyb}.$$

Clusters were ranked according to the number of contiguous oligonucleotide sequences that passed through the filter set ("contig" length).

Figure 4:
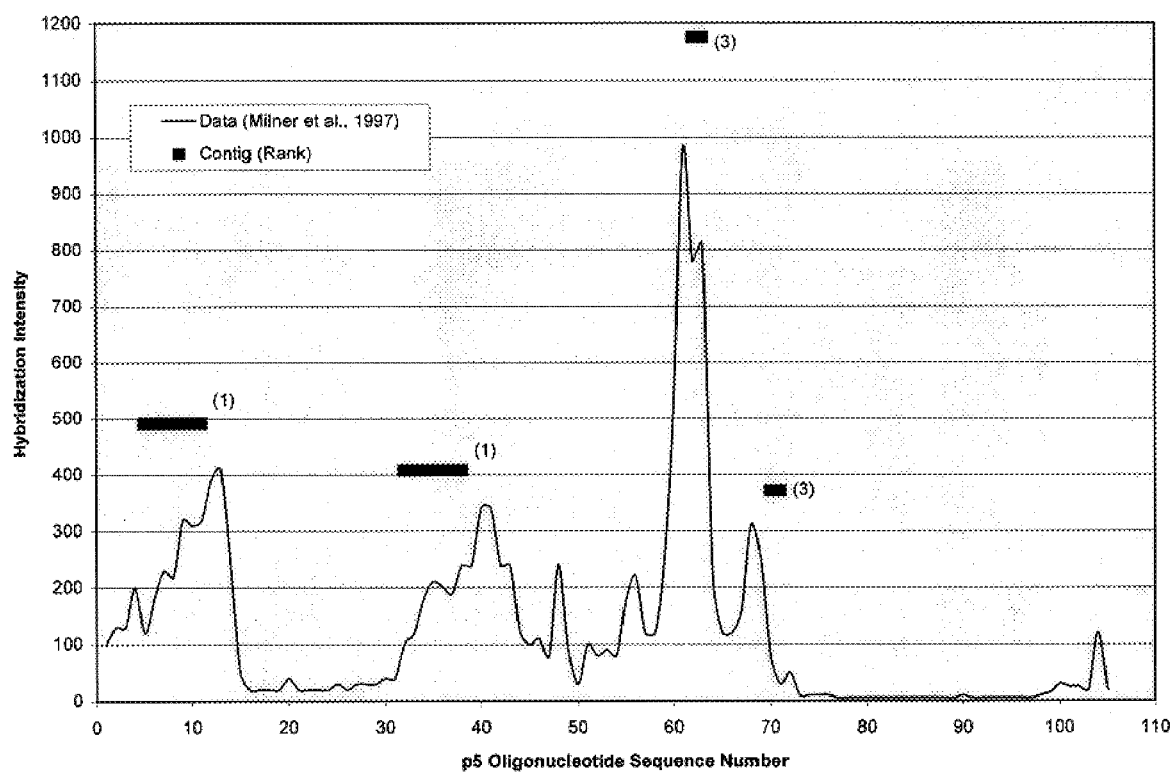
FIG. 4 shows the observed hybridization patterns for oligonucleotides selected using a method in accordance with the present invention and additional oligonucleotides to a portion of the rabbit β-globin gene (radiolabeled antisense RNA target).

Results:

The detailed analysis results for rabbit β-globin are presented in Table 3; a graphical summary of the results is shown in FIG. 4. In Table 3, values of $T_m$ and $\Delta G_{MFOLD}$ that were excluded by the filter set are shown with a line through them, and table entries for contig length are shown in gray when the oligonucleotide sequence in question was not in a contig. The top 20% of the observed hybridization intensities are shown underlined.

TABLE 3

| Position | Oligonucleotide Sequence | SEQ ID NO: | $T_m$(° C.) | $\Delta G_{MFOLD}$ (kcal/mole) | Contig Length | Hybridization Intensity (Milner et al., 1997) |
|---|---|---|---|---|---|---|
| 1 | TTCTTCCACATTCACCT | 40 | ~~53.62~~ | 5.00 | | 100 |
| 2 | TCTTCCACATTCACCTT | 41 | ~~53.62~~ | 5.00 | | 130 |
| 3 | CTTCCACATTCACCTTG | 42 | ~~52.19~~ | 0.90 | | 130 |
| 4 | TTCCACATTCACCTTGC | 43 | ~~54.50~~ | 0.50 | | 200 |
| 5 | TCCACATTCACCTTGCC | 44 | 58.46 | 0.50 | 7 | 120 |
| 6 | CCACATTCACCTTGCCC | 45 | 61.10 | 0.50 | 7 | 180 |
| 7 | CACATTCACCTTGCCCC | 46 | 61.10 | 0.50 | 7 | <u>230</u> |
| 8 | ACATTCACCTTGCCCCA | 47 | 61.10 | 0.50 | 7 | <u>220</u> |
| 9 | CATTCACCTTGCCCCAC | 48 | 61.10 | 0.90 | 7 | <u>320</u> |
| 10 | ATTCACCTTGCCCCACA | 49 | 61.10 | 0.70 | 7 | <u>310</u> |
| 11 | TTCACCTTGCCCCACAG | 50 | 61.33 | 0.50 | 7 | <u>320</u> |
| 12 | TCACCTTGCCCCACAGG | 51 | 63.70 | ~~0.60~~ | | <u>390</u> |
| 13 | CACCTTGCCCCACAGGG | 52 | 64.85 | ~~-1.60~~ | | <u>410</u> |
| 14 | ACCTTGCCCCACAGGGC | 53 | 68.01 | ~~-4.10~~ | | <u>240</u> |
| 15 | CCTTGCCCCACAGGGCA | 54 | 68.63 | ~~-5.40~~ | | 50 |
| 16 | CTTGCCCCACAGGGCAG | 55 | 64.95 | ~~-5.60~~ | | 20 |

TABLE 3-continued

| Position | Oligonucleotide Sequence | SEQ ID NO: | T$_m$(° C.) | ΔG$_{MFOLD}$ (kcal/mole) | Contig Length | Hybridization Intensity (Milner et al., 1997) |
|---|---|---|---|---|---|---|
| 17 | TTGCCCCACAGGGCAGT | 56 | 66.31 | ~~-5.60~~ | | 20 |
| 18 | TGCCCCACAGGGCAGTG | 57 | 65.79 | ~~-5.40~~ | | 20 |
| 19 | GCCCCACAGGGCAGTGA | 58 | 67.37 | ~~-4.10~~ | | 20 |
| 20 | CCCCACAGGGCAGTGAC | 59 | 63.42 | ~~-1.60~~ | | 40 |
| 21 | CCCACAGGGCAGTGACC | 60 | 63.42 | ~~-1.40~~ | | 20 |
| 22 | CCACAGGGCAGTGACCG | 61 | 59.85 | ~~-1.40~~ | | 20 |
| 23 | CACAGGGCAGTGACCGC | 62 | 60.14 | ~~-1.00~~ | | 20 |
| 24 | ACAGGGCAGTGACCGCA | 63 | 60.14 | ~~-0.50~~ | | 20 |
| 25 | CAGGGCAGTGACCGCAG | 64 | 59.76 | ~~-0.50~~ | | 30 |
| 26 | AGGGCAGTGACCGCAGA | 65 | 59.83 | ~~-0.50~~ | | 20 |
| 27 | GGGCAGTGACCGCAGAC | 66 | 60.22 | ~~-0.50~~ | | 30 |
| 28 | GGCAGTGACCGCAGACT | 67 | 59.53 | ~~-0.50~~ | | 30 |
| 29 | GCAGTGACCGCAGACTT | 68 | 57.06 | ~~-0.40~~ | | 30 |
| 30 | CAGTGACCGCAGACTTC | 69 | ~~53.99~~ | ~~-0.40~~ | | 40 |
| 31 | AGTGACCGCAGACTTCT | 70 | ~~54.71~~ | -0.20 | | 40 |
| 32 | GTGACCGCAGACTTCTC | 71 | 55.99 | 0.60 | 7 | 100 |
| 33 | TGACCGCAGACTTCTCC | 72 | 57.01 | 0.60 | 7 | 120 |
| 34 | GACCGCAGACTTCTCCT | 73 | 59.22 | 0.60 | 7 | 180 |
| 35 | ACCGCAGACTTCTCCTC | 74 | 59.28 | 0.60 | 7 | 210 |
| 36 | CCGCAGACTTCTCCTCA | 75 | 60.07 | 0.60 | 7 | 200 |
| 37 | CGCAGACTTCTCCTCAC | 76 | 56.34 | 0.60 | 7 | 190 |
| 38 | GCAGACTTCTCCTCACT | 77 | 57.79 | 0.60 | 7 | <u>240</u> |
| 39 | CAGACTTCTCCTCACTG | 78 | ~~52.93~~ | 0.60 | | <u>240</u> |
| 40 | AGACTTCTCCTCACTGG | 79 | ~~54.41~~ | 0.00 | | <u>340</u> |
| 41 | GACTTCTCCTCACTGGA | 80 | 55.77 | ~~-1.40~~ | | <u>340</u> |
| 42 | ACTTCTCCTCACTGGAC | 81 | ~~54.05~~ | ~~-1.60~~ | | <u>240</u> |
| 43 | CTTCTCCTCACTGGACA | 82 | 55.75 | ~~-1.60~~ | | <u>240</u> |
| 44 | TTCTCCTCACTGGACAG | 83 | ~~53.66~~ | ~~-1.60~~ | | 120 |

TABLE 3-continued

| Position | Oligonucleotide Sequence | SEQ ID NO: | $T_m$(° C.) | $\Delta G_{MFOLD}$ (kcal/mole) | Contig Length | Hybridization Intensity (Milner et al., 1997) |
|---|---|---|---|---|---|---|
| 45 | TCTCCTCACTGGACAGA | 84 | ~~54.02~~ | ~~-1.60~~ | | 100 |
| 46 | CTCCTCACTGGACAGAT | 85 | ~~53.36~~ | ~~-1.60~~ | | 110 |
| 47 | TCCTCACTGGACAGATG | 86 | ~~51.10~~ | ~~-1.40~~ | | 80 |
| 48 | CCTCACTGGACAGATGC | 87 | ~~54.25~~ | 0.00 | | <u>240</u> |
| 49 | CTCACTGGACAGATGCA | 88 | ~~51.26~~ | 0.20 | | 90 |
| 50 | TCACTGGACAGATGCAC | 89 | ~~49.63~~ | 0.20 | | 30 |
| 51 | CACTGGACAGATGCACC | 90 | ~~52.74~~ | 0.50 | | 100 |
| 52 | ACTGGACAGATGCACCA | 91 | ~~52.74~~ | ~~-0.50~~ | | 80 |
| 53 | CTGGACAGATGCACCAT | 92 | ~~52.10~~ | ~~-1.00~~ | | 90 |
| 54 | TGGACAGATGCACCATT | 93 | ~~50.39~~ | ~~-0.00~~ | | 80 |
| 55 | GGACAGATGCACCATTC | 94 | ~~51.75~~ | 0.30 | | 180 |
| 56 | GACAGATGCACCATTCT | 95 | ~~51.05~~ | -0.10 | | 220 |
| 57 | ACAGATGCACCATTCTG | 96 | ~~49.56~~ | ~~-1.80~~ | | 120 |
| 58 | CAGATGCACCATTCTGT | 97 | ~~52.19~~ | ~~-2.10~~ | | 120 |
| 59 | AGATGCACCATTCTGTC | 98 | ~~52.06~~ | -0.10 | | <u>250</u> |
| 60 | GATGCACCATTCTGTCT | 99 | ~~54.18~~ | 0.30 | | <u>520</u> |
| 61 | ATGCACCATTCTGTCTG | 100 | ~~52.60~~ | 0.40 | | <u>980</u> |
| 62 | TGCACCATTCTGTCTGT | 101 | 56.05 | 0.20 | 2 | <u>780</u> |
| 63 | GCACCATTCTGTCTGTT | 102 | 56.52 | 0.20 | 2 | <u>810</u> |
| 64 | CACCATTCTGTCTGTTT | 103 | ~~52.06~~ | 0.20 | | <u>220</u> |
| 65 | ACCATTCTGTCTGTTTT | 104 | ~~50.83~~ | 0.20 | | 120 |
| 66 | CCATTCTGTCTGTTTTG | 105 | ~~50.10~~ | 0.20 | | 120 |
| 67 | CATTCTGTCTGTTTTGG | 106 | ~~48.42~~ | 0.60 | | 160 |
| 68 | ATTCTGTCTGTTTTGGG | 107 | ~~49.91~~ | 1.70 | | <u>310</u> |
| 69 | TTCTGTCTGTTTTGGGG | 108 | ~~53.10~~ | 1.70 | | <u>250</u> |
| 70 | TCTGTCTGTTTTGGGGG | 109 | 55.90 | 1.70 | 2 | 80 |
| 71 | CTGTCTGTTTTGGGGGA | 110 | 55.91 | 1.40 | 2 | 30 |
| 72 | TGTCTGTTTTGGGGGAT | 111 | ~~53.55~~ | 0.90 | | 50 |

TABLE 3-continued

| Position | Oligonucleotide Sequence | SEQ ID NO: | T$_m$(° C.) | ΔG$_{MFOLD}$ (kcal/mole) | Contig Length | Hybridization Intensity (Milner et al., 1997) |
|---|---|---|---|---|---|---|
| 73 | GTCTGTTTTGGGGGATT | 112 | ~~54.00~~ | 0.90 | | 10 |
| 74 | TCTGTTTTGGGGGATTG | 113 | ~~50.50~~ | 1.10 | | 10 |
| 75 | CTGTTTTGGGGGATTGC | 114 | ~~53.77~~ | 2.20 | | 10 |
| 76 | TGTTTTGGGGGATTGCA | 115 | ~~53.04~~ | 1.20 | | 10 |
| 77 | GTTTTGGGGGATTGCAA | 116 | ~~51.01~~ | 0.00 | | 5 |
| 78 | TTTTGGGGGATTGCAAG | 117 | ~~47.99~~ | -0.20 | | 5 |
| 79 | TTTGGGGGATTGCAAGT | 118 | ~~50.00~~ | -0.20 | | 5 |
| 80 | TTGGGGGATTGCAAGTA | 119 | ~~49.00~~ | 0.00 | | 5 |
| 81 | TGGGGGATTGCAAGTAA | 120 | ~~47.55~~ | 1.20 | | 5 |
| 82 | GGGGGATTGCAAGTAAA | 121 | ~~45.76~~ | 1.40 | | 5 |
| 83 | GGGGATTGCAAGTAAAC | 122 | ~~43.54~~ | 1.40 | | 5 |
| 84 | GGGATTGCAAGTAAACA | 123 | ~~42.32~~ | 1.30 | | 5 |
| 85 | GGATTGCAAGTAAACAC | 124 | ~~40.11~~ | 0.90 | | 5 |
| 86 | GATTGCAAGTAAACACA | 125 | ~~38.94~~ | 0.50 | | 5 |
| 87 | ATTGCAAGTAAACACAG | 126 | ~~37.61~~ | 0.50 | | 5 |
| 88 | TTGCAAGTAAACACAGT | 127 | ~~40.35~~ | 0.50 | | 5 |
| 89 | TGCAAGTAAACACAGTT | 128 | ~~40.35~~ | 0.30 | | 5 |
| 90 | GCAAGTAAACACAGTTG | 129 | ~~40.35~~ | 0.10 | | 10 |
| 91 | CAAGTAAACACAGTTGT | 130 | ~~38.98~~ | -0.30 | | 5 |
| 92 | AAGTAAACACAGTTGTG | 131 | ~~37.40~~ | ~~-0.90~~ | | 5 |
| 93 | AGTAAACACAGTTGTGT | 132 | ~~42.02~~ | ~~-2.30~~ | | 5 |
| 94 | GTAAACACAGTTGTGTC | 133 | ~~43.15~~ | ~~-2.50~~ | | 5 |
| 95 | TAAACACAGTTGTGTCA | 134 | ~~41.73~~ | ~~-2.50~~ | | 5 |
| 96 | AAACACAGTTGTGTCAA | 135 | ~~40.67~~ | ~~-2.50~~ | | 5 |
| 97 | AACACAGTTGTGTCAAA | 136 | ~~40.67~~ | ~~-2.50~~ | | 5 |
| 98 | ACACAGTTGTGTCAAAA | 137 | ~~40.67~~ | ~~-2.30~~ | | 10 |

TABLE 3-continued

| Position | Oligonucleotide Sequence | SEQ ID NO: | $T_m$ (° C.) | $\Delta G_{MFOLD}$ (kcal/mole) | Contig Length | Hybridization Intensity (Milner et al., 1997) |
|---|---|---|---|---|---|---|
| 99 | CACAGTTGTGTCAAAAG | 138 | ~~40.20~~ | ~~-1.20~~ | | 15 |
| 100 | ACAGTTGTGTCAAAAGC | 139 | ~~42.93~~ | ~~-0.50~~ | | 30 |
| 101 | CAGTTGTGTCAAAAGCA | 140 | ~~43.99~~ | 0.20 | | 25 |
| 102 | AGTTGTGTCAAAAGCAA | 141 | ~~40.67~~ | -0.10 | | 25 |
| 103 | GTTGTGTCAAAAGCAAG | 142 | ~~40.67~~ | -0.30 | | 20 |
| 104 | TTGTGTCAAAAGCAAGT | 143 | ~~40.67~~ | -0.10 | | 120 |
| 105 | TGTGTCAAAAGCAAGTG | 144 | ~~40.40~~ | 0.50 | | 20 |

In FIG. 4, the hybridization intensity observed experimentally is plotted as a function of oligonucleotide starting position in the target-complementary sequence that was input into p5. The identified contigs are plotted as horizontal bars, with the contig rank (by length) shown in parentheses next to each bar. It is clear from Table 3 and FIG. 4 that the prediction algorithm identified contigs that overlap all of the "top 20%" hybridization intensity peaks observed. Iterative experimental improvement of these predictions would converge on each of the observed intensity maxima in 3–4 iterations.

Figure 5:
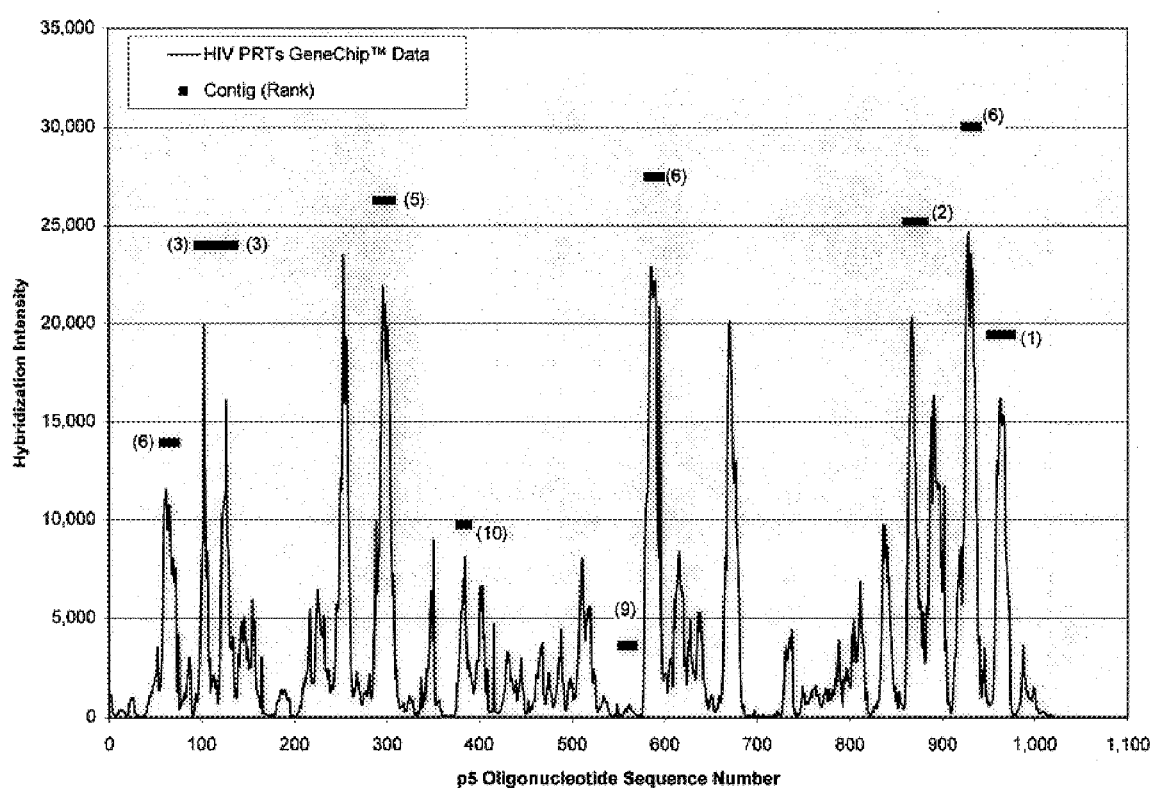
FIG. 5 shows the observed hybridization patterns for oligonucleotides selected using a method in accordance with the present invention and additional oligonucleotides to the HIV PRT gene (fluorescein-labeled sense RNA target).
Figure 6:
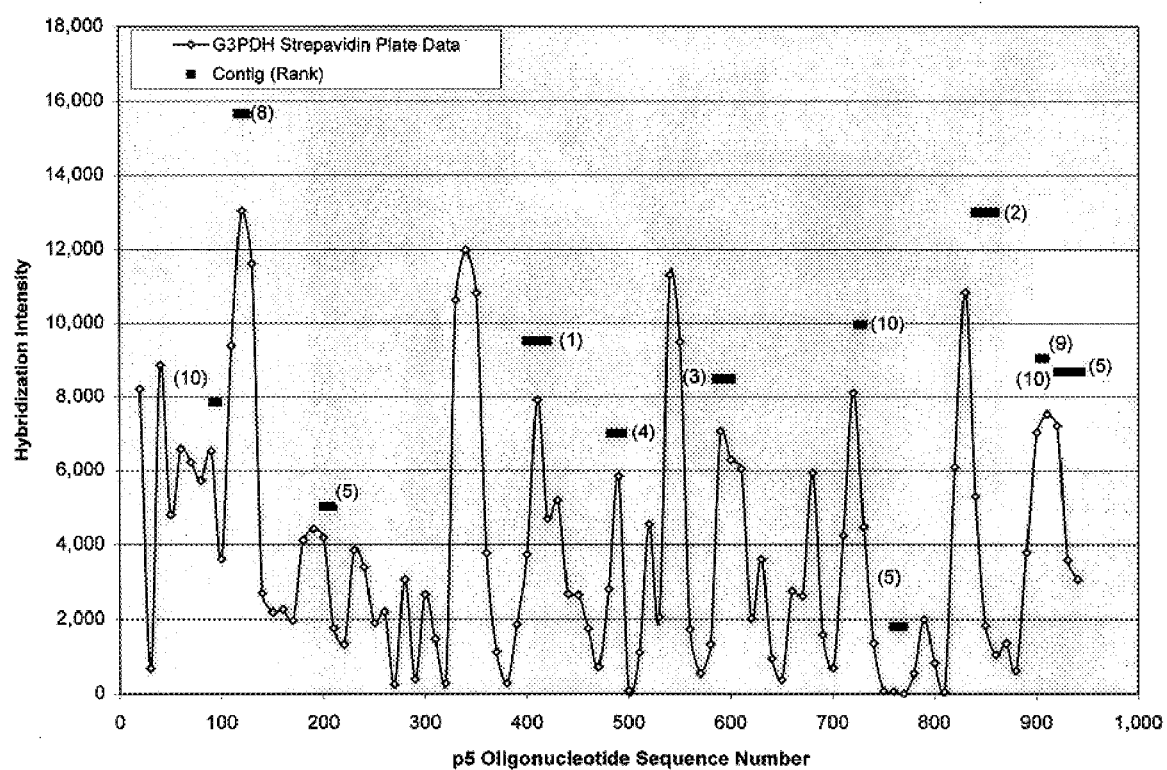
FIG. 6 shows the observed hybridization patterns for oligonucleotides selected using a method in accordance with the present invention and additional oligonucleotides to the G3PDH gene (fluorescein-labeled antisense RNA target).
Figure 7:
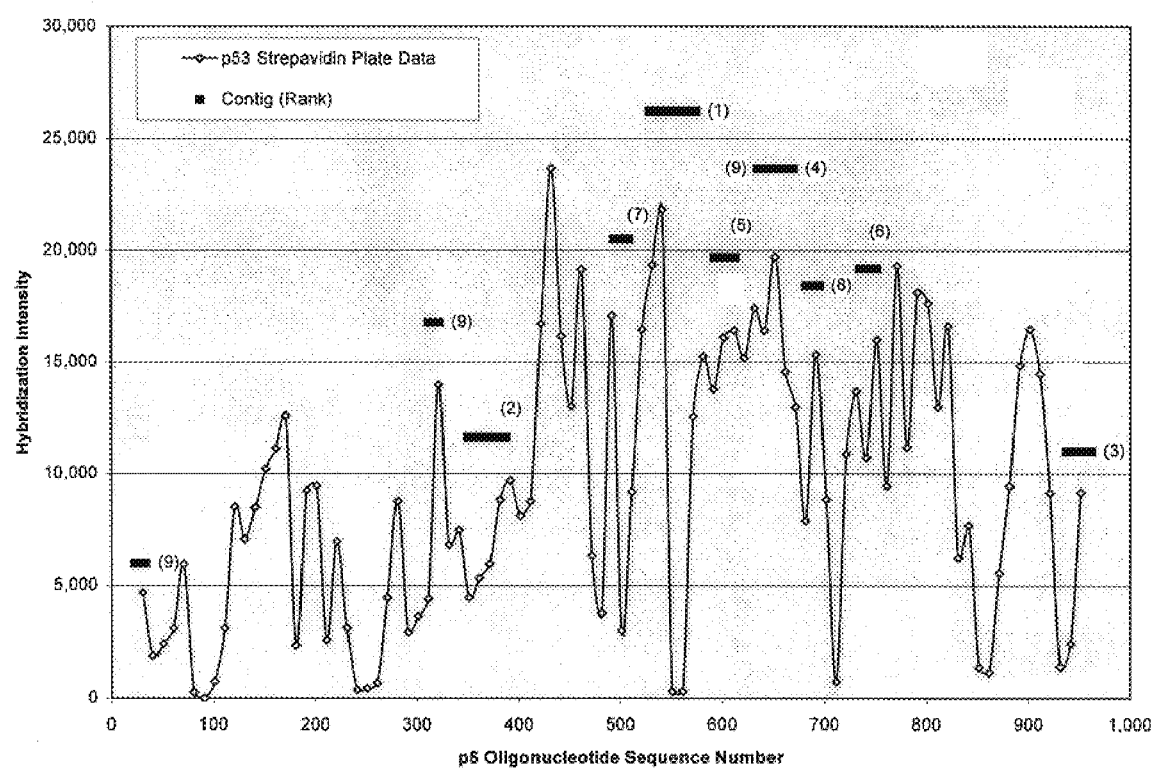
FIG. 7 shows the observed hybridization patterns for oligonucleotides selected using a method in accordance with the present invention and additional oligonucleotides to the p53 gene (fluorescein-labeled antisense RNA target).

Prediction worksheets for HIV PRT, G3PDH and p53 were prepared in a manner similar to that for rabbit β-globin as shown in Table 3, except that the probes were longer as indicated above and that approximately 1,000 probes were analyzed for each of these genes. The results of these analyses are shown in FIG. 5 (HIV PRT), FIG. 6 (G3PDH) and FIG. 7 (p53). In FIG. 5, data are plotted for all possible 20-mer oligonucleotide probes. In FIGS. 6 and 7, data were available for only every $10^{th}$ 25-mer probe, and the actual data points are plotted as open diamonds.

It is clear from FIGS. 5–7 that the hybridization efficiency prediction algorithm of the present invention performed well in the task of identifying regions with observed high hybridization intensity. In each case, the 4 longest contigs point to good-to-excellent regions for experimental investigation. It should be noted that the contigs usually bracket observed intensity peaks; experimental iterative refinement would therefore be expected to converge in 2–3 iterations. By this is meant that certain oligonucleotides from the identified contigs are prepared and subjected to evaluation in actual hybridization experiments. Based on the results of such experiments, the observed signal is evaluated to determine whether the oligonucleotides are hybridizing to the left of, the right of, or on the center of a peak with respect to the graphed data. The next iteration is carried out to experimentally evaluate the hybridization efficiency of probes that are inferred to lie closer to the peak of hybridization efficiency, based on the data from the previous iteration. Iteration is continued until the signal level is deemed acceptable by the user, or the local hybridization efficiency maximum is reached (i.e. the best probe in the cluster identified by the method of the current invention has been experimentally identified). A detailed illustration of this process is shown in Example 3.

It should be noted that clusters of predictions that overlap the maxima of observed peaks of hybridization efficiency will often yield user-acceptable probes on the first iteration. Thus, the method of the present invention is much more efficient than current methods in which every potential probe is synthesized. For instance, in the HIV PRT example shown in FIG. 5, at least 3 good probes would be identified after synthesis of ~10 test probes (i.e. statistical sampling of the 3 longest contigs). This is much more efficient than the ~1,000 probes represented by the data in FIG. 5.

Example 2

Synopsis:

Data from a labeled RNA target hybridization to an Affymetrix GeneChip™ HIV PRT-sense probe array (GeneChip™ HIV PRT 440s, Affymetrix Corporation, Santa Clara, Calif.) were compared to the predictions of the window-averaged composite dimensionless score version of the method of the present invention.

Materials and Methods:

Data were obtained as described for the Affymetrix GeneChip™ HIV PRT-sense probe array (GeneChip™ HIV PRT 440s, Affymetrix Corporation, Santa Clara, Calif.) in Example 1. The DNA sequence (SEQ ID NO: 37) complementary to the fluorescein-labeled RNA target was divided into overlapping 20-mer oligonucleotide sequences spaced one nucleotide apart, using the prototype application p5; p5 was also used to calculate the predicted values of the RNA/DNA heteroduplex melting temperature ($T_m$) and the free energy of the most stable predicted probe intramolecular structure, $\Delta G_{MFOLD}$, as described in Example 1. The probe sequences and parameter values were then transferred to a Microsoft Excel spreadsheet, which was used to complete the predictions of efficient and inefficient probes. The weight was obtained by optimizing the performance of the algorithm with the data of Milner et al., supra, as the training data using the Microsoft® Excel® spreadsheet software. The composite score was calculated using a weight of 0.62 for the dimensionless Tm score and a weight of 0.38 for the $\Delta G_{MFOLD}$ dimensionless score. The windowed-averaging was performed using a window width of 7 and Microsoft® Excel® spreadsheet software. Finally, the oligonucleotide sequences having the top 10% of the window-averaged composite dimensionless scores were predicted to be effi cient probes, while the oligonucleotide sequences having the bottom 10% of the window-averaged composite dimensionless scores were predicted to be inefficient probes.

Figure 8:
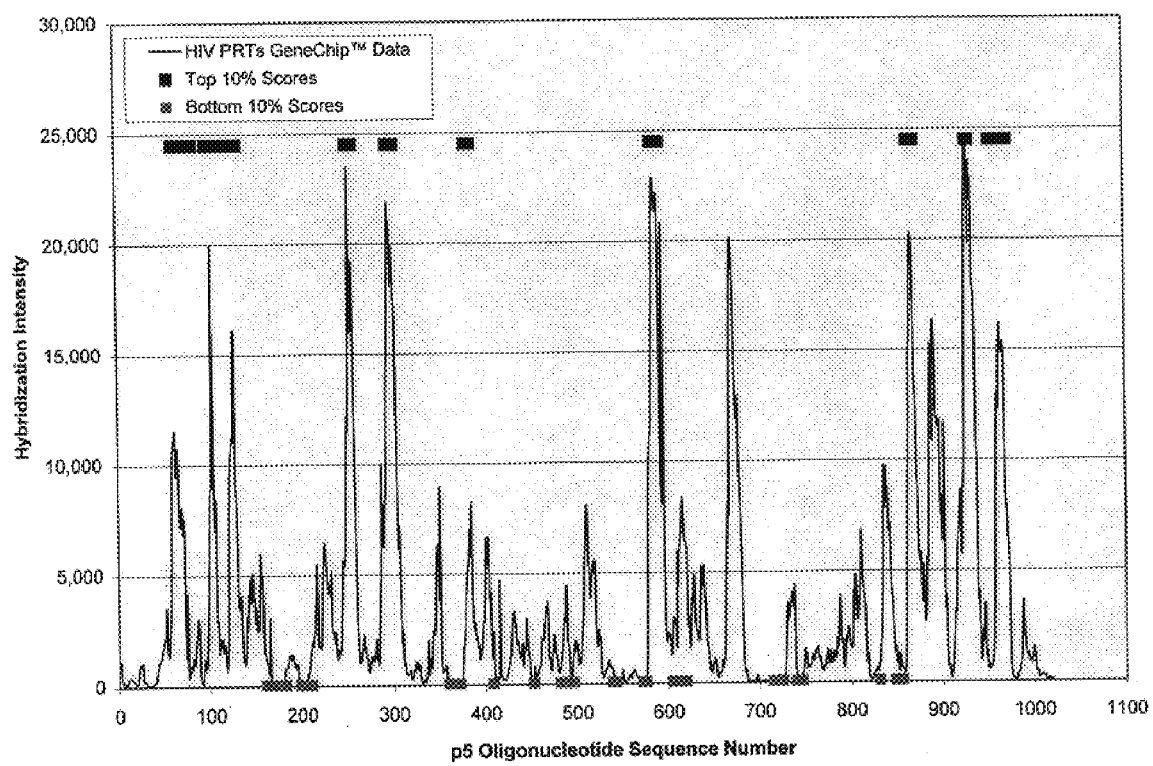
FIG. 8 shows the observed hybridization patterns for oligonucleotides selected using a method in accordance with the present invention and additional oligonucleotides to the HIV PRTs gene (using data from the GeneChip™ data).

Results:

The calculated parameters and scores are shown in Table 4; the algorithm predictions are also shown diagrammatically in FIG. 8. In Table 4, window-averaged composite score values that were in the top 10% of the distribution of values are shown in bold type, values that were in the bottom 10% are shown in italics, and all other values are shown with a line through them. It is clear from both Table 4 and FIG. 8 that the window-averaged composite dimensionless score embodiment of the current invention correctly predicted both efficient and inefficient hybridization probes for HIV PRT sense-strand RNA. As in Example 1, statistical sampling of contiguous stretches of predicted "good" probes would lead to convergence of the design process to the best probes in each region in 2–4 design iterations.

TABLE 4

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 1 | GTACTGTCCATTTATCAGGA | 145 | 64.16 | −0.10 | 0.557 | −0.199 | 0.269 | | 1152.2 |
| 2 | TACTGTCCATTTATCAGGAT | 146 | 60.91 | −0.40 | 0.080 | −0.460 | −0.125 | | 1040.7 |
| 3 | ACTGTCCATTTATCAGGATG | 147 | 61.41 | −0.90 | 0.152 | −0.895 | −0.246 | | 291.9 |
| 4 | CTGTCCATTTATCAGGATGG | 148 | 63.46 | −0.90 | 0.453 | −0.895 | −0.059 | −0.168 | 221.8 |
| 5 | TGTCCATTTATCAGGATGGA | 149 | 62.82 | −0.90 | 0.360 | −0.895 | −0.117 | −0.281 | 148.3 |
| 6 | GTCCATTTATCAGGATGGAG | 150 | 63.15 | −1.90 | 0.408 | −1.764 | −0.418 | −0.308 | 84.6 |
| 7 | TCCATTTATCAGGATGGAGT | 151 | 63.15 | −2.10 | 0.408 | −1.938 | −0.484 | −0.252 | 128.7 |
| 8 | CCATTTATCAGGATGGAGTT | 152 | 62.03 | −1.90 | 0.245 | −1.764 | −0.519 | −0.242 | 94.6 |
| 9 | CATTTATCAGGATGGAGTTC | 153 | 59.53 | −0.60 | −0.122 | −0.634 | −0.317 | −0.236 | 157.5 |
| 10 | ATTTATCAGGATGGAGTTCA | 154 | 59.53 | 0.80 | −0.122 | 0.583 | 0.146 | −0.227 | 316.9 |
| 11 | TTTATCAGGATGGAGTTCAT | 155 | 59.53 | 0.40 | −0.122 | 0.236 | 0.014 | −0.194 | 360.2 |
| 12 | TTATCAGGATGGAGTTCATA | 156 | 58.58 | 0.40 | −0.262 | 0.236 | −0.073 | −0.105 | 403.8 |
| 13 | TATCAGGATGGAGTTCATAA | 157 | 56.21 | 0.20 | −0.609 | 0.062 | −0.354 | −0.014 | 382.5 |
| 14 | ATCAGGATGGAGTTCATAAC | 158 | 57.34 | 0.20 | −0.444 | 0.062 | −0.252 | −0.004 | 324.4 |
| 15 | TCAGGATGGAGTTCATAACC | 159 | 61.25 | 0.20 | 0.129 | 0.062 | 0.104 | −0.035 | 320.5 |
| 16 | CAGGATGGAGTTCATAACCC | 160 | 63.57 | 0.20 | 0.470 | 0.062 | 0.315 | −0.101 | 238.9 |
| 17 | AGGATGGAGTTCATAACCCA | 161 | 63.57 | −0.10 | 0.470 | −0.199 | 0.216 | −0.157 | 202.3 |
| 18 | GGATGGAGTTCATAACCCAT | 162 | 63.34 | −1.30 | 0.436 | −1.243 | −0.202 | −0.120 | 113.6 |
| 19 | GATGGAGTTCATAACCCATC | 163 | 62.24 | −2.00 | 0.275 | −1.851 | −0.533 | −0.099 | 97.7 |
| 20 | ATGGAGTTCATAACCCATCC | 164 | 64.62 | −3.30 | 0.624 | −2.982 | −0.746 | −0.100 | 143.3 |
| 21 | TGGAGTTCATAACCCATCCC | 165 | 68.18 | −2.00 | 1.146 | −1.851 | 0.007 | −0.109 | 484.6 |
| 22 | GGAGTTCATAACCCATCCCA | 166 | 69.39 | −1.60 | 1.324 | −1.504 | 0.249 | −0.058 | 857.6 |
| 23 | GAGTTCATAACCCATCCCAA | 167 | 64.93 | −0.20 | 0.670 | −0.286 | 0.307 | −0.053 | 991.4 |
| 24 | AGTTCATAACCCATCCCAAA | 168 | 61.82 | 0.20 | 0.213 | 0.062 | 0.155 | −0.173 | 907.0 |
| 25 | GTTCATAACCCATCCCAAAG | 169 | 61.82 | 0.20 | 0.213 | 0.062 | 0.155 | −0.137 | 887.9 |
| 26 | TTCATAACCCATCCCAAAGG | 170 | 61.36 | 0.60 | 0.145 | 0.410 | 0.246 | −0.053 | 1015.3 |
| 27 | TCATAACCCATCCCAAAGGA | 171 | 62.21 | −0.10 | 0.270 | −0.199 | 0.092 | 0.040 | 279.7 |
| 28 | CATAACCCATCCCAAAGGAA | 172 | 59.26 | −0.30 | −0.163 | −0.373 | −0.243 | −0.124 | 210.7 |
| 29 | ATAACCCATCCCAAAGGAAT | 173 | 58.19 | −0.30 | −0.320 | −0.373 | −0.340 | −0.204 | 179.9 |
| 30 | TAACCCATCCCAAAGGAATG | 174 | 58.13 | −0.30 | −0.328 | −0.373 | −0.345 | −0.309 | 91.8 |
| 31 | AACCCATCCCAAAGGAATGG | 175 | 60.78 | −1.30 | 0.061 | −1.243 | −0.435 | −0.412 | 44.6 |
| 32 | ACCCATCCCAAAGGAATGGA | 176 | 63.69 | −2.00 | 0.487 | −1.551 | −0.401 | −0.488 | 42.9 |
| 33 | CCCATCCCAAAGGAATGGAG | 177 | 63.40 | −2.20 | 0.445 | −2.025 | −0.494 | −0.542 | 45.0 |
| 34 | CCATCCCAAAGGAATGGAGG | 178 | 62.34 | −2.30 | 0.290 | −2.112 | −0.623 | −0.579 | 45.3 |
| 35 | CATCCCAAAGGAATGGAGGT | 179 | 61.72 | −2.60 | 0.199 | −2.373 | −0.778 | −0.587 | 47.9 |
| 36 | ATCCCAAAGGAATGGAGGTT | 180 | 60.90 | −2.20 | 0.079 | −2.025 | −0.721 | −0.580 | 49.2 |
| 37 | TCCCAAAGGAATGGAGGTTC | 181 | 62.24 | −2.20 | 0.274 | −2.025 | −0.600 | −0.585 | 74.2 |
| 38 | CCCAAAGGAATGGAGGTTCT | 182 | 62.71 | −2.00 | 0.344 | −1.851 | −0.490 | −0.572 | 125.5 |
| 39 | CCAAAGGAATGGAGGTTCTT | 183 | 59.47 | −0.70 | −0.132 | −0.721 | −0.356 | −0.485 | 183.3 |
| 40 | CAAAGGAATGGAGGTTCTTT | 184 | 56.10 | −0.30 | −0.627 | −0.373 | −0.530 | −0.380 | 261.4 |
| 41 | AAAGGAATGGAGGTTCTTTC | 185 | 56.11 | −0.30 | −0.625 | −0.373 | −0.529 | −0.277 | 518.3 |
| 42 | AAGGAATGGAGGTTCTTTCT | 186 | 60.05 | −0.30 | −0.046 | −0.373 | −0.170 | −0.206 | 716.5 |
| 43 | AGGAATGGAGGTTCTTTCTG | 187 | 62.09 | −0.30 | 0.253 | −0.373 | 0.015 | −0.164 | 1056.0 |
| 44 | GGAATGGAGGTTCTTTCTGA | 188 | 63.23 | −0.30 | 0.420 | −0.373 | 0.119 | −0.025 | 1084.3 |
| 45 | GAATGGAGGTTCTTTCTGAT | 189 | 60.56 | 0.10 | 0.028 | −0.025 | 0.008 | −0.119 | 1241.1 |
| 46 | AATGGAGGTTCTTTCTGATG | 190 | 59.12 | 0.30 | −0.183 | 0.149 | −0.057 | −0.217 | 1278.8 |
| 47 | ATGGAGGTTCTTTCTGATGT | 191 | 64.58 | 0.30 | 0.618 | 0.149 | 0.440 | −0.258 | 1616.0 |
| 48 | TGGAGGTTCTTTCTGATGTT | 192 | 64.98 | 0.30 | 0.677 | 0.149 | 0.476 | −0.270 | 1677.5 |
| 49 | GGAGGTTCTTTCTGATGTTT | 193 | 65.49 | 0.30 | 0.751 | 0.149 | 0.522 | −0.300 | 1963.1 |
| 50 | GAGGTTCTTTCTGATGTTTT | 194 | 63.04 | 0.30 | 0.392 | 0.149 | 0.300 | −0.301 | 2126.1 |
| 51 | AGGTTCTTTCTGATGTTTTT | 195 | 61.97 | 0.30 | 0.235 | 0.149 | 0.202 | −0.231 | 2143.3 |
| 52 | GGTTCTTTCTGATGTTTTTT | 196 | 62.11 | 0.30 | 0.256 | 0.149 | 0.215 | −0.180 | 3540.6 |
| 53 | GTTCTTTCTGATGTTTTTTG | 197 | 59.21 | 0.30 | −0.170 | 0.149 | −0.049 | −0.164 | 1728.7 |
| 54 | TTCTTTCTGATGTTTTTTGT | 198 | 59.21 | 0.30 | −0.170 | 0.149 | −0.049 | −0.151 | 1364.3 |
| 55 | TCTTTCTGATGTTTTTTGTC | 199 | 60.35 | 0.50 | −0.002 | 0.323 | 0.121 | −0.183 | 1788.4 |
| 56 | CTTTCTGATGTTTTTTGTCT | 200 | 60.96 | 1.20 | 0.086 | 0.931 | 0.407 | −0.253 | 2670.9 |
| 57 | TTTCTGATGTTTTTTGTCTG | 201 | 58.76 | 1.20 | −0.235 | 0.931 | 0.208 | −0.338 | 3336.2 |
| 58 | TTCTGATGTTTTTTGTCTGG | 202 | 61.17 | 1.20 | 0.118 | 0.931 | 0.427 | −0.440 | 6683.6 |
| 59 | TCTGATGTTTTTTGTCTGGT | 203 | 64.20 | 1.20 | 0.562 | 0.931 | 0.702 | −0.537 | 10227.0 |
| 60 | CTGATGTTTTTTGTCTGGTG | 204 | 62.51 | 1.20 | 0.315 | 0.931 | 0.549 | −0.625 | 10965.0 |
| 61 | TGATGTTTTTTGTCTGGTGT | 205 | 63.80 | 1.20 | 0.504 | 0.931 | 0.666 | −0.778 | 11133.0 |
| 62 | GATGTTTTTTGTCTGGTGTG | 206 | 63.80 | 1.60 | 0.504 | 1.279 | 0.798 | 0.894 | 11503.0 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip ™ Data |
|---|---|---|---|---|---|---|---|---|---|
| 63 | ATGTTTTTTGTCTGGTGTGG | 207 | 65.18 | 1.90 | 0.705 | 1.540 | 1.023 | 0.894 | 9492.8 |
| 64 | TGTTTTTTGTCTGGTGTGGT | 208 | 68.78 | 1.70 | 1.234 | 1.366 | 1.284 | 0.914 | 10704.0 |
| 65 | GTTTTTTGTCTGGTGTGGTA | 209 | 68.28 | 1.70 | 1.161 | 1.366 | 1.239 | 0.933 | 10741.0 |
| 66 | TTTTTTGTCTGGTGTGGTAA | 210 | 62.37 | 1.70 | 0.294 | 1.366 | 0.701 | 0.950 | 9187.5 |
| 67 | TTTTTGTCTGGTGTGGTAAG | 211 | 62.23 | 1.70 | 0.273 | 1.366 | 0.689 | 0.941 | 7871.0 |
| 68 | TTTTGTCTGGTGTGGTAAGT | 212 | 65.28 | 1.20 | 0.721 | 0.931 | 0.801 | 0.921 | 7209.1 |
| 69 | TTTGTCTGGTGTGGTAAGTC | 213 | 66.56 | 1.20 | 0.908 | 0.931 | 0.917 | 0.959 | 8052.3 |
| 70 | TTGTCTGGTGTGGTAAGTCC | 214 | 70.25 | 0.30 | 1.449 | 0.149 | 0.955 | 1.022 | 7230.6 |
| 71 | TGTCTGGTGTGGTAAGTCCC | 215 | 73.77 | −0.10 | 1.966 | −0.199 | 1.143 | 0.998 | 6809.5 |
| 72 | GTCTGGTGTGGTAAGTCCCC | 216 | 77.74 | −0.10 | 2.549 | −0.199 | 1.504 | 0.913 | 7442.8 |
| 73 | TCTGGTGTGGTAAGTCCCCA | 217 | 75.28 | −0.50 | 2.187 | −0.547 | 1.148 | 0.824 | 2627.7 |
| 74 | CTGGTGTGGTAAGTCCCCAC | 218 | 74.18 | −2.10 | 2.026 | −1.938 | 0.519 | 0.781 | 1315.0 |
| 75 | TGGTGTGGTAAGTCCCCACC | 219 | 75.80 | −3.50 | 2.263 | −3.156 | 0.204 | 0.680 | 4182.3 |
| 76 | GGTGTGGTAAGTCCCCACCT | 220 | 77.89 | −3.80 | 2.571 | −3.417 | 0.296 | 0.518 | 474.7 |
| 77 | GTGTGGTAAGTCCCCACCTC | 221 | 77.05 | −2.50 | 2.448 | −2.286 | 0.649 | 0.429 | 682.4 |
| 78 | TGTGGTAAGTCCCCACCTCA | 222 | 74.71 | −2.50 | 2.105 | −2.286 | 0.436 | 0.465 | 679.1 |
| 79 | GTGGTAAGTCCCCACCTCAA | 223 | 72.54 | −2.10 | 1.785 | −1.938 | 0.370 | 0.584 | 924.0 |
| 80 | TGGTAAGTCCCCACCTCAAC | 224 | 69.94 | −0.90 | 1.404 | −0.895 | 0.531 | 0.667 | 835.5 |
| 81 | GGTAAGTCCCCACCTCAACA | 225 | 71.14 | −0.50 | 1.580 | −0.547 | 0.772 | 0.687 | 1213.6 |
| 82 | GTAAGTCCCCACCTCAACAG | 226 | 68.97 | 0.90 | 1.262 | 0.670 | 1.037 | 0.763 | 1106.1 |
| 83 | TAAGTCCCCACCTCAACAGA | 227 | 67.18 | 0.90 | 0.999 | 0.670 | 0.874 | 0.872 | 1009.0 |
| 84 | AAGTCCCCACCTCAACAGAT | 228 | 67.68 | 0.50 | 1.073 | 0.323 | 0.788 | 0.908 | 1656.2 |
| 85 | AGTCCCCACCTCAACAGATG | 229 | 69.68 | 0.50 | 1.366 | 0.323 | 0.970 | 0.831 | 2178.3 |
| 86 | GTCCCCACCTCAACAGATGT | 230 | 72.56 | 0.20 | 1.789 | 0.062 | 1.132 | 0.679 | 2567.0 |
| 87 | TCCCCACCTCAACAGATGTT | 231 | 69.77 | −0.10 | 1.379 | −0.199 | 0.779 | 0.522 | 3000.5 |
| 88 | CCCCACCTCAACAGATGTTG | 232 | 68.19 | −1.30 | 1.148 | −1.243 | 0.240 | 0.354 | 2025.4 |
| 89 | CCCACCTCAACAGATGTTGT | 233 | 67.78 | −2.00 | 1.087 | −1.851 | −0.030 | 0.164 | 429.2 |
| 90 | CCACCTCAACAGATGTTGTC | 234 | 65.65 | −2.00 | 0.775 | −1.851 | −0.223 | 0.041 | 157.9 |
| 91 | CACCTCAACAGATGTTGTCT | 235 | 63.85 | −2.00 | 0.511 | −1.851 | −0.387 | 0.244 | 135.3 |
| 92 | ACCTCAACAGATGTTGTCTC | 236 | 64.11 | −2.00 | 0.549 | −1.851 | −0.363 | 0.339 | 330.8 |
| 93 | CCTCAACAGATGTTGTCTCA | 237 | 64.77 | −2.00 | 0.646 | −1.851 | −0.303 | 0.370 | 900.0 |
| 94 | CTCAACAGATGTTGTCTCAG | 238 | 61.08 | −2.00 | 0.104 | −1.851 | −0.639 | 0.300 | 1177.0 |
| 95 | TCAACAGATGTTGTCTCAGC | 239 | 63.40 | −2.00 | 0.444 | −1.851 | −0.428 | 0.117 | 795.1 |
| 96 | CAACAGATGTTGTCTCAGCT | 240 | 63.91 | −1.60 | 0.520 | −1.504 | −0.249 | 0.081 | 889.2 |
| 97 | AACAGATGTTGTCTCAGCTC | 241 | 64.19 | −0.10 | 0.560 | −0.199 | 0.272 | 0.287 | 1703.6 |
| 98 | ACAGATGTTGTCTCAGCTCC | 242 | 70.61 | 0.00 | 1.503 | −0.112 | 0.889 | 0.598 | 3115.2 |
| 99 | CAGATGTTGTCTCAGCTCCT | 243 | 72.08 | 0.00 | 1.719 | −0.112 | 1.023 | 0.847 | 4445.0 |
| 100 | AGATGTTGTCTCAGCTCCTC | 244 | 72.66 | 0.20 | 1.803 | 0.062 | 1.141 | 1.070 | 6762.8 |
| 101 | GATGTTGTCTCAGCTCCTCT | 245 | 74.49 | 0.90 | 2.071 | 0.670 | 1.539 | 1.227 | 8845.0 |
| 102 | ATGTTGTCTCAGCTCCTCTA | 246 | 72.38 | 0.80 | 1.763 | 0.583 | 1.314 | 1.253 | 9010.6 |
| 103 | TGTTGTCTCAGCTCCTCTAT | 247 | 72.38 | 0.80 | 1.763 | 0.583 | 1.314 | 1.260 | 19941.0 |
| 104 | GTTGTCTCAGCTCCTCTATT | 248 | 72.97 | 0.80 | 1.849 | 0.583 | 1.368 | 1.257 | 12577.0 |
| 105 | TTGTCTCAGCTCCTCTATTT | 249 | 69.70 | 0.80 | 1.369 | 0.583 | 1.071 | 1.149 | 7503.3 |
| 106 | TGTCTCAGCTCCTCTATTTT | 250 | 69.70 | 0.80 | 1.369 | 0.583 | 1.071 | 1.098 | 7033.8 |
| 107 | GTCTCAGCTCCTCTATTTTT | 251 | 70.26 | 0.80 | 1.451 | 0.583 | 1.121 | 1.024 | 8276.7 |
| 108 | TCTCAGCTCCTCTATTTTTG | 252 | 66.57 | 0.80 | 0.910 | 0.583 | 0.786 | 0.942 | 2899.0 |
| 109 | CTCAGCTCCTCTATTTTTGT | 253 | 68.39 | 0.80 | 1.177 | 0.583 | 0.952 | 0.923 | 2935.0 |
| 110 | TCAGCTCCTCTATTTTTGTT | 254 | 66.69 | 0.80 | 0.927 | 0.583 | 0.796 | 0.930 | 1512.8 |
| 111 | CAGCTCCTCTATTTTTGTTC | 255 | 66.69 | 0.80 | 0.927 | 0.583 | 0.796 | 0.872 | 1708.8 |
| 112 | AGCTCCTCTATTTTTGTTCT | 256 | 67.52 | 1.00 | 1.050 | 0.757 | 0.939 | 0.833 | 1977.3 |
| 113 | GCTCCTCTATTTTTGTTCTA | 257 | 66.63 | 1.80 | 0.919 | 1.453 | 1.122 | 0.809 | 2114.8 |
| 114 | CTCCTCTATTTTTGTTCTAT | 258 | 62.13 | 1.80 | 0.259 | 1.453 | 0.713 | 0.766 | 1527.3 |
| 115 | TCCTCTATTTTTGTTCTATG | 259 | 59.97 | 1.80 | 0.058 | 1.453 | 0.516 | 0.695 | 1536.8 |
| 116 | CCTCTATTTTTGTTCTATGC | 260 | 62.84 | 1.80 | 0.363 | 1.453 | 0.777 | 0.642 | 1824.5 |
| 117 | CTCTATTTTTGTTCTATGCT | 261 | 60.87 | 1.50 | 0.074 | 1.192 | 0.499 | 0.588 | 1169.2 |
| 118 | TCTATTTTTGTTCTATGCTG | 262 | 58.71 | 1.50 | −0.244 | 1.192 | 0.302 | 0.649 | 683.7 |
| 119 | CTATTTTTGTTCTATGCTGC | 263 | 61.60 | 1.50 | 0.181 | 1.192 | 0.565 | 0.765 | 1306.8 |
| 120 | TATTTTTGTTCTATGCTGCC | 264 | 63.53 | 1.50 | 0.464 | 1.192 | 0.741 | 0.831 | 2523.6 |
| 121 | ATTTTTGTTCTATGCTGCCC | 265 | 67.96 | 1.50 | 1.113 | 1.192 | 1.143 | 0.931 | 6682.0 |
| 122 | TTTTTGTTCTATGCTGCCCT | 266 | 69.96 | 1.50 | 1.407 | 1.192 | 1.325 | 1.060 | 9417.4 |
| 123 | TTTTGTTCTATGCTGCCCTA | 267 | 69.01 | 1.50 | 1.267 | 1.192 | 1.239 | 1.151 | 10339.0 |
| 124 | TTTGTTCTATGCTGCCCTAT | 268 | 68.62 | 1.50 | 1.210 | 1.192 | 1.203 | 1.254 | 10750.0 |
| 125 | TTGTTCTATGCTGCCCTATT | 269 | 68.62 | 1.50 | 1.210 | 1.192 | 1.203 | 1.282 | 11180.0 |
| 126 | TGTTCTATGCTGCCCTATTT | 270 | 68.62 | 1.50 | 1.210 | 1.192 | 1.203 | 1.271 | 11060.0 |
| 127 | GTTCTATGCTGCCCTATTTC | 271 | 70.37 | 1.80 | 1.468 | 1.453 | 1.462 | 1.221 | 16074.0 |
| 128 | TTCTATGCTGCCCTATTTCT | 272 | 69.00 | 1.80 | 1.266 | 1.453 | 1.337 | 1.144 | 9183.8 |
| 129 | TCTATGCTGCCCTATTTCTA | 273 | 68.05 | 1.80 | 1.127 | 1.453 | 1.251 | 1.082 | 8617.8 |
| 130 | CTATGCTGCCCTATTTCTAA | 274 | 64.38 | 1.70 | 0.589 | 1.366 | 0.884 | 1.040 | 7286.8 |
| 131 | TATGCTGCCCTATTTCTAAG | 275 | 62.71 | 1.50 | 0.344 | 1.192 | 0.666 | 0.978 | 3642.4 |
| 132 | ATGCTGCCCTATTTCTAAGT | 276 | 66.39 | 0.80 | 0.883 | 0.583 | 0.769 | 0.883 | 3799.7 |
| 133 | TGCTGCCCTATTTCTAAGTC | 277 | 67.95 | 0.80 | 1.112 | 0.583 | 0.911 | 0.749 | 3408.3 |
| 134 | GCTGCCCTATTTCTAAGTCA | 278 | 69.25 | 0.80 | 1.303 | 0.583 | 1.030 | 0.644 | 4017.4 |
| 135 | CTGCCCTATTTCTAAGTCAG | 279 | 65.26 | 0.80 | 0.718 | 0.583 | 0.667 | 0.536 | 2197.2 |
| 136 | TGCCCTATTTCTAAGTCAGA | 280 | 64.63 | −0.10 | 0.626 | −0.199 | 0.312 | 0.412 | 1125.0 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 137 | GCCCTATTTCTAAGTCAGAT | 281 | 64.73 | −0.60 | 0.639 | −0.634 | 0.156 | −0.244 | 1306.3 |
| 138 | CCCTATTTCTAAGTCAGATC | 282 | 61.98 | −0.60 | 0.236 | −0.634 | −0.094 | −0.024 | 1019.5 |
| 139 | CCTATTTCTAAGTCAGATCC | 283 | 61.98 | −0.60 | 0.236 | −0.634 | −0.094 | −0.129 | 1852.3 |
| 140 | CTATTTCTAAGTCAGATCCT | 284 | 60.05 | −0.60 | −0.046 | −0.634 | −0.270 | −0.214 | 3159.3 |
| 141 | TATTTCTAAGTCAGATCCTA | 285 | 57.43 | −0.60 | −0.430 | −0.634 | −0.508 | −0.281 | 2604.8 |
| 142 | ATTTCTAAGTCAGATCCTAC | 286 | 58.59 | −0.60 | −0.261 | −0.634 | −0.402 | −0.315 | 3986.1 |
| 143 | TTTCTAAGTCAGATCCTACA | 287 | 59.91 | −0.60 | −0.068 | −0.634 | −0.283 | −0.285 | 4500.7 |
| 144 | TTCTAAGTCAGATCCTACAT | 288 | 59.55 | −0.60 | −0.120 | −0.634 | −0.315 | −0.233 | 4754.5 |
| 145 | TCTAAGTCAGATCCTACATA | 289 | 58.62 | −0.40 | −0.257 | −0.460 | −0.334 | −0.165 | 3802.1 |
| 146 | CTAAGTCAGATCCTACATAC | 290 | 57.80 | 1.20 | −0.377 | 0.931 | 0.120 | −0.111 | 5069.4 |
| 147 | TAAGTCAGATCCTACATACA | 291 | 57.13 | 1.30 | −0.476 | 1.018 | 0.092 | −0.059 | 3965.2 |
| 148 | AAGTCAGATCCTACATACAA | 292 | 55.78 | 1.30 | −0.673 | 1.018 | −0.030 | −0.031 | 3862.3 |
| 149 | AGTCAGATCCTACATACAAA | 293 | 55.78 | 1.30 | −0.673 | 1.018 | −0.030 | −0.020 | 2868.9 |
| 150 | GTCAGATCCTACATACAAAT | 294 | 55.62 | 1.70 | −0.697 | 1.366 | 0.087 | −0.089 | 3542.9 |
| 151 | TCAGATCCTACATACAAATC | 295 | 54.02 | 1.50 | −0.932 | 1.192 | −0.125 | −0.122 | 2477.1 |
| 152 | CAGATCCTACATACAAATCA | 296 | 54.07 | 1.10 | −0.924 | 0.844 | −0.252 | −0.091 | 2522.4 |
| 153 | AGATCCTACATACAAATCAT | 297 | 52.83 | 1.10 | −1.106 | 0.844 | −0.365 | −0.045 | 2554.6 |
| 154 | GATCCTACATACAAATCATC | 298 | 53.87 | 1.50 | −0.953 | 1.192 | −0.138 | −0.031 | 3580.0 |
| 155 | ATCCTACATACAAATCATCC | 299 | 56.33 | 1.80 | −0.591 | 1.453 | 0.185 | −0.067 | 5937.7 |
| 156 | TCCTACATACAAATCATCCA | 300 | 57.54 | 1.80 | −0.415 | 1.453 | 0.295 | −0.111 | 4606.7 |
| 157 | CCTACATACAAATCATCCAT | 301 | 56.32 | 1.80 | −0.594 | 1.453 | 0.184 | −0.159 | 4877.2 |
| 158 | CTACATACAAATCATCCATG | 302 | 52.68 | 1.10 | −1.128 | 0.844 | −0.379 | −0.278 | 2608.6 |
| 159 | TACATACAAATCATCCATGT | 303 | 53.56 | 0.30 | −0.999 | 0.149 | −0.563 | −0.469 | 1491.7 |
| 160 | ACATACAAATCATCCATGTA | 304 | 53.56 | −0.10 | −0.999 | −0.199 | −0.695 | −0.644 | 1364.3 |
| 161 | CATACAAATCATCCATGTAT | 305 | 53.07 | −0.80 | −1.071 | −0.808 | −0.971 | −0.751 | 1089.8 |
| 162 | ATACAAATCATCCATGTATT | 306 | 52.11 | −1.10 | −1.211 | −1.069 | −1.157 | −0.818 | 1008.6 |
| 163 | TACAAATCATCCATGTATTG | 307 | 52.08 | −0.40 | −1.215 | −0.460 | −0.928 | −0.891 | 624.8 |
| 164 | ACAAATCATCCATGTATTGA | 308 | 53.86 | 0.20 | −0.955 | 0.062 | −0.568 | −0.921 | 535.8 |
| 165 | CAAATCATCCATGTATTGAT | 309 | 53.36 | −0.50 | −1.027 | −0.547 | −0.845 | −0.860 | 3019.6 |
| 166 | AAATCATCCATGTATTGATA | 310 | 51.57 | −0.70 | −1.291 | −0.721 | −1.074 | −0.753 | 214.0 |
| 167 | AATCATCCATGTATTGATAG | 311 | 53.47 | −0.70 | −1.012 | −0.721 | −0.901 | −0.685 | 212.7 |
| 168 | ATCATCCATGTATTGATAGA | 312 | 56.66 | −0.50 | −0.543 | −0.547 | −0.545 | −0.709 | 165.2 |
| 169 | TCATCCATGTATTGATAGAT | 313 | 56.66 | −0.10 | −0.543 | −0.199 | −0.412 | −0.686 | 166.0 |
| 170 | CATCCATGTATTGATAGATA | 314 | 54.80 | 0.30 | −0.817 | 0.149 | −0.450 | −0.622 | 151.0 |
| 171 | ATCCATGTATTGATAGATAA | 315 | 51.69 | 0.30 | −1.273 | 0.149 | −0.733 | −0.621 | 101.8 |
| 172 | TCCATGTATTGATAGATAAC | 316 | 52.19 | 0.30 | −1.199 | 0.149 | −0.687 | −0.721 | 84.0 |
| 173 | CCATGTATTGATAGATAACT | 317 | 52.89 | 0.30 | −1.097 | 0.149 | −0.623 | −0.850 | 130.3 |
| 174 | CATGTATTGATAGATAACTA | 318 | 48.47 | 0.70 | −1.746 | 0.496 | −0.894 | −0.937 | 67.8 |
| 175 | ATGTATTGATAGATAACTAT | 319 | 47.12 | 0.00 | −1.944 | −0.112 | −1.248 | −1.006 | 65.7 |
| 176 | TGTATTGATAGATAACTATG | 320 | 47.11 | −0.20 | −1.945 | −0.286 | −1.315 | −1.048 | 90.0 |
| 177 | GTATTGATAGATAACTATGT | 321 | 49.90 | −0.20 | −1.536 | −0.286 | −1.061 | −1.099 | 125.9 |
| 178 | TATTGATAGATAACTATGTC | 322 | 48.24 | −0.20 | −1.779 | −0.286 | −1.212 | −1.083 | 132.6 |
| 179 | ATTGATAGATAACTATGTCT | 323 | 50.78 | −0.20 | −1.407 | −0.286 | −0.981 | −0.998 | 167.4 |
| 180 | TTGATAGATAACTATGTCTG | 324 | 50.75 | −0.20 | −1.411 | −0.286 | −0.984 | −0.916 | 219.0 |
| 181 | TGATAGATAACTATGTCTGG | 325 | 53.01 | −0.20 | −1.080 | −0.286 | −0.778 | −0.866 | 722.6 |
| 182 | GATAGATAACTATGTCTGGA | 326 | 54.36 | −0.20 | −0.881 | −0.286 | −0.655 | −0.774 | 825.1 |
| 183 | ATAGATAACTATGTCTGGAT | 327 | 53.04 | −0.10 | −1.074 | −0.199 | −0.742 | −0.679 | 844.4 |
| 184 | TAGATAACTATGTCTGGATT | 328 | 53.37 | −0.10 | −1.027 | −0.199 | −0.712 | −0.569 | 912.6 |
| 185 | AGATAACTATGTCTGGATTT | 329 | 54.27 | 0.10 | −0.895 | −0.025 | −0.565 | −0.449 | 1301.8 |
| 186 | GATAACTATGTCTGGATTTT | 330 | 54.43 | 0.80 | −0.870 | 0.583 | −0.318 | −0.335 | 1367.4 |
| 187 | ATAACTATGTCTGGATTTTG | 331 | 53.08 | 1.50 | −1.070 | 1.192 | −0.210 | −0.177 | 1284.2 |
| 188 | TAACTATGTCTGGATTTTGT | 332 | 56.05 | 1.50 | −0.634 | 1.192 | 0.060 | −0.026 | 1162.5 |
| 189 | AACTATGTCTGGATTTTGTT | 333 | 56.97 | 1.50 | −0.499 | 1.192 | 0.144 | −0.081 | 1396.7 |
| 190 | ACTATGTCTGGATTTTGTTT | 334 | 59.38 | 1.50 | −0.145 | 1.192 | 0.363 | −0.176 | 1348.3 |
| 191 | CTATGTCTGGATTTTGTTTT | 335 | 59.16 | 1.50 | −0.177 | 1.192 | 0.343 | −0.261 | 1092.8 |
| 192 | TATGTCTGGATTTTGTTTTT | 336 | 57.45 | 1.50 | −0.428 | 1.192 | 0.188 | −0.234 | 912.6 |
| 193 | ATGTCTGGATTTTGTTTTTT | 337 | 58.41 | 1.70 | −0.287 | 1.368 | 0.341 | −0.123 | 994.3 |
| 194 | TGTCTGGATTTTGTTTTTTA | 338 | 57.81 | 2.00 | −0.375 | 1.627 | 0.386 | −0.079 | 840.7 |
| 195 | GTCTGGATTTTGTTTTTAA | 339 | 55.82 | 1.00 | −0.667 | 0.757 | −0.126 | −0.311 | 941.9 |
| 196 | TCTGGATTTTGTTTTTAAA | 340 | 50.98 | 0.80 | −1.377 | 0.583 | −0.632 | −0.488 | 84.9 |
| 197 | CTGGATTTTGTTTTTAAAA | 341 | 48.16 | 0.30 | −1.790 | 0.149 | −1.054 | −0.670 | 78.6 |
| 198 | TGGATTTTGTTTTTAAAAG | 342 | 46.41 | 0.10 | −2.048 | −0.025 | −1.279 | −0.851 | 93.2 |
| 199 | GGATTTTGTTTTTAAAAGG | 343 | 48.87 | 0.10 | −1.686 | −0.025 | −1.055 | −0.933 | 56.0 |
| 200 | GATTTTGTTTTTAAAAGGC | 344 | 50.22 | 0.10 | −1.488 | −0.025 | −0.932 | −0.912 | 49.9 |
| 201 | ATTTTGTTTTTAAAAGGCT | 345 | 50.84 | 0.10 | −1.397 | −0.025 | −0.876 | −0.843 | 55.0 |
| 202 | TTTTGTTTTTAAAAGGCTC | 346 | 52.03 | 0.30 | −1.223 | 0.149 | −0.702 | −0.768 | 64.6 |
| 203 | TTTGTTTTTAAAAGGCTCT | 347 | 53.64 | 0.50 | −0.987 | 0.323 | −0.489 | −0.724 | 162.8 |
| 204 | TTGTTTTTAAAAGGCTCTA | 348 | 52.76 | 0.50 | −1.115 | 0.323 | −0.569 | −0.706 | 265.8 |
| 205 | TGTTTTTAAAAGGCTCTAA | 349 | 50.71 | 0.50 | −1.417 | 0.323 | −0.756 | −0.677 | 288.5 |
| 206 | GTTTTTAAAAGGCTCTAAG | 350 | 50.86 | 0.50 | −1.395 | 0.323 | −0.742 | −0.672 | 548.4 |
| 207 | TTTTTAAAAGGCTCTAAGA | 351 | 49.40 | 0.70 | −1.609 | 0.496 | −0.809 | −0.698 | 524.7 |
| 208 | TTTTAAAAGGCTCTAAGAT | 352 | 49.11 | 1.20 | −1.651 | 0.931 | −0.670 | −0.746 | 937.9 |
| 209 | TTTAAAAGGCTCTAAGATT | 353 | 49.11 | 1.20 | −1.651 | 0.931 | −0.670 | −0.790 | 1440.3 |
| 210 | TTAAAAGGCTCTAAGATTT | 354 | 49.11 | 1.20 | −1.651 | 0.931 | −0.670 | −0.820 | 1633.3 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 211 | TTAAAAGGCTCTAAGATTTT | 355 | 49.11 | 0.50 | −1.651 | 0.323 | −0.901 | −0.735 | 1987.4 |
| 212 | TAAAAGGCTCTAAGATTTTT | 356 | 49.11 | 0.00 | −1.651 | −0.112 | −1.067 | −0.627 | 1792.3 |
| 213 | AAAAGGCTCTAAGATTTTTG | 357 | 49.63 | 0.20 | −1.575 | 0.062 | −0.953 | −0.495 | 2218.9 |
| 214 | AAAGGCTCTAAGATTTTTGT | 358 | 54.13 | 1.20 | −0.914 | 0.931 | −0.213 | −0.365 | 2371.4 |
| 215 | AAGGCTCTAAGATTTTTGTC | 359 | 57.38 | 1.20 | −0.439 | 0.931 | 0.082 | −0.238 | 3308.9 |
| 216 | AGGCTCTAAGATTTTTGTCA | 360 | 60.78 | 0.80 | 0.061 | 0.583 | 0.260 | −0.087 | 4070.5 |
| 217 | GGCTCTAAGATTTTTGTCAT | 361 | 60.56 | 0.80 | 0.028 | 0.583 | 0.239 | −0.048 | 5394.5 |
| 218 | GCTCTAAGATTTTTGTCATG | 362 | 57.81 | 0.80 | −0.376 | 0.583 | −0.011 | −0.051 | 2025.5 |
| 219 | CTCTAAGATTTTTGTCATGC | 363 | 57.81 | 0.80 | −0.376 | 0.583 | −0.011 | −0.006 | 1741.9 |
| 220 | TCTAAGATTTTTGTCATGCT | 364 | 57.81 | 0.80 | −0.376 | 0.583 | −0.011 | −0.065 | 1707.6 |
| 221 | CTAAGATTTTTGTCATGCTA | 365 | 55.87 | 0.80 | −0.660 | 0.583 | −0.187 | −0.089 | 1783.0 |
| 222 | TAAGATTTTTGTCATGCTAC | 366 | 54.43 | 0.80 | −0.872 | 0.583 | −0.319 | −0.076 | 3131.4 |
| 223 | AAGATTTTTGTCATGCTACT | 367 | 56.99 | 0.60 | −0.495 | 0.410 | −0.151 | −0.082 | 4892.5 |
| 224 | AGATTTTTGTCATGCTACTT | 368 | 59.39 | 0.60 | −0.144 | 0.410 | 0.067 | −0.053 | 5856.4 |
| 225 | GATTTTTGTCATGCTACTTT | 369 | 59.54 | 0.60 | −0.122 | 0.410 | 0.080 | −0.015 | 6439.0 |
| 226 | ATTTTTGTCATGCTACTTTG | 370 | 58.09 | 0.60 | −0.334 | 0.410 | −0.051 | −0.069 | 5820.3 |
| 227 | TTTTTGTCATGCTACTTTGG | 371 | 60.78 | 0.60 | 0.060 | 0.410 | 0.193 | −0.095 | 5189.6 |
| 228 | TTTTGTCATGCTACTTTGGA | 372 | 61.79 | 0.60 | 0.209 | 0.410 | 0.285 | −0.079 | 4721.7 |
| 229 | TTTGTCATGCTACTTTGGAA | 373 | 59.35 | 0.60 | −0.149 | 0.410 | 0.063 | −0.075 | 4221.0 |
| 230 | TTGTCATGCTACTTTGGAAT | 374 | 59.00 | 0.60 | −0.200 | 0.410 | 0.032 | −0.056 | 4279.0 |
| 231 | TGTCATGCTACTTTGGAATA | 375 | 58.10 | 0.60 | −0.333 | 0.410 | −0.051 | −0.004 | 4102.0 |
| 232 | GTCATGCTACTTTGGAATAT | 376 | 58.16 | 0.90 | −0.324 | 0.670 | 0.054 | −0.022 | 5069.8 |
| 233 | TCATGCTACTTTGGAATATT | 377 | 55.52 | 0.90 | −0.711 | 0.670 | −0.186 | −0.015 | 2407.9 |
| 234 | CATGCTACTTTGGAATATTG | 378 | 54.23 | 1.30 | −0.900 | 1.018 | −0.171 | −0.016 | 2443.0 |
| 235 | ATGCTACTTTGGAATATTGC | 379 | 56.90 | 1.40 | −0.508 | 1.105 | 0.105 | −0.058 | 2324.3 |
| 236 | TGCTACTTTGGAATATTGCT | 380 | 58.82 | 0.90 | −0.227 | 0.670 | 0.114 | −0.099 | 1894.1 |
| 237 | GCTACTTTGGAATATTGCTG | 381 | 58.82 | 1.30 | −0.227 | 1.018 | 0.246 | −0.180 | 2363.8 |
| 238 | CTACTTTGGAATATTGCTGG | 382 | 57.35 | 1.70 | −0.443 | 1.366 | 0.244 | −0.270 | 1363.0 |
| 239 | TACTTTGGAATATTGCTGGT | 383 | 58.39 | 1.70 | −0.290 | 1.366 | 0.339 | −0.299 | 1217.5 |
| 240 | ACTTTGGAATATTGCTGGTG | 384 | 58.88 | 1.70 | −0.217 | 1.366 | 0.384 | −0.340 | 1621.8 |
| 241 | CTTTGGAATATTGCTGGTGA | 385 | 59.64 | 1.70 | −0.106 | 1.366 | 0.453 | −0.346 | 1438.2 |
| 242 | TTTGGAATATTGCTGGTGAT | 386 | 57.72 | 1.80 | −0.388 | 1.453 | 0.311 | −0.345 | 1608.0 |
| 243 | TTGGAATATTGCTGGTGATC | 387 | 58.73 | 1.80 | −0.241 | 1.453 | 0.403 | −0.302 | 2334.6 |
| 244 | TGGAATATTGCTGGTGATCC | 388 | 62.18 | 0.50 | 0.266 | 0.323 | 0.288 | −0.241 | 3776.7 |
| 245 | GGAATATTGCTGGTGATCCT | 389 | 64.19 | −0.20 | 0.561 | −0.286 | 0.239 | −0.216 | 5648.7 |
| 246 | GAATATTGCTGGTGATCCTT | 390 | 61.99 | −0.20 | 0.238 | −0.286 | 0.039 | −0.261 | 5358.8 |
| 247 | AATATTGCTGGTGATCCTTT | 391 | 61.03 | −0.20 | 0.097 | −0.286 | −0.049 | −0.316 | 5517.2 |
| 248 | ATATTGCTGGTGATCCTTTC | 392 | 64.63 | −0.20 | 0.625 | −0.286 | 0.279 | −0.368 | 6246.4 |
| 249 | TATTGCTGGTGATCCTTTCC | 393 | 68.48 | −0.20 | 1.190 | −0.286 | 0.629 | −0.444 | 9975.1 |
| 250 | ATTGCTGGTGATCCTTTCCA | 394 | 70.22 | −0.20 | 1.446 | −0.286 | 0.788 | −0.599 | 11990.0 |
| 251 | TTGCTGGTGATCCTTTCCAT | 395 | 70.22 | −0.60 | 1.446 | −0.634 | 0.655 | −0.756 | 11543.0 |
| 252 | TGCTGGTGATCCTTTCCATC | 396 | 71.48 | −0.60 | 1.631 | −0.634 | 0.770 | 0.862 | 14125.0 |
| 253 | GCTGGTGATCCTTTCCATCC | 397 | 75.32 | −0.60 | 2.193 | −0.634 | 1.119 | 0.936 | 23489.0 |
| 254 | CTGGTGATCCTTTCCATCCC | 398 | 74.58 | −0.60 | 2.085 | −0.634 | 1.052 | 1.022 | 15975.0 |
| 255 | TGGTGATCCTTTCCATCCCT | 399 | 74.58 | −0.70 | 2.085 | −0.721 | 1.019 | 1.082 | 16053.0 |
| 256 | GGTGATCCTTTCCATCCCTG | 400 | 74.58 | −0.30 | 2.085 | −0.373 | 1.151 | 1.136 | 19205.0 |
| 257 | GTGATCCTTTCCATCCCTGT | 401 | 75.40 | 0.20 | 2.206 | 0.062 | 1.391 | 1.080 | 17872.0 |
| 258 | TGATCCTTTCCATCCCTGTG | 402 | 71.89 | 0.20 | 1.691 | 0.062 | 1.072 | 0.955 | 12871.0 |
| 259 | GATCCTTTCCATCCCTGTGG | 403 | 74.58 | −0.30 | 2.085 | −0.373 | 1.151 | −0.809 | 8792.7 |
| 260 | ATCCTTTCCATCCCTGTGGA | 404 | 74.58 | −1.60 | 2.085 | −1.504 | 0.721 | −0.653 | 5609.6 |
| 261 | TCCTTTCCATCCCTGTGGAA | 405 | 72.27 | −2.60 | 1.746 | −2.373 | 0.181 | −0.451 | 3018.0 |
| 262 | CCTTTCCATCCCTGTGGAAG | 406 | 71.00 | −2.80 | 1.559 | −2.547 | −0.001 | −0.308 | 1802.6 |
| 263 | CTTTCCATCCCTGTGGAAGC | 407 | 71.60 | −2.80 | 1.648 | −2.547 | 0.054 | −0.205 | 1074.0 |
| 264 | TTTCCATCCCTGTGGAAGCA | 408 | 70.81 | −2.80 | 1.532 | −2.547 | −0.018 | −0.120 | 1132.5 |
| 265 | TTCCATCCCTGTGGAAGCAC | 409 | 71.02 | −2.60 | 1.562 | −2.373 | 0.067 | −0.071 | 1454.5 |
| 266 | TCCATCCCTGTGGAAGCACA | 410 | 71.74 | −1.70 | 1.669 | −1.591 | 0.430 | −0.032 | 1676.8 |
| 267 | CCATCCCTGTGGAAGCACAT | 411 | 70.20 | −2.20 | 1.443 | −2.025 | 0.125 | −0.026 | 2268.9 |
| 268 | CATCCCTGTGGAAGCACATT | 412 | 67.07 | −2.20 | 0.983 | −2.025 | −0.160 | −0.004 | 1682.6 |
| 269 | ATCCCTGTGGAAGCACATTG | 413 | 65.82 | −2.20 | 0.801 | −2.025 | −0.273 | −0.070 | 1753.9 |
| 270 | TCCCTGTGGAAGCACATTGT | 414 | 68.98 | −2.20 | 1.263 | −2.025 | 0.014 | −0.220 | 1281.8 |
| 271 | CCCTGTGGAAGCACATTGTA | 415 | 66.92 | −2.20 | 0.962 | −2.025 | −0.173 | −0.344 | 1227.8 |
| 272 | CCTGTGGAAGCACATTGTAC | 416 | 63.84 | −2.20 | 0.509 | −2.025 | −0.454 | −0.337 | 700.3 |
| 273 | CTGTGGAAGCACATTGTACT | 417 | 62.01 | −2.20 | 0.241 | −2.025 | −0.620 | −0.307 | 618.7 |
| 274 | TGTGGAAGCACATTGTACTG | 418 | 59.99 | −2.00 | −0.056 | −1.851 | −0.738 | −0.324 | 771.5 |
| 275 | GTGGAAGCACATTGTACTGA | 419 | 61.39 | −0.50 | 0.149 | −0.547 | −0.115 | −0.347 | 1180.6 |
| 276 | TGGAAGCACATTGTACTGAT | 420 | 58.35 | 0.50 | −0.296 | 0.323 | −0.061 | −0.331 | 1160.5 |
| 277 | GGAAGCACATTGTACTGATA | 421 | 57.86 | 0.50 | −0.368 | 0.323 | −0.106 | −0.239 | 1314.7 |
| 278 | GAAGCACATTGTACTGATAT | 422 | 55.32 | 0.50 | −0.740 | 0.323 | −0.336 | −0.141 | 1102.5 |
| 279 | AAGCACATTGTACTGATATC | 423 | 55.30 | 0.50 | −0.744 | 0.323 | −0.339 | −0.209 | 1222.1 |
| 280 | AGCACATTGTACTGATATCT | 424 | 59.26 | 0.50 | −0.162 | 0.323 | 0.022 | −0.302 | 1893.2 |
| 281 | GCACATTGTACTGATATCTA | 425 | 58.48 | 0.50 | −0.277 | 0.323 | −0.049 | −0.398 | 2097.7 |
| 282 | CACATTGTACTGATATCTAA | 426 | 52.51 | 0.50 | −1.152 | 0.323 | −0.592 | −0.446 | 1237.8 |
| 283 | ACATTGTACTGATATCTAAT | 427 | 51.20 | 0.50 | −1.345 | 0.323 | −0.711 | −0.443 | 959.5 |
| 284 | CATTGTACTGATATCTAATC | 428 | 51.89 | 0.10 | −1.244 | −0.025 | −0.781 | −0.472 | 1149.1 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 285 | ATTGTACTGATATCTAATCC | 429 | 54.53 | −0.30 | −0.856 | −0.373 | −0.672 | −0.490 | 2351.3 |
| 286 | TTGTACTGATATCTAATCCC | 430 | 58.41 | −0.30 | −0.287 | −0.373 | −0.320 | −0.436 | 4191.6 |
| 287 | TGTACTGATATCTAATCCCT | 431 | 59.99 | −0.30 | −0.055 | −0.373 | −0.176 | −0.320 | 5565.8 |
| 288 | GTACTGATATCTAATCCCTG | 432 | 59.99 | −0.30 | −0.055 | −0.373 | −0.176 | −0.202 | 9980.2 |
| 289 | TACTGATATCTAATCCCTGG | 433 | 59.52 | −0.30 | −0.124 | −0.373 | −0.218 | −0.084 | 6318.9 |
| 290 | ACTGATATCTAATCCCTGGT | 434 | 63.07 | −0.30 | 0.397 | −0.373 | 0.104 | −0.023 | 7749.5 |
| 291 | CTGATATCTAATCCCTGGTG | 435 | 62.43 | −0.30 | 0.303 | −0.373 | 0.046 | −0.184 | 8165.3 |
| 292 | TGATATCTAATCCCTGGTGT | 436 | 63.60 | −0.30 | 0.474 | −0.373 | 0.152 | −0.365 | 9107.6 |
| 293 | GATATCTAATCCCTGGTGTC | 437 | 65.19 | 0.10 | 0.707 | −0.025 | 0.429 | −0.566 | 13914.0 |
| 294 | ATATCTAATCCCTGGTGTCT | 438 | 65.82 | 1.50 | 0.800 | 1.192 | 0.949 | −0.698 | 15093.0 |
| 295 | TATCTAATCCCTGGTGTCTC | 439 | 67.41 | 1.50 | 1.033 | 1.192 | 1.093 | −0.822 | 18647.0 |
| 296 | ATCTAATCCCTGGTGTCTCA | 440 | 69.20 | 1.30 | 1.296 | 1.018 | 1.190 | 0.904 | 21810.0 |
| 297 | TCTAATCCCTGGTGTCTCAT | 441 | 69.20 | 0.80 | 1.296 | 0.583 | 1.025 | 0.996 | 20102.0 |
| 298 | CTAATCCCTGGTGTCTCATT | 442 | 67.98 | 0.80 | 1.117 | 0.583 | 0.914 | 1.052 | 20967.0 |
| 299 | TAATCCCTGGTGTCTCATTG | 443 | 65.90 | 0.80 | 0.811 | 0.583 | 0.725 | 1.092 | 18200.0 |
| 300 | AATCCCTGGTGTCTCATTGT | 444 | 69.78 | 0.80 | 1.380 | 0.583 | 1.077 | 1.088 | 19845.0 |
| 301 | ATCCCTGGTGTCTCATTGTT | 445 | 72.61 | 0.80 | 1.797 | 0.583 | 1.336 | 1.057 | 19231.0 |
| 302 | TCCCTGGTGTCTCATTGTTT | 446 | 73.04 | 0.80 | 1.860 | 0.583 | 1.375 | 0.981 | 17629.0 |
| 303 | CCCTGGTGTCTCATTGTTTA | 447 | 70.72 | 0.80 | 1.519 | 0.583 | 1.164 | 0.918 | 17009.0 |
| 304 | CCTGGTGTCTCATTGTTTAT | 448 | 66.82 | 0.80 | 0.946 | 0.583 | 0.808 | −0.800 | 11580.0 |
| 305 | CTGGTGTCTCATTGTTTATA | 449 | 62.17 | 0.80 | 0.264 | 0.583 | 0.386 | −0.600 | 8374.6 |
| 306 | TGGTGTCTCATTGTTTATAC | 450 | 60.65 | 0.90 | 0.042 | 0.670 | 0.281 | −0.355 | 6153.3 |
| 307 | GGTGTCTCATTGTTTATACT | 451 | 62.88 | 0.20 | 0.369 | 0.062 | 0.252 | −0.177 | 7134.0 |
| 308 | GTGTCTCATTGTTTATACTA | 452 | 59.43 | 0.20 | −0.138 | 0.062 | −0.062 | −0.050 | 4435.2 |
| 309 | TGTCTCATTGTTTATACTAG | 453 | 56.35 | 0.20 | −0.589 | 0.062 | −0.342 | −0.043 | 2035.5 |
| 310 | GTCTCATTGTTTATACTAGG | 454 | 59.21 | 0.20 | −0.170 | 0.062 | −0.082 | −0.149 | 2466.6 |
| 311 | TCTCATTGTTTATACTAGGT | 455 | 59.21 | 0.20 | −0.170 | 0.062 | −0.082 | −0.268 | 1080.9 |
| 312 | CTCATTGTTTATACTAGGTA | 456 | 57.15 | 0.20 | −0.472 | 0.062 | −0.269 | −0.325 | 956.0 |
| 313 | TCATTGTTTATACTAGGTAT | 457 | 55.08 | 0.20 | −0.776 | 0.062 | −0.458 | −0.302 | 529.4 |
| 314 | CATTGTTTATACTAGGTATG | 458 | 53.70 | 0.20 | −0.978 | 0.062 | −0.583 | −0.328 | 471.4 |
| 315 | ATTGTTTATACTAGGTATGG | 459 | 55.01 | 0.20 | −0.785 | 0.062 | −0.463 | −0.389 | 510.4 |
| 316 | TTGTTTATACTAGGTATGGT | 460 | 58.17 | 0.20 | −0.322 | 0.062 | −0.176 | −0.486 | 531.0 |
| 317 | TGTTTATACTAGGTATGGTA | 461 | 57.21 | 0.20 | −0.463 | 0.062 | −0.264 | −0.560 | 613.3 |
| 318 | GTTTATACTAGGTATGGTAA | 462 | 55.23 | 0.00 | −0.753 | −0.112 | −0.510 | −0.620 | 685.1 |
| 319 | TTTATACTAGGTATGGTAAA | 463 | 50.42 | 0.00 | −1.459 | −0.112 | −0.947 | −0.639 | 300.0 |
| 320 | TTATACTAGGTATGGTAAAT | 464 | 50.12 | 0.00 | −1.504 | −0.112 | −0.975 | −0.672 | 316.1 |
| 321 | TATACTAGGTATGGTAAATG | 465 | 49.79 | 0.00 | −1.551 | −0.112 | −1.004 | −0.655 | 387.5 |
| 322 | ATACTAGGTATGGTAAATGC | 466 | 54.30 | 0.00 | −0.889 | −0.112 | −0.594 | −0.557 | 685.7 |
| 323 | TACTAGGTATGGTAAATGCA | 467 | 55.59 | 0.20 | −0.700 | 0.062 | −0.411 | −0.430 | 759.6 |
| 324 | ACTAGGTATGGTAAATGCAG | 468 | 56.32 | 0.80 | −0.593 | 0.583 | −0.146 | −0.291 | 1050.2 |
| 325 | CTAGGTATGGTAAATGCAGT | 469 | 58.78 | 1.10 | −0.232 | 0.844 | 0.177 | −0.157 | 1020.4 |
| 326 | TAGGTATGGTAAATGCAGTA | 470 | 56.24 | 1.10 | −0.605 | 0.844 | −0.054 | −0.109 | 742.6 |
| 327 | AGGTATGGTAAATGCAGTAT | 471 | 56.81 | 1.10 | −0.521 | 0.844 | −0.002 | −0.132 | 889.6 |
| 328 | GGTATGGTAAATGCAGTATA | 472 | 56.07 | 1.10 | −0.631 | 0.844 | −0.070 | −0.182 | 858.8 |
| 329 | GTATGGTAAATGCAGTATAC | 473 | 54.02 | 1.10 | −0.931 | 0.844 | −0.256 | −0.262 | 379.0 |
| 330 | TATGGTAAATGCAGTATACT | 474 | 53.06 | 0.40 | −1.071 | 0.236 | −0.575 | −0.257 | 166.7 |
| 331 | ATGGTAAATGCAGTATACTT | 475 | 53.94 | 0.40 | −0.943 | 0.236 | −0.495 | −0.249 | 215.3 |
| 332 | TGGTAAATGCAGTATACTTC | 476 | 55.21 | 0.40 | −0.757 | 0.236 | −0.380 | −0.303 | 103.2 |
| 333 | GGTAAATGCAGTATACTTCC | 477 | 59.15 | 0.40 | −0.178 | 0.236 | −0.021 | −0.326 | 246.3 |
| 334 | GTAAATGCAGTATACTTCCT | 478 | 58.53 | 0.80 | −0.269 | 0.583 | 0.055 | −0.303 | 163.4 |
| 335 | TAAATGCAGTATACTTCCTG | 479 | 55.54 | 0.10 | −0.708 | −0.025 | −0.448 | −0.264 | 294.1 |
| 336 | AAATGCAGTATACTTCCTGA | 480 | 57.36 | −0.30 | −0.441 | −0.373 | −0.415 | −0.229 | 531.4 |
| 337 | AATGCAGTATACTTCCTGAA | 481 | 57.36 | −0.30 | −0.441 | −0.373 | −0.415 | −0.233 | 1995.5 |
| 338 | ATGCAGTATACTTCCTGAAG | 482 | 59.50 | −0.30 | −0.128 | −0.373 | −0.221 | −0.279 | 510.1 |
| 339 | TGCAGTATACTTCCTGAAGT | 483 | 62.63 | −0.90 | 0.332 | −0.895 | −0.134 | −0.264 | 555.4 |
| 340 | GCAGTATACTTCCTGAAGTC | 484 | 64.24 | −1.10 | 0.568 | −1.069 | −0.054 | −0.238 | 1214.0 |
| 341 | CAGTATACTTCCTGAAGTCT | 485 | 61.94 | −1.10 | 0.230 | −1.069 | −0.263 | −0.237 | 825.7 |
| 342 | AGTATACTTCCTGAAGTCTT | 486 | 61.00 | −1.10 | 0.094 | −1.069 | −0.348 | −0.261 | 1582.6 |
| 343 | GTATACTTCCTGAAGTCTTC | 487 | 62.28 | −1.10 | 0.281 | −1.069 | −0.232 | −0.278 | 2391.8 |
| 344 | TATACTTCCTGAAGTCTTCA | 488 | 60.34 | −1.10 | −0.004 | −1.069 | −0.409 | −0.273 | 2276.3 |
| 345 | ATACTTCCTGAAGTCTTCAT | 489 | 60.91 | −1.20 | 0.080 | −1.156 | −0.389 | −0.252 | 2702.8 |
| 346 | TACTTCCTGAAGTCTTCATC | 490 | 62.40 | −1.20 | 0.299 | −1.156 | −0.254 | −0.274 | 3781.7 |
| 347 | ACTTCCTGAAGTCTTCATCT | 491 | 65.05 | −1.20 | 0.686 | −1.156 | −0.014 | −0.314 | 5343.4 |
| 348 | CTTCCTGAAGTCTTCATCTA | 492 | 63.86 | −1.20 | 0.512 | −1.156 | −0.122 | −0.314 | 6309.0 |
| 349 | TTCCTGAAGTCTTCATCTAA | 493 | 59.70 | −1.20 | −0.098 | −1.156 | −0.500 | −0.332 | 6372.4 |
| 350 | TCCTGAAGTCTTCATCTAAG | 494 | 59.55 | −1.20 | −0.120 | −1.156 | −0.513 | −0.369 | 3835.3 |
| 351 | CCTGAAGTCTTCATCTAAGG | 495 | 60.76 | −1.20 | 0.057 | −1.156 | −0.404 | −0.423 | 8925.5 |
| 352 | CTGAAGTCTTCATCTAAGGG | 496 | 59.48 | −1.20 | −0.130 | −1.156 | −0.520 | −0.472 | 1211.8 |
| 353 | TGAAGTCTTCATCTAAGGGA | 497 | 58.84 | −1.00 | −0.224 | −0.982 | −0.512 | −0.414 | 609.4 |
| 354 | GAAGTCTTCATCTAAGGGAA | 498 | 56.91 | −0.10 | −0.507 | −0.199 | −0.390 | −0.358 | 629.1 |
| 355 | AAGTCTTCATCTAAGGGAAC | 499 | 56.13 | −0.10 | −0.622 | −0.199 | −0.461 | −0.341 | 749.3 |
| 356 | AGTCTTCATCTAAGGGAACT | 500 | 60.12 | −0.10 | −0.036 | −0.199 | −0.098 | −0.371 | 805.6 |
| 357 | GTCTTCATCTAAGGGAACTG | 501 | 59.84 | −0.10 | −0.077 | −0.199 | −0.124 | −0.449 | 817.0 |
| 358 | TCTTCATCTAAGGGAACTGA | 502 | 58.11 | −0.10 | −0.331 | −0.199 | −0.281 | −0.536 | 327.1 |

TABLE 4-continued

| p5 Probe Position | DNA Probe Sequence | SEQ ID NO: | RNA/DNA T$_m$ (° C.) | G$_{MFOLD}$ (kcal/mole @ 35° C.) | T$_m$ Score | ΔG$_{MFOLD}$ Score | Composite Score | Window-Averaged Composite Score | HIV PRT GeneChip™ Data |
|---|---|---|---|---|---|---|---|---|---|
| 359 | CTTCATCTAAGGGAACTGAA | 503 | 54.95 | −0.60 | −0.794 | −0.634 | −0.733 | *−0.645* | 320.0 |
| 360 | TTCATCTAAGGGAACTGAAA | 504 | 51.39 | −0.60 | −1.316 | −0.634 | −1.057 | *−0.822* | 84.1 |
| 361 | TCATCTAAGGGAACTGAAAA | 505 | 49.50 | 0.10 | −1.595 | −0.025 | −0.998 | *−1.002* | 67.7 |
| 362 | CATCTAAGGGAACTGAAAAA | 506 | 46.98 | 0.10 | −1.963 | −0.025 | −1.227 | *−1.171* | 62.2 |
| 363 | ATCTAAGGGAACTGAAAAAT | 507 | 45.78 | 0.10 | −2.140 | −0.025 | −1.336 | *−1.298* | 78.9 |
| 364 | TCTAAGGGAACTGAAAAATA | 508 | 45.27 | 0.10 | −2.214 | −0.025 | −1.382 | *−1.328* | 43.2 |
| 365 | CTAAGGGAACTGAAAAATAT | 509 | 44.36 | 0.10 | −2.349 | −0.025 | −1.466 | *−1.322* | 50.4 |
| 366 | TAAGGGAACTGAAAAATATG | 510 | 42.71 | 0.10 | −2.591 | −0.025 | −1.616 | *−1.242* | 43.7 |
| 367 | AAGGGAACTGAAAAATATGC | 511 | 46.54 | 0.10 | −2.028 | −0.025 | −1.267 | *−1.163* | 45.6 |
| 368 | AGGGAACTGAAAAATATGCA | 512 | 49.21 | 0.30 | −1.637 | 0.149 | −0.958 | *−1.119* | 49.8 |
| 369 | GGGAACTGAAAAATATGCAT | 513 | 49.11 | 1.20 | −1.651 | 0.931 | −0.670 | *−1.082* | 53.2 |
| 370 | GGAACTGAAAAATATGCATC | 514 | 47.87 | 1.20 | −1.834 | 0.931 | −0.783 | *−0.958* | 56.6 |
| 371 | GAACTGAAAAATATGCATCA | 515 | 46.82 | 0.60 | −1.987 | 0.410 | −1.076 | *−0.844* | 45.3 |
| 372 | AACTGAAAAATATGCATCAC | 516 | 46.12 | 0.40 | −2.090 | 0.236 | −1.206 | *−0.773* | 56.3 |
| 373 | ACTGAAAAATATGCATCACC | 517 | 51.18 | 0.40 | −1.347 | 0.236 | −0.746 | *−0.702* | 61.7 |
| 374 | CTGAAAAATATGCATCACCC | 518 | 54.20 | 0.40 | −0.905 | 0.236 | −0.471 | *−0.616* | 224.5 |
| 375 | TGAAAAATATGCATCACCCA | 519 | 53.65 | 0.60 | −0.985 | 0.410 | −0.455 | *−0.476* | 413.0 |
| 376 | GAAAAATATGCATCACCCAC | 520 | 54.14 | 1.30 | −0.913 | 1.018 | −0.179 | *−0.289* | 1584.0 |
| 377 | AAAAATATGCATCACCCACA | 521 | 54.14 | 1.30 | −0.913 | 1.018 | −0.179 | *−0.097* | 1846.7 |
| 378 | AAAATATGCATCACCCACAT | 522 | 55.78 | 1.10 | −0.673 | 0.844 | −0.096 | *−0.096* | 2445.8 |
| 379 | AAATATGCATCACCCACATC | 523 | 58.72 | 0.90 | −0.241 | 0.670 | 0.105 | *−0.291* | 3709.4 |
| 380 | AATATGCATCACCCACATCC | 524 | 64.13 | 0.90 | 0.552 | 0.670 | 0.597 | *−0.494* | 4548.4 |
| 381 | ATATGCATCACCCACATCCA | 525 | 67.27 | 0.90 | 1.013 | 0.670 | 0.883 | *−0.680* | 5254.1 |
| 382 | TATGCATCACCCACATCCAG | 526 | 67.53 | 0.90 | 1.051 | 0.670 | 0.906 | 0.864 | 5527.2 |
| 383 | ATGCATCACCCACATCCAGT | 527 | 71.21 | 0.90 | 1.590 | 0.670 | 1.241 | 0.991 | 6916.9 |
| 384 | TGCATCACCCACATCCAGTA | 528 | 70.68 | 0.70 | 1.513 | 0.496 | 1.127 | 1.030 | 5861.4 |
| 385 | GCATCACCCACATCCAGTAC | 529 | 71.39 | 0.70 | 1.617 | 0.496 | 1.191 | 1.043 | 8078.4 |
| 386 | CATCACCCACATCCAGTACT | 530 | 69.16 | 0.70 | 1.290 | 0.496 | 0.988 | 1.013 | 4148.8 |
| 387 | ATCACCCACATCCAGTACTG | 531 | 67.91 | 0.70 | 1.107 | 0.496 | 0.875 | 0.913 | 3317.1 |
| 388 | TCACCCACATCCAGTACTGT | 532 | 71.15 | 0.10 | 1.582 | −0.025 | 0.971 | *−0.830* | 2486.4 |
| 389 | CACCCACATCCAGTACTGTT | 533 | 69.94 | −0.40 | 1.404 | −0.460 | 0.696 | *−0.714* | 2746.4 |
| 390 | ACCCACATCCAGTACTGTTA | 534 | 68.25 | −0.40 | 1.157 | −0.460 | 0.543 | *−0.506* | 2133.0 |
| 391 | CCCACATCCAGTACTGTTAC | 535 | 68.25 | −0.40 | 1.157 | −0.460 | 0.543 | *−0.297* | 2197.0 |
| 392 | CCACATCCAGTACTGTTACT | 536 | 66.50 | −0.40 | 0.900 | −0.460 | 0.383 | *−0.066* | 1824.0 |
| 393 | CACATCCAGTACTGTTACTG | 537 | 62.61 | −1.90 | 0.329 | −1.764 | −0.467 | *−0.137* | 1675.2 |
| 394 | ACATCCAGTACTGTTACTGA | 538 | 62.71 | −2.30 | 0.344 | −2.112 | −0.590 | *−0.313* | 1219.8 |
| 395 | CATCCAGTACTGTTACTGAT | 539 | 62.12 | −2.30 | 0.258 | −2.112 | −0.643 | *−0.504* | 1414.0 |
| 396 | ATCCAGTACTGTTACTGATT | 540 | 61.21 | −2.30 | 0.124 | −2.112 | −0.726 | *−0.700* | 1710.7 |
| 397 | TCCAGTACTGTTACTGATTT | 541 | 61.58 | −2.30 | 0.178 | −2.112 | −0.692 | *−0.713* | 2280.7 |
| 398 | CCAGTACTGTTACTGATTTT | 542 | 60.48 | −2.30 | 0.017 | −2.112 | −0.792 | *−0.659* | 2847.7 |
| 399 | CAGTACTGTTACTGATTTTT | 543 | 56.84 | −1.90 | −0.518 | −1.764 | −0.992 | *−0.635* | 2830.2 |
| 400 | AGTACTGTTACTGATTTTTT | 544 | 55.82 | −0.30 | −0.666 | −0.373 | −0.555 | *−0.588* | 4336.3 |
| 401 | GTACTGTTACTGATTTTTTC | 545 | 57.04 | 0.40 | −0.488 | 0.236 | −0.213 | *−0.548* | 6581.1 |
| 402 | TACTGTTACTGATTTTTTCT | 546 | 55.95 | −0.10 | −0.649 | −0.199 | −0.478 | *−0.516* | 5406.6 |
| 403 | ACTGTTACTGATTTTTTCTT | 547 | 56.89 | −0.10 | −0.510 | −0.199 | −0.392 | *−0.450* | 6083.1 |
| 404 | CTGTTACTGATTTTTTCTTT | 548 | 56.67 | −0.10 | −0.542 | −0.199 | −0.412 | *−0.482* | 6585.7 |
| 405 | TGTTACTGATTTTTTCTTTT | 549 | 54.96 | −0.10 | −0.793 | −0.199 | −0.567 | *−0.575* | 3923.2 |
| 406 | GTTACTGATTTTTTCTTTTT | 550 | 55.36 | −0.10 | −0.734 | −0.199 | −0.531 | *−0.646* | 4093.5 |
| 407 | TTACTGATTTTTTCTTTTTT | 551 | 52.62 | −0.10 | −1.136 | −0.199 | −0.780 | *−0.730* | 1381.5 |
| 408 | TACTGATTTTTTCTTTTTTA | 552 | 51.70 | −0.10 | −1.272 | −0.199 | −0.864 | *−0.784* | 1194.3 |
| 409 | ACTGATTTTTTCTTTTTAA | 553 | 50.45 | −0.10 | −1.454 | −0.199 | −0.977 | *−0.746* | 2371.3 |
| 410 | CTGATTTTTTCTTTTTAAC | 554 | 50.45 | −0.10 | −1.454 | −0.199 | −0.977 | *−0.682* | 395.9 |
| 411 | TGATTTTTTCTTTTTAACC | 555 | 52.50 | −0.10 | −1.155 | −0.199 | −0.792 | *−0.583* | 230.7 |
| 412 | GATTTTTTCTTTTTAACCC | 556 | 56.43 | 0.30 | −0.578 | 0.149 | −0.302 | *−0.423* | 314.9 |
| 413 | ATTTTTCTTTTTAACCCT | 557 | 57.05 | 0.80 | −0.487 | 0.583 | −0.080 | *−0.246* | 276.1 |
| 414 | TTTTTCTTTTTAACCCTG | 558 | 56.99 | 0.80 | −0.495 | 0.583 | −0.085 | *−0.046* | 273.3 |
| 415 | TTTTCTTTTTAACCCTGC | 559 | 60.68 | 0.80 | 0.045 | 0.583 | 0.250 | *−0.093* | 628.4 |
| 416 | TTTTCTTTTTAACCCTGCG | 560 | 60.85 | 0.80 | 0.071 | 0.583 | 0.265 | *−0.155* | 4661.4 |
| 417 | TTTCTTTTTAACCCTGCGG | 561 | 62.93 | 0.70 | 0.377 | 0.496 | 0.422 | *−0.167* | 411.2 |
| 418 | TTCTTTTTAACCCTGCGGG | 562 | 65.01 | −0.60 | 0.681 | −0.634 | 0.181 | *−0.156* | 289.5 |
| 419 | TCTTTTTAACCCTGCGGGA | 563 | 65.91 | −1.00 | 0.813 | −0.982 | 0.131 | *−0.130* | 244.8 |
| 420 | CTTTTTAACCCTGCGGGAT | 564 | 64.52 | −1.00 | 0.610 | −0.982 | 0.005 | *−0.096* | 250.7 |
| 421 | TTTTTAACCCTGCGGGATG | 565 | 62.66 | −1.00 | 0.337 | −0.982 | −0.164 | *−0.067* | 207.8 |
| 422 | TTTTAACCCTGCGGGATGT | 566 | 65.23 | −1.00 | 0.713 | −0.982 | 0.069 | *−0.106* | 255.8 |
| 423 | TTTAACCCTGCGGGATGTG | 567 | 64.80 | −1.00 | 0.651 | −0.982 | 0.030 | *−0.142* | 356.8 |
| 424 | TTAACCCTGCGGGATGTGG | 568 | 66.83 | −1.00 | 0.949 | −0.982 | 0.215 | *−0.201* | 497.8 |
| 425 | TAACCCTGCGGGATGTGGT | 569 | 69.50 | −1.00 | 1.339 | −0.982 | 0.457 | *−0.318* | 754.3 |
| 426 | AACCCTGCGGGATGTGGTA | 570 | 68.63 | −1.00 | 1.212 | −0.982 | 0.378 | *−0.434* | 902.4 |
| 427 | ACCCTGCGGGATGTGGTAT | 571 | 69.14 | −1.00 | 1.286 | −0.982 | 0.424 | *−0.555* | 1186.6 |
| 428 | CCCTGCGGGATGTGGTATT | 572 | 71.66 | −1.00 | 1.657 | −0.982 | 0.654 | *−0.595* | 1514.9 |
| 429 | CCTGCGGGATGTGGTATTC | 573 | 72.66 | −0.60 | 1.804 | −0.634 | 0.878 | *−0.569* | 2407.6 |
| 430 | CTGCGGGATGTGGTATTCC | 574 | 72.66 | −0.60 | 1.804 | −0.634 | 0.878 | *−0.526* | 3019.4 |
| 431 | TGCGGGATGTGGTATTCCT | 575 | 71.02 | −1.30 | 1.563 | −1.243 | 0.497 | *−0.426* | 3275.3 |
| 432 | GCGGGATGTGGTATTCCTA | 576 | 68.54 | −1.30 | 1.199 | −1.243 | 0.271 | *−0.291* | 2830.8 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 433 | GCGGGATGTGGTATTCCTAA | 577 | 66.48 | −1.30 | 0.896 | −1.243 | 0.083 | −0.108 | 2620.5 |
| 434 | CGGGATGTGGTATTCCTAAT | 578 | 62.46 | −1.30 | 0.307 | −1.243 | −0.282 | −0.058 | 1827.8 |
| 435 | GGGATGTGGTATTCCTAATT | 579 | 62.37 | −1.30 | 0.294 | −1.243 | −0.290 | −0.211 | 1957.4 |
| 436 | GGATGTGGTATTCCTAATTG | 580 | 59.71 | −0.90 | −0.097 | −0.895 | −0.400 | −0.330 | 1686.2 |
| 437 | GATGTGGTATTCCTAATTGA | 581 | 58.45 | −0.20 | −0.281 | −0.286 | −0.283 | −0.396 | 1395.0 |
| 438 | ATGTGGTATTCCTAATTGAA | 582 | 55.24 | −0.20 | −0.752 | −0.286 | −0.575 | −0.444 | 1245.7 |
| 439 | TGTGGTATTCCTAATTGAAC | 583 | 55.76 | −0.30 | −0.675 | −0.373 | −0.561 | −0.473 | 1314.0 |
| 440 | GTGGTATTCCTAATTGAACT | 584 | 57.73 | −0.30 | −0.387 | −0.373 | −0.382 | −0.470 | 1818.7 |
| 441 | TGGTATTCCTAATTGAACTT | 585 | 55.15 | −0.30 | −0.765 | −0.373 | −0.616 | −0.474 | 880.3 |
| 442 | GGTATTCCTAATTGAACTTC | 586 | 56.47 | −0.30 | −0.572 | −0.373 | −0.496 | −0.413 | 1419.0 |
| 443 | GTATTCCTAATTGAACTTCC | 587 | 57.76 | −0.30 | −0.383 | −0.373 | −0.379 | −0.343 | 1567.9 |
| 444 | TATTCCTAATTGAACTTCCC | 588 | 58.57 | −0.30 | −0.264 | −0.373 | −0.306 | −0.248 | 1959.4 |
| 445 | ATTCCTAATTGAACTTCCCA | 589 | 60.26 | −0.30 | −0.016 | −0.373 | −0.152 | −0.161 | 2971.8 |
| 446 | TTCCTAATTGAACTTCCCAG | 590 | 60.45 | −0.10 | 0.013 | −0.199 | −0.068 | −0.200 | 1898.5 |
| 447 | TCCTAATTGAACTTCCCAGA | 591 | 61.36 | 0.70 | 0.146 | 0.496 | 0.279 | −0.300 | 1392.3 |
| 448 | CCTAATTGAACTTCCCAGAA | 592 | 58.27 | 0.70 | −0.308 | 0.496 | −0.002 | −0.397 | 1143.2 |
| 449 | CTAATTGAACTTCCCAGAAG | 593 | 54.92 | −0.70 | −0.800 | −0.721 | −0.770 | −0.467 | 427.7 |
| 450 | TAATTGAACTTCCCAGAAGT | 594 | 55.84 | −1.90 | −0.664 | −1.764 | −1.082 | −0.545 | 148.5 |
| 451 | AATTGAACTTCCCAGAAGTC | 595 | 57.61 | −2.10 | −0.404 | −1.938 | −0.987 | −0.677 | 259.1 |
| 452 | ATTGAACTTCCCAGAAGTCT | 596 | 61.42 | −2.10 | 0.154 | −1.938 | −0.641 | −0.751 | 241.9 |
| 453 | TTGAACTTCCCAGAAGTCTT | 597 | 61.76 | −2.10 | 0.205 | −1.938 | −0.609 | −0.730 | 808.1 |
| 454 | TGAACTTCCCAGAAGTCTTG | 598 | 61.34 | −2.10 | 0.143 | −1.938 | −0.648 | −0.586 | 351.6 |
| 455 | GAACTTCCCAGAAGTCTTGA | 599 | 62.71 | −2.10 | 0.344 | −1.938 | −0.523 | −0.415 | 499.7 |
| 456 | AACTTCCCAGAAGTCTTGAG | 600 | 61.63 | −2.10 | 0.186 | −1.938 | −0.621 | −0.262 | 407.4 |
| 457 | ACTTCCCAGAAGTCTTGAGT | 601 | 66.97 | −1.90 | 0.969 | −1.764 | −0.069 | −0.138 | 492.1 |
| 458 | CTTCCCAGAAGTCTTGAGTT | 602 | 66.75 | −1.00 | 0.937 | −0.982 | 0.208 | −0.019 | 736.1 |
| 459 | TTCCCAGAAGTCTTGAGTTC | 603 | 66.31 | −0.20 | 0.872 | −0.286 | 0.432 | −0.058 | 815.2 |
| 460 | TCCCAGAAGTCTTGAGTTCT | 604 | 67.98 | −1.20 | 1.116 | −1.156 | 0.253 | −0.101 | 888.8 |
| 461 | CCCAGAAGTCTTGAGTTCTC | 605 | 67.98 | −1.40 | 1.116 | −1.330 | 0.187 | −0.049 | 2021.6 |
| 462 | CCAGAAGTCTTGAGTTCTCT | 606 | 66.10 | −1.40 | 0.842 | −1.330 | 0.017 | −0.013 | 1988.5 |
| 463 | CAGAAGTCTTGAGTTCTCTT | 607 | 62.41 | −1.40 | 0.300 | −1.330 | −0.319 | −0.082 | 2008.8 |
| 464 | AGAAGTCTTGAGTTCTCTTA | 608 | 60.43 | −1.20 | 0.009 | −1.156 | −0.434 | −0.105 | 2631.8 |
| 465 | GAAGTCTTGAGTTCTCTTAT | 609 | 60.20 | −0.50 | −0.025 | −0.547 | −0.223 | −0.151 | 3052.8 |
| 466 | AAGTCTTGAGTTCTCTTATT | 610 | 59.12 | 0.30 | −0.183 | 0.149 | −0.057 | −0.212 | 3509.3 |
| 467 | AGTCTTGAGTTCTCTTATTA | 611 | 60.75 | 0.30 | 0.056 | 0.149 | 0.091 | −0.211 | 3221.6 |
| 468 | GTCTTGAGTTCTCTTATTAA | 612 | 58.29 | 0.30 | −0.305 | 0.149 | −0.132 | −0.216 | 3677.1 |
| 469 | TCTTGAGTTCTCTTATTAAG | 613 | 55.25 | 0.30 | −0.751 | 0.149 | −0.409 | −0.238 | 1176.6 |
| 470 | CTTGAGTTCTCTTATTAAGT | 614 | 57.04 | 0.10 | −0.488 | −0.025 | −0.312 | −0.255 | 1168.1 |
| 471 | TTGAGTTCTCTTATTAAGTT | 615 | 55.29 | 0.10 | −0.745 | −0.025 | −0.471 | −0.292 | 666.3 |
| 472 | TGAGTTCTCTTATTAAGTTC | 616 | 56.35 | 0.10 | −0.589 | −0.025 | −0.375 | −0.271 | 674.0 |
| 473 | GAGTTCTCTTATTAAGTTCT | 617 | 58.57 | 0.10 | −0.263 | −0.025 | −0.173 | −0.256 | 1471.4 |
| 474 | AGTTCTCTTATTAAGTTCTC | 618 | 58.61 | 0.10 | −0.257 | −0.025 | −0.169 | −0.240 | 1493.5 |
| 475 | GTTCTCTTATTAAGTTCTCT | 619 | 60.59 | 0.10 | 0.032 | −0.025 | 0.011 | −0.247 | 2191.5 |
| 476 | TTCTCTTATTAAGTTCTCTG | 620 | 57.16 | 0.10 | −0.471 | −0.025 | −0.301 | −0.317 | 1410.3 |
| 477 | TCTCTTATTAAGTTCTCTGA | 621 | 58.23 | 0.10 | −0.314 | −0.025 | −0.204 | −0.413 | 1262.8 |
| 478 | CTCTTATTAAGTTCTCTGAA | 622 | 54.79 | 0.10 | −0.817 | −0.025 | −0.516 | −0.519 | 1072.9 |
| 479 | TCTTATTAAGTTCTCTGAAA | 623 | 50.95 | 0.10 | −1.382 | −0.025 | −0.866 | −0.629 | 540.9 |
| 480 | CTTATTAAGTTCTCTGAAAT | 624 | 49.77 | 0.50 | −1.554 | 0.323 | −0.841 | −0.695 | 539.2 |
| 481 | TTATTAAGTTCTCTGAAATC | 625 | 48.99 | 0.50 | −1.668 | 0.323 | −0.912 | −0.768 | 709.0 |
| 482 | TATTAAGTTCTCTGAAATCT | 626 | 50.64 | 0.50 | −1.427 | 0.323 | −0.762 | −0.775 | 978.1 |
| 483 | ATTAAGTTCTCTGAAATCTA | 627 | 50.64 | 0.50 | −1.427 | 0.323 | −0.762 | −0.732 | 1217.7 |
| 484 | TTAAGTTCTCTGAAATCTAC | 628 | 51.15 | 0.50 | −1.352 | 0.323 | −0.716 | −0.693 | 1748.1 |
| 485 | TAAGTTCTCTGAAATCTACT | 629 | 52.79 | 0.50 | −1.112 | 0.323 | −0.567 | −0.646 | 2511.5 |
| 486 | AAGTTCTCTGAAATCTACTA | 630 | 52.79 | 0.50 | −1.112 | 0.323 | −0.567 | −0.643 | 2997.2 |
| 487 | AGTTCTCTGAAATCTACTAA | 631 | 52.79 | 0.50 | −1.112 | 0.323 | −0.567 | −0.663 | 2887.6 |
| 488 | GTTCTCTGAAATCTACTAAT | 632 | 52.65 | 0.50 | −1.133 | 0.323 | −0.580 | −0.725 | 4421.3 |
| 489 | TTCTCTGAAATCTACTAATT | 633 | 50.14 | 0.70 | −1.500 | 0.496 | −0.741 | −0.832 | 1937.7 |
| 490 | TCTCTGAAATCTACTAATTT | 634 | 50.14 | 0.20 | −1.500 | 0.062 | −0.906 | −0.962 | 1773.3 |
| 491 | CTCTGAAATCTACTAATTTT | 635 | 49.31 | −0.30 | −1.622 | −0.373 | −1.147 | −1.102 | 1491.1 |
| 492 | TCTGAAATCTACTAATTTTC | 636 | 48.55 | −0.60 | −1.734 | −0.634 | −1.316 | −1.171 | 376.6 |
| 493 | CTGAAATCTACTAATTTTCT | 637 | 49.31 | −1.30 | −1.622 | −1.243 | −1.478 | −1.178 | 371.9 |
| 494 | TGAAATCTACTAATTTTCTC | 638 | 48.55 | −1.30 | −1.734 | −1.243 | −1.547 | −1.092 | 415.2 |
| 495 | GAAATCTACTAATTTTCTCC | 639 | 52.45 | −0.90 | −1.161 | −0.895 | −1.060 | −0.938 | 1097.9 |
| 496 | AAATCTACTAATTTTCTCCA | 640 | 52.47 | −0.10 | −1.158 | −0.199 | −0.794 | −0.778 | 1429.1 |
| 497 | AATCTACTAATTTTCTCCAT | 641 | 54.25 | 0.90 | −0.897 | 0.670 | −0.301 | −0.620 | 1812.5 |
| 495 | ATCTACTAATTTTCTCCATT | 642 | 56.46 | 1.00 | −0.572 | 0.757 | −0.067 | −0.485 | 1943.4 |
| 499 | TCTACTAATTTTCTCCATTT | 643 | 56.80 | 0.50 | −0.523 | 0.323 | −0.202 | −0.421 | 1506.1 |
| 500 | CTACTAATTTTCTCCATTTA | 644 | 54.93 | 0.50 | −0.797 | 0.323 | −0.372 | −0.376 | 1694.7 |
| 501 | TACTAATTTTCTCCATTTAG | 645 | 53.14 | 0.30 | −1.060 | 0.149 | −0.600 | −0.396 | 946.7 |
| 502 | ACTAATTTTCTCCATTTAGT | 646 | 56.69 | −0.70 | −0.539 | −0.721 | −0.605 | −0.407 | 1114.3 |
| 503 | CTAATTTTCTCCATTTAGTA | 647 | 55.57 | 0.00 | −0.704 | −0.112 | −0.479 | −0.369 | 963.9 |
| 504 | TAATTTTCTCCATTTAGTAC | 648 | 54.12 | 0.50 | −0.917 | 0.323 | −0.446 | −0.274 | 1347.9 |
| 505 | AATTTTCTCCATTTAGTACT | 649 | 56.69 | 0.70 | −0.539 | 0.496 | −0.145 | −0.130 | 2067.7 |
| 506 | ATTTTCTCCATTTAGTACTG | 650 | 58.66 | 0.80 | −0.250 | 0.583 | 0.067 | −0.037 | 2724.2 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip ™ Data |
|---|---|---|---|---|---|---|---|---|---|
| 507 | TTTTCTCCATTTAGTACTGT | 651 | 61.92 | 0.60 | 0.228 | 0.410 | 0.297 | −0.186 | 3367.9 |
| 508 | TTTCTCCATTTAGTACTGTC | 652 | 63.10 | 0.60 | 0.401 | 0.410 | 0.404 | −0.314 | 5235.8 |
| 509 | TTCTCCATTTAGTACTGTCT | 653 | 64.84 | 0.60 | 0.656 | 0.410 | 0.562 | −0.377 | 6423.5 |
| 510 | TCTCCATTTAGTACTGTCTT | 654 | 64.84 | 0.60 | 0.656 | 0.410 | 0.562 | −0.396 | 7758.9 |
| 511 | CTCCATTTAGTACTGTCTTT | 655 | 63.63 | 0.60 | 0.479 | 0.410 | 0.453 | −0.342 | 8001.5 |
| 512 | TCCATTTAGTACTGTCTTTT | 656 | 61.92 | 0.60 | 0.228 | 0.410 | 0.297 | −0.273 | 5512.4 |
| 513 | CCATTTAGTACTGTCTTTTT | 657 | 60.78 | 0.60 | 0.061 | 0.410 | 0.194 | −0.210 | 5300.0 |
| 514 | CATTTAGTACTGTCTTTTTT | 658 | 57.04 | 0.80 | −0.489 | 0.583 | −0.081 | −0.147 | 3902.1 |
| 515 | ATTTAGTACTGTCTTTTTTC | 659 | 57.08 | 0.80 | −0.482 | 0.583 | −0.077 | −0.099 | 4641.8 |
| 516 | TTTAGTACTGTCTTTTTTCT | 660 | 59.26 | 0.80 | −0.162 | 0.583 | 0.121 | −0.084 | 4888.4 |
| 517 | TTAGTACTGTCTTTTTTCTT | 661 | 59.26 | 0.80 | −0.162 | 0.583 | 0.121 | −0.160 | 5477.3 |
| 518 | TAGTACTGTCTTTTTTCTTT | 662 | 59.26 | 0.80 | −0.162 | 0.583 | 0.121 | −0.242 | 5064.9 |
| 519 | AGTACTGTCTTTTTTCTTTA | 663 | 59.26 | 1.00 | −0.162 | 0.757 | 0.187 | −0.310 | 5580.3 |
| 520 | GTACTGTCTTTTTTCTTTAT | 664 | 59.04 | 2.70 | −0.195 | 2.236 | 0.729 | −0.400 | 5478.3 |
| 521 | TACTGTCTTTTTTCTTTATG | 665 | 55.71 | 2.90 | −0.683 | 2.410 | 0.492 | −0.480 | 2275.5 |
| 522 | ACTGTCTTTTTTCTTTATGG | 666 | 59.07 | 1.70 | −0.190 | 1.366 | 0.402 | −0.524 | 1730.8 |
| 523 | CTGTCTTTTTTCTTTATGGC | 667 | 62.92 | 1.70 | 0.374 | 1.366 | 0.751 | −0.449 | 2405.5 |
| 524 | TGTCTTTTTTCTTTATGGCA | 668 | 62.14 | 1.70 | 0.260 | 1.366 | 0.680 | −0.258 | 1942.0 |
| 525 | GTCTTTTTTCTTTATGGCAA | 669 | 60.05 | 1.50 | −0.047 | 1.192 | 0.424 | −0.068 | 2085.6 |
| 526 | TCTTTTTTCTTTATGGCAAA | 670 | 54.99 | 0.60 | −0.788 | 0.410 | −0.333 | −0.106 | 493.2 |
| 527 | CTTTTTTCTTTATGGCAAAT | 671 | 53.75 | 0.10 | −0.971 | −0.025 | −0.612 | −0.309 | 532.7 |
| 528 | TTTTTTCTTTATGGCAAATA | 672 | 51.30 | 0.10 | −1.331 | −0.025 | −0.835 | −0.507 | 280.0 |
| 529 | TTTTTCTTTATGGCAAATAC | 673 | 51.49 | 0.10 | −1.302 | −0.025 | −0.817 | −0.640 | 440.8 |
| 530 | TTTTCTTTATGGCAAATACT | 674 | 53.08 | 0.10 | −1.069 | −0.025 | −0.672 | −0.652 | 463.1 |
| 531 | TTTCTTTATGGCAAATACTG | 675 | 52.74 | 0.10 | −1.119 | −0.025 | −0.704 | −0.639 | 579.0 |
| 532 | TTCTTTATGGCAAATACTGG | 676 | 54.90 | 0.10 | −0.802 | −0.025 | −0.507 | −0.572 | 673.7 |
| 533 | TCTTTATGGCAAATACTGGA | 677 | 55.85 | 0.10 | −0.663 | −0.025 | −0.421 | −0.504 | 837.0 |
| 534 | CTTTATGGCAAATACTGGAG | 678 | 54.78 | 0.10 | −0.820 | −0.025 | −0.518 | −0.490 | 1061.9 |
| 535 | TTTATGGCAAATACTGGAGT | 679 | 55.74 | 0.30 | −0.679 | 0.149 | −0.365 | −0.507 | 855.0 |
| 536 | TTATGGCAAATACTGGAGTA | 680 | 54.87 | 0.60 | −0.806 | 0.410 | −0.344 | −0.562 | 775.0 |
| 537 | TATGGCAAATACTGGAGTAT | 681 | 54.56 | 0.00 | −0.852 | −0.112 | −0.571 | −0.591 | 773.6 |
| 538 | ATGGCAAATACTGGAGTATT | 682 | 55.42 | −1.00 | −0.726 | −0.982 | −0.823 | −0.647 | 702.5 |
| 539 | TGGCAAATACTGGAGTATTG | 683 | 55.37 | −1.20 | −0.733 | −1.156 | −0.893 | −0.775 | 387.5 |
| 540 | GGCAAATACTGGAGTATTGT | 684 | 58.33 | −1.20 | −0.298 | −1.156 | −0.624 | −0.924 | 435.3 |
| 541 | GCAAATACTGGAGTATTGTA | 685 | 55.24 | −1.20 | −0.753 | −1.156 | −0.906 | −0.974 | 93.7 |
| 542 | CAAATACTGGAGTATTGTAT | 686 | 51.30 | −1.20 | −1.331 | −1.156 | −1.264 | −0.913 | 50.0 |
| 543 | AAATACTGGAGTATTGTATG | 687 | 49.96 | −1.20 | −1.527 | −1.156 | −1.386 | −0.809 | 50.4 |
| 544 | AATACTGGAGTATTGTATGG | 688 | 54.30 | −1.00 | −0.890 | −0.982 | −0.925 | −0.688 | 64.7 |
| 545 | ATACTGGAGTATTGTATGGA | 689 | 57.60 | −0.30 | −0.406 | −0.373 | −0.394 | −0.483 | 76.0 |
| 546 | TACTGGAGTATTGTATGGAT | 690 | 57.60 | 0.40 | −0.406 | 0.236 | −0.162 | −0.236 | 86.0 |
| 547 | ACTGGAGTATTGTATGGATT | 691 | 58.53 | 1.30 | −0.269 | 1.018 | 0.220 | −0.009 | 123.4 |
| 548 | CTGGAGTATTGTATGGATTC | 692 | 59.39 | 2.00 | −0.144 | 1.627 | 0.529 | −0.135 | 121.5 |
| 549 | TGGAGTATTGTATGGATTCT | 693 | 59.39 | 1.80 | −0.144 | 1.453 | 0.463 | −0.210 | 641.3 |
| 550 | GGAGTATTGTATGGATTCTC | 694 | 60.95 | 0.60 | 0.086 | 0.410 | 0.209 | −0.286 | 161.5 |
| 551 | GAGTATTGTATGGATTCTCA | 695 | 59.52 | 0.60 | −0.124 | 0.410 | 0.079 | −0.321 | 129.9 |
| 552 | AGTATTGTATGGATTCTCAG | 696 | 58.31 | 1.10 | −0.302 | 0.844 | 0.134 | −0.371 | 88.7 |
| 553 | GTATTGTATGGATTCTCAGG | 697 | 60.87 | 1.10 | 0.074 | 0.844 | 0.367 | −0.462 | 112.5 |
| 554 | TATTGTATGGATTCTCAGGC | 698 | 61.97 | 1.10 | 0.236 | 0.844 | 0.467 | −0.575 | 134.6 |
| 555 | ATTGTATGGATTCTCAGGCC | 699 | 66.52 | 1.10 | 0.902 | 0.844 | 0.880 | −0.669 | 191.6 |
| 556 | TTGTATGGATTCTCAGGCCC | 700 | 70.34 | 0.70 | 1.463 | 0.496 | 1.096 | −0.714 | 254.5 |
| 557 | TGTATGGATTCTCAGGCCCA | 701 | 71.11 | 0.20 | 1.577 | 0.062 | 1.001 | −0.738 | 332.2 |
| 558 | GTATGGATTCTCAGGCCCAA | 702 | 68.95 | 0.00 | 1.259 | −0.112 | 0.738 | −0.761 | 415.6 |
| 559 | TATGGATTCTCAGGCCCAAT | 703 | 65.78 | 0.00 | 0.795 | −0.112 | 0.450 | −0.774 | 285.0 |
| 560 | ATGGATTCTCAGGCCCAATT | 704 | 66.68 | 0.00 | 0.925 | −0.112 | 0.531 | −0.737 | 464.0 |
| 561 | TGGATTCTCAGGCCCAATTT | 705 | 67.04 | 0.20 | 0.979 | 0.062 | 0.630 | −0.663 | 492.5 |
| 562 | GGATTCTCAGGCCCAATTTT | 706 | 67.51 | 1.10 | 1.048 | 0.844 | 0.970 | −0.624 | 639.7 |
| 563 | GATTCTCAGGCCCAATTTTT | 707 | 65.34 | 1.30 | 0.729 | 1.018 | 0.839 | −0.595 | 512.4 |
| 564 | ATTCTCAGGCCCAATTTTTG | 708 | 63.94 | 0.60 | 0.524 | 0.410 | 0.481 | −0.513 | 393.4 |
| 565 | TTCTCAGGCCCAATTTTTGA | 709 | 65.24 | 0.20 | 0.716 | 0.062 | 0.467 | −0.394 | 334.3 |
| 566 | TCTCAGGCCCAATTTTTGAA | 710 | 62.85 | 0.20 | 0.364 | 0.062 | 0.249 | −0.181 | 308.2 |
| 567 | CTCAGGCCCAATTTTTGAAA | 711 | 59.62 | 0.20 | −0.109 | 0.062 | −0.044 | −0.048 | 199.2 |
| 568 | TCAGGCCCAATTTTTGAAAT | 712 | 57.85 | 0.20 | −0.369 | 0.062 | −0.205 | −0.223 | 164.3 |
| 569 | CAGGCCCAATTTTTGAAATT | 713 | 56.95 | −0.50 | −0.501 | −0.547 | −0.518 | −0.412 | 125.6 |
| 570 | AGGCCCAATTTTTGAAATTT | 714 | 56.09 | −1.00 | −0.627 | −0.982 | −0.762 | −0.571 | 102.6 |
| 571 | GGCCCAATTTTTGAAATTTT | 715 | 56.23 | −1.00 | −0.606 | −0.982 | −0.749 | −0.688 | 91.6 |
| 572 | GCCCAATTTTTGAAATTTTC | 716 | 55.07 | −1.00 | −0.777 | −0.982 | −0.855 | −0.806 | 76.2 |
| 573 | CCCAATTTTTGAAATTTTCC | 717 | 54.96 | −1.00 | −0.792 | −0.982 | −0.864 | −0.881 | 78.8 |
| 574 | CCAATTTTTGAAATTTTCCT | 718 | 54.96 | −1.00 | −0.792 | −0.982 | −0.864 | −0.841 | 84.8 |
| 575 | CAATTTTTGAAATTTTCCCT | 719 | 53.17 | −1.00 | −1.055 | −0.982 | −1.027 | −0.755 | 162.0 |
| 576 | AATTTTTGAAATTTTCCCTT | 720 | 52.25 | −0.80 | −1.190 | −0.808 | −1.045 | −0.634 | 539.5 |
| 577 | ATTTTTGAAATTTTCCCTTC | 721 | 55.17 | 0.10 | −0.762 | −0.025 | −0.482 | −0.511 | 1787.3 |
| 578 | TTTTTGAAATTTTCCCTTCC | 722 | 58.88 | 0.10 | −0.219 | −0.025 | −0.145 | −0.389 | 6354.2 |
| 579 | TTTTGAAATTTTCCCTTCCT | 723 | 60.39 | 0.10 | 0.004 | −0.025 | −0.007 | −0.243 | 9513.6 |
| 580 | TTTGAAATTTTCCCTTCCTT | 724 | 60.39 | 0.10 | 0.004 | −0.025 | −0.007 | −0.062 | 10660.0 |

TABLE 4-continued

| p5 Probe Position | DNA Probe Sequence | SEQ ID NO: | RNA/DNA $T_m$ (°C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip ™ Data |
|---|---|---|---|---|---|---|---|---|---|
| 581 | TTGAAATTTTCCCTTCCTTT | 725 | 60.39 | 0.10 | 0.004 | −0.025 | −0.007 | −0.107 | 11202.0 |
| 582 | TGAAATTTTCCCTTCCTTTT | 726 | 60.39 | 0.10 | 0.004 | −0.025 | −0.007 | −0.293 | 11543.0 |
| 583 | GAAATTTTCCCTTCCTTTTC | 727 | 61.81 | 0.40 | 0.212 | 0.236 | 0.221 | −0.596 | 14774.0 |
| 584 | AAATTTTCCCTTCCTTTTCC | 728 | 64.17 | 1.20 | 0.557 | 0.931 | 0.699 | 0.952 | 18197.0 |
| 585 | AATTTTCCCTTCCTTTTCCA | 729 | 67.39 | 1.70 | 1.030 | 1.366 | 1.158 | 1.307 | 21410.0 |
| 586 | ATTTTCCCTTCCTTTTCCAT | 730 | 69.58 | 4.00 | 1.351 | 3.366 | 2.117 | 1.679 | 22869.0 |
| 587 | TTTTCCCTTCCTTTTCCATT | 731 | 69.96 | 5.00 | 1.408 | 4.236 | 2.482 | 2.039 | 21818.0 |
| 588 | TTTCCCTTCCTTTTCCATTT | 732 | 69.96 | 5.00 | 1.408 | 4.236 | 2.482 | 2.113 | 21341.0 |
| 589 | TTCCCTTCCTTTTCCATTTC | 733 | 71.19 | 5.00 | 1.588 | 4.236 | 2.594 | 2.085 | 22063.0 |
| 590 | TCCCTTCCTTTTCCATTTCT | 734 | 72.77 | 5.00 | 1.820 | 4.236 | 2.738 | 1.863 | 22152.0 |
| 591 | CCCTTCCTTTTCCATTTCTG | 735 | 71.01 | 0.90 | 1.561 | 0.670 | 1.223 | 1.571 | 20764.0 |
| 592 | CCTTCCTTTTCCATTTCTGT | 736 | 70.68 | 0.20 | 1.513 | 0.062 | 0.961 | 1.289 | 12579.0 |
| 593 | CTTCCTTTTCCATTTCTGTA | 737 | 66.30 | 0.20 | 0.870 | 0.062 | 0.563 | 0.945 | 9036.3 |
| 594 | TTCCTTTTCCATTTCTGTAC | 738 | 64.87 | 0.20 | 0.660 | 0.062 | 0.433 | −0.505 | 8251.8 |
| 595 | TCCTTTTCCATTTCTGTACA | 739 | 65.74 | 0.20 | 0.788 | 0.062 | 0.512 | −0.257 | 20788.0 |
| 596 | CCTTTTCCATTTCTGTACAA | 740 | 62.11 | 0.20 | 0.256 | 0.062 | 0.182 | −0.024 | 7073.9 |
| 597 | CTTTTCCATTTCTGTACAAA | 741 | 56.39 | 0.20 | −0.583 | 0.062 | −0.338 | −0.153 | 2932.4 |
| 598 | TTTTCCATTTCTGTACAAAT | 742 | 54.49 | 0.20 | −0.862 | 0.062 | −0.511 | −0.300 | 1897.3 |
| 599 | TTTCCATTTCTGTACAAATT | 743 | 54.49 | −0.30 | −0.862 | −0.373 | −0.676 | −0.449 | 2158.1 |
| 600 | TTCCATTTCTGTACAAATTT | 744 | 54.49 | −0.30 | −0.862 | −0.373 | −0.676 | −0.608 | 2215.9 |
| 601 | TCCATTTCTGTACAAATTTC | 745 | 55.43 | −0.30 | −0.724 | −0.373 | −0.591 | −0.695 | 2168.6 |
| 602 | CCATTTCTGTACAAATTTCT | 746 | 56.07 | −0.30 | −0.631 | −0.373 | −0.533 | −0.708 | 2025.8 |
| 603 | CATTTCTGTACAAATTTCTA | 747 | 51.65 | −0.30 | −1.278 | −0.373 | −0.934 | −0.708 | 1277.2 |
| 604 | ATTTCTGTACAAATTTCTAC | 748 | 50.83 | −0.10 | −1.398 | −0.199 | −0.943 | −0.736 | 1944.8 |
| 605 | TTTCTGTACAAATTTCTACT | 749 | 52.78 | 0.40 | −1.112 | 0.236 | −0.600 | −0.790 | 2504.3 |
| 606 | TTCTGTACAAATTTCTACTA | 750 | 51.90 | 0.40 | −1.242 | 0.236 | −0.681 | −0.876 | 2941.5 |
| 607 | TCTGTACAAATTTCTACTAA | 751 | 49.84 | 0.40 | −1.544 | 0.236 | −0.868 | −0.846 | 2694.8 |
| 608 | CTGTACAAATTTCTACTAAT | 752 | 48.73 | 0.40 | −1.707 | 0.236 | −0.969 | −0.827 | 2610.7 |
| 609 | TGTACAAATTTCTACTAATG | 753 | 46.88 | 0.40 | −1.979 | 0.236 | −1.137 | −0.845 | 1678.1 |
| 610 | GTACAAATTTCTACTAATGC | 754 | 50.66 | 0.60 | −1.424 | 0.410 | −0.727 | −0.854 | 5877.3 |
| 611 | TACAAATTTCTACTAATGCT | 755 | 49.82 | 0.60 | −1.547 | 0.410 | −0.803 | −0.849 | 4461.0 |
| 612 | ACAAATTTCTACTAATGCTT | 756 | 50.65 | 0.60 | −1.425 | 0.410 | −0.728 | −0.816 | 5943.2 |
| 613 | CAAATTTCTACTAATGCTTT | 757 | 50.46 | 0.60 | −1.453 | 0.410 | −0.745 | −0.753 | 6492.9 |
| 614 | AAATTTCTACTAATGCTTTT | 758 | 49.47 | 0.60 | −1.599 | 0.410 | −0.836 | −0.745 | 6875.0 |
| 615 | AATTTCTACTAATGCTTTTA | 759 | 50.61 | 0.60 | −1.431 | 0.410 | −0.731 | −0.727 | 7950.3 |
| 616 | ATTTCTACTAATGCTTTTAT | 760 | 52.40 | 0.20 | −1.169 | 0.062 | −0.701 | −0.719 | 8314.8 |
| 617 | TTTCTACTAATGCTTTTATT | 761 | 52.72 | 0.20 | −1.122 | 0.062 | −0.672 | −0.720 | 6885.8 |
| 618 | TTCTACTAATGCTTTTATTT | 762 | 52.72 | 0.20 | −1.122 | 0.062 | −0.672 | −0.730 | 6443.2 |
| 619 | TCTACTAATGCTTTTATTTT | 763 | 52.72 | 0.20 | −1.122 | 0.062 | −0.672 | −0.731 | 6331.1 |
| 620 | CTACTAATGCTTTTATTTTT | 764 | 51.81 | 0.20 | −1.255 | 0.062 | −0.755 | −0.718 | 5952.5 |
| 621 | TACTAATGCTTTTATTTTTC | 765 | 50.18 | 0.20 | −1.494 | 0.062 | −0.903 | −0.721 | 2662.8 |
| 622 | ACTAATGCTTTTATTTTTCT | 766 | 51.96 | 0.20 | −1.233 | 0.062 | −0.741 | −0.667 | 3034.0 |
| 623 | CTAATGCTTTTATTTTTCTT | 767 | 53.41 | 0.20 | −1.021 | 0.062 | −0.609 | −0.513 | 2198.5 |
| 624 | TAATGCTTTTATTTTTCTTC | 768 | 51.76 | 0.40 | −1.263 | 0.236 | −0.694 | −0.315 | 1670.1 |
| 625 | AATGCTTTTATTTTTCTTCT | 769 | 53.61 | 1.10 | −0.992 | 0.844 | −0.294 | −0.038 | 3039.4 |
| 626 | ATGCTTTTATTTTTCTTCTG | 770 | 57.66 | 2.10 | −0.397 | 1.714 | 0.405 | −0.177 | 3873.8 |
| 627 | TGCTTTTATTTTTCTTCTGT | 771 | 57.60 | 2.80 | −0.406 | 2.323 | 0.631 | −0.363 | 3609.7 |
| 628 | GCTTTTATTTTTCTTCTGTC | 772 | 60.96 | 3.10 | 0.087 | 2.583 | 1.036 | −0.464 | 4891.4 |
| 629 | CTTTTATTTTTCTTCTGTCA | 773 | 57.96 | 3.10 | −0.353 | 2.583 | 0.763 | −0.480 | 3071.6 |
| 630 | TTTTATTTTTCTTCTGTCAA | 774 | 57.22 | 3.10 | −0.461 | 2.583 | 0.696 | −0.391 | 2667.2 |
| 631 | TTTATTTTTCTTCTGTCAAT | 775 | 54.81 | 1.70 | −0.816 | 1.366 | 0.013 | −0.312 | 2293.1 |
| 632 | TTATTTTTCTTCTGTCAATG | 776 | 54.46 | 1.20 | −0.866 | 0.931 | −0.183 | −0.232 | 2123.0 |
| 633 | TATTTTTCTTCTGTCAATGG | 777 | 54.08 | 1.20 | −0.922 | 0.931 | −0.218 | −0.237 | 1914.7 |
| 634 | ATTTTTCTTCTGTCAATGGC | 778 | 57.36 | 1.20 | −0.442 | 0.931 | 0.080 | −0.263 | 2174.1 |
| 635 | TTTTTCTTCTGTCAATGGCC | 779 | 61.67 | 1.20 | 0.192 | 0.931 | 0.473 | −0.372 | 3659.7 |
| 636 | TTTTCTTCTGTCAATGGCCA | 780 | 65.26 | 1.20 | 0.717 | 0.931 | 0.799 | −0.509 | 5217.7 |
| 637 | TTTCTTCTGTCAATGGCCAT | 781 | 66.11 | 1.20 | 0.843 | 0.931 | 0.877 | −0.569 | 4559.7 |
| 638 | TTCTTCTGTCAATGGCCATT | 782 | 65.73 | 1.00 | 0.787 | 0.757 | 0.776 | −0.576 | 4347.7 |
| 639 | TCTTCTGTCAATGGCCATTG | 783 | 65.73 | 1.00 | 0.787 | 0.757 | 0.776 | −0.506 | 5267.4 |
| 640 | CTTCTGTCAATGGCCATTGT | 784 | 65.26 | −0.60 | 0.718 | −0.634 | 0.204 | −0.389 | 3922.8 |
| 641 | TTCTGTCAATGGCCATTGTT | 785 | 66.97 | −1.30 | 0.968 | −1.243 | 0.128 | −0.235 | 3608.6 |
| 642 | TCTGTCAATGGCCATTGTTT | 786 | 65.36 | −1.30 | 0.733 | −1.243 | −0.018 | −0.044 | 1881.6 |
| 643 | CTGTCAATGGCCATTGTTTA | 787 | 65.36 | −1.30 | 0.733 | −1.243 | −0.018 | −0.139 | 1658.0 |
| 644 | TGTCAATGGCCATTGTTTAA | 788 | 63.32 | −1.30 | 0.433 | −1.243 | −0.204 | −0.255 | 1369.8 |
| 645 | GTCAATGGCCATTGTTTAAC | 789 | 59.38 | −1.30 | −0.144 | −1.243 | −0.562 | −0.353 | 605.8 |
| 646 | TCAATGGCCATTGTTTAACT | 790 | 59.99 | −1.30 | −0.055 | −1.243 | −0.506 | −0.357 | 933.2 |
| 647 | CAATGGCCATTGTTTAACTT | 791 | 58.93 | −1.30 | −0.211 | −1.243 | −0.603 | −0.331 | 441.8 |
| 648 | AATGGCCATTGTTTAACTTT | 792 | 57.97 | −0.90 | −0.352 | −0.895 | −0.558 | −0.281 | 545.6 |
| 649 | ATGGCCATTGTTTAACTTTA | 793 | 57.07 | 0.90 | −0.483 | 0.670 | −0.045 | −0.173 | 781.4 |
| 650 | TGGCCATTGTTTAACTTTT | 794 | 59.31 | 0.90 | −0.156 | 0.670 | 0.158 | −0.092 | 1027.3 |
| 651 | GGCCATTGTTTAACTTTTG | 795 | 59.24 | 0.90 | −0.165 | 0.670 | 0.152 | −0.021 | 1102.5 |
| 652 | GCCATTGTTTAACTTTTGG | 796 | 61.84 | 0.30 | 0.216 | 0.149 | 0.190 | −0.156 | 935.7 |
| 653 | CCATTGTTTAACTTTTGGG | 797 | 61.84 | −0.10 | 0.216 | −0.199 | 0.058 | −0.218 | 403.7 |
| 654 | CATTGTTTAACTTTTGGGGC | 798 | 61.84 | 0.30 | 0.216 | 0.149 | 0.190 | −0.251 | 269.3 |

TABLE 4-continued

| p5 Probe Position | DNA Probe Sequence | SEQ ID NO: | RNA/DNA T$_m$ (° C.) | G$_{MFOLD}$ (kcal/mole @ 35° C.) | T$_m$ Score | ΔG$_{MFOLD}$ Score | Composite Score | Window-Averaged Composite Score | HIV PRT GeneChip ™ Data |
|---|---|---|---|---|---|---|---|---|---|
| 655 | CATTGTTTAACTTTTGGGCC | 799 | 61.84 | 0.90 | 0.216 | 0.670 | 0.389 | -0.299 | 296.8 |
| 656 | ATTGTTTAACTTTTGGGCCA | 800 | 61.84 | 0.90 | 0.216 | 0.670 | 0.389 | -0.367 | 449.4 |
| 657 | TTGTTTAACTTTTGGGCCAT | 801 | 61.84 | 0.90 | 0.216 | 0.670 | 0.389 | -0.377 | 448.1 |
| 658 | TGTTTAACTTTTGGGCCATC | 802 | 62.91 | 0.90 | 0.373 | 0.670 | 0.486 | -0.340 | 584.9 |
| 659 | GTTTAACTTTTGGGCCATCC | 803 | 66.73 | 0.40 | 0.934 | 0.236 | 0.669 | -0.275 | 1032.4 |
| 660 | TTTAACTTTTGGGCCATCCA | 804 | 64.79 | -0.70 | 0.649 | -0.721 | 0.128 | -0.235 | 737.8 |
| 661 | TTAACTTTTGGGCCATCCAT | 805 | 64.44 | -1.20 | 0.598 | -1.156 | -0.069 | -0.271 | 950.2 |
| 662 | TAACTTTTGGGCCATCCATT | 806 | 64.44 | -1.20 | 0.598 | -1.156 | -0.069 | -0.310 | 1308.0 |
| 663 | AACTTTTGGGCCATCCATTC | 807 | 66.42 | -1.20 | 0.888 | -1.156 | 0.111 | -0.296 | 2360.1 |
| 664 | ACTTTTGGGCCATCCATTCC | 808 | 72.21 | -1.20 | 1.738 | -1.156 | 0.638 | -0.387 | 4946.0 |
| 665 | CTTTTGGGCCATCCATTCCT | 809 | 73.53 | -1.20 | 1.930 | -1.156 | 0.758 | -0.480 | 6789.2 |
| 666 | TTTTGGGCCATCCATTCCTG | 810 | 71.49 | -1.20 | 1.632 | -1.156 | 0.573 | -0.560 | 8150.6 |
| 667 | TTTGGGCCATCCATTCCTGG | 811 | 73.62 | -1.20 | 1.945 | -1.156 | 0.766 | -0.622 | 7589.0 |
| 668 | TTGGGCCATCCATTCCTGGC | 812 | 77.43 | -2.80 | 2.504 | -2.547 | 0.584 | -0.580 | 13914.0 |
| 669 | TGGGCCATCCATTCCTGGCT | 813 | 78.94 | -3.50 | 2.725 | -3.156 | 0.490 | -0.500 | 17513.0 |
| 670 | GGGCCATCCATTCCTGGCTT | 814 | 79.51 | -3.50 | 2.809 | -3.156 | 0.542 | -0.449 | 19883.0 |
| 671 | GGCCATCCATTCCTGGCTTT | 815 | 77.37 | -3.50 | 2.494 | -3.156 | 0.347 | -0.324 | 20103.0 |
| 672 | GCCATCCATTCCTGGCTTTA | 816 | 74.28 | -3.10 | 2.040 | -2.808 | 0.198 | -0.214 | 18622.9 |
| 673 | CCATCCATTCCTGGCTTTAA | 817 | 67.92 | -1.30 | 1.109 | -1.243 | 0.215 | -0.122 | 16915.0 |
| 674 | CATCCATTCCTGGCTTTAAT | 818 | 64.36 | -1.30 | 0.585 | -1.243 | -0.109 | -0.028 | 13910.0 |
| 675 | ATCCATTCCTGGCTTTAATT | 819 | 63.53 | -1.30 | 0.464 | -1.243 | -0.185 | -0.009 | 12524.0 |
| 676 | TCCATTCCTGGCTTTAATTT | 820 | 63.88 | -1.30 | 0.516 | -1.243 | -0.152 | -0.005 | 11890.0 |
| 677 | CCATTCCTGGCTTTAATTTT | 821 | 62.81 | -0.90 | 0.359 | -0.895 | -0.118 | -0.040 | 12839.0 |
| 678 | CATTCCTGGCTTTAATTTTA | 822 | 58.55 | 0.90 | -0.266 | 0.670 | 0.090 | -0.126 | 9726.8 |
| 679 | ATTCCTGGCTTTAATTTTAC | 823 | 57.84 | 1.50 | -0.371 | 1.192 | 0.223 | -0.238 | 8499.7 |
| 680 | TTCCTGGCTTTAATTTTACT | 824 | 59.78 | 1.90 | -0.086 | 1.540 | 0.532 | -0.336 | 6800.4 |
| 681 | TCCTGGCTTTAATTTTACTG | 825 | 59.37 | 1.90 | -0.146 | 1.540 | 0.494 | -0.396 | 5445.6 |
| 682 | CCTGGCTTTAATTTTACTGG | 826 | 60.53 | 1.90 | 0.024 | 1.540 | 0.600 | -0.434 | 2901.6 |
| 683 | CTGGCTTTAATTTTACTGGT | 827 | 59.77 | 1.90 | -0.087 | 1.540 | 0.531 | -0.431 | 1174.2 |
| 684 | TGGCTTTAATTTTACTGGTA | 828 | 57.25 | 1.90 | -0.458 | 1.540 | 0.301 | -0.268 | 521.3 |
| 685 | GGCTTTAATTTTACTGGTAC | 829 | 57.86 | 1.90 | -0.368 | 1.540 | 0.357 | -0.066 | 611.1 |
| 686 | GCTTTAATTTTACTGGTACA | 830 | 56.55 | 1.80 | -0.560 | 1.453 | 0.205 | -0.148 | 287.6 |
| 687 | CTTTAATTTTACTGGTACAG | 831 | 52.66 | 0.40 | -1.130 | 0.236 | -0.611 | -0.330 | 109.5 |
| 688 | TTTAATTTTACTGGTACAGT | 832 | 53.62 | -0.80 | -0.989 | -0.808 | -0.920 | -0.454 | 59.5 |
| 689 | TTAATTTTACTGGTACAGTC | 833 | 54.59 | -1.00 | -0.847 | -0.982 | -0.898 | -0.540 | 62.1 |
| 690 | TAATTTTACTGGTACAGTCT | 834 | 56.28 | -1.00 | -0.599 | -0.982 | -0.745 | -0.632 | 59.4 |
| 691 | AATTTTACTGGTACAGTCTC | 835 | 58.27 | -1.00 | -0.308 | -0.982 | -0.564 | -0.613 | 68.0 |
| 692 | ATTTTACTGGTACAGTCTCA | 836 | 61.78 | -1.00 | 0.207 | -0.982 | -0.245 | -0.561 | 72.9 |
| 693 | TTTTACTGGTACAGTCTCAA | 837 | 59.61 | -1.00 | -0.111 | -0.982 | -0.442 | -0.515 | 62.2 |
| 694 | TTTACTGGTACAGTCTCAAT | 838 | 59.25 | -1.00 | -0.164 | -0.982 | -0.475 | -0.439 | 64.5 |
| 695 | TTACTGGTACAGTCTCAATA | 839 | 58.30 | -1.00 | -0.303 | -0.982 | -0.561 | -0.318 | 53.5 |
| 696 | TACTGGTACAGTCTCAATAG | 840 | 58.15 | -1.00 | -0.326 | -0.982 | -0.575 | -0.166 | 57.8 |
| 697 | ACTGGTACAGTCTCAATAGG | 841 | 61.44 | -0.80 | 0.157 | -0.808 | -0.210 | -0.034 | 341.0 |
| 698 | CTGGTACAGTCTCAATAGGG | 842 | 63.55 | 0.10 | 0.467 | -0.025 | 0.280 | -0.186 | 54.8 |
| 699 | TGGTACAGTCTCAATAGGGC | 843 | 65.89 | 1.10 | 0.810 | 0.844 | 0.823 | -0.279 | 47.1 |
| 700 | GGTACAGTCTCAATAGGGCT | 844 | 68.08 | 0.90 | 1.131 | 0.670 | 0.956 | -0.383 | 59.7 |
| 701 | GTACAGTCTCAATAGGGCTA | 845 | 64.73 | 0.70 | 0.640 | 0.496 | 0.586 | -0.425 | 47.0 |
| 702 | TACAGTCTCAATAGGGCTAA | 846 | 59.35 | 0.70 | -0.149 | 0.496 | 0.096 | -0.425 | 49.3 |
| 703 | ACAGTCTCAATAGGGCTAAT | 847 | 59.91 | 0.70 | -0.067 | 0.496 | 0.147 | -0.388 | 55.0 |
| 704 | CAGTCTCAATAGGGCTAATG | 848 | 59.29 | 0.70 | -0.158 | 0.496 | 0.091 | -0.275 | 49.0 |
| 705 | AGTCTCAATAGGGCTAATGG | 849 | 60.62 | 0.90 | 0.037 | 0.670 | 0.278 | -0.220 | 45.7 |
| 706 | GTCTCAATAGGGCTAATGGA | 850 | 63.00 | 1.10 | 0.386 | 0.844 | 0.560 | -0.189 | 115.6 |
| 707 | TCTCAATAGGGCTAATGGGA | 851 | 61.22 | 0.40 | 0.125 | 0.236 | 0.167 | -0.133 | 50.6 |
| 708 | CTCAATAGGGCTAATGGGAA | 852 | 57.97 | 1.40 | -0.352 | 1.105 | 0.202 | -0.075 | 48.0 |
| 709 | TCAATAGGGCTAATGGGAAA | 853 | 54.39 | 1.40 | -0.877 | 1.105 | -0.124 | -0.028 | 50.5 |
| 710 | CAATAGGGCTAATGGGAAAA | 854 | 51.64 | 1.80 | -1.281 | 1.453 | -0.242 | -0.191 | 44.1 |
| 711 | AATAGGGCTAATGGGAAAAT | 855 | 50.45 | 1.90 | -1.454 | 1.540 | -0.316 | -0.298 | 43.1 |
| 712 | ATAGGGCTAATGGGAAAATT | 856 | 52.34 | 1.00 | -1.178 | 0.757 | -0.442 | -0.432 | 45.2 |
| 713 | TAGGGCTAATGGGAAAATTT | 857 | 52.63 | 0.50 | -1.135 | 0.323 | -0.581 | -0.569 | 47.4 |
| 714 | AGGGCTAATGGGAAAATTTA | 858 | 52.63 | 0.50 | -1.135 | 0.323 | -0.581 | -0.717 | 50.0 |
| 715 | GGGCTAATGGGAAAATTTAA | 859 | 50.89 | 0.50 | -1.390 | 0.323 | -0.739 | -0.867 | 47.8 |
| 716 | GGCTAATGGGAAAATTTAAA | 860 | 47.14 | 0.50 | -1.940 | 0.323 | -1.080 | -1.022 | 50.2 |
| 717 | GCTAATGGGAAAATTTAAAG | 861 | 45.00 | 0.50 | -2.254 | 0.323 | -1.275 | -1.096 | 43.0 |
| 718 | CTAATGGGAAAATTTAAAGT | 862 | 43.95 | 0.50 | -2.408 | 0.323 | -1.371 | -1.088 | 57.0 |
| 719 | TAATGGGAAAATTTAAAGTG | 863 | 42.27 | 0.50 | -2.655 | 0.323 | -1.524 | -1.072 | 58.7 |
| 720 | AATGGGAAAATTTAAAGTGC | 864 | 46.18 | 0.70 | -2.081 | 0.496 | -1.102 | -1.011 | 183.6 |
| 721 | ATGGGAAAATTTAAAGTGCA | 865 | 48.90 | 1.70 | -1.682 | 1.366 | -0.524 | -0.924 | 303.4 |
| 722 | TGGGAAAATTTAAAGTGCAA | 866 | 47.39 | 1.80 | -1.903 | 1.453 | -0.628 | -0.837 | 135.7 |
| 723 | GGGAAAATTTAAAGTGCAAC | 867 | 47.84 | 1.60 | -1.838 | 1.279 | -0.653 | -0.766 | 241.7 |
| 724 | GGAAAATTTAAAGTGCAACC | 868 | 49.12 | 1.20 | -1.649 | 0.931 | -0.669 | -0.737 | 132.5 |
| 725 | GAAAATTTAAAGTGCAACCA | 869 | 48.09 | 1.20 | -1.801 | 0.931 | -0.763 | -0.758 | 128.8 |
| 726 | AAAATTTAAAGTGCAACCAA | 870 | 45.57 | 1.10 | -2.171 | 0.844 | -1.025 | -0.720 | 141.0 |
| 727 | AAATTTAAAGTGCAACCAAT | 871 | 46.97 | 1.10 | -1.965 | 0.844 | -0.897 | -0.679 | 282.0 |
| 728 | AATTTAAAGTGCAACCAATC | 872 | 49.46 | 1.10 | -1.599 | 0.844 | -0.671 | -0.629 | 948.6 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 729 | ATTTAAAGTGCAACCAATCT | 873 | 52.84 | 1.10 | −1.104 | 0.844 | −0.363 | −0.567 | 1815.1 |
| 730 | TTTAAAGTGCAACCAATCTG | 874 | 52.81 | 1.10 | −1.109 | 0.844 | −0.366 | −0.426 | 3188.2 |
| 731 | TTAAAGTGCAACCAATCTGA | 875 | 53.71 | 1.00 | −0.976 | 0.757 | −0.317 | −0.262 | 3566.1 |
| 732 | TAAAGTGCAACCAATCTGAG | 876 | 53.56 | 1.00 | −0.999 | 0.757 | −0.331 | −0.087 | 2925.1 |
| 733 | AAAGTGCAACCAATCTGAGT | 877 | 56.81 | 1.00 | −0.522 | 0.757 | −0.036 | −0.014 | 3233.2 |
| 734 | AAGTGCAACCAATCTGAGTC | 878 | 59.99 | 1.00 | −0.055 | 0.757 | 0.254 | −0.085 | 3615.6 |
| 735 | AGTGCAACCAATCTGAGTCA | 879 | 63.25 | 1.00 | 0.422 | 0.757 | 0.550 | −0.165 | 3994.8 |
| 736 | GTGCAACCAATCTGAGTCAA | 880 | 61.00 | 1.00 | 0.093 | 0.757 | 0.345 | −0.138 | 4033.0 |
| 737 | TGCAACCAATCTGAGTCAAC | 881 | 58.62 | 1.00 | −0.257 | 0.757 | 0.128 | −0.008 | 3380.2 |
| 738 | GCAACCAATCTGAGTCAACA | 882 | 59.87 | 1.00 | −0.073 | 0.757 | 0.242 | −0.173 | 4288.7 |
| 739 | CAACCAATCTGAGTCAACAG | 883 | 56.22 | −0.30 | −0.608 | −0.373 | −0.519 | −0.445 | 744.1 |
| 740 | AACCAATCTGAGTCAACAGA | 884 | 56.24 | −1.60 | −0.605 | −1.504 | −0.946 | −0.757 | 392.2 |
| 741 | ACCAATCTGAGTCAACAGAT | 885 | 58.10 | −2.30 | −0.332 | −2.112 | −1.009 | −1.030 | 158.1 |
| 742 | CCAATCTGAGTCAACAGATT | 886 | 57.90 | −3.30 | −0.362 | −2.982 | −1.357 | −1.219 | 70.8 |
| 743 | CAATCTGAGTCAACAGATTT | 887 | 54.41 | −3.80 | −0.874 | −3.417 | −1.840 | −1.262 | 190.0 |
| 744 | AATCTGAGTCAACAGATTTC | 888 | 54.37 | −3.60 | −0.880 | −3.243 | −1.778 | −1.168 | 87.7 |
| 745 | ATCTGAGTCAACAGATTTCT | 889 | 58.37 | −2.60 | −0.293 | −2.373 | −1.084 | −1.017 | 152.7 |
| 746 | TCTGAGTCAACAGATTTCTT | 890 | 58.73 | −1.90 | −0.241 | −1.764 | −0.820 | −0.797 | 270.5 |
| 747 | CTGAGTCAACAGATTTCTTC | 891 | 58.73 | −0.30 | −0.241 | −0.373 | −0.291 | −0.553 | 498.7 |
| 748 | TGAGTCAACAGATTTCTTCC | 892 | 60.70 | 0.20 | 0.049 | 0.062 | 0.054 | −0.321 | 891.0 |
| 749 | GAGTCAACAGATTTCTTCCA | 893 | 62.06 | 0.20 | 0.248 | 0.062 | 0.177 | −0.221 | 1509.8 |
| 750 | AGTCAACAGATTTCTTCCAA | 894 | 58.66 | 0.20 | −0.250 | 0.062 | −0.132 | −0.182 | 1009.3 |
| 751 | GTCAACAGATTTCTTCCAAT | 895 | 58.47 | 0.20 | −0.279 | 0.062 | −0.149 | −0.235 | 1198.0 |
| 752 | TCAACAGATTTCTTCCAATT | 896 | 55.86 | 0.20 | −0.661 | 0.062 | −0.387 | −0.315 | 680.5 |
| 753 | CAACAGATTTCTTCCAATTA | 897 | 54.08 | 0.20 | −0.922 | 0.062 | −0.548 | −0.381 | 762.5 |
| 754 | AACAGATTTCTTCCAATTAT | 898 | 52.82 | 0.20 | −1.107 | 0.062 | −0.663 | −0.415 | 689.8 |
| 755 | ACAGATTTCTTCCAATTATG | 899 | 54.58 | 0.20 | −0.849 | 0.062 | −0.503 | −0.445 | 715.1 |
| 756 | CAGATTTCTTCCAATTATGT | 900 | 56.99 | 0.20 | −0.496 | 0.062 | −0.284 | −0.460 | 833.8 |
| 757 | AGATTTCTTCCAATTATGTT | 901 | 56.02 | 0.20 | −0.638 | 0.062 | −0.372 | −0.445 | 1067.7 |
| 758 | GATTTCTTCCAATTATGTTG | 902 | 55.80 | 0.30 | −0.670 | 0.149 | −0.359 | −0.401 | 1225.9 |
| 759 | ATTTCTTCCAATTATGTTGA | 903 | 55.80 | −0.10 | −0.670 | −0.199 | −0.491 | −0.382 | 1028.7 |
| 760 | TTTCTTCCAATTATGTTGAC | 904 | 56.34 | −0.10 | −0.591 | −0.199 | −0.442 | −0.378 | 1419.0 |
| 761 | TTCTTCCAATTATGTTGACA | 905 | 57.29 | −0.10 | −0.452 | −0.199 | −0.356 | −0.348 | 1437.4 |
| 762 | TCTTCCAATTATGTTGACAG | 906 | 57.14 | −0.10 | −0.474 | −0.199 | −0.369 | −0.325 | 1518.3 |
| 763 | CTTCCAATTATGTTGACAGG | 907 | 58.36 | −0.10 | −0.295 | −0.199 | −0.259 | −0.262 | 1560.3 |
| 764 | TTCCAATTATGTTGACAGGT | 908 | 59.43 | −0.10 | −0.138 | −0.199 | −0.161 | −0.244 | 1100.0 |
| 765 | TCCAATTATGTTGACAGGTG | 909 | 59.02 | −0.10 | −0.198 | −0.199 | −0.198 | −0.216 | 1096.4 |
| 766 | CCAATTATGTTGACAGGTGT | 910 | 60.68 | −0.10 | 0.046 | −0.199 | −0.047 | −0.124 | 1103.4 |
| 767 | CAATTATGTTGACAGGTGTA | 911 | 56.24 | 0.30 | −0.605 | 0.149 | −0.319 | −0.005 | 738.1 |
| 768 | AATTATGTTGACAGGTGTAG | 912 | 55.09 | 1.10 | −0.774 | 0.844 | −0.159 | −0.054 | 596.7 |
| 769 | ATTATGTTGACAGGTGTAGG | 913 | 59.83 | 1.10 | −0.079 | 0.844 | 0.272 | −0.161 | 548.1 |
| 770 | TTATGTTGACAGGTGTAGGT | 914 | 63.16 | 1.10 | 0.409 | 0.844 | 0.575 | −0.274 | 701.1 |
| 771 | TATGTTGACAGGTGTAGGTC | 915 | 64.38 | −0.20 | 0.588 | −0.286 | 0.256 | −0.420 | 724.7 |
| 772 | ATGTTGACAGGTGTAGGTCC | 916 | 69.08 | −0.60 | 1.278 | −0.634 | 0.551 | −0.506 | 1129.8 |
| 773 | TGTTGACAGGTGTAGGTCCT | 917 | 71.21 | −0.60 | 1.591 | −0.634 | 0.745 | −0.537 | 1214.0 |
| 774 | GTTGACAGGTGTAGGTCCTA | 918 | 70.75 | −0.60 | 1.523 | −0.634 | 0.703 | −0.520 | 1425.4 |
| 775 | TTGACAGGTGTAGGTCCTAC | 919 | 67.83 | −0.60 | 1.095 | −0.634 | 0.438 | −0.499 | 838.8 |
| 776 | TGACAGGTGTAGGTCCTACT | 920 | 69.52 | −0.90 | 1.343 | −0.895 | 0.493 | −0.427 | 1173.1 |
| 777 | GACAGGTGTAGGTCCTACTA | 921 | 69.06 | −0.90 | 1.275 | −0.895 | 0.450 | −0.304 | 1367.0 |
| 778 | ACAGGTGTAGGTCCTACTAA | 922 | 65.30 | −0.90 | 0.723 | −0.895 | 0.108 | −0.192 | 872.0 |
| 779 | CAGGTGTAGGTCCTACTAAT | 923 | 64.69 | −0.90 | 0.634 | −0.895 | 0.053 | −0.109 | 897.6 |
| 780 | AGGTGTAGGTCCTACTAATA | 924 | 62.84 | −0.90 | 0.362 | −0.895 | −0.115 | −0.024 | 962.2 |
| 781 | GGTGTAGGTCCTACTAATAC | 925 | 63.19 | −0.90 | 0.414 | −0.895 | −0.083 | −0.090 | 1382.6 |
| 782 | GTGTAGGTCCTACTAATACT | 926 | 62.53 | −0.90 | 0.317 | −0.895 | −0.143 | −0.099 | 1132.9 |
| 783 | TGTAGGTCCTACTAATACTG | 927 | 59.27 | −0.90 | −0.160 | −0.895 | −0.439 | −0.095 | 1180.7 |
| 784 | GTAGGTCCTACTAATACTGT | 928 | 62.53 | −0.50 | 0.317 | −0.547 | −0.011 | −0.020 | 1932.9 |
| 785 | TAGGTCCTACTAATACTGTA | 929 | 58.77 | 0.70 | −0.234 | 0.496 | 0.043 | −0.042 | 1634.4 |
| 786 | AGGTCCTACTAATACTGTAC | 930 | 59.91 | 0.50 | −0.067 | 0.323 | 0.081 | −0.067 | 2488.1 |
| 787 | GGTCCTACTAATACTGTACC | 931 | 63.54 | 0.50 | 0.466 | 0.323 | 0.411 | −0.116 | 3560.9 |
| 788 | GTCCTACTAATACTGTACCT | 932 | 62.91 | 0.50 | 0.373 | 0.323 | 0.354 | −0.048 | 3850.1 |
| 789 | TCCTACTAATACTGTACCTA | 933 | 59.31 | 0.50 | −0.155 | 0.323 | 0.026 | −0.041 | 1879.0 |
| 790 | CCTACTAATACTGTACCTAT | 934 | 57.99 | 0.50 | −0.348 | 0.323 | −0.093 | −0.053 | 1920.4 |
| 791 | CTACTAATACTGTACCTATA | 935 | 53.68 | 0.50 | −0.981 | 0.323 | −0.486 | −0.094 | 1131.2 |
| 792 | TACTAATACTGTACCTATAG | 936 | 51.92 | 0.70 | −1.240 | 0.496 | −0.580 | −0.147 | 756.5 |
| 793 | ACTAATACTGTACCTATAGC | 937 | 56.45 | 1.20 | −0.574 | 0.931 | −0.002 | −0.142 | 1881.3 |
| 794 | CTAATACTGTACCTATAGCT | 938 | 57.85 | 1.20 | −0.369 | 0.931 | 0.125 | −0.102 | 2033.6 |
| 795 | TAATACTGTACCTATAGCTT | 939 | 56.25 | 1.20 | −0.604 | 0.931 | −0.021 | −0.006 | 1853.9 |
| 796 | AATACTGTACCTATAGCTTT | 940 | 57.14 | 1.20 | −0.473 | 0.931 | 0.060 | −0.111 | 2462.6 |
| 797 | ATACTGTACCTATAGCTTTA | 941 | 58.55 | 1.20 | −0.266 | 0.931 | 0.189 | −0.183 | 2436.8 |
| 798 | TACTGTACCTATAGCTTTAT | 942 | 58.55 | 1.20 | −0.266 | 0.931 | 0.189 | −0.220 | 1865.2 |
| 799 | ACTGTACCTATAGCTTTATG | 943 | 59.06 | 1.20 | −0.192 | 0.931 | 0.235 | −0.331 | 1682.1 |
| 800 | CTGTACCTATAGCTTTATGT | 944 | 61.64 | 1.30 | 0.187 | 1.018 | 0.503 | −0.405 | 1551.3 |
| 801 | TGTACCTATAGCTTTATGTC | 945 | 61.08 | 1.10 | 0.105 | 0.844 | 0.386 | −0.484 | 1600.1 |
| 802 | GTACCTATAGCTTTATGTCC | 946 | 65.16 | 1.10 | 0.703 | 0.844 | 0.757 | −0.572 | 4094.6 |

TABLE 4-continued

| p5 Probe Position | DNA Probe Sequence | SEQ ID NO: | RNA/DNA $T_m$ (° C.) | $G_{MFOLD}$ (kcal/mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 803 | TACCTATAGCTTTATGTCCA | 947 | 63.16 | 1.10 | 0.409 | 0.844 | 0.575 | −0.597 | 2794.2 |
| 804 | ACCTATAGCTTTATGTCCAC | 948 | 64.30 | 1.30 | 0.577 | 1.018 | 0.745 | −0.575 | 4754.9 |
| 805 | CCTATAGCTTTATGTCCACA | 949 | 64.94 | 1.30 | 0.671 | 1.018 | 0.803 | −0.554 | 4185.4 |
| 806 | CTATAGCTTTATGTCCACAG | 950 | 61.34 | 1.10 | 0.143 | 0.844 | 0.409 | −0.484 | 3284.3 |
| 807 | TATAGCTTTATGTCCACAGA | 951 | 60.70 | 1.10 | 0.048 | 0.844 | 0.351 | −0.453 | 2819.7 |
| 808 | ATAGCTTTATGTCCACAGAT | 952 | 61.27 | 0.60 | 0.132 | 0.410 | 0.238 | −0.414 | 3545.1 |
| 809 | TAGCTTTATGTCCACAGATT | 953 | 61.63 | 0.60 | 0.186 | 0.410 | 0.271 | −0.337 | 4232.6 |
| 810 | AGCTTTATGTCCACAGATTT | 954 | 62.57 | 0.60 | 0.324 | 0.410 | 0.356 | −0.283 | 5252.8 |
| 811 | GCTTTATGTCCACAGATTTC | 955 | 63.85 | 0.60 | 0.511 | 0.410 | 0.472 | −0.232 | 6823.9 |
| 812 | CTTTATGTCCACAGATTTCT | 956 | 61.56 | 0.60 | 0.176 | 0.410 | 0.265 | −0.193 | 4829.8 |
| 813 | TTTATGTCCACAGATTTCTA | 957 | 58.97 | 0.60 | −0.205 | 0.410 | 0.029 | −0.173 | 4333.7 |
| 814 | TTATGTCCACAGATTTCTAT | 958 | 58.62 | 0.60 | −0.257 | 0.410 | −0.004 | −0.144 | 3801.0 |
| 815 | TATGTCCACAGATTTCTATG | 959 | 58.20 | 0.60 | −0.318 | 0.410 | −0.041 | −0.142 | 3528.2 |
| 816 | ATGTCCACAGATTTCTATGA | 960 | 60.12 | 0.60 | −0.036 | 0.410 | 0.134 | −0.129 | 2080.0 |
| 817 | TGTCCACAGATTTCTATGAG | 961 | 60.34 | 0.60 | −0.004 | 0.410 | 0.153 | −0.145 | 913.8 |
| 818 | GTCCACAGATTTCTATGAGT | 962 | 63.68 | 0.60 | 0.486 | 0.410 | 0.457 | −0.122 | 1228.3 |
| 819 | TCCACAGATTTCTATGAGTA | 963 | 59.83 | 0.80 | −0.078 | 0.583 | 0.173 | −0.067 | 238.1 |
| 820 | CCACAGATTTCTATGAGTAT | 964 | 58.43 | 1.10 | −0.285 | 0.844 | 0.144 | −0.078 | 219.4 |
| 821 | CACAGATTTCTATGAGTATC | 965 | 55.78 | 0.90 | −0.673 | 0.670 | −0.162 | −0.169 | 138.6 |
| 822 | ACAGATTTCTATGAGTATCT | 966 | 56.48 | −0.10 | −0.571 | −0.199 | −0.430 | −0.273 | 112.7 |
| 823 | CAGATTTCTATGAGTATCTG | 967 | 55.85 | −1.30 | −0.663 | −1.243 | −0.883 | −0.327 | 133.8 |
| 824 | AGATTTCTATGAGTATCTGA | 968 | 55.87 | −0.10 | −0.659 | −0.199 | −0.485 | −0.387 | 296.8 |
| 825 | GATTTCTATGAGTATCTGAT | 969 | 55.69 | 0.60 | −0.686 | 0.410 | −0.270 | −0.442 | 279.7 |
| 826 | ATTTCTATGAGTATCTGATC | 970 | 55.67 | 0.80 | −0.689 | 0.583 | −0.206 | −0.498 | 484.4 |
| 827 | TTTCTATGAGTATCTGATCA | 971 | 57.06 | 0.20 | −0.485 | 0.062 | −0.277 | −0.510 | 502.0 |
| 828 | TTCTATGAGTATCTGATCAT | 972 | 56.70 | −0.50 | −0.538 | −0.547 | −0.541 | −0.569 | 637.3 |
| 829 | TCTATGAGTATCTGATCATA | 973 | 55.75 | −1.10 | −0.678 | −1.069 | −0.826 | −0.657 | 489.0 |
| 830 | CTATGAGTATCTGATCATAC | 974 | 54.95 | −1.30 | −0.794 | −1.243 | −0.965 | −0.712 | 808.7 |
| 831 | TATGAGTATCTGATCATACT | 975 | 54.95 | −1.10 | −0.794 | −1.069 | −0.899 | −0.738 | 903.2 |
| 832 | ATGAGTATCTGATCATACTG | 976 | 55.49 | −1.20 | −0.715 | −1.156 | −0.883 | −0.707 | 1709.3 |
| 833 | TGAGTATCTGATCATACTGT | 977 | 58.64 | −1.20 | −0.254 | −1.156 | −0.597 | −0.601 | 2103.9 |
| 834 | GAGTATCTGATCATACTGTC | 978 | 60.20 | −1.20 | −0.025 | −1.156 | −0.455 | −0.468 | 3973.4 |
| 835 | AGTATCTGATCATACTGTCT | 979 | 60.88 | −1.00 | 0.076 | −0.982 | −0.326 | −0.330 | 6462.3 |
| 836 | GTATCTGATCATACTGTCTT | 980 | 61.03 | −0.30 | 0.097 | −0.373 | −0.081 | −0.167 | 9749.0 |
| 837 | TATCTGATCATACTGTCTTA | 981 | 57.16 | 0.90 | −0.470 | 0.670 | −0.037 | −0.059 | 7817.2 |
| 838 | ATCTGATCATACTGTCTTAC | 982 | 58.34 | 0.90 | −0.298 | 0.670 | 0.070 | −0.007 | 9683.1 |
| 539 | TCTGATCATACTGTCTTACT | 983 | 60.42 | 0.90 | 0.008 | 0.670 | 0.259 | −0.055 | 8089.0 |
| 840 | CTGATCATACTGTCTTACTT | 984 | 59.32 | 0.90 | −0.154 | 0.670 | 0.159 | −0.067 | 8696.8 |
| 841 | TGATCATACTGTCTTACTTT | 985 | 57.63 | 0.90 | −0.401 | 0.670 | 0.006 | −0.064 | 6880.5 |
| 842 | GATCATACTGTCTTACTTTG | 986 | 57.63 | 0.90 | −0.401 | 0.670 | 0.006 | −0.020 | 7033.7 |
| 843 | ATCATACTGTCTTACTTTGA | 987 | 57.63 | 0.90 | −0.401 | 0.670 | 0.006 | −0.093 | 5406.5 |
| 844 | TCATACTGTCTTACTTTGAT | 988 | 57.63 | 0.70 | −0.401 | 0.496 | −0.060 | −0.215 | 4239.4 |
| 845 | CATACTGTCTTACTTTGATA | 989 | 55.68 | 0.70 | −0.688 | 0.496 | −0.238 | −0.378 | 3727.4 |
| 846 | ATACTGTCTTACTTTGATAA | 990 | 52.44 | 0.70 | −1.163 | 0.496 | −0.533 | −0.550 | 2665.5 |
| 847 | TACTGTCTTACTTTGATAAA | 991 | 50.65 | 0.70 | −1.426 | 0.496 | −0.696 | −0.696 | 1817.8 |
| 848 | ACTGTCTTACTTTGATAAAA | 992 | 49.49 | −0.30 | −1.595 | −0.373 | −1.131 | −0.809 | 1335.9 |
| 849 | CTGTCTTACTTTGATAAAAC | 993 | 49.49 | −0.50 | −1.595 | −0.547 | −1.197 | −0.916 | 1526.2 |
| 850 | TGTCTTACTTTGATAAAACC | 994 | 51.45 | −0.50 | −1.309 | −0.547 | −1.019 | −0.949 | 822.7 |
| 851 | GTCTTACTTTGATAAAACCT | 995 | 53.32 | −0.50 | −1.034 | −0.547 | −0.849 | −0.966 | 1227.4 |
| 852 | TCTTACTTTGATAAAACCTC | 996 | 51.75 | −0.50 | −1.264 | −0.547 | −0.991 | −0.946 | 503.0 |
| 853 | CTTACTTTGATAAAACCTCC | 997 | 54.28 | −0.50 | −0.894 | −0.547 | −0.762 | −0.910 | 1174.3 |
| 854 | TTACTTTGATAAAACCTCCA | 998 | 53.70 | −0.50 | −0.978 | −0.547 | −0.814 | −0.901 | 885.5 |
| 855 | TACTTTGATAAAACCTCCAA | 999 | 51.79 | −0.50 | −1.259 | −0.547 | −0.988 | −0.916 | 650.6 |
| 856 | ACTTTGATAAAACCTCCAAT | 1000 | 52.29 | −0.50 | −1.185 | −0.547 | −0.943 | −0.826 | 615.4 |
| 857 | CTTTGATAAAACCTCCAATT | 1001 | 52.11 | −0.50 | −1.212 | −0.547 | −0.959 | −0.728 | 563.4 |
| 858 | TTTGATAAAACCTCCAATTC | 1002 | 51.46 | −0.30 | −1.307 | −0.373 | −0.952 | −0.561 | 420.9 |
| 859 | TTGATAAAACCTCCAATTCC | 1003 | 54.68 | 0.60 | −0.834 | 0.410 | −0.362 | −0.298 | 536.6 |
| 860 | TGATAAAACCTCCAATTCCC | 1004 | 57.79 | 0.60 | −0.378 | 0.410 | −0.079 | −0.022 | 1417.8 |
| 861 | GATAAAACCTCCAATTCCCC | 1005 | 61.15 | 1.00 | 0.114 | 0.757 | 0.359 | −0.258 | 4351.2 |
| 862 | ATAAAACCTCCAATTCCCCT | 1006 | 63.24 | 1.90 | 0.421 | 1.540 | 0.846 | −0.560 | 7738.7 |
| 863 | TAAAACCTCCAATTCcCCCT | 1007 | 64.88 | 1.90 | 0.663 | 1.540 | 0.996 | −0.817 | 11136.0 |
| 864 | AAAACCTCCAATTCCCCCTA | 1008 | 64.88 | 1.90 | 0.663 | 1.540 | 0.996 | 1.074 | 14811.0 |
| 865 | AAACCTCCAATTCCCCCTAT | 1009 | 66.73 | 1.90 | 0.933 | 1.540 | 1.164 | 1.261 | 15751.0 |
| 866 | AACCTCCAATTCCCCCTATC | 1010 | 70.07 | 1.80 | 1.424 | 1.453 | 1.435 | 1.330 | 19661.0 |
| 867 | ACCTCCAATTCCCCCTATCA | 1011 | 73.21 | 1.80 | 1.883 | 1.453 | 1.720 | 1.335 | 20301.0 |
| 868 | CCTCCAATTCCCCCTATCAT | 1012 | 72.64 | 1.80 | 1.801 | 1.453 | 1.669 | 1.327 | 19376.0 |
| 869 | CTCCAATTCCCCCTATCATT | 1013 | 69.66 | 1.60 | 1.364 | 1.279 | 1.332 | 1.254 | 17642.0 |
| 870 | TCCAATTCCCCCTATCATTT | 1014 | 68.21 | 1.10 | 1.150 | 0.844 | 1.034 | 1.093 | 13751.0 |
| 871 | CCAATTCCCCCTATCATTTT | 1015 | 67.12 | 1.10 | 0.991 | 0.844 | 0.935 | 0.931 | 12669.0 |
| 872 | CAATTCCCCCTATCATTTTT | 1016 | 64.02 | 1.10 | 0.536 | 0.844 | 0.653 | −0.818 | 9255.9 |
| 873 | AATTCCCCCTATCATTTTTG | 1017 | 62.80 | 0.40 | 0.357 | 0.236 | 0.311 | −0.753 | 8929.1 |
| 874 | ATTCCCCCTATCATTTTTGG | 1018 | 67.28 | 0.00 | 1.014 | −0.112 | 0.586 | −0.715 | 6148.2 |
| 875 | TTCCCCCTATCATTTTTGGT | 1019 | 70.46 | 0.00 | 1.480 | −0.112 | 0.875 | −0.664 | 5468.0 |
| 876 | TCCCCCTATCATTTTTGGTT | 1020 | 70.46 | 0.00 | 1.480 | −0.112 | 0.875 | −0.653 | 5803.7 |

TABLE 4-continued

| p5 Probe Position | DNA Probe Sequence | SEQ ID NO: | RNA/DNA T$_m$ (° C.) | G$_{MFOLD}$ (kcal/mole @ 35° C.) | T$_m$ Score | ΔG$_{MFOLD}$ Score | Composite Score | Window-Averaged Composite Score | HIV PRT GeneChip™ Data |
|---|---|---|---|---|---|---|---|---|---|
| 877 | CCCCCTATCATTTTTGGTTT | 1021 | 69.27 | 0.00 | 1.307 | −0.112 | 0.768 | 0.658 | 5192.0 |
| 878 | CCCCTATCATTTTTGGTTTC | 1022 | 67.18 | 0.00 | 1.000 | −0.112 | 0.577 | 0.549 | 3557.4 |
| 879 | CCCTATCATTTTTGGTTTCC | 1023 | 67.18 | 0.00 | 1.000 | −0.112 | 0.577 | 0.392 | 5274.3 |
| 880 | CCTATCATTTTTGGTTTCCA | 1024 | 64.63 | 0.00 | 0.625 | −0.112 | 0.345 | 0.270 | 3787.9 |
| 881 | CTATCATTTTTGGTTTCCAT | 1025 | 60.77 | −0.50 | 0.059 | −0.547 | −0.171 | 0.167 | 2726.8 |
| 882 | TATCATTTTTGGTTTCCATC | 1026 | 60.20 | −0.50 | −0.025 | −0.547 | −0.223 | 0.092 | 3249.9 |
| 883 | ATCATTTTTGGTTTCCATCT | 1027 | 62.83 | −0.50 | 0.361 | −0.547 | 0.016 | 0.051 | 5548.9 |
| 884 | TCATTTTTGGTTTCCATCTT | 1028 | 63.21 | −0.50 | 0.416 | −0.547 | 0.050 | 0.071 | 5290.0 |
| 885 | CATTTTTGGTTTCCATCTTC | 1029 | 63.21 | −0.50 | 0.416 | −0.547 | 0.050 | 0.157 | 7451.0 |
| 886 | ATTTTTGGTTTCCATCTTCC | 1030 | 65.88 | −0.50 | 0.809 | −0.547 | 0.293 | 0.262 | 11578.0 |
| 887 | TTTTTGGTTTCCATCTTCCT | 1031 | 67.93 | −0.50 | 1.109 | −0.547 | 0.480 | 0.366 | 13722.0 |
| 888 | TTTTGGTTTCCATCTTCCTG | 1032 | 67.42 | −0.50 | 1.035 | −0.547 | 0.434 | 0.475 | 15064.0 |
| 889 | TTTGGTTTCCATCTTCCTGG | 1033 | 69.71 | −0.90 | 1.370 | −0.895 | 0.509 | 0.554 | 10869.0 |
| 890 | TTGGTTTCCATCTTCCTGGC | 1034 | 73.74 | −1.30 | 1.962 | −1.243 | 0.744 | 0.535 | 16035.0 |
| 891 | TGGTTTCCATCTTCCTGGCA | 1035 | 74.48 | −1.30 | 2.071 | −1.243 | 0.812 | 0.457 | 16304.0 |
| 892 | GGTTTCCATCTTCCTGGCAA | 1036 | 72.21 | −1.30 | 1.737 | −1.243 | 0.605 | 0.406 | 14885.0 |
| 893 | GTTTCCATCTTCCTGGCAAA | 1037 | 67.37 | −1.30 | 1.027 | −1.243 | 0.165 | 0.358 | 11910.0 |
| 894 | TTTCCATCTTCCTGGCAAAC | 1038 | 64.82 | −1.30 | 0.653 | −1.243 | −0.067 | 0.290 | 11929.0 |
| 895 | TTCCATCTTCCTGGCAAACT | 1039 | 66.34 | −1.30 | 0.877 | −1.243 | 0.071 | 0.252 | 11517.0 |
| 896 | TCCATCTTCCTGGCAAACTC | 1040 | 67.47 | −1.30 | 1.042 | −1.243 | 0.174 | 0.237 | 11822.0 |
| 897 | CCATCTTCCTGGCAAACTCA | 1041 | 67.12 | −0.90 | 0.991 | −0.895 | 0.274 | 0.285 | 11710.0 |
| 898 | CATCTTCCTGGCAAACTCAT | 1042 | 63.55 | 0.90 | 0.466 | 0.670 | 0.544 | 0.357 | 7635.3 |
| 899 | ATCTTCCTGGCAAACTCATT | 1043 | 62.71 | 1.00 | 0.343 | 0.757 | 0.501 | 0.409 | 8378.2 |
| 900 | TCTTCCTGGCAAACTCATTT | 1044 | 63.06 | 0.90 | 0.395 | 0.670 | 0.500 | 0.446 | 6321.4 |
| 901 | CTTCCTGGCAAACTCATTTC | 1045 | 63.06 | 0.70 | 0.395 | 0.496 | 0.434 | 0.468 | 7659.0 |
| 902 | TTCCTGGCAAACTCATTTCT | 1046 | 63.06 | 0.70 | 0.395 | 0.496 | 0.434 | 0.429 | 11621.0 |
| 903 | TCCTGGCAAACTCATTTCTT | 1047 | 63.06 | 0.70 | 0.395 | 0.496 | 0.434 | 0.363 | 3389.0 |
| 904 | CCTGGCAAACTCATTTCTTC | 1048 | 63.06 | 0.70 | 0.395 | 0.496 | 0.434 | 0.273 | 3870.6 |
| 905 | CTGGCAAACTCATTTCTTCT | 1049 | 61.24 | 0.70 | 0.127 | 0.496 | 0.268 | 0.160 | 1992.7 |
| 906 | TGGCAAACTCATTTCTTCTA | 1050 | 58.74 | 0.70 | −0.239 | 0.496 | 0.040 | 0.015 | 698.3 |
| 907 | GGCAAACTCATTTCTTCTAA | 1051 | 56.86 | 0.70 | −0.514 | 0.496 | −0.130 | 0.201 | 718.3 |
| 908 | GCAAACTCATTTCTTCTAAT | 1052 | 54.36 | 0.70 | −0.882 | 0.496 | −0.358 | 0.339 | 372.3 |
| 909 | CAAACTCATTTCTTCTAATA | 1053 | 49.93 | 0.60 | −1.530 | 0.410 | −0.793 | 0.430 | 180.6 |
| 910 | AAACTCATTTCTTCTAATAC | 1054 | 49.11 | 0.60 | −1.651 | 0.410 | −0.868 | 0.455 | 430.0 |
| 911 | AACTCATTTCTTCTAATACT | 1055 | 52.79 | 0.60 | −1.111 | 0.410 | −0.533 | 0.491 | 904.3 |
| 912 | ACTCATTTCTTCTAATACTG | 1056 | 54.63 | 0.60 | −0.842 | 0.410 | −0.366 | 0.510 | 1663.5 |
| 913 | CTCATTTCTTCTAATACTGT | 1057 | 57.14 | 0.60 | −0.474 | 0.410 | −0.138 | 0.459 | 2694.2 |
| 914 | TCATTTCTTCTAATACTGTA | 1058 | 54.51 | 0.60 | −0.859 | 0.410 | −0.377 | 0.361 | 3222.9 |
| 915 | CATTTCTTCTAATACTGTAT | 1059 | 53.21 | 0.60 | −1.049 | 0.410 | −0.495 | 0.310 | 3142.8 |
| 916 | ATTTCTTCTAATACTGTATC | 1060 | 53.13 | 0.80 | −1.061 | 0.583 | −0.436 | 0.270 | 5867.0 |
| 917 | TTTCTTCTAATACTGTATCA | 1061 | 54.51 | 1.20 | −0.859 | 0.931 | −0.179 | 0.253 | 6641.4 |
| 918 | TTCTTCTAATACTGTATCAT | 1062 | 54.17 | 1.30 | −0.908 | 1.018 | −0.176 | 0.229 | 7151.9 |
| 919 | TCTTCTAATACTGTATCATC | 1063 | 55.17 | 1.30 | −0.762 | 1.018 | −0.086 | 0.139 | 8134.9 |
| 920 | CTTCTAATACTGTATCATCT | 1064 | 55.86 | 1.30 | −0.661 | 1.018 | −0.023 | 0.048 | 8551.4 |
| 921 | TTCTAATACTGTATCATCTG | 1065 | 53.80 | 1.30 | −0.964 | 1.018 | −0.211 | 0.003 | 5741.7 |
| 922 | TCTAATACTGTATCATCTGC | 1066 | 57.65 | 1.30 | −0.398 | 1.018 | 0.140 | 0.101 | 8575.9 |
| 923 | CTAATACTGTATCATCTGCT | 1067 | 58.28 | 1.30 | −0.307 | 1.018 | 0.197 | 0.248 | 8980.3 |
| 924 | TAATACTGTATCATCTGCTC | 1068 | 57.65 | 1.30 | −0.398 | 1.018 | 0.140 | 0.384 | 10762.0 |
| 925 | AATACTGTATCATCTGCTCC | 1069 | 62.19 | 1.30 | 0.268 | 1.018 | 0.553 | 0.566 | 17037.0 |
| 926 | ATACTGTATCATCTGCTCCT | 1070 | 66.43 | 1.30 | 0.889 | 1.018 | 0.938 | 0.682 | 20970.0 |
| 927 | TACTGTATCATCTGCTCCTG | 1071 | 66.32 | 1.30 | 0.874 | 1.018 | 0.929 | 0.763 | 23084.0 |
| 928 | ACTGTATCATCTGCTCCTGT | 1072 | 70.36 | 0.60 | 1.466 | 0.410 | 1.065 | 0.875 | 24474.0 |
| 929 | CTGTATCATCTGCTCCTGTA | 1073 | 69.13 | 0.60 | 1.286 | 0.410 | 0.953 | 0.910 | 22217.0 |
| 930 | TGTATCATCTGCTCCTGTAT | 1074 | 67.04 | 0.60 | 0.979 | 0.410 | 0.763 | 0.890 | 19829.0 |
| 931 | GTATCATCTGCTCCTGTATC | 1075 | 68.85 | 0.60 | 1.244 | 0.410 | 0.927 | 0.842 | 23548.0 |
| 932 | TATCATCTGCTCCTGTATCT | 1076 | 67.44 | 0.60 | 1.037 | 0.410 | 0.799 | 0.773 | 21759.0 |
| 933 | ATCATCTGCTCCTGTATCTA | 1077 | 67.44 | 0.60 | 1.037 | 0.410 | 0.799 | 0.725 | 22711.0 |
| 934 | TCATCTGCTCCTGTATCTAA | 1078 | 65.13 | 0.60 | 0.699 | 0.410 | 0.589 | 0.706 | 18134.0 |
| 935 | CATCTGCTCCTGTATCTAAT | 1079 | 63.60 | 1.00 | 0.475 | 0.757 | 0.582 | 0.611 | 17772.0 |
| 936 | ATCTGCTCCTGTATCTAATA | 1080 | 61.77 | 1.60 | 0.207 | 1.279 | 0.614 | 0.502 | 17134.0 |
| 937 | TCTGCTCCTGTATCTAATAG | 1081 | 62.01 | 1.60 | 0.241 | 1.279 | 0.635 | 0.389 | 10969.0 |
| 938 | CTGCTCCTGTATCTAATAGA | 1082 | 61.90 | 0.50 | 0.225 | 0.323 | 0.262 | 0.336 | 9556.3 |
| 939 | TGCTCCTGTATCTAATAGAG | 1083 | 60.12 | 0.30 | −0.036 | 0.149 | 0.034 | 0.264 | 3739.9 |
| 940 | GCTCCTGTATCTAATAGAGC | 1084 | 64.50 | −1.00 | 0.607 | −0.982 | 0.003 | 0.187 | 4088.3 |
| 941 | CTCCTGTATCTAATAGAGCT | 1085 | 62.21 | 0.30 | 0.271 | 0.149 | 0.224 | 0.106 | 2263.0 |
| 942 | TCCTGTATCTAATAGAGCTT | 1086 | 60.56 | 0.30 | 0.028 | 0.149 | 0.074 | 0.080 | 1018.0 |
| 943 | CCTGTATCTAATAGAGCTTC | 1087 | 60.56 | 0.30 | 0.028 | 0.149 | 0.074 | 0.091 | 1319.1 |
| 944 | CTGTATCTAATAGAGCTTCC | 1088 | 60.56 | 0.30 | 0.028 | 0.149 | 0.074 | 0.070 | 2347.8 |
| 945 | TGTATCTAATAGAGCTTCCT | 1089 | 60.56 | 0.30 | 0.028 | 0.149 | 0.074 | 0.018 | 1871.6 |
| 946 | GTATCTAATAGAGCTTCCTT | 1090 | 61.00 | 0.30 | 0.092 | 0.149 | 0.114 | 0.010 | 3469.1 |
| 947 | TATCTAATAGAGCTTCCTTT | 1091 | 58.20 | 0.30 | −0.318 | 0.149 | −0.141 | 0.030 | 1114.6 |
| 948 | ATCTAATAGAGCTTCCTTTA | 1092 | 58.20 | 0.30 | −0.318 | 0.149 | −0.141 | 0.057 | 1358.4 |
| 949 | TCTAATAGAGCTTCCTTTAG | 1093 | 58.39 | 0.30 | −0.289 | 0.149 | −0.123 | 0.078 | 665.4 |
| 950 | CTAATAGAGCTTCCTTTAGT | 1094 | 60.12 | 0.00 | −0.036 | −0.112 | −0.065 | 0.019 | 807.4 |

TABLE 4-continued

| p5 Probe Position | DNA Probe Sequence | SEQ ID NO: | RNA/DNA $T_m$ (° C.) | $G_{MFOLD}$ (kcal/ mole @ 35° C.) | $T_m$ Score | $\Delta G_{MFOLD}$ Score | Composite Score | Window-Averaged Composite Score | HIV PRT GeneChip™ Data |
|---|---|---|---|---|---|---|---|---|---|
| 951 | TAATAGAGCTTCCTTTAGTT | 1095 | 58.46 | 0.30 | −0.280 | 0.149 | −0.117 | −0.128 | 608.7 |
| 952 | AATAGAGCTTCCTTTAGTTG | 1096 | 58.97 | 0.30 | −0.205 | 0.149 | −0.070 | −0.332 | 623.8 |
| 953 | ATAGAGCTTCCTTTAGTTGC | 1097 | 65.53 | 0.30 | 0.758 | 0.149 | 0.526 | −0.576 | 674.5 |
| 954 | TAGAGCTTCCTTTAGTTGCC | 1098 | 69.50 | 0.30 | 1.340 | 0.149 | 0.887 | 0.841 | 814.3 |
| 955 | AGAGCTTCCTTTAGTTGCCC | 1099 | 73.89 | 0.30 | 1.983 | 0.149 | 1.286 | 1.157 | 1183.8 |
| 956 | GAGCTTCCTTTAGTTGCCCC | 1100 | 77.20 | 0.30 | 2.470 | 0.149 | 1.588 | 1.454 | 2219.4 |
| 957 | AGCTTCCTTTAGTTGCCCCC | 1101 | 79.38 | 0.30 | 2.789 | 0.149 | 1.785 | 1.650 | 4642.2 |
| 958 | GCTTCCTTTAGTTGCCCCCC | 1102 | 82.41 | 0.40 | 3.234 | 0.236 | 2.095 | 1.765 | 8804.8 |
| 959 | CTTCCTTTAGTTGCCCCCCT | 1103 | 80.06 | 0.80 | 2.889 | 0.583 | 2.013 | 1.823 | 11331.0 |
| 960 | TTCCTTTAGTTGCCCCCCTA | 1104 | 77.67 | 1.10 | 2.539 | 0.844 | 1.895 | 1.818 | 12976.0 |
| 961 | TCCTTTAGTTGCCCCCCTAT | 1105 | 77.27 | 0.60 | 2.480 | 0.410 | 1.693 | 1.765 | 12369.0 |
| 962 | CCTTTAGTTGCCCCCCTATC | 1106 | 77.27 | 0.60 | 2.480 | 0.410 | 1.693 | 1.669 | 15090.0 |
| 963 | CTTTAGTTGCCCCCCTATCT | 1107 | 75.74 | 0.60 | 2.255 | 0.410 | 1.554 | 1.581 | 16130.0 |
| 964 | TTTAGTTGCCCCCCTATCTT | 1108 | 74.23 | 0.60 | 2.033 | 0.410 | 1.416 | 1.545 | 15304.0 |
| 965 | TTAGTTGCCCCCCTATCTTT | 1109 | 74.23 | 0.60 | 2.033 | 0.410 | 1.416 | 1.539 | 14829.0 |
| 966 | TAGTTGCCCCCCTATCTTTA | 1110 | 73.31 | 0.80 | 1.899 | 0.583 | 1.399 | 1.490 | 15309.0 |
| 967 | AGTTGCCCCCCTATCTTTAT | 1111 | 73.83 | 1.40 | 1.976 | 1.105 | 1.645 | 1.498 | 15205.0 |
| 968 | GTTGCCCCCCTATCTTTATT | 1112 | 73.91 | 1.40 | 1.986 | 1.105 | 1.652 | 1.524 | 14192.0 |
| 969 | TTGCCCCCCTATCTTTATTG | 1113 | 70.59 | 1.40 | 1.500 | 1.105 | 1.350 | 1.515 | 8699.5 |
| 970 | TGCCCCCCTATCTTTATTGT | 1114 | 73.39 | 1.40 | 1.911 | 1.105 | 1.605 | 1.461 | 7786.6 |
| 971 | GCCCCCCTATCTTTATTGTG | 1115 | 73.39 | 1.40 | 1.911 | 1.105 | 1.605 | 1.328 | 6709.1 |
| 972 | CCCCCCTATCTTTATTGTGA | 1116 | 70.61 | 1.40 | 1.502 | 1.105 | 1.351 | 1.165 | 6198.4 |
| 973 | CCCCCTATCTTTATTGTGAC | 1117 | 67.66 | 1.20 | 1.070 | 0.931 | 1.017 | 0.999 | 4910.2 |
| 974 | CCCCTATCTTTATTGTGACG | 1118 | 64.37 | 1.20 | 0.587 | 0.931 | 0.718 | −0.780 | 850.0 |
| 975 | CCCTATCTTTATTGTGACGA | 1119 | 62.05 | 1.20 | 0.248 | 0.931 | 0.507 | −0.570 | 404.9 |
| 976 | CCTATCTTTATTGTGACGAG | 1120 | 58.56 | 1.20 | −0.265 | 0.931 | 0.190 | −0.436 | 166.6 |
| 977 | CTATCTTTATTGTGACGAGG | 1121 | 57.28 | 1.20 | −0.452 | 0.931 | 0.073 | −0.376 | 126.9 |
| 978 | TATCTTTATTGTGACGAGGG | 1122 | 57.91 | 1.20 | −0.361 | 0.931 | 0.130 | −0.279 | 92.6 |
| 979 | ATCTTTATTGTGACGAGGGG | 1123 | 61.03 | 1.20 | 0.097 | 0.931 | 0.414 | −0.173 | 97.9 |
| 980 | TCTTTATTGTGACGAGGGGT | 1124 | 64.18 | 0.90 | 0.559 | 0.670 | 0.601 | −0.097 | 122.3 |
| 981 | CTTTATTGTGACGAGGGGTC | 1125 | 64.18 | −0.80 | 0.559 | −0.808 | 0.039 | −0.013 | 267.0 |
| 982 | TTTATTGTGACGAGGGGTCG | 1126 | 62.63 | −1.20 | 0.332 | −1.156 | −0.233 | −0.073 | 396.2 |
| 983 | TTATTGTGACGAGGGGTCGT | 1127 | 65.37 | −2.30 | 0.734 | −2.112 | −0.348 | −0.145 | 446.0 |
| 984 | TATTGTGACGAGGGGTCGTT | 1128 | 65.37 | −2.80 | 0.734 | −2.547 | −0.513 | −0.202 | 661.9 |
| 985 | ATTGTGACGAGGGGTCGTTG | 1129 | 65.82 | −2.80 | 0.800 | −2.547 | −0.472 | −0.163 | 864.5 |
| 986 | TTGTGACGAGGGGTCGTTGC | 1130 | 70.01 | −2.80 | 1.414 | −2.547 | −0.091 | −0.156 | 1465.7 |
| 987 | TGTGACGAGGGGTCGTTGCC | 1131 | 73.21 | −2.80 | 1.884 | −2.547 | 0.200 | −0.157 | 2836.9 |
| 988 | GTGACGAGGGGTCGTTGCCA | 1132 | 74.44 | −2.80 | 2.065 | −2.547 | 0.312 | −0.137 | 3589.7 |
| 989 | TGACGAGGGGTCGTTGCCAA | 1133 | 69.05 | −2.80 | 1.274 | −2.547 | −0.178 | −0.058 | 2100.4 |
| 990 | GACGAGGGGTCGTTGCCAAA | 1134 | 67.10 | −2.80 | 0.988 | −2.547 | −0.355 | −0.042 | 1948.7 |
| 991 | ACGAGGGGTCGTTGCCAAAG | 1135 | 66.13 | −2.60 | 0.845 | −2.373 | −0.378 | −0.125 | 1384.3 |
| 992 | CGAGGGGTCGTTGCCAAAGA | 1136 | 66.81 | −1.40 | 0.945 | −1.330 | 0.081 | −0.187 | 1192.0 |
| 993 | GAGGGGTCGTTGCCAAAGAG | 1137 | 66.84 | 0.20 | 0.950 | 0.062 | 0.612 | −0.304 | 1221.0 |
| 994 | AGGGGTCGTTGCCAAAGAGT | 1138 | 68.70 | 0.20 | 1.223 | 0.062 | 0.782 | −0.427 | 953.2 |
| 995 | GGGGTCGTTGCCAAAGAGTG | 1139 | 68.32 | 0.20 | 1.167 | 0.062 | 0.747 | −0.515 | 988.6 |
| 996 | GGGTCGTTGCCAAAGAGTGA | 1140 | 67.11 | 0.20 | 0.989 | 0.062 | 0.636 | −0.476 | 937.8 |
| 997 | GGTCGTTGCCAAAGAGTGAT | 1141 | 64.59 | 0.50 | 0.620 | 0.323 | 0.507 | −0.333 | 852.1 |
| 998 | GTCGTTGCCAAAGAGTGATC | 1142 | 63.51 | 0.00 | 0.461 | −0.112 | 0.243 | −0.176 | 1189.4 |
| 999 | TCGTTGCCAAAGAGTGATCT | 1143 | 62.35 | −1.00 | 0.291 | −0.982 | −0.192 | −0.012 | 1501.7 |
| 1000 | CGTTGCCAAAGAGTGATCTG | 1144 | 60.92 | −1.20 | 0.081 | −1.156 | −0.389 | −0.156 | 1360.9 |
| 1001 | GTTGCCAAAGAGTGATCTGA | 1145 | 61.71 | −1.20 | 0.198 | −1.156 | −0.317 | −0.263 | 1112.9 |
| 1002 | TTGCCAAAGAGTGATCTGAG | 1146 | 58.90 | −1.20 | −0.215 | −1.156 | −0.572 | −0.353 | 468.3 |
| 1003 | TGCCAAAGAGTGATCTGAGG | 1147 | 61.08 | −1.20 | 0.104 | −1.156 | −0.375 | −0.454 | 400.1 |
| 1004 | GCCAAAGAGTGATCTGAGGG | 1148 | 63.68 | −1.50 | 0.485 | −1.417 | −0.237 | −0.541 | 401.6 |
| 1005 | CCAAAGAGTGATCTGAGGGA | 1149 | 60.94 | −1.20 | 0.084 | −1.156 | −0.387 | −0.575 | 199.9 |
| 1006 | CAAAGAGTGATCTGAGGGAA | 1150 | 55.32 | −1.20 | −0.741 | −1.156 | −0.899 | −0.530 | 202.1 |
| 1007 | AAAGAGTGATCTGAGGGAAG | 1151 | 54.21 | −1.20 | −0.903 | −1.156 | −0.999 | −0.491 | 258.7 |
| 1008 | AAGAGTGATCTGAGGGAAGT | 1152 | 59.12 | −1.20 | −0.183 | −1.156 | −0.552 | −0.475 | 274.7 |
| 1009 | AGAGTGATCTGAGGGAAGTT | 1153 | 61.60 | −1.00 | 0.181 | −0.982 | −0.261 | −0.463 | 297.2 |
| 1010 | GAGTGATCTGAGGGAAGTTA | 1154 | 60.78 | −0.30 | 0.061 | −0.373 | −0.104 | −0.414 | 250.6 |
| 1011 | AGTGATCTGAGGGAAGTTAA | 1155 | 57.35 | 0.60 | −0.443 | 0.410 | −0.119 | −0.318 | 231.3 |
| 1012 | GTGATCTGAGGGAAGTTAAA | 1156 | 55.25 | 0.60 | −0.751 | 0.410 | −0.310 | −0.286 | 214.5 |
| 1013 | TGATCTGAGGGAAGTTAAAG | 1157 | 52.55 | 0.60 | −1.147 | 0.410 | −0.556 | −0.295 | 102.3 |
| 1014 | GATCTGAGGGAAGTTAAAGG | 1158 | 55.09 | 0.60 | −0.774 | 0.410 | −0.324 | −0.330 | 102.3 |
| 1015 | ATCTGAGGGAAGTTAAAGGA | 1159 | 55.09 | 0.60 | −0.774 | 0.410 | −0.324 | −0.367 | 49.4 |
| 1016 | TCTGAGGGAAGTTAAAGGAT | 1160 | 55.09 | 0.60 | −0.774 | 0.410 | −0.324 | −0.379 | 104.3 |
| 1017 | CTGAGGGAAGTTAAAGGATA | 1161 | 53.32 | 1.00 | −1.034 | 0.757 | −0.353 | −0.370 | 46.3 |
| 1018 | TGAGGGAAGTTAAAGGATAC | 1162 | 51.95 | 1.30 | −1.235 | 1.018 | −0.378 | −0.360 | 50.9 |
| 1019 | GAGGGAAGTTAAAGGATACA | 1163 | 53.26 | 0.90 | −1.043 | 0.670 | −0.392 | | 58.2 |
| 1020 | AGGGAAGTTAAAGGATACAG | 1164 | 52.14 | 0.90 | −1.207 | 0.670 | −0.494 | | 50.5 |
| 1021 | GGGAAGTTAAAGGATACAGT | 1165 | 54.81 | 0.90 | −0.815 | 0.670 | −0.251 | | 53.1 |

Example 3

Synopsis:

The method of the present invention is particularly useful as a guide to the iterative refinement of probes. One of the specific predictions made for rabbit β-globin in Example 1 is used to provide an example of such a refinement.

Materials and Methods:

The contig spanning positions 5–11 of a portion of the rabbit β-globin gene (Example 1, Table 3) was analyzed, using the experimentally measured data to simulate the results of successive experimental measurements. The iterative refinement was performed using a rule-based algorithm, outlined below. This algorithm is used by way of example only; other algorithms for efficiently finding local maxima are well known to the art and could be employed to perform this task.

Given experimental data for probes from the $1^{st}$ quartile, median and $3^{rd}$ quartile of a contig, as well as a user-set signal threshold for further consideration of a probe, 1) If all 3 measurements are below the user-specified signal threshold, discard the prediction.
2) If at least one of the measurements is above the user-specified threshold, determine which point yields the maximum signal.
   a) If the maximum point is the $1^{st}$ quartile probe, then make three new measurements for probes with the same spacing as that used in the preceding iteration, but displaced so that the third probe is identical to the original $1^{st}$ quartile probe. In other words, repeat the search with the same pattern and spacing, but displace the pattern in the direction of increasing signal found in the first experiment.
   b) If the maximum point is the $3^{rd}$ quartile probe, then make three new measurements for probes with the same spacing as that used in the preceding iteration, but displaced so that the first probe is identical to the original $3^{rd}$ quartile probe. In other words, repeat the search with the same pattern and spacing, but displace the pattern in the direction of increasing signal found in the first experiment.
   c) If the maximum point is the median probe, then repeat the experiment, keeping the median point the same, but shrinking the spacing between probes by a factor of 2.
3) Continue iteration until a maximum is found, or the user judges the signal level observed to be acceptable. Use the experimental value measured for the probe duplicated in successive iterations to tie together the successive data sets, via a simple normalization procedure, described below. Where appropriate, consider all of the data (i.e. all of the iterations) when deciding how to proceed, or whether the peak hybridization intensity has been found.

Results:

Iterative refinement of the contig spanning positions 5–11 in Table 3 proceeds as follows:

Iteration 1: Probes are synthesized at positions 6, 8 and 10, yielding the experimental hybridization intensities 180, 220 and 310, respectively.

Iteration 2: Following rule 2b), probes are synthesized at positions 10, 12 and 14. Note that the redundant measurement at position 10 serves as a bridge between experiments, and allows comparison of the two sets by normalizing the intensities by multiplying the second iteration measurements by the ratio of the intensity observed for the probe at position 10 in the first iteration to the value observed in the second iteration. In the simplest case, the ratio is 1; in any case, the second iteration yields the normalized values 310, 390, 240 for probe positions 10, 12 and 14, respectively.

Iteration 3: By rule 2c), measurements are performed for probes at positions 11, 12 and 13; after normalization, these yield the normalized hybridization intensities 320, 390 and 410, respectively. Combination of these results with the results from iteration 2, probe position 14, yields the conclusion that the best probe for this intensity peak is the probe that starts at sequence position 13. The overall result is that iterative improvement converges in three iterations, and requires the synthesis of seven test probes, one of which is the local optimal probe. In addition, the first and second iterations yield probes that exhibit 75% and 95% of the local maximum hybridization intensities, respectively. In many applications, either of these probes would be considered acceptable.

The above examples 1 and 2 demonstrate that two different implementations of the method of the present invention are capable of efficiently predicting regions of high hybridization efficiency in a variety of polynucleotide targets. Many of the predictions yield acceptable probe sequences on the first design iteration, and all would yield optimized probe sets after 2–4 rounds of iterative refinement, as demonstrated in Example 3. The performance demonstrated in these examples greatly exceeds the performance of current methods. Finally, the examples demonstrate that the predictions can be performed by a software application that has been implemented and installed on a Pentium®-based computer workstation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for predicting the potential of an oligonucleotide to hybridze to a target nucleotide sequence, said method comprising:
  (a) identifying a predetermined number of unique oligonucleotides of at least 5 nucleotides in length within a nucleotide sequence of at least 30 nucleotides in length that is hybridizable with said target nucleotide sequence, said oligonucleotides being chosen to sample the entire length of said nucleotide sequence,
  (b) determining and evaluating for each of said oligonucleotides at least one parameter that is independently predictive of the ability of each of said oligonucleotides to hybridize to said target nucleotide sequence,
  (c) selecting a subset of oligonucleotides within said predetermined number of unique oligonucleotides based on an examination of said parameter and application of a rule that rejects some of said oligonucleotides of step (b),
  (d) identifying oligonucleotides in said selected subset, viewed according to order of position along said nucleotide sequence, that are clustered along a region of said nucleotide sequence, and,
  (e) selecting, from said oliaonucleotides identified in step (d), oligonucleotides of higher hybridization potential for said target nucleotide sequence wherein the larger the size of said clusters, the higher said hybridization potential.

2. A method according to claim 1 which comprises ranking said oligonucleotides of step (e) based on the size of said clusters of oligonucleotides.

3. A method according to claim 1 wherein said unique oligonucleotides are of identical length N.

4. A method according to claim 3 wherein said unique oligonucleotides are spaced one nucleotide apart, said predetermined number comprising L−N+1 oligonucleotides, where L is the length of the hybridizable sequence.

5. A method according to claim 1 wherein said parameter is selected from the group consisting of composition factors, thermodynamic factors, chemosynthetic efficiencies and kinetic factors.

6. A method according to claim 1 wherein said parameter is a composition factor selected from the group consisting of mole fraction (G+C) and percent (G+C).

7. A method according to claim 1 wherein said parameter is a thermodynamic factor selected from the group consisting of predicted duplex melting temperature, predicted enthalpy of duplex formation, predicted entropy of duplex formation, predicted free energy of duplex formation, predicted melting temperature of the most stable intramolecular structure of the oligonucleotide or its complement, predicted enthalpy of the most stable intramolecular structure of the oligonucleotide or its complement, predicted entropy of the most stable intramolecular structure of the oligonucleotide or its complement, predicted free energy of the most stable intramolecular structure of the oligonucleotide or its complement, predicted melting temperature of the most stable hairpin structure of the oligonucleotide or its complement, predicted enthalpy of the most stable hairpin structure of the oligonucleotide or its complement, predicted entropy of the most stable hairpin structure of the oligonucleotide or its complement, predicted free energy of the most stable hairpin structure of the oligonucleotide or its complement, thermodynamic partition function for intramolecular structure of the oligonucleotide or its complement.

8. A method according to claim 1 wherein said parameter is a chemosynthetic efficiency selected from the group consisting of coupling efficiencies and efficiency of the synthesis of a target nucleotide sequence or an oligonucleotide probe.

9. A method according to claim 1 wherein said parameter is a kinetic factor selected from the group consisting of steric factors calculated via molecular modeling, rate constants calculated via molecular dynamics simulations, rate constants calculated via semi-empirical kinetic modeling, associative rate constants, dissociative rate constants, enthalpies of activation, entropies of activation, and free energies of activation.

10. A method according to claim 1 wherein said parameter is derived from a factor by mathematical transformation of said factor.

11. A method according to claim 1 which comprises ranking said clustered oligonucleotides of step (e) based on the size of said clusters of oligonucleotides and selecting a subset of said clustered oligonucleotides.

12. A method according to claim 11 wherein said subset consists of any number of oligonucleotides within said cluster of oligonucleotides.

13. A method according to claim 11 wherein the subset of said clustered oligonucleotides are selected to statistically sample the cluster.

14. A method according to claim 13 wherein said statistical sample consists of oligonucleotides spaced at the first quartile, median and third quartile of the cluster of oligonucleotides.

15. A method according to claim 1 wherein said parameters are determined for said oligonucleotides by means of a computer program.

16. A method according to claim 1 wherein said oligonucleotides are attached to a surface.

17. A method according to claim 1 wherein said oligonucleotides are DNA.

18. A method according to claim 1 wherein said oligonucleotides are RNA.

19. A method according to claim 1 wherein said oligonucleotides contain chemically modified nucleotides.

20. A method according to claim 1 wherein said target nucleotide sequence is RNA.

21. A method according to claim 1 wherein said target nucleotide sequence is DNA.

22. A method according to claim 1 wherein said target nucleotide sequence contains chemically modified nucleotides.

23. A method according to claim 1 wherein said parameter is, for each oligonucleotide/target nucleotide sequence duplex, the difference between the predicted duplex melting temperature corrected for salt concentration and the temperature of hybridization of each of said oligonucleotides with said target nucleotide sequence.

24. A method according to claim 1 wherein step (c) comprises identifying a subset of oligonucleotides within said predetermined number of unique oligonucleotides by establishing cut-off values for said parameter.

25. A method according to claim 1 wherein said step (c) comprises identifying a subset of oligonucleotides within said predetermined number of unique oligonucleotides by converting the values of said parameters into a dimensionless number wherein the following equations are used for converting the values of said parameters into a dimensionless number:

$$S_{i,x} = \frac{x_i - \langle x \rangle}{\sigma_{\{x\}}},$$

where $S_{i,x}$ is the dimensionless score derived from parameter x calculated for oligonucleotide i, $x_i$ is the value of parameter x calculated for oligonucleotide i, $\langle x \rangle$ is the average of parameter x calculated for all of the oligonucleotides under consideration for a given nucleotide sequence target, and $\sigma_{\{x\}}$ is the standard deviation of parameter x calculated for all of the oligonucleotides under consideration for a given nucleotide sequence target, and is given by the equation $$\sigma_{\{x\}} = \sqrt{\frac{\sum_{j=1}^{L-N+1} (x_j - \langle x \rangle)^2}{L - N}},$$

where the target sequence is of length L and the oligonucleotides are of length N.

26. A method according to claim 25 wherein said value is converted into a dimensionless number by determining a dimensionless score for each parameter resulting in a distribution of scores having a mean value of zero and a standard deviation of one.

27. A method according to claim 26 which comprises optimizing a method according to calculation for said parameter based on said individual scores.

28. A method according to claim 1 wherein step (b) comprises determining at least two parameters wherein said parameters are poorly correlated with respect to one another.

29. A method according to claim 28 wherein said parameters are derived from a combination of factors by mathematical transformation of those factors.

30. A method according to claim 1 wherein step (b) comprises determining two parameters at least one of said parameters being the association free energy between a subsequence within each of said oligonucleotides and its complementary sequence on said target nucleotide sequence.

31. A method according to claim 30 wherein said subsequence is 3 to 9 nucleotides in length.

32. A method according to claim 30 wherein said subsequence is 5 to 7 nucleotides in length.

33. A method according to claim 30 wherein said subsequence is at least three nucleotides from the terminus of said oligonucleotides.

34. A method according to claim 30 wherein said subsequence is at least three nucleotides from a surface to which said oligonucleotides are attached.

35. A method according to claim 30 wherein said oligonucleotides are attached to a surface and said subsequence is at least five nucleotides from the terminus of said oligonucleotides that is attached to said surface and at least three nucleotides from the free end of said oligonucleotides.

36. A method according to claim 30 wherein the association free energy of the members of a set of subsequences within each of said oligonucleotides is determined and said subsequence having the minimum value is identified.

37. A method according to claim 1 which comprises including oligonucleotides that are adjacent to said oligonucleotides in said subset that are clustered along a region of said target nucleotide sequence.

38. A method according to claim 1 which comprises (i) identifying a subset of oligonucleotides within said predetermined number of unique oligonucleotides establishing by cut-off values for each of said parameters.

39. A method according to claim 1 which comprises determining the sizes of said clusters of step (d) by counting the number of contiguous oligonucleotides in said region of said hybridizable sequence.

40. A method according to claim 1 which comprises determining the sizes of said clusters of step (d) by counting the number of oligonucleotides in said subset that begin in a region of predetermined length in said hybridizable sequence.

41. A method for predicting the potential of an oligonucleotide to hybridize to a complementary target nucleotide sequence, said method comprising:
    (a) identifying a set of overlapping oligonucleotides of at least 5 nucleotides in length from a nucleotide sequence of at least 30 nucleotides in length that is complementary to said target nucleotide sequence,
    (b) determining and evaluating for each of said oligonucleotides at least two parameters that are independently predictive of the ability of each of said oligonucleotides to hybridize to said target nucleotide sequence wherein said parameters are poorly correlated with respect to one another,
    (c) selecting a subset of oligonucleotides within said set of oligonucleotides based on an examination of said parameters and application of a rule that rejects some of said oligonucleotides of step (b),
    (d) identifying oligonucleotides in said selected subset, viewed according to order of position along said nucleotide sequence, that are clustered along a region of said complementary nucleotide sequence, and
    (e) selecting, from said oligonucleotides identified in step (d), oligonucleotides of higher hybridization potential for said target nucleotide sequence wherein the larger the size of said clusters, the higher said hybridization potential.

42. A method according to claim 41 which comprises ranking said oligonucleotides of step (e) based on the size of said clusters of oligonucleotides.

43. A method according to claim 41 which comprises determining the sizes of said clusters of step (e) by counting the number of contiguous oligonucleotides in said region of said complementary sequence.

44. A method according to claim 41 which comprises determining the sizes of said clusters of step (e) by counting the number of oligonucleotides in said subset that begin in a region of set length in said complementary sequence.

45. A method according to claim 41 wherein said overlapping oligonucleotides are of identical length N.

46. A method according to claim 45 wherein said overlapping oligonucleotides are spaced one nucleotide apart, said set comprising L−N+1 oligonucleotides, where L is the length of the complementary sequence.

47. A method according to claim 41 wherein said parameters are each independently selected from the group consisting of composition factors, thermodynamic factors, chemosynthetic efficiencies and kinetic factors.

48. A method according to claim 41 wherein said parameters are composition factors selected from the group consisting of mole fraction (G+C) and percent (G+C).

49. A method according to claim 41 wherein said parameters are thermodynamic factors selected from the group consisting of predicted duplex melting temperature, predicted enthalpy of duplex formation, predicted entropy of duplex formation, predicted free energy of duplex formation, predicted melting temperature of the most stable intramolecular structure of the oligonucleotide or its complement, predicted enthalpy of the most stable intramolecular structure of the oligonucleotide or its complement, predicted entropy of the most stable intramolecular structure of the oligonucleotide or its complement, predicted free energy of the most stable intramolecular structure of the oligonucleotide or its complement, predicted melting temperature of the most stable hairpin structure of the oligonucleotide or its complement, predicted enthalpy of the most stable hairpin structure of the oligonucleotide or its complement, predicted entropy of the most stable hairpin structure of the oligonucleotide or its complement, predicted free energy of the most stable hairpin structure of the oligonucleotide or its complement, thermodynamic partition function for intramolecular structure of the oligonucleotide or its complement.

50. A method according to claim 41 wherein any of said parameters is derived from a factor by mathematical transformation of said factor.

51. A method according to claim 49 wherein any of said parameters is derived from a combination of factors by mathematical transformation of those factors.

52. A method according to claim 41 wherein said parameters are chemosynthetic efficiencies selected from the group consisting of coupling efficiencies and efficiencies of the syntheses of a target nucleotide sequence or an oligonucleotide probe.

53. method according to claim 41 wherein said parameters are kinetic factors selected from the group consisting of steric factors calculated via molecular modeling, rate constants calculated via molecular dynamics simulations, rate constants calculated via semi-empirical kinetic modeling, associative rate constants, dissociative rate constants, enthalpies of activation, entropies of activation, and free energies of activation.

54. A method according to claim 41 which comprises ranking said clustered oligonucleotides of step (e) based on the size of said clusters of oligonucleotides and selecting a subset of said clustered oligonucleotides.

55. A method according to claim 54 wherein said subset consists of any number of oligonucleotides within said cluster of oligonucleotides.

56. A method according to claim 54 wherein the subset of said clustered oligonucleotides are selected to statistically sample the cluster.

57. A method according to claim 54 wherein said statistical sample consists of oligonucleotides spaced at the first quartile, median and third quartile of the cluster of oligonucleotides.

58. A method according to claim 41 wherein said parameters are determined for said oligonucleotides by means of a computer program.

59. A method according to claim 41 wherein said oligonucleotides are attached to a surface.

60. A method according to claim 41 wherein said oligonucleotides are DNA.

61. A method according to claim 41 wherein said oligonucleotides are RNA.

62. A method according to claim 41 wherein said oligonucleotides contain chemically modified nucleotides.

63. A method according to claim 41 wherein said target nucleotide sequence is RNA.

64. A method according to claim 41 wherein said target nucleotide sequence is DNA.

65. A method according to claim 41 wherein said target nucleotide sequence contains chemically modified nucleotides.

66. A method according to claim 41 wherein said parameter is, for each oligonucloetide/target nucleotide sequence duplex, the difference between the predicted duplex melting temperature corrected for salt concentration and the temperature of hybridization of each of said oligonucleotides with said target nucleotide sequence.

67. method according to claim 41 wherein step (c) comprises identifying a subset of oligonucleotides within said set of oligonucleotides by establishing cut-off values for each set of parameters.

68. A method according to claim 41 wherein said step (c) comprises identifying a subset of oligonucleotides within said set of oligonucleotides by converting the values of said parameters into a dimensionless number wherein the following equations are used for converting the values of said parameters into a dimensionless number:

$$s_{i,x} = \frac{x_i - \langle x \rangle}{\sigma_{\{x\}}},$$

where $S_{i,x}$ is the dimensionless score derived from parameter x calculated for oligonucleotide i, $x_i$ is the value of parameter x calculated for oligonucleotide i, <x> is the average of parameter x calculated for all of the oligonucleotides under consideration for a given nucleotide sequence target, and $\sigma_{\{x\}}$ is the standard deviation of parameter x calculated for all of the oligonucleotides under consideration for a given nucleotide sequence target, and is given by the equation $$\sigma_{\{x\}} = \sqrt{\frac{\sum_{j=1}^{L-N+1}(x_j - \langle x \rangle)^2}{L-N}},$$

where the target sequence is of length L and the oligonucleotides are of length N.

69. A method according to claim 66 wherein said values are converted into dimensionless numbers by (a) determining a dimensionless score for each parameter resulting in a distribution of scores having a mean value of zero and a standard deviation of one and (b) calculating a combination score by evaluating a weighted average of the individual scores.

70. A method according to claim 69 wherein step (b) comprises optimizing the weighting factors based on comparison of said individual scores to a calibration data set.

71. A method according to claim 41 wherein step (b) comprises determining two parameters at least one of said parameters being the association free energy between a subsequence within each of said oligonucleotides and its complementary sequence on said target nucleotide sequence.

72. A method according to claim 71 wherein said subsequence is 3 to 9 nucleotides in length.

73. A method according to claim 71 wherein said subsequence is 5 to 7 nucleotides in length.

74. A method according to claim 71 wherein said subsequence is at least three nucleotides from the terminus of said oligonucleotides.

75. A method according to claim 71 wherein said oligonucleotides are attached to a surface and said subsequence is at least five nucleotides from the terminus of said oligonucleotides that is attached to said surface and at least three nucleotides from the free end of said oligonucleotides.

76. A method according to claim 71 wherein the association free energy of the members of a set of subsequences within each of said oligonucleotides is determined and said subsequence having the minimum value is identified.

77. A method according to claim 41 which comprises including in said evaluation oligonucleotides that are adjacent to said oligonucleotides in said subset that are clustered along a region of said target nucleotide sequence.

78. A method for predicting the potential of an oligonucleotide to hybridize to a complementary target nucleotide sequence, said method comprising:
 (a) obtaining, from a nucleotide sequence of at least 30 nucleotides in length complementary to said target nucleotide sequence, a set of overlapping oligonucleotides of at least 5 nucleotides in length and of identical length N and spaced one nucleotide apart, said set comprising L–N+1 oligonucleotides,
 (b) determining and evaluating for each of said oligonucleotides the parameters: (i) the predicted melt temperature of the duplex of said oligonucleotide and said target nucleotide sequence corrected for salt concentration and (ii) predicted free energy of the most stable intramolecular structure of the oligonucleotide at the temperature of hybridization of each of said oligonucleotides with said target nucleotide sequence,
 (c) identifying a subset of oligonucleotides within said set of oligonucleotides based on an examination of said parameters by establishing cut-off values for each of said parameters,
 (d) ranking oligonucleotides in said subset of step (c), viewed according to order of position along said nucleotide sequence, that are clustered along a region of said complementary nucleotide sequence based on the size of said clusters of oligonucleotides, and
 (e) selecting, based on said ranking, a subset of said clustered oligonucleotides identified in step (d) having higher hybridization potential for said target nucleotide sequence wherein the larger the size of said clusters, the higher said hybridization potential.

79. A method according to claim 78 wherein said subset consists of any number of oligonucleotides within said cluster of oligonucleotides.

80. A method according to claim 78 wherein the subset of said clustered oligonucleotides are selected to statistically sample the cluster.

81. A method according to claim 78 wherein said parameters are derived from a factor by mathematical transformation of said factor.

82. A method according to claim 78 wherein the melting temperature of step (b) is transform by subtracting the temperature of hybridization.

83. A method according to claim 78 which comprises determining the sizes of said clusters of step (d) by counting the number of contiguous oligonucleotides in said region of said complementary sequence.

84. A method according to claim 78 wherein said statistical sample consists of oligonucleotides spaced at the first quartile, median and third quartile of the cluster of oligonucleotides.

85. A method according to claim 78 wherein said parameters are determined for said oligonucleotides by means of a computer program.

86. A method according to claim 78 wherein said oligonucleotides are attached to a surface.

87. A method according to claim 78 wherein said oligonucleotides are DNA.

88. A method according to claim 78 wherein said oligonucleotides are RNA.

89. A method according to claim 78 wherein said oligonucleotides contain chemically modified nucleotides.

90. A method according to claim 78 wherein said target nucleotide sequence is RNA.

91. A method according to claim 78 wherein said target nucleotide sequence is DNA.

92. A method according to claim 78 wherein said target nucleotide sequence contains chemically modified nucleotides.

93. A method according to claim 68 wherein a combination score $S_i$ is calculated by evaluating a weighted average of the individual values of the dimensionless scores $S_{i,x}$ by the equation:

$$S_i = \sum_{\{x\}} q_x s_{i,x},$$

where $q_x$ is the weight assigned to the score derived from parameter x, the individual values of $q_x$ are always greater than zero, and the sum of the weights $q_x$ is unity.

94. A method according to claim 78 where clustering is determined by calculating a moving window-averaged combination score $<S_i>$ for the ith probe by the equation:

$$\langle S_i \rangle = \frac{1}{w} \sum_{j=i-\frac{w-1}{2}}^{i+\frac{w-1}{2}} S_j, \quad w = \text{an odd integer},$$

where w is the length of the window for averaging, and then applying a cutoff filter to the value of $<S_i>$.

95. A method according to claim 93 wherein optimization of the weights $q_x$ is performed by varying the values of the weights so that the correlation coefficient $\rho_{\{<Si>\},\{Vi\}}$ between the set of window-averaged combination scores $\{<S_i>\}$ and a set of calibration experimental measurements $\{V_i\}$ is maximized wherein the correlation coefficient $\rho_{\{<Si>\},\{Vi\}}$ is calculated from the equation $$\rho_{x,y} = \frac{\text{Covariance}(x, y)}{\sqrt{\text{Variance}(x)\text{Variance}(y)}},$$

where $x=<S_i>$, $y=V_i$ and the Covariance (x,y) is defined by $$\text{Covariance}(x, y) = \frac{1}{N}\sum_{i=1}^{N}(x_i - \mu_x)(y_i - \mu_y)$$

wherein the quantities $\mu_x$ and $\mu_y$ are the averages of the quantities x and y, while the variances are the squares of the standard deviations.

96. A method according to claim 95 wherein the cutoff filter selects the lowest values of the window-averaged combination score $<S_i>$ and the clustered probes so identified are predicted to exhibit low hybridization efficiency.

97. A computer based method for predicting the potential of an oligonucleotide to hybridize to a target nucleotide sequence, said method comprising:

(a) identifying under computer control a predetermined number of unique oligonucleotides of at least 5 nucleotides in length within a nucleotide sequence of at least 30 nucleotides in length that is hybridizable with said target nucleotide sequence, said oligonucleotides being chosen to sample the entire length of said nucleotide sequence, (b) under computer control, determining and evaluating for each of said oligonucleotides a value for at least one parameter that is independently predictive of the ability of each of said oligonucleotides to hybridize to said target nucleotide sequence and storing said parameter values, (c) selecting under computer control, from said stored parameter values, a subset of oligonucleotides within said predetermined number of unique oligonucleotides based on an examination of said parameter and application of a rule that rejects some of said oligonucleotides of step (b), (d) identifying under computer control oligonucleotides in said selected subset, viewed according to order of position along said nucleotide sequence, that are clustered along a region of said nucleotide sequence that is hybridizable to said target nucleotide sequence, and (e) under computer control selecting, from said oligonucleotides identified in step (d), oligonucleotides of higher hybridization potential for said target nucleotide sequence wherein the larger the size of said clusters, the higher said hybridization potential.

98. A method according to claim 97 wherein the identified subset of oligonucleotide sequences is electronically transferred to an oligonucleotide array manufacturing system.

* * * * *

SEQUENCE LISTING (1) GENERAL INFORMATION:

(iii) NUMBER OF SEQUENCES: 1165

(2) INFORMATION FOR SEQ ID NO: 1:

(i) SEQUENCE CHARACTERISTICS:

(A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (ix) FEATURE:
        (A) NAME/KEY: stem_loop
        (B) LOCATION: 2..21

(xi) SEQUENCE DESCRIPTION: SEQ ID NO: 1:

ACTGGCAATC ACAATTGCCA GTAA                                               24

(2) INFORMATION FOR SEQ ID NO: 2:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (vi) ORIGINAL SOURCE:
        (A) ORGANISM: Saccharomyces cerevisiae (ix) FEATURE:
        (A) NAME/KEY: tRNA
        (B) LOCATION: 1..75
        (C) IDENTIFICATION METHOD: experimental
        (D) OTHER INFORMATION: /function= "transfer RNA"
            /product= "tRNA-Ala"
            /evidence= EXPERIMENTAL
            /anticodon= (pos: 34 .. 36, aa: Ala)
            /citation= ([1|2])

(ix) FEATURE:
        (A) NAME/KEY: modified_base
        (B) LOCATION: 9
        (C) IDENTIFICATION METHOD: experimental
        (D) OTHER INFORMATION: /evidence= EXPERIMENTAL
            /frequency= 0.9999
            /mod_base= m1g
            /citation= ([1|2])

(ix) FEATURE:
        (A) NAME/KEY: modified_base
        (B) LOCATION: 16
        (C) IDENTIFICATION METHOD: experimental
        (D) OTHER INFORMATION: /evidence= EXPERIMENTAL
            /frequency= 0.9999
            /mod_base= d
            /citation= ([1|2])

(ix) FEATURE:
        (A) NAME/KEY: modified_base
        (B) LOCATION: 20
        (C) IDENTIFICATION METHOD: experimental
        (D) OTHER INFORMATION: /evidence= EXPERIMENTAL
            /frequency= 0.9999
            /mod_base= d
            /citation= ([1|2])

(ix) FEATURE:
        (A) NAME/KEY: modified_base
        (B) LOCATION: 26
        (C) IDENTIFICATION METHOD: experimental
        (D) OTHER INFORMATION: /evidence= EXPERIMENTAL

```
    /frequency= 0.9999
    /mod_base= m22g
    /citation= ([1|2])

(ix) FEATURE:
    (A) NAME/KEY: modified_base
    (B) LOCATION: 34
    (C) IDENTIFICATION METHOD: experimental
    (D) OTHER INFORMATION: /evidence= EXPERIMENTAL
        /frequency= 0.9999
        /mod_base= i
        /citation= ([1|2])

(ix) FEATURE:
    (A) NAME/KEY: modified_base
    (B) LOCATION: 37
    (C) IDENTIFICATION METHOD: experimental
    (D) OTHER INFORMATION: /evidence= EXPERIMENTAL
        /frequency= 0.9999
        /mod_base= m1i
        /citation= ([1|2])

(ix) FEATURE:
    (A) NAME/KEY: modified_base
    (B) LOCATION: 38
    (C) IDENTIFICATION METHOD: experimental
    (D) OTHER INFORMATION: /evidence= EXPERIMENTAL
        /frequency= 0.9999
        /mod_base= p
        /citation= ([1|2])

(ix) FEATURE:
    (A) NAME/KEY: modified_base
    (B) LOCATION: 46
    (C) IDENTIFICATION METHOD: experimental
    (D) OTHER INFORMATION: /evidence= EXPERIMENTAL
        /frequency= 0.9999
        /mod_base= d
        /citation= ([1|2])

(ix) FEATURE:
    (A) NAME/KEY: modified_base
    (B) LOCATION: 53
    (C) IDENTIFICATION METHOD: experimental
    (D) OTHER INFORMATION: /evidence= EXPERIMENTAL
        /frequency= 0.9999
        /mod_base= t
        /citation= ([1|2])

(ix) FEATURE:
    (A) NAME/KEY: modified_base
    (B) LOCATION: 54
    (C) IDENTIFICATION METHOD: experimental
    (D) OTHER INFORMATION: /evidence= EXPERIMENTAL
        /frequency= 0.9999
        /mod_base= p
        /citation= ([1|2])

(x) PUBLICATION INFORMATION:
    (A) AUTHORS: Holley, R. W.
                 Apgar, J.
                 Everett, G. A.
                 Madison, J. T.
                 Marquisee, M.
                 Merrill, S. H.
                 Penswick, J. R.
                 Zamir, A.
    (B) TITLE: Structure of a ribonucleic acid
    (C) JOURNAL: Science
    (D) VOLUME: 147
    (F) PAGES: 1462-1465
    (G) DATE: 1965
    (K) RELEVANT RESIDUES IN SEQ ID NO: 2: FROM 1 TO 75

(x) PUBLICATION INFORMATION:
    (A) AUTHORS: Penswick, J. R.
                 Martin, R.
                 Dirheimer, G.
    (B) TITLE: Evidence supporting a revised sequence for
```

```
            yeast alanine tRNA
       (C) JOURNAL: FEBS Lett.
       (D) VOLUME: 50
       (F) PAGES: 28-31
       (G) DATE: 1975
       (K) RELEVANT RESIDUES IN SEQ ID NO: 2: FROM 1 TO 75

(xi) SEQUENCE DESCRIPTION: SEQ ID NO: 2:

GGGCGUGUGG CGUAGUCGGU AGCGCGCUCC CUUGGCGUGG GAGAGUCUCC GGUUCGAUUC     60

CGGACUCGUC CACCA                                                     75

(2) INFORMATION FOR SEQ ID NO: 3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 3:

ATGGACTTAG CATTCG                                                    16

(2) INFORMATION FOR SEQ ID NO: 4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 4:

ATGGACTTAG CA                                                        12

(2) INFORMATION FOR SEQ ID NO: 5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 5:

TGGACTTAGC AT                                                        12

(2) INFORMATION FOR SEQ ID NO: 6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: YES (iv) ANTI-SENSE: NO (xi) SEQUENCE DESCRIPTION: SEQ ID NO: 6:

GGACTTAGCA TT                                                                12

(2) INFORMATION FOR SEQ ID NO: 7:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 7:

GACTTAGCAT TC                                                                12

(2) INFORMATION FOR SEQ ID NO: 8:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 8:

ACTTAGCATT CG                                                                12

(2) INFORMATION FOR SEQ ID NO: 9:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 9:

GTCCAAAAAG GGTCAGTCTA CCTCCCGCCA TAAAAAACTC ATGTTCAAGA                        50

(2) INFORMATION FOR SEQ ID NO: 10:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 10:

GTCCAAAAAG GGTCAGTCTA CCTCC                                              25

(2) INFORMATION FOR SEQ ID NO: 11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 11:

TCCAAAAAGG GTCAGTCTAC CTCCC                                              25

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 12:

CCAAAAAGGG TCAGTCTACC TCCCG                                              25

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 13:

CAAAAGGGT CAGTCTACCT CCCGC                                               25

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO

```
        (xi) SEQUENCE DESCRIPTION: SEQ ID NO: 14:

AAAAAGGGTC AGTCTACCTC CCGCC                                              25

(2) INFORMATION FOR SEQ ID NO: 15:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 15:

AAAAGGGTCA GTCTACCTCC CGCCA                                              25

(2) INFORMATION FOR SEQ ID NO: 16:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 16:

AAAGGGTCAG TCTACCTCCC GCCAT                                              25

(2) INFORMATION FOR SEQ ID NO: 17:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 17:

AAGGGTCAGT CTACCTCCCG CCATA                                              25

(2) INFORMATION FOR SEQ ID NO: 18:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 18:

AGGGTCAGTC TACCTCCCGC CATAA                                              25
```

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 19:

GGGTCAGTCT ACCTCCCGCC ATAAA                                   25

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 20:

GGTCAGTCTA CCTCCCGCCA TAAAA                                   25

(2) INFORMATION FOR SEQ ID NO: 21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 21:

GTCAGTCTAC CTCCCGCCAT AAAAA                                   25

(2) INFORMATION FOR SEQ ID NO: 22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 22:

TCAGTCTACC TCCCGCCATA AAAAA                                   25

(2) INFORMATION FOR SEQ ID NO: 23:

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 23:

CAGTCTACCT CCCGCCATAA AAAAC                                              25

(2) INFORMATION FOR SEQ ID NO: 24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 24:

AGTCTACCTC CCGCCATAAA AAACT                                              25

(2) INFORMATION FOR SEQ ID NO: 25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 25:

GTCTACCTCC CGCCATAAAA AACTC                                              25

(2) INFORMATION FOR SEQ ID NO: 26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 26:

TCTACCTCCC GCCATAAAAA ACTCA                                              25

(2) INFORMATION FOR SEQ ID NO: 27:

(i) SEQUENCE CHARACTERISTICS:
        (A) LENGTH: 25 base pairs
```

```
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 27:

CTACCTCCCG CCATAAAAAA CTCAT                                              25

(2) INFORMATION FOR SEQ ID NO: 28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 28:

TACCTCCCGC CATAAAAAAC TCATG                                              25

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 29:

ACCTCCCGCC ATAAAAACT CATGT                                               25

(2) INFORMATION FOR SEQ ID NO: 30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 30:

CCTCCCGCCA TAAAAACTC ATGTT                                               25

(2) INFORMATION FOR SEQ ID NO: 31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear
```

```
        (ii) MOLECULE TYPE: cDNA (iii) HYPOTHETICAL: YES (iv) ANTI-SENSE: NO (xi) SEQUENCE DESCRIPTION: SEQ ID NO: 31:

CTCCCGCCAT AAAAAACTCA TGTTC                                              25

(2) INFORMATION FOR SEQ ID NO: 32:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 32:

TCCCGCCATA AAAAACTCAT GTTCA                                              25

(2) INFORMATION FOR SEQ ID NO: 33:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 33:

CCCGCCATAA AAAACTCATG TTCAA                                              25

(2) INFORMATION FOR SEQ ID NO: 34:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 34:

CCGCCATAAA AAACTCATGT TCAAG                                              25

(2) INFORMATION FOR SEQ ID NO: 35:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: cDNA
```

(iii) HYPOTHETICAL: YES (iv) ANTI-SENSE: NO (xi) SEQUENCE DESCRIPTION: SEQ ID NO: 35:

CGCCATAAAA AACTCATGTT CAAGA                                               25

(2) INFORMATION FOR SEQ ID NO: 36:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Oryctolagus cuniculus (ix) FEATURE:
        (A) NAME/KEY: 5'UTR
        (B) LOCATION: 1..53

(ix) FEATURE:
        (A) NAME/KEY: CDS
        (B) LOCATION: 54..122
        (D) OTHER INFORMATION: /codon_start= 54
            /product= "rabbit beta1 globin, N-terminus"
            /citation= ([1])

(x) PUBLICATION INFORMATION:
        (A) AUTHORS: Rohrbaugh, M. L.
                III Johnson, J. E.
                James, M. D.
                Hardison, R. C.
        (B) TITLE: Transcriptional unit of the rabbit beta1
            globin gene
        (C) JOURNAL: Mol. Cell. Biol.
        (D) VOLUME: 5
        (F) PAGES: 147-160
        (G) DATE: 1985
        (K) RELEVANT RESIDUES IN SEQ ID NO: 36: FROM 1 TO 122

(xi) SEQUENCE DESCRIPTION: SEQ ID NO: 36:

ACACTTGCTT TTGACACAAC TGTGTTTACT TGCAATCCCC CAAAACAGAC AGA ATG            56
                                                         Met
                                                           1

GTG CAT CTG TCC AGT GAG GAG AAG TCT GCG GTC ACT GCC CTG TGG GGC          104
Val His Leu Ser Ser Glu Glu Lys Ser Ala Val Thr Ala Leu Trp Gly
          5                  10                  15

AAG GTG AAT GTG GAA GAA                                                  122
Lys Val Asn Val Glu Glu
         20

(2) INFORMATION FOR SEQ ID NO: 37:

(i) SEQUENCE CHARACTERISTICS:
        (A) LENGTH: 1040 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Human immunodefficiency virus
         (B) STRAIN: type I
         (C) INDIVIDUAL ISOLATE: BH10

(ix) FEATURE:
         (A) NAME/KEY: misc_RNA
         (B) LOCATION: 1..1040
         (C) IDENTIFICATION METHOD: experimental
         (D) OTHER INFORMATION: /partial
             /function= "protease & reverse transcriptase
             regions"
             /product= "pol polyprotein (partial)"
             /evidence= EXPERIMENTAL
             /citation= ([1])

(x) PUBLICATION INFORMATION:
         (A) AUTHORS: Wong-Stahl, F.
                      Gallo, R. C.
                      Chang, N. T.
                      Ghrayeb, J.
                      Papas, T. S.
                      Lautenberger, J. A.
                      Pearson, M. L.
                      Jr. Petteway, S. R.
                      Ivanoff, L.
                      Baumeister, K.
         (B) TITLE: Complete nucleotide sequence of the AIDS
             virus, HTLV-III
         (C) JOURNAL: Nature
         (D) VOLUME: 313
         (F) PAGES: 277-284
         (G) DATE: 1985
         (K) RELEVANT RESIDUES IN SEQ ID NO: 37: FROM 1 TO 1040

(xi) SEQUENCE DESCRIPTION: SEQ ID NO: 37:

```
TGTACTGTCC ATTTATCAGG ATGGAGTTCA TAACCCATCC AAAGGAATGG AGGTTCTTTC      60

TGATGTTTTT TGTCTGGTGT GGTAAGTCCC CACCTCAACA GATGTTGTCT CAGCTCCTCT     120

ATTTTTGTTC TATGCTGCCC TATTTCTAAG TCAGATCCTA CATACAAATC ATCCATGTAT     180

TGATAGATAA CTATGTCTGG ATTTTGTTTT TTAAAAGGCT CTAAGATTTT TGTCATGCTA     240

CTTTGGAATA TTGCTGGTGA TCCTTTCCAT CCCTGTGGAA GCACATTGTA CTGATATCTA     300

ATCCCTGGTG TCTCATTGTT TATACTAGGT ATGGTAAATG CAGTATACTT CCTGAAGTCT     360

TCATCTAAGG GAACTGAAAA ATATGCATCA CCCACATCCA GTACTGTTAC TGATTTTTTC     420

TTTTTTAACC CTGCGGGATG TGGTATTCCT AATTGAACTT CCCAGAAGTC TTGAGTTCTC     480

TTATTAAGTT CTCTGAAATC TACTAATTTT CTCCATTTAG TACTGTCTTT TTTCTTTATG     540

GCAAATACTG GAGTATTGTA TGGATTCTCA GGCCCAATTT TTGAAATTTT CCCTTCCTTT     600

TCCATTTCTG TACAAATTTC TACTAATGCT TTTATTTTTT CTTCTGTCAA TGGCCATTGT     660

TTAACTTTTG GGCCATCCAT TCCTGGCTTT AATTTTACTG GTACAGTCTC AATAGGGCTA     720

ATGGGAAAAT TTAAAGTGCA ACCAATCTGA GTCAACAGAT TCTTCCAAT TATGTTGACA      780

GGTGTAGGTC CTACTAATAC TGTACCTATA GCTTTATGTC CACAGATTTC TATGAGTATC     840

TGATCATACT GTCTTACTTT GATAAAACCT CCAATTCCCC CTATCATTTT TGGTTTCCAT     900

CTTCCTGGCA AACTCATTTC TTCTAATACT GTATCATCTG CTCCTGTATC TAATAGAGCT     960

TCCTTTAGTT GCCCCCCTAT CTTTATTGTG ACGAGGGGTC GTTGCCAAAG AGTGATCTGA    1020

GGGAAGTTAA AGGATACAGT                                                 1040
```

(2) INFORMATION FOR SEQ ID NO: 38:

(i) SEQUENCE CHARACTERISTICS:
         (A) LENGTH: 999 base pairs
         (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 1..982
        (C) IDENTIFICATION METHOD: experimental
        (D) OTHER INFORMATION: /partial
            /codon_start= 2
            /function= "glycolysis"
            /product= "Glyceraldehydephosphate Dehydrogenase"
            /evidence= EXPERIMENTAL
            /standard_name= "G3PDH"
            /citation= ([1])

(ix) FEATURE:
        (A) NAME/KEY: promoter
        (B) LOCATION: 983..999
        (D) OTHER INFORMATION: /function= "promoter for T7 RNA
            polymerase"

(x) PUBLICATION INFORMATION:
        (A) AUTHORS: Arcari, P.
                     Martinelli, R.
                     Salvatore, F.
        (B) TITLE: The complete sequence of a full length cDNA
            for human liver glyceraldehyde-3-phosphate
            dehydrogenase: evidence for multiple mRNA species
        (C) JOURNAL: Nucleic Acids Res.
        (D) VOLUME: 12
        (E) ISSUE: 23
        (F) PAGES: 9179-9189
        (G) DATE: 1984
        (K) RELEVANT RESIDUES IN SEQ ID NO: 38: FROM 1 TO 999

(xi) SEQUENCE DESCRIPTION: SEQ ID NO: 38:
```

| | | | | | | | | | | | | | | | | |
|---|---|---|---|---|---|---|---|---|---|---|---|---|---|---|---|---|
| G | AAG | GTC | GGA | GTC | AAC | GGA | TTT | GGT | CGT | ATT | GGG | CGC | CTG | GTC | ACC | 46 |
| | Lys | Val | Gly | Val | Asn | Gly | Phe | Gly | Arg | Ile | Gly | Arg | Leu | Val | Thr | |
| | 1 | | | 5 | | | | | 10 | | | | | 15 | | |
| AGG | GCT | GCT | TTT | AAC | TCT | GGT | AAA | GTG | GAT | ATT | GTT | GCC | ATC | AAT | GAC | 94 |
| Arg | Ala | Ala | Phe | Asn | Ser | Gly | Lys | Val | Asp | Ile | Val | Ala | Ile | Asn | Asp | |
| | | | | 20 | | | | | 25 | | | | | 30 | | |
| CCC | TTC | ATT | GAC | CTC | AAC | TAC | ATG | GTT | TAC | ATG | TTC | CAA | TAT | GAT | TCC | 142 |
| Pro | Phe | Ile | Asp | Leu | Asn | Tyr | Met | Val | Tyr | Met | Phe | Gln | Tyr | Asp | Ser | |
| | | 35 | | | | | 40 | | | | | 45 | | | | |
| ACC | CAT | GGC | AAA | TTC | CAT | GGC | ACC | GTC | AAG | GCT | GAG | AAC | GGG | AAG | CTT | 190 |
| Thr | His | Gly | Lys | Phe | His | Gly | Thr | Val | Lys | Ala | Glu | Asn | Gly | Lys | Leu | |
| | | 50 | | | | | 55 | | | | | 60 | | | | |
| GTC | ATC | AAT | GGA | AAT | CCC | ATC | ACC | ATC | TTC | CAG | GAG | CGA | GAT | CCC | TCC | 238 |
| Val | Ile | Asn | Gly | Asn | Pro | Ile | Thr | Ile | Phe | Gln | Glu | Arg | Asp | Pro | Ser | |
| | 65 | | | | | 70 | | | | | 75 | | | | | |
| AAA | ATC | AAG | TGG | GGC | GAT | GCT | GGC | GCT | GAG | TAC | GTC | GTG | GAG | TCC | ACT | 286 |
| Lys | Ile | Lys | Trp | Gly | Asp | Ala | Gly | Ala | Glu | Tyr | Val | Val | Glu | Ser | Thr | |
| 80 | | | | | 85 | | | | | 90 | | | | | 95 | |
| GGC | GTC | TTC | ACC | ACC | ATG | GAG | AAG | GCT | GGG | GCT | CAT | TTG | CAG | GGG | GGA | 334 |
| Gly | Val | Phe | Thr | Thr | Met | Glu | Lys | Ala | Gly | Ala | His | Leu | Gln | Gly | Gly | |
| | | | | 100 | | | | | 105 | | | | | 110 | | |
| GCC | AAA | AGG | GTC | ATC | ATC | TCT | GCC | CCC | TCT | GCT | GAT | GCC | CCC | ATG | TTC | 382 |
| Ala | Lys | Arg | Val | Ile | Ile | Ser | Ala | Pro | Ser | Ala | Asp | Ala | Pro | Met | Phe | |
| | | | 115 | | | | | 120 | | | | | 125 | | | |
| GTC | ATG | GGT | GTG | AAC | CAT | GAG | AAG | TAT | GAC | AAC | AGC | CTC | AAG | ATC | ATC | 430 |

```
Val Met Gly Val Asn His Glu Lys Tyr Asp Asn Ser Leu Lys Ile Ile
        130                 135                 140

AGC AAT GCC TCC TGC ACC ACC AAC TGC TTA GCA CCC CTG GCC AAG GTC      478
Ser Asn Ala Ser Cys Thr Thr Asn Cys Leu Ala Pro Leu Ala Lys Val
        145                 150                 155

ATC CAT GAC AAC TTT GGT ATC GTG GAA GGA CTC ATG ACC ACA GTC CAT      526
Ile His Asp Asn Phe Gly Ile Val Glu Gly Leu Met Thr Thr Val His
160                 165                 170                 175

GCC ATC ACT GCC ACC CAG AAG ACT GTG GAT GGC CCC TCC GGG AAA CTG      574
Ala Ile Thr Ala Thr Gln Lys Thr Val Asp Gly Pro Ser Gly Lys Leu
                180                 185                 190

TGG CGT GAT GGC CGC GGG GCT CTC CAG AAC ATC ATC CCT GCC TCT ACT      622
Trp Arg Asp Gly Arg Gly Ala Leu Gln Asn Ile Ile Pro Ala Ser Thr
            195                 200                 205

GGC GCT GCC AAG GCT GTG GGC AAG GTC ATC CCT GAG CTA GAC GGG AAG      670
Gly Ala Ala Lys Ala Val Gly Lys Val Ile Pro Glu Leu Asp Gly Lys
        210                 215                 220

CTC ACT GGC ATG GCC TTC CGT GTC CCC ACT GCC AAC GTG TCA GTG GTG      718
Leu Thr Gly Met Ala Phe Arg Val Pro Thr Ala Asn Val Ser Val Val
    225                 230                 235

GAC CTG ACC TGC CGT CTA GAA AAA CCT GCC AAA TAT GAT GAC ATC AAG      766
Asp Leu Thr Cys Arg Leu Glu Lys Pro Ala Lys Tyr Asp Asp Ile Lys
240                 245                 250                 255

AAG GTG GTG AAG CAG GCG TCG GAG GGC CCC CTC AAA GGC ATC CTG GGC      814
Lys Val Val Lys Gln Ala Ser Glu Gly Pro Leu Lys Gly Ile Leu Gly
                260                 265                 270

TAC ACT GAG CAC CAG GTG GTC TCC TCT GAC TTC AAC AGC GAC ACC CAC      862
Tyr Thr Glu His Gln Val Val Ser Ser Asp Phe Asn Ser Asp Thr His
            275                 280                 285

TCC TCC ACC TTT GAC GCT GGG GCT GGC ATT GCC CTC AAC GAC CAC TTT      910
Ser Ser Thr Phe Asp Ala Gly Ala Gly Ile Ala Leu Asn Asp His Phe
        290                 295                 300

GTC AAG CTC ATT TCC TGG TAT GAC AAC GAA TTT GGC TAC AGC AAC AGG      958
Val Lys Leu Ile Ser Trp Tyr Asp Asn Glu Phe Gly Tyr Ser Asn Arg
    305                 310                 315

GTG GTG GAC CTC ATG GCC CAC ATG CTATAGTGAG TCGTATT                   999
Val Val Asp Leu Met Ala His Met
320                 325

(2) INFORMATION FOR SEQ ID NO: 39:

(i) SEQUENCE CHARACTERISTICS:
        (A) LENGTH: 1049 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 1..372
        (C) IDENTIFICATION METHOD: experimental
        (D) OTHER INFORMATION: /partial
            /codon_start= 1
            /function= "tumor suppressor"
            /product= "p53 (C-terminal portion)"
            /evidence= EXPERIMENTAL
            /gene= "HSP53G"
```

/standard_name= "p53"

(ix) FEATURE:
    (A) NAME/KEY: 3'UTR
    (B) LOCATION: 373..1049
    (D) OTHER INFORMATION: /citation= ([1])

(x) PUBLICATION INFORMATION:
    (A) AUTHORS: Futreal, P. A.
                 Barrett, J. C.
                 Wiseman, R. W.
    (B) TITLE: An Alu polymorphism intragenic to the TP53 gene
    (C) JOURNAL: Nucleic Acids Res.
    (D) VOLUME: 19
    (E) ISSUE: 24
    (F) PAGES: 6977-
    (G) DATE: 1991
    (K) RELEVANT RESIDUES IN SEQ ID NO: 39: FROM 1 TO 1049

(xi) SEQUENCE DESCRIPTION: SEQ ID NO: 39:

```
GAG GTG CGT GTT TGT GCC TGT CCT GGG AGA GAC CGG CGC ACA GAG GAA        48
Glu Val Arg Val Cys Ala Cys Pro Gly Arg Asp Arg Arg Thr Glu Glu
 1               5                  10                  15

GAG AAT CTC CGC AAG AAA GGG GAG CCT CAC CAC GAG CTG CCC CCA GGG        96
Glu Asn Leu Arg Lys Lys Gly Glu Pro His His Glu Leu Pro Pro Gly
                20                  25                  30

AGC ACT AAG CGA GCA CTG CCC AAC AAC ACC AGC TCC TCT CCC CAG CCA       144
Ser Thr Lys Arg Ala Leu Pro Asn Asn Thr Ser Ser Ser Pro Gln Pro
            35                  40                  45

AAG AAG AAA CCA CTG GAT GGA GAA TAT TTC ACC CTT CAG ATC CGT GGG       192
Lys Lys Lys Pro Leu Asp Gly Glu Tyr Phe Thr Leu Gln Ile Arg Gly
 50                  55                  60

CGT GAG CGC TTC GAG ATG TTC CGA GAG CTG AAT GAG GCC TTG GAA CTC       240
Arg Glu Arg Phe Glu Met Phe Arg Glu Leu Asn Glu Ala Leu Glu Leu
 65                  70                  75                  80

AAG GAT GCC CAG GCT GGG AAG GAG CCA GGG GGG AGC AGG GCT CAC TCC       288
Lys Asp Ala Gln Ala Gly Lys Glu Pro Gly Gly Ser Arg Ala His Ser
                85                  90                  95

AGC CAC CTG AAG TCC AAA AAG GGT CAG TCT ACC TCC CGC CAT AAA AAA       336
Ser His Leu Lys Ser Lys Lys Gly Gln Ser Thr Ser Arg His Lys Lys
            100                 105                 110

CTC ATG TTC AAG ACA GAA GGG CCT GAC TCA GAC TGA CATTCTCCAC            382
Leu Met Phe Lys Thr Glu Gly Pro Asp Ser Asp *
        115                 120

TTCTTGTTCC CCACTGACAG CCTCCCTCCC CCATCTCTCC CTCCCCTGCC ATTTTGGGTT     442

TTGGGTCTTT GAACCCTTGC TTGCAATAGG TGTGCGTCAG AAGCACCCAG GACTTCCATT     502

TGCTTTGTCC CGGGGCTCCA CTGAACAAGT TGGCCTGCAC TGGTGTTTTG TTGTGGGGAG     562

GAGGATGGGG AGTAGGACAT ACCAGCTTAG ATTTTAAGGT TTTTACTGTG AGGGATGTTT     622

GGGAGATGTA AGAAATGTTC TTGCAGTTAA GGGTTAGTTT ACAATCAGCC ACATTCTAGG     682

TAGGTAGGGG CCCACTTCAC CGTACTAACC AGGGAAGCTG TCCCTCATGT TGAATTTTCT     742

CTAACTTCAA GGCCCATATC TGTGAAATGC TGGCATTTGC ACCTACCTCA CAGAGTGCAT     802

TGTGAGGGTT AATGAAATAA TGTACATCTG GCCTTGAAAC CACCTTTTAT TACATGGGGT     862

CTAAAACTTG ACCCCCTTGA GGGTGCCTGT TCCCTCTCCC TCTCCCTGTT GGCTGGTGGG     922

TTGGTAGTTT CTACAGTTGG GCAGCTGGTT AGGTAGAGGG AGTTGTCAAG TCTTGCTGGC     982

CCAGCCAAAC CCTGTCTGAC AACCTCTTGG TCGACCTTAG TACCTAAAAG GAAATCTCAC    1042

CCCATCC                                                              1049
```

(2) INFORMATION FOR SEQ ID NO: 40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 40:

TTCTTCCACA TTCACCT                                              17

(2) INFORMATION FOR SEQ ID NO: 41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 41:

TCTTCCACAT TCACCTT                                              17

(2) INFORMATION FOR SEQ ID NO: 42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 42:

CTTCCACATT CACCTTG                                              17

(2) INFORMATION FOR SEQ ID NO: 43:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 43:

TTCCACATTC ACCTTGC                                              17

(2) INFORMATION FOR SEQ ID NO: 44:

(i) SEQUENCE CHARACTERISTICS:

(A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 44:

TCCACATTCA CCTTGCC                                                    17

(2) INFORMATION FOR SEQ ID NO: 45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 45:

CCACATTCAC CTTGCCC                                                    17

(2) INFORMATION FOR SEQ ID NO: 46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 46:

CACATTCACC TTGCCCC                                                    17

(2) INFORMATION FOR SEQ ID NO: 47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 47:

ACATTCACCT TGCCCCA                                                    17

(2) INFORMATION FOR SEQ ID NO: 48:

(i) SEQUENCE CHARACTERISTICS:
        (A) LENGTH: 17 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:48:

CATTCACCTT GCCCCAC                                              17

(2) INFORMATION FOR SEQ ID NO: 49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 49:

ATTCACCTTG CCCCACA                                              17

(2) INFORMATION FOR SEQ ID NO: 50:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 50:

TTCACCTTGC CCCACAG                                              17

(2) INFORMATION FOR SEQ ID NO: 51:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 51:

TCACCTTGCC CCACAGG                                              17

(2) INFORMATION FOR SEQ ID NO: 52:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 52:

CACCTTGCCC CACAGGG                                              17

(2) INFORMATION FOR SEQ ID NO: 53:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 53:

ACCTTGCCCC ACAGGGC                                              17

(2) INFORMATION FOR SEQ ID NO: 54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 54:

CCTTGCCCCA CAGGGCA                                              17

(2) INFORMATION FOR SEQ ID NO: 55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 55:

CTTGCCCCAC AGGGCAG                                              17

(2) INFORMATION FOR SEQ ID NO: 56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 56:

TTGCCCCACA GGGCAGT                                                      17

(2) INFORMATION FOR SEQ ID NO: 57:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 57:

TGCCCCACAG GGCAGTG                                                      17

(2) INFORMATION FOR SEQ ID NO: 58:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 58:

GCCCCACAGG GCAGTGA                                                      17

(2) INFORMATION FOR SEQ ID NO: 59:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 59:

CCCCACAGGG CAGTGAC                                                      17

(2) INFORMATION FOR SEQ ID NO: 60:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 60:

```
CCCACAGGGC AGTGACC                                                    17
```

(2) INFORMATION FOR SEQ ID NO: 61:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 61:

```
CCACAGGGCA GTGACCG                                                    17
```

(2) INFORMATION FOR SEQ ID NO: 62:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 62:

```
CACAGGGCAG TGACCGC                                                    17
```

(2) INFORMATION FOR SEQ ID NO: 63:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 63:

```
ACAGGGCAGT GACCGCA                                                    17
```

(2) INFORMATION FOR SEQ ID NO: 64:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 64:

```
CAGGGCAGTG ACCGCAG                                                    17
```

(2) INFORMATION FOR SEQ ID NO: 65:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 65:

AGGGCAGTGA CCGCAGA                                    17

(2) INFORMATION FOR SEQ ID NO: 66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 66:

GGGCAGTGAC CGCAGAC                                    17

(2) INFORMATION FOR SEQ ID NO: 67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 67:

GGCAGTGACC GCAGACT                                    17

(2) INFORMATION FOR SEQ ID NO: 68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 68:

GCAGTGACCG CAGACTT                                    17

(2) INFORMATION FOR SEQ ID NO: 69:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 69:

CAGTGACCGC AGACTTC                                                      17

(2) INFORMATION FOR SEQ ID NO: 70:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 70:

AGTGACCGCA GACTTCT                                                      17

(2) INFORMATION FOR SEQ ID NO: 71:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 71:

GTGACCGCAG ACTTCTC                                                      17

(2) INFORMATION FOR SEQ ID NO: 72:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 72:

TGACCGCAGA CTTCTCC                                                      17

(2) INFORMATION FOR SEQ ID NO: 73:

(i) SEQUENCE CHARACTERISTICS:
        (A) LENGTH: 17 base pairs
        (B) TYPE: nucleic acid (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 73:

GACCGCAGAC TTCTCCT                                                              17

(2) INFORMATION FOR SEQ ID NO: 74:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 74:

ACCGCAGACT TCTCCTC                                                              17

(2) INFORMATION FOR SEQ ID NO: 75:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 75:

CCGCAGACTT CTCCTCA                                                              17

(2) INFORMATION FOR SEQ ID NO: 76:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 76:

CGCAGACTTC TCCTCAC                                                              17

(2) INFORMATION FOR SEQ ID NO: 77:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 77:

GCAGACTTCT CCTCACT                                                    17

(2) INFORMATION FOR SEQ ID NO: 78:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 78:

CAGACTTCTC CTCACTG                                                    17

(2) INFORMATION FOR SEQ ID NO: 79:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 79:

AGACTTCTCC TCACTGG                                                    17

(2) INFORMATION FOR SEQ ID NO: 80:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 80:

GACTTCTCCT CACTGGA                                                    17

(2) INFORMATION FOR SEQ ID NO: 81:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 81:

ACTTCTCCTC ACTGGAC                                                     17

(2) INFORMATION FOR SEQ ID NO: 82:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 82:

CTTCTCCTCA CTGGACA                                                     17

(2) INFORMATION FOR SEQ ID NO: 83:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 83:

TTCTCCTCAC TGGACAG                                                     17

(2) INFORMATION FOR SEQ ID NO: 84:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 84:

TCTCCTCACT GGACAGA                                                     17

(2) INFORMATION FOR SEQ ID NO: 85:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 85:

CTCCTCACTG GACAGAT                                                                                       17

(2) INFORMATION FOR SEQ ID NO: 86:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 86:

TCCTCACTGG ACAGATG                                                                                       17

(2) INFORMATION FOR SEQ ID NO: 87:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 87:

CCTCACTGGA CAGATGC                                                                                       17

(2) INFORMATION FOR SEQ ID NO: 88:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 88:

CTCACTGGAC AGATGCA                                                                                       17

(2) INFORMATION FOR SEQ ID NO: 89:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 89:

TCACTGGACA GATGCAC                                                                                       17

(2) INFORMATION FOR SEQ ID NO: 90:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 90:

CACTGGACAG ATGCACC                                                17

(2) INFORMATION FOR SEQ ID NO: 91:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 91:

ACTGGACAGA TGCACCA                                                17

(2) INFORMATION FOR SEQ ID NO: 92:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 92:

CTGGACAGAT GCACCAT                                                17

(2) INFORMATION FOR SEQ ID NO: 93:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 93:

TGGACAGATG CACCATT                                                17

(2) INFORMATION FOR SEQ ID NO: 94:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 94:

GGACAGATGC ACCATTC                                                       17

(2) INFORMATION FOR SEQ ID NO: 95:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 95:

GACAGATGCA CCATTCT                                                       17

(2) INFORMATION FOR SEQ ID NO: 96:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 96:

ACAGATGCAC CATTCTG                                                       17

(2) INFORMATION FOR SEQ ID NO: 97:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 97:

CAGATGCACC ATTCTGT                                                       17

(2) INFORMATION FOR SEQ ID NO: 98:

(i) SEQUENCE CHARACTERISTICS:
        (A) LENGTH: 17 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 98:

AGATGCACCA TTCTGTC                                                17

(2) INFORMATION FOR SEQ ID NO: 99:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 99:

GATGCACCAT TCTGTCT                                                17

(2) INFORMATION FOR SEQ ID NO: 100:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 100:

ATGCACCATT CTGTCTG                                                17

(2) INFORMATION FOR SEQ ID NO: 101:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 101:

TGCACCATTC TGTCTGT                                                17

(2) INFORMATION FOR SEQ ID NO: 102:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 102:

GCACCATTCT GTCTGTT                                                          17

(2) INFORMATION FOR SEQ ID NO: 103:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 103:

CACCATTCTG TCTGTTT                                                          17

(2) INFORMATION FOR SEQ ID NO: 104:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 104:

ACCATTCTGT CTGTTTT                                                          17

(2) INFORMATION FOR SEQ ID NO: 105:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 105:

CCATTCTGTC TGTTTTG                                                          17

(2) INFORMATION FOR SEQ ID NO: 106:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: cDNA -continued (iii) HYPOTHETICAL: NO (iv) ANTI-SENSE: NO (xi) SEQUENCE DESCRIPTION: SEQ ID NO: 106:

CATTCTGTCT GTTTTGG                                                17

(2) INFORMATION FOR SEQ ID NO: 107:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 107:

ATTCTGTCTG TTTTGGG                                                17

(2) INFORMATION FOR SEQ ID NO: 108:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 108:

TTCTGTCTGT TTTGGGG                                                17

(2) INFORMATION FOR SEQ ID NO: 109:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 109:

TCTGTCTGTT TTGGGGG                                                17

(2) INFORMATION FOR SEQ ID NO: 110:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 110:

CTGTCTGTTT TGGGGGA                                                              17

(2) INFORMATION FOR SEQ ID NO: 111:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 111:

TGTCTGTTTT GGGGGAT                                                              17

(2) INFORMATION FOR SEQ ID NO: 112:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 112:

GTCTGTTTTG GGGGATT                                                              17

(2) INFORMATION FOR SEQ ID NO: 113:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 113:

TCTGTTTTGG GGGATTG                                                              17

(2) INFORMATION FOR SEQ ID NO: 114:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 114:

```
CTGTTTTGGG GGATTGC                                                    17

(2) INFORMATION FOR SEQ ID NO: 115:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 115:

TGTTTTGGGG GATTGCA                                                    17

(2) INFORMATION FOR SEQ ID NO: 116:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 116:

GTTTTGGGGG ATTGCAA                                                    17

(2) INFORMATION FOR SEQ ID NO: 117:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 117:

TTTTGGGGGA TTGCAAG                                                    17

(2) INFORMATION FOR SEQ ID NO: 118:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 118:

TTTGGGGGAT TGCAAGT                                                    17
```

(2) INFORMATION FOR SEQ ID NO: 119:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 119:

TTGGGGGATT GCAAGTA                                                17

(2) INFORMATION FOR SEQ ID NO: 120:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 120:

TGGGGGATTG CAAGTAA                                                17

(2) INFORMATION FOR SEQ ID NO: 121:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 121:

GGGGGATTGC AAGTAAA                                                17

(2) INFORMATION FOR SEQ ID NO: 122:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 122:

GGGGATTGCA AGTAAAC                                                17

(2) INFORMATION FOR SEQ ID NO: 123:

(i) SEQUENCE CHARACTERISTICS:

(A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 123:

GGGATTGCAA GTAAACA                                              17

(2) INFORMATION FOR SEQ ID NO: 124:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 124:

GGATTGCAAG TAAACAC                                              17

(2) INFORMATION FOR SEQ ID NO: 125:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 125:

GATTGCAAGT AAACACA                                              17

(2) INFORMATION FOR SEQ ID NO: 126:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 126:

ATTGCAAGTA AACACAG                                              17

(2) INFORMATION FOR SEQ ID NO: 127:

(i) SEQUENCE CHARACTERISTICS:
        (A) LENGTH: 17 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 127:

TTGCAAGTAA ACACAGT                                                              17

(2) INFORMATION FOR SEQ ID NO: 128:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 128:

TGCAAGTAAA CACAGTT                                                              17

(2) INFORMATION FOR SEQ ID NO: 129:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 129:

GCAAGTAAAC ACAGTTG                                                              17

(2) INFORMATION FOR SEQ ID NO: 130:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 130:

CAAGTAAACA CAGTTGT                                                              17

(2) INFORMATION FOR SEQ ID NO: 131:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 131:

AAGTAAACAC AGTTGTG                                                                17

(2) INFORMATION FOR SEQ ID NO: 132:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 132:

AGTAAACACA GTTGTGT                                                                17

(2) INFORMATION FOR SEQ ID NO: 133:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 133:

GTAAACACAG TTGTGTC                                                                17

(2) INFORMATION FOR SEQ ID NO: 134:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 134:

TAAACACAGT TGTGTCA                                                                17

(2) INFORMATION FOR SEQ ID NO: 135:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 135:

AAACACAGTT GTGTCAA                                                    17

(2) INFORMATION FOR SEQ ID NO: 136:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 136:

AACACAGTTG TGTCAAA                                                    17

(2) INFORMATION FOR SEQ ID NO: 137:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 137:

ACACAGTTGT GTCAAAA                                                    17

(2) INFORMATION FOR SEQ ID NO: 138:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 138:

CACAGTTGTG TCAAAAG                                                    17

(2) INFORMATION FOR SEQ ID NO: 139:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 139:

```
ACAGTTGTGT CAAAAGC                                                      17

(2) INFORMATION FOR SEQ ID NO: 140:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 140:

CAGTTGTGTC AAAAGCA                                                      17

(2) INFORMATION FOR SEQ ID NO: 141:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 141:

AGTTGTGTCA AAGCAA                                                       17

(2) INFORMATION FOR SEQ ID NO: 142:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 142:

GTTGTGTCAA AAGCAAG                                                      17

(2) INFORMATION FOR SEQ ID NO: 143:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 143:

TTGTGTCAAA AGCAAGT                                                      17
```

(2) INFORMATION FOR SEQ ID NO: 144:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 144:

TGTGTCAAAA GCAAGTG                                    17

(2) INFORMATION FOR SEQ ID NO: 145:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 145:

GTACTGTCCA TTTATCAGGA                               20

(2) INFORMATION FOR SEQ ID NO: 146:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 146:

TACTGTCCAT TTATCAGGAT                               20

(2) INFORMATION FOR SEQ ID NO: 147:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 147:

ACTGTCCATT TATCAGGATG                               20

(2) INFORMATION FOR SEQ ID NO: 148:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 148:

CTGTCCATTT ATCAGGATGG                                                    20

(2) INFORMATION FOR SEQ ID NO: 149:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 149:

TGTCCATTTA TCAGGATGGA                                                    20

(2) INFORMATION FOR SEQ ID NO: 150:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 150:

GTCCATTTAT CAGGATGGAG                                                    20

(2) INFORMATION FOR SEQ ID NO: 151:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 151:

TCCATTTATC AGGATGGAGT                                                    20

(2) INFORMATION FOR SEQ ID NO: 152:

(i) SEQUENCE CHARACTERISTICS:
        (A) LENGTH: 20 base pairs
        (B) TYPE: nucleic acid
```

(C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 152:

CCATTTATCA GGATGGAGTT                                              20

(2) INFORMATION FOR SEQ ID NO: 153:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 153:

CATTTATCAG GATGGAGTTC                                              20

(2) INFORMATION FOR SEQ ID NO: 154:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 154:

ATTTATCAGG ATGGAGTTCA                                              20

(2) INFORMATION FOR SEQ ID NO: 155:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 155:

TTTATCAGGA TGGAGTTCAT                                              20

(2) INFORMATION FOR SEQ ID NO: 156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 156:

TTATCAGGAT GGAGTTCATA                                                        20

(2) INFORMATION FOR SEQ ID NO: 157:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 157:

TATCAGGATG GAGTTCATAA                                                        20

(2) INFORMATION FOR SEQ ID NO: 158:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 158:

ATCAGGATGG AGTTCATAAC                                                        20

(2) INFORMATION FOR SEQ ID NO: 159:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 159:

TCAGGATGGA GTTCATAACC                                                        20

(2) INFORMATION FOR SEQ ID NO: 160:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 160:

CAGGATGGAG TTCATAACCC                                               20

(2) INFORMATION FOR SEQ ID NO: 161:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 161:

AGGATGGAGT TCATAACCCA                                               20

(2) INFORMATION FOR SEQ ID NO: 162:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 162:

GGATGGAGTT CATAACCCAT                                               20

(2) INFORMATION FOR SEQ ID NO: 163:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 163:

GATGGAGTTC ATAACCCATC                                               20

(2) INFORMATION FOR SEQ ID NO: 164:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO -continued (xi) SEQUENCE DESCRIPTION: SEQ ID NO: 164:

ATGGAGTTCA TAACCCATCC                                                    20

(2) INFORMATION FOR SEQ ID NO: 165:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 165:

TGGAGTTCAT AACCCATCCC                                                    20

(2) INFORMATION FOR SEQ ID NO: 166:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 166:

GGAGTTCATA ACCCATCCCA                                                    20

(2) INFORMATION FOR SEQ ID NO: 167:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 167:

GAGTTCATAA CCCATCCCAA                                                    20

(2) INFORMATION FOR SEQ ID NO: 168:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 168:

AGTTCATAAC CCATCCCAAA                                                    20

(2) INFORMATION FOR SEQ ID NO: 169:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 169:

GTTCATAACC CATCCCAAAG                                          20

(2) INFORMATION FOR SEQ ID NO: 170:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 170:

TTCATAACCC ATCCCAAAGG                                          20

(2) INFORMATION FOR SEQ ID NO: 171:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 171:

TCATAACCCA TCCCAAAGGA                                          20

(2) INFORMATION FOR SEQ ID NO: 172:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 172:

CATAACCCAT CCCAAAGGAA                                          20

(2) INFORMATION FOR SEQ ID NO: 173:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 173:

ATAACCCATC CCAAAGGAAT                                           20

(2) INFORMATION FOR SEQ ID NO: 174:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 174:

TAACCCATCC CAAAGGAATG                                           20

(2) INFORMATION FOR SEQ ID NO: 175:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 175:

AACCCATCCC AAAGGAATGG                                           20

(2) INFORMATION FOR SEQ ID NO: 176:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 176:

ACCCATCCCA AAGGAATGGA                                           20

(2) INFORMATION FOR SEQ ID NO: 177:

(i) SEQUENCE CHARACTERISTICS:
        (A) LENGTH: 20 base pairs

```
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 177:

CCCATCCCAA AGGAATGGAG                                              20

(2) INFORMATION FOR SEQ ID NO: 178:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 178:

CCATCCCAAA GGAATGGAGG                                              20

(2) INFORMATION FOR SEQ ID NO: 179:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 179:

CATCCCAAAG GAATGGAGGT                                              20

(2) INFORMATION FOR SEQ ID NO: 180:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 180:

ATCCCAAAGG AATGGAGGTT                                              20

(2) INFORMATION FOR SEQ ID NO: 181:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 181:

TCCCAAAGGA ATGGAGGTTC                                                    20

(2) INFORMATION FOR SEQ ID NO: 182:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 182:

CCCAAAGGAA TGGAGGTTCT                                                    20

(2) INFORMATION FOR SEQ ID NO: 183:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 183:

CCAAAGGAAT GGAGGTTCTT                                                    20

(2) INFORMATION FOR SEQ ID NO: 184:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 184:

CAAAGGAATG GAGGTTCTTT                                                    20

(2) INFORMATION FOR SEQ ID NO: 185:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 185:

AAAGGAATGG AGGTTCTTTC                                                           20

(2) INFORMATION FOR SEQ ID NO: 186:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 186:

AAGGAATGGA GGTTCTTTCT                                                           20

(2) INFORMATION FOR SEQ ID NO: 187:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 187:

AGGAATGGAG GTTCTTTCTG                                                           20

(2) INFORMATION FOR SEQ ID NO: 188:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 188:

GGAATGGAGG TTCTTTCTGA                                                           20

(2) INFORMATION FOR SEQ ID NO: 189:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 189:

GAATGGAGGT TCTTTCTGAT                                                       20

(2) INFORMATION FOR SEQ ID NO: 190:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 190:

AATGGAGGTT CTTTCTGATG                                                       20

(2) INFORMATION FOR SEQ ID NO: 191:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 191:

ATGGAGGTTC TTTCTGATGT                                                       20

(2) INFORMATION FOR SEQ ID NO: 192:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 192:

TGGAGGTTCT TTCTGATGTT                                                       20

(2) INFORMATION FOR SEQ ID NO: 193:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 193:

```
GGAGGTTCTT TCTGATGTTT                                                      20

(2) INFORMATION FOR SEQ ID NO: 194:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 194:

GAGGTTCTTT CTGATGTTTT                                                      20

(2) INFORMATION FOR SEQ ID NO: 195:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 195:

AGGTTCTTTC TGATGTTTTT                                                      20

(2) INFORMATION FOR SEQ ID NO: 196:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 196:

GGTTCTTTCT GATGTTTTTT                                                      20

(2) INFORMATION FOR SEQ ID NO: 197:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 197:

GTTCTTTCTG ATGTTTTTTG                                                      20
```

(2) INFORMATION FOR SEQ ID NO: 198:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 198:

TTCTTTCTGA TGTTTTTTGT                                              20

(2) INFORMATION FOR SEQ ID NO: 199:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 199:

TCTTTCTGAT GTTTTTTGTC                                              20

(2) INFORMATION FOR SEQ ID NO: 200:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 200:

CTTTCTGATG TTTTTTGTCT                                              20

(2) INFORMATION FOR SEQ ID NO: 201:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 201:

TTTCTGATGT TTTTTGTCTG                                              20

(2) INFORMATION FOR SEQ ID NO: 202:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 202:

TTCTGATGTT TTTTGTCTGG                                            20

(2) INFORMATION FOR SEQ ID NO: 203:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 203:

TCTGATGTTT TTTGTCTGGT                                            20

(2) INFORMATION FOR SEQ ID NO: 204:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 204:

CTGATGTTTT TTGTCTGGTG                                            20

(2) INFORMATION FOR SEQ ID NO: 205:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 205:

TGATGTTTTT TGTCTGGTGT                                            20

(2) INFORMATION FOR SEQ ID NO: 206:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 206:

GATGTTTTTT GTCTGGTGTG                                                    20

(2) INFORMATION FOR SEQ ID NO: 207:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 207:

ATGTTTTTTG TCTGGTGTGG                                                    20

(2) INFORMATION FOR SEQ ID NO: 208:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 208:

TGTTTTTTGT CTGGTGTGGT                                                    20

(2) INFORMATION FOR SEQ ID NO: 209:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 209:

GTTTTTTGTC TGGTGTGGTA                                                    20

(2) INFORMATION FOR SEQ ID NO: 210:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 210:

TTTTTTGTCT GGTGTGGTAA                                                    20

(2) INFORMATION FOR SEQ ID NO: 211:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 211:

TTTTTGTCTG GTGTGGTAAG                                                    20

(2) INFORMATION FOR SEQ ID NO: 212:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 212:

TTTTGTCTGG TGTGGTAAGT                                                    20

(2) INFORMATION FOR SEQ ID NO: 213:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 213:

TTTGTCTGGT GTGGTAAGTC                                                    20

(2) INFORMATION FOR SEQ ID NO: 214:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 214:

TTGTCTGGTG TGGTAAGTCC                                              20

(2) INFORMATION FOR SEQ ID NO: 215:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 215:

TGTCTGGTGT GGTAAGTCCC                                              20

(2) INFORMATION FOR SEQ ID NO: 216:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 216:

GTCTGGTGTG GTAAGTCCCC                                              20

(2) INFORMATION FOR SEQ ID NO: 217:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 217:

TCTGGTGTGG TAAGTCCCCA                                              20

(2) INFORMATION FOR SEQ ID NO: 218:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 218:

```
CTGGTGTGGT AAGTCCCCAC                                              20

(2) INFORMATION FOR SEQ ID NO: 219:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 219:

TGGTGTGGTA AGTCCCCACC                                              20

(2) INFORMATION FOR SEQ ID NO: 220:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 220:

GGTGTGGTAA GTCCCCACCT                                              20

(2) INFORMATION FOR SEQ ID NO: 221:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 221:

GTGTGGTAAG TCCCCACCTC                                              20

(2) INFORMATION FOR SEQ ID NO: 222:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 222:

TGTGGTAAGT CCCCACCTCA                                              20
```

(2) INFORMATION FOR SEQ ID NO: 223:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 223:

GTGGTAAGTC CCCACCTCAA                                            20

(2) INFORMATION FOR SEQ ID NO: 224:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 224:

TGGTAAGTCC CCACCTCAAC                                            20

(2) INFORMATION FOR SEQ ID NO: 225:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 225:

GGTAAGTCCC CACCTCAACA                                            20

(2) INFORMATION FOR SEQ ID NO: 226:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 226:

GTAAGTCCCC ACCTCAACAG                                            20

(2) INFORMATION FOR SEQ ID NO: 227:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 227:

TAAGTCCCCA CCTCAACAGA                                              20

(2) INFORMATION FOR SEQ ID NO: 228:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 228:

AAGTCCCCAC CTCAACAGAT                                              20

(2) INFORMATION FOR SEQ ID NO: 229:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 229:

AGTCCCCACC TCAACAGATG                                              20

(2) INFORMATION FOR SEQ ID NO: 230:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 230:

GTCCCCACCT CAACAGATGT                                              20

(2) INFORMATION FOR SEQ ID NO: 231:

(i) SEQUENCE CHARACTERISTICS:
        (A) LENGTH: 20 base pairs
        (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 231:

TCCCCACCTC AACAGATGTT                                               20

(2) INFORMATION FOR SEQ ID NO: 232:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 232:

CCCCACCTCA ACAGATGTTG                                               20

(2) INFORMATION FOR SEQ ID NO: 233:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 233:

CCCACCTCAA CAGATGTTGT                                               20

(2) INFORMATION FOR SEQ ID NO: 234:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 234:

CCACCTCAAC AGATGTTGTC                                               20

(2) INFORMATION FOR SEQ ID NO: 235:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 235:

CACCTCAACA GATGTTGTCT                                                    20

(2) INFORMATION FOR SEQ ID NO: 236:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 236:

ACCTCAACAG ATGTTGTCTC                                                    20

(2) INFORMATION FOR SEQ ID NO: 237:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 237:

CCTCAACAGA TGTTGTCTCA                                                    20

(2) INFORMATION FOR SEQ ID NO: 238:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 238:

CTCAACAGAT GTTGTCTCAG                                                    20

(2) INFORMATION FOR SEQ ID NO: 239:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 239:

TCAACAGATG TTGTCTCAGC                                                    20

(2) INFORMATION FOR SEQ ID NO: 240:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 240:

CAACAGATGT TGTCTCAGCT                                                    20

(2) INFORMATION FOR SEQ ID NO: 241:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 241:

AACAGATGTT GTCTCAGCTC                                                    20

(2) INFORMATION FOR SEQ ID NO: 242:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 242:

ACAGATGTTG TCTCAGCTCC                                                    20

(2) INFORMATION FOR SEQ ID NO: 243:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO -continued (xi) SEQUENCE DESCRIPTION: SEQ ID NO: 243:

CAGATGTTGT CTCAGCTCCT                                               20

(2) INFORMATION FOR SEQ ID NO: 244:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 244:

AGATGTTGTC TCAGCTCCTC                                               20

(2) INFORMATION FOR SEQ ID NO: 245:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 245:

GATGTTGTCT CAGCTCCTCT                                               20

(2) INFORMATION FOR SEQ ID NO: 246:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 246:

ATGTTGTCTC AGCTCCTCTA                                               20

(2) INFORMATION FOR SEQ ID NO: 247:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 247:

TGTTGTCTCA GCTCCTCTAT                                               20

(2) INFORMATION FOR SEQ ID NO: 248:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 248:

GTTGTCTCAG CTCCTCTATT        20

(2) INFORMATION FOR SEQ ID NO: 249:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 249:

TTGTCTCAGC TCCTCTATTT        20

(2) INFORMATION FOR SEQ ID NO: 250:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 250:

TGTCTCAGCT CCTCTATTTT        20

(2) INFORMATION FOR SEQ ID NO: 251:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 251:

GTCTCAGCTC CTCTATTTTT        20

(2) INFORMATION FOR SEQ ID NO: 252:

```
        (i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 252:

TCTCAGCTCC TCTATTTTTG                                                      20

(2) INFORMATION FOR SEQ ID NO: 253:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 253:

CTCAGCTCCT CTATTTTTGT                                                      20

(2) INFORMATION FOR SEQ ID NO: 254:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 254:

TCAGCTCCTC TATTTTTGTT                                                      20

(2) INFORMATION FOR SEQ ID NO: 255:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 255:

CAGCTCCTCT ATTTTTGTTC                                                      20

(2) INFORMATION FOR SEQ ID NO: 256:

(i) SEQUENCE CHARACTERISTICS:
             (A) LENGTH: 20 base pairs
```

```
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 256:

AGCTCCTCTA TTTTTGTTCT                                                  20

(2) INFORMATION FOR SEQ ID NO: 257:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 257:

GCTCCTCTAT TTTTGTTCTA                                                  20

(2) INFORMATION FOR SEQ ID NO: 258:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 258:

CTCCTCTATT TTTGTTCTAT                                                  20

(2) INFORMATION FOR SEQ ID NO: 259:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 259:

TCCTCTATTT TGTTCTATG                                                   20

(2) INFORMATION FOR SEQ ID NO: 260:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 260:

CCTCTATTTT TGTTCTATGC                                                   20

(2) INFORMATION FOR SEQ ID NO: 261:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 261:

CTCTATTTTT GTTCTATGCT                                                   20

(2) INFORMATION FOR SEQ ID NO: 262:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 262:

TCTATTTTTG TTCTATGCTG                                                   20

(2) INFORMATION FOR SEQ ID NO: 263:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 263:

CTATTTTGT TCTATGCTGC                                                    20

(2) INFORMATION FOR SEQ ID NO: 264:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 264:

TATTTTTGTT CTATGCTGCC                                                    20

(2) INFORMATION FOR SEQ ID NO: 265:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 265:

ATTTTTGTTC TATGCTGCCC                                                    20

(2) INFORMATION FOR SEQ ID NO: 266:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 266:

TTTTTGTTCT ATGCTGCCCT                                                    20

(2) INFORMATION FOR SEQ ID NO: 267:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 267:

TTTTGTTCTA TGCTGCCCTA                                                    20

(2) INFORMATION FOR SEQ ID NO: 268:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 268:

TTTGTTCTAT GCTGCCCTAT                    20

(2) INFORMATION FOR SEQ ID NO: 269:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 269:

TTGTTCTATG CTGCCCTATT                    20

(2) INFORMATION FOR SEQ ID NO: 270:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 270:

TGTTCTATGC TGCCCTATTT                    20

(2) INFORMATION FOR SEQ ID NO: 271:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 271:

GTTCTATGCT GCCCTATTTC                    20

(2) INFORMATION FOR SEQ ID NO: 272:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 272:

```
TTCTATGCTG CCCTATTTCT                                                    20

(2) INFORMATION FOR SEQ ID NO: 273:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 273:

TCTATGCTGC CCTATTTCTA                                                    20

(2) INFORMATION FOR SEQ ID NO: 274:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 274:

CTATGCTGCC CTATTTCTAA                                                    20

(2) INFORMATION FOR SEQ ID NO: 275:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 275:

TATGCTGCCC TATTTCTAAG                                                    20

(2) INFORMATION FOR SEQ ID NO: 276:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 276:

ATGCTGCCCT ATTTCTAAGT                                                    20
```

(2) INFORMATION FOR SEQ ID NO: 277:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 277:

TGCTGCCCTA TTTCTAAGTC                                                20

(2) INFORMATION FOR SEQ ID NO: 278:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 278:

GCTGCCCTAT TTCTAAGTCA                                                20

(2) INFORMATION FOR SEQ ID NO: 279:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 279:

CTGCCCTATT TCTAAGTCAG                                                20

(2) INFORMATION FOR SEQ ID NO: 280:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 280:

TGCCCTATTT CTAAGTCAGA                                                20

(2) INFORMATION FOR SEQ ID NO: 281:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 281:

GCCCTATTTC TAAGTCAGAT                                            20

(2) INFORMATION FOR SEQ ID NO: 282:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 282:

CCCTATTTCT AAGTCAGATC                                            20

(2) INFORMATION FOR SEQ ID NO: 283:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 283:

CCTATTTCTA AGTCAGATCC                                            20

(2) INFORMATION FOR SEQ ID NO: 284:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 284:

CTATTTCTAA GTCAGATCCT                                            20

(2) INFORMATION FOR SEQ ID NO: 285:

(i) SEQUENCE CHARACTERISTICS:
        (A) LENGTH: 20 base pairs
        (B) TYPE: nucleic acid
        (C) STRANDEDNESS: single -continued (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 285:

TATTTCTAAG TCAGATCCTA                                            20

(2) INFORMATION FOR SEQ ID NO: 286:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 286:

ATTTCTAAGT CAGATCCTAC                                            20

(2) INFORMATION FOR SEQ ID NO: 287:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 287:

TTTCTAAGTC AGATCCTACA                                            20

(2) INFORMATION FOR SEQ ID NO: 288:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 288:

TTCTAAGTCA GATCCTACAT                                            20

(2) INFORMATION FOR SEQ ID NO: 289:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 289:

TCTAAGTCAG ATCCTACATA                                                   20

(2) INFORMATION FOR SEQ ID NO: 290:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 290:

CTAAGTCAGA TCCTACATAC                                                   20

(2) INFORMATION FOR SEQ ID NO: 291:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 291:

TAAGTCAGAT CCTACATACA                                                   20

(2) INFORMATION FOR SEQ ID NO: 292:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 292:

AAGTCAGATC CTACATACAA                                                   20

(2) INFORMATION FOR SEQ ID NO: 293:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 293:

AGTCAGATCC TACATACAAA                                                    20

(2) INFORMATION FOR SEQ ID NO: 294:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 294:

GTCAGATCCT ACATACAAAT                                                    20

(2) INFORMATION FOR SEQ ID NO: 295:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 295:

TCAGATCCTA CATACAAATC                                                    20

(2) INFORMATION FOR SEQ ID NO: 296:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 296:

CAGATCCTAC ATACAAATCA                                                    20

(2) INFORMATION FOR SEQ ID NO: 297:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 297:

```
AGATCCTACA TACAAATCAT                                              20

(2) INFORMATION FOR SEQ ID NO: 298:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 298:

GATCCTACAT ACAAATCATC                                              20

(2) INFORMATION FOR SEQ ID NO: 299:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 299:

ATCCTACATA CAAATCATCC                                              20

(2) INFORMATION FOR SEQ ID NO: 300:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 300:

TCCTACATAC AAATCATCCA                                              20

(2) INFORMATION FOR SEQ ID NO: 301:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 301:

CCTACATACA AATCATCCAT                                              20
```

(2) INFORMATION FOR SEQ ID NO: 302:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 302:

CTACATACAA ATCATCCATG          20

(2) INFORMATION FOR SEQ ID NO: 303:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 303:

TACATACAAA TCATCCATGT          20

(2) INFORMATION FOR SEQ ID NO: 304:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 304:

ACATACAAAT CATCCATGTA          20

(2) INFORMATION FOR SEQ ID NO: 305:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 305:

CATACAAATC ATCCATGTAT          20

(2) INFORMATION FOR SEQ ID NO: 306:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 306:

ATACAAATCA TCCATGTATT                                              20

(2) INFORMATION FOR SEQ ID NO: 307:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 307:

TACAAATCAT CCATGTATTG                                              20

(2) INFORMATION FOR SEQ ID NO: 308:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 308:

ACAAATCATC CATGTATTGA                                              20

(2) INFORMATION FOR SEQ ID NO: 309:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 309:

CAAATCATCC ATGTATTGAT                                              20

(2) INFORMATION FOR SEQ ID NO: 310:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 310:

AAATCATCCA TGTATTGATA                                                         20

(2) INFORMATION FOR SEQ ID NO: 311:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 311:

AATCATCCAT GTATTGATAG                                                         20

(2) INFORMATION FOR SEQ ID NO: 312:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 312:

ATCATCCATG TATTGATAGA                                                         20

(2) INFORMATION FOR SEQ ID NO: 313:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 313:

TCATCCATGT ATTGATAGAT                                                         20

(2) INFORMATION FOR SEQ ID NO: 314:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 314:

CATCCATGTA TTGATAGATA                                            20

(2) INFORMATION FOR SEQ ID NO: 315:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 315:

ATCCATGTAT TGATAGATAA                                            20

(2) INFORMATION FOR SEQ ID NO: 316:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 316:

TCCATGTATT GATAGATAAC                                            20

(2) INFORMATION FOR SEQ ID NO: 317:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 317:

CCATGTATTG ATAGATAACT                                            20

(2) INFORMATION FOR SEQ ID NO: 318:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 318:

CATGTATTGA TAGATAACTA                                                         20

(2) INFORMATION FOR SEQ ID NO: 319:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 319:

ATGTATTGAT AGATAACTAT                                                         20

(2) INFORMATION FOR SEQ ID NO: 320:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 320:

TGTATTGATA GATAACTATG                                                         20

(2) INFORMATION FOR SEQ ID NO: 321:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 321:

GTATTGATAG ATAACTATGT                                                         20

(2) INFORMATION FOR SEQ ID NO: 322:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 322:

TATTGATAGA TAACTATGTC                                         20

(2) INFORMATION FOR SEQ ID NO: 323:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 323:

ATTGATAGAT AACTATGTCT                                         20

(2) INFORMATION FOR SEQ ID NO: 324:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 324:

TTGATAGATA ACTATGTCTG                                         20

(2) INFORMATION FOR SEQ ID NO: 325:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 325:

TGATAGATAA CTATGTCTGG                                         20

(2) INFORMATION FOR SEQ ID NO: 326:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 326:

GATAGATAAC TATGTCTGGA                                         20

(2) INFORMATION FOR SEQ ID NO: 327:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 327:

ATAGATAACT ATGTCTGGAT                                              20

(2) INFORMATION FOR SEQ ID NO: 328:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 328:

TAGATAACTA TGTCTGGATT                                              20

(2) INFORMATION FOR SEQ ID NO: 329:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 329:

AGATAACTAT GTCTGGATTT                                              20

(2) INFORMATION FOR SEQ ID NO: 330:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 330:

GATAACTATG TCTGGATTTT                                              20

(2) INFORMATION FOR SEQ ID NO: 331:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 331:

ATAACTATGT CTGGATTTTG                                                    20

(2) INFORMATION FOR SEQ ID NO: 332:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 332:

TAACTATGTC TGGATTTTGT                                                    20

(2) INFORMATION FOR SEQ ID NO: 333:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 333:

AACTATGTCT GGATTTTGTT                                                    20

(2) INFORMATION FOR SEQ ID NO: 334:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 334:

ACTATGTCTG GATTTGTTT                                                     20

(2) INFORMATION FOR SEQ ID NO: 335:

(i) SEQUENCE CHARACTERISTICS:
            (A) LENGTH: 20 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 335:

CTATGTCTGG ATTTTGTTTT                                             20

(2) INFORMATION FOR SEQ ID NO: 336:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 336:

TATGTCTGGA TTTTGTTTTT                                             20

(2) INFORMATION FOR SEQ ID NO: 337:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 337:

ATGTCTGGAT TTTGTTTTTT                                             20

(2) INFORMATION FOR SEQ ID NO: 338:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 338:

TGTCTGGATT TGTTTTTTA                                              20

(2) INFORMATION FOR SEQ ID NO: 339:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 339:

GTCTGGATTT TGTTTTTTAA                                              20

(2) INFORMATION FOR SEQ ID NO: 340:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 340:

TCTGGATTTT GTTTTTTAAA                                              20

(2) INFORMATION FOR SEQ ID NO: 341:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 341:

CTGGATTTTG TTTTTTAAAA                                              20

(2) INFORMATION FOR SEQ ID NO: 342:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 342:

TGGATTTTGT TTTTTAAAAG                                              20

(2) INFORMATION FOR SEQ ID NO: 343:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 343:

GGATTTTGTT TTTTAAAAGG                                                           20

(2) INFORMATION FOR SEQ ID NO: 344:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 344:

GATTTTGTTT TTTAAAAGGC                                                           20

(2) INFORMATION FOR SEQ ID NO: 345:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 345:

ATTTTGTTTT TTAAAAGGCT                                                           20

(2) INFORMATION FOR SEQ ID NO: 346:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 346:

TTTTGTTTTT TAAAAGGCTC                                                           20

(2) INFORMATION FOR SEQ ID NO: 347:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 347:

TTTGTTTTTT AAAAGGCTCT                                       20

(2) INFORMATION FOR SEQ ID NO: 348:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 348:

TTGTTTTTTA AAAGGCTCTA                                       20

(2) INFORMATION FOR SEQ ID NO: 349:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 349:

TGTTTTTTAA AAGGCTCTAA                                       20

(2) INFORMATION FOR SEQ ID NO: 350:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 350:

GTTTTTTAAA AGGCTCTAAG                                       20

(2) INFORMATION FOR SEQ ID NO: 351:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 351:

```
TTTTTTAAAA GGCTCTAAGA                                                       20

(2) INFORMATION FOR SEQ ID NO: 352:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 352:

TTTTTAAAAG GCTCTAAGAT                                                       20

(2) INFORMATION FOR SEQ ID NO: 353:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 353:

TTTTAAAAGG CTCTAAGATT                                                       20

(2) INFORMATION FOR SEQ ID NO: 354:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 354:

TTTAAAAGGC TCTAAGATTT                                                       20

(2) INFORMATION FOR SEQ ID NO: 355:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 355:

TTAAAAGGCT CTAAGATTTT                                                       20
```

```
(2) INFORMATION FOR SEQ ID NO: 356:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 356:

TAAAAGGCTC TAAGATTTTT                                                  20

(2) INFORMATION FOR SEQ ID NO: 357:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 357:

AAAAGGCTCT AAGATTTTTG                                                  20

(2) INFORMATION FOR SEQ ID NO: 358:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 358:

AAAGGCTCTA AGATTTTTGT                                                  20

(2) INFORMATION FOR SEQ ID NO: 359:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 359:

AAGGCTCTAA GATTTTTGTC                                                  20

(2) INFORMATION FOR SEQ ID NO: 360:

(i) SEQUENCE CHARACTERISTICS:
```

(A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 360:

AGGCTCTAAG ATTTTTGTCA                                              20

(2) INFORMATION FOR SEQ ID NO: 361:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 361:

GGCTCTAAGA TTTTTGTCAT                                              20

(2) INFORMATION FOR SEQ ID NO: 362:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 362:

GCTCTAAGAT TTTTGTCATG                                              20

(2) INFORMATION FOR SEQ ID NO: 363:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 363:

CTCTAAGATT TTTGTCATGC                                              20

(2) INFORMATION FOR SEQ ID NO: 364:

(i) SEQUENCE CHARACTERISTICS:
            (A) LENGTH: 20 base pairs
            (B) TYPE: nucleic acid
            (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 364:

TCTAAGATTT TTGTCATGCT                                                   20

(2) INFORMATION FOR SEQ ID NO: 365:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 365:

CTAAGATTTT TGTCATGCTA                                                   20

(2) INFORMATION FOR SEQ ID NO: 366:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 366:

TAAGATTTTT GTCATGCTAC                                                   20

(2) INFORMATION FOR SEQ ID NO: 367:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 367:

AAGATTTTTG TCATGCTACT                                                   20

(2) INFORMATION FOR SEQ ID NO: 368:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 368:

AGATTTTTGT CATGCTACTT                                                         20

(2) INFORMATION FOR SEQ ID NO: 369:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 369:

GATTTTTGTC ATGCTACTTT                                                         20

(2) INFORMATION FOR SEQ ID NO: 370:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 370:

ATTTTTGTCA TGCTACTTTG                                                         20

(2) INFORMATION FOR SEQ ID NO: 371:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 371:

TTTTTGTCAT GCTACTTTGG                                                         20

(2) INFORMATION FOR SEQ ID NO: 372:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 372:

TTTTGTCATG CTACTTTGGA                                                                              20

(2) INFORMATION FOR SEQ ID NO: 373:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 373:

TTTGTCATGC TACTTTGGAA                                                                              20

(2) INFORMATION FOR SEQ ID NO: 374:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 374:

TTGTCATGCT ACTTTGGAAT                                                                              20

(2) INFORMATION FOR SEQ ID NO: 375:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 375:

TGTCATGCTA CTTTGGAATA                                                                              20

(2) INFORMATION FOR SEQ ID NO: 376:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 376:

GTCATGCTAC TTTGGAATAT                                                           20

(2) INFORMATION FOR SEQ ID NO: 377:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 377:

TCATGCTACT TTGGAATATT                                                           20

(2) INFORMATION FOR SEQ ID NO: 378:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 378:

CATGCTACTT TGGAATATTG                                                           20

(2) INFORMATION FOR SEQ ID NO: 379:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 379:

ATGCTACTTT GGAATATTGC                                                           20

(2) INFORMATION FOR SEQ ID NO: 380:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 380:

TGCTACTTTG GAATATTGCT                                                           20

(2) INFORMATION FOR SEQ ID NO: 381:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 381:

GCTACTTTGG AATATTGCTG                                          20

(2) INFORMATION FOR SEQ ID NO: 382:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 382:

CTACTTTGGA ATATTGCTGG                                          20

(2) INFORMATION FOR SEQ ID NO: 383:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 383:

TACTTTGGAA TATTGCTGGT                                          20

(2) INFORMATION FOR SEQ ID NO: 384:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 384:

ACTTTGGAAT ATTGCTGGTG                                          20

(2) INFORMATION FOR SEQ ID NO: 385:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 385:

CTTTGGAATA TTGCTGGTGA                                               20

(2) INFORMATION FOR SEQ ID NO: 386:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 386:

TTTGGAATAT TGCTGGTGAT                                               20

(2) INFORMATION FOR SEQ ID NO: 387:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 387:

TTGGAATATT GCTGGTGATC                                               20

(2) INFORMATION FOR SEQ ID NO: 388:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 388:

TGGAATATTG CTGGTGATCC                                               20

(2) INFORMATION FOR SEQ ID NO: 389:

(i) SEQUENCE CHARACTERISTICS:
        (A) LENGTH: 20 base pairs
        (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 389:

GGAATATTGC TGGTGATCCT                                              20

(2) INFORMATION FOR SEQ ID NO: 390:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 390:

GAATATTGCT GGTGATCCTT                                              20

(2) INFORMATION FOR SEQ ID NO: 391:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 391:

AATATTGCTG GTGATCCTTT                                              20

(2) INFORMATION FOR SEQ ID NO: 392:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 392:

ATATTGCTGG TGATCCTTTC                                              20

(2) INFORMATION FOR SEQ ID NO: 393:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 393:

TATTGCTGGT GATCCTTTCC                                                    20

(2) INFORMATION FOR SEQ ID NO: 394:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 394:

ATTGCTGGTG ATCCTTTCCA                                                    20

(2) INFORMATION FOR SEQ ID NO: 395:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 395:

TTGCTGGTGA TCCTTTCCAT                                                    20

(2) INFORMATION FOR SEQ ID NO: 396:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 396:

TGCTGGTGAT CCTTTCCATC                                                    20

(2) INFORMATION FOR SEQ ID NO: 397:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 397:

GCTGGTGATC CTTTCCATCC                                                        20

(2) INFORMATION FOR SEQ ID NO: 398:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 398:

CTGGTGATCC TTTCCATCCC                                                        20

(2) INFORMATION FOR SEQ ID NO: 399:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 399:

TGGTGATCCT TTCCATCCCT                                                        20

(2) INFORMATION FOR SEQ ID NO: 400:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 400:

GGTGATCCTT TCCATCCCTG                                                        20

(2) INFORMATION FOR SEQ ID NO: 401:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 401:

GTGATCCTTT CCATCCCTGT                                                     20

(2) INFORMATION FOR SEQ ID NO: 402:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 402:

TGATCCTTTC CATCCCTGTG                                                     20

(2) INFORMATION FOR SEQ ID NO: 403:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 403:

GATCCTTTCC ATCCCTGTGG                                                     20

(2) INFORMATION FOR SEQ ID NO: 404:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 404:

ATCCTTTCCA TCCCTGTGGA                                                     20

(2) INFORMATION FOR SEQ ID NO: 405:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 405:

TCCTTTCCAT CCCTGTGGAA                                                     20

(2) INFORMATION FOR SEQ ID NO: 406:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 406:

CCTTTCCATC CCTGTGGAAG                                                    20

(2) INFORMATION FOR SEQ ID NO: 407:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 407:

CTTTCCATCC CTGTGGAAGC                                                    20

(2) INFORMATION FOR SEQ ID NO: 408:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 408:

TTTCCATCCC TGTGGAAGCA                                                    20

(2) INFORMATION FOR SEQ ID NO: 409:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 409:

TTCCATCCCT GTGGAAGCAC                                                    20

(2) INFORMATION FOR SEQ ID NO: 410:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 410:

TCCATCCCTG TGGAAGCACA                                                     20

(2) INFORMATION FOR SEQ ID NO: 411:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 411:

CCATCCCTGT GGAAGCACAT                                                     20

(2) INFORMATION FOR SEQ ID NO: 412:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 412:

CATCCCTGTG GAAGCACATT                                                     20

(2) INFORMATION FOR SEQ ID NO: 413:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 413:

ATCCCTGTGG AAGCACATTG                                                     20

(2) INFORMATION FOR SEQ ID NO: 414:

(i) SEQUENCE CHARACTERISTICS:
            (A) LENGTH: 20 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 414:

TCCCTGTGGA AGCACATTGT                                                    20

(2) INFORMATION FOR SEQ ID NO: 415:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 415:

CCCTGTGGAA GCACATTGTA                                                    20

(2) INFORMATION FOR SEQ ID NO: 416:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 416:

CCTGTGGAAG CACATTGTAC                                                    20

(2) INFORMATION FOR SEQ ID NO: 417:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 417:

CTGTGGAAGC ACATTGTACT                                                    20

(2) INFORMATION FOR SEQ ID NO: 418:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 418:

TGTGGAAGCA CATTGTACTG                                                             20

(2) INFORMATION FOR SEQ ID NO: 419:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 419:

GTGGAAGCAC ATTGTACTGA                                                             20

(2) INFORMATION FOR SEQ ID NO: 420:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 420:

TGGAAGCACA TTGTACTGAT                                                             20

(2) INFORMATION FOR SEQ ID NO: 421:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 421:

GGAAGCACAT TGTACTGATA                                                             20

(2) INFORMATION FOR SEQ ID NO: 422:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 422:

GAAGCACATT GTACTGATAT                                              20

(2) INFORMATION FOR SEQ ID NO: 423:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 423:

AAGCACATTG TACTGATATC                                              20

(2) INFORMATION FOR SEQ ID NO: 424:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 424:

AGCACATTGT ACTGATATCT                                              20

(2) INFORMATION FOR SEQ ID NO: 425:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 425:

GCACATTGTA CTGATATCTA                                              20

(2) INFORMATION FOR SEQ ID NO: 426:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 426:

CACATTGTAC TGATATCTAA                                              20

(2) INFORMATION FOR SEQ ID NO: 427:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 427:

ACATTGTACT GATATCTAAT                                              20

(2) INFORMATION FOR SEQ ID NO: 428:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 428:

CATTGTACTG ATATCTAATC                                              20

(2) INFORMATION FOR SEQ ID NO: 429:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 429:

ATTGTACTGA TATCTAATCC                                              20

(2) INFORMATION FOR SEQ ID NO: 430:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 430:

TTGTACTGAT ATCTAATCCC                                                    20

(2) INFORMATION FOR SEQ ID NO: 431:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 431:

TGTACTGATA TCTAATCCCT                                                    20

(2) INFORMATION FOR SEQ ID NO: 432:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 432:

GTACTGATAT CTAATCCCTG                                                    20

(2) INFORMATION FOR SEQ ID NO: 433:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 433:

TACTGATATC TAATCCCTGG                                                    20

(2) INFORMATION FOR SEQ ID NO: 434:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 434:

ACTGATATCT AATCCCTGGT                                                    20

(2) INFORMATION FOR SEQ ID NO: 435:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 435:

CTGATATCTA ATCCCTGGTG                                              20

(2) INFORMATION FOR SEQ ID NO: 436:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 436:

TGATATCTAA TCCCTGGTGT                                              20

(2) INFORMATION FOR SEQ ID NO: 437:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 437:

GATATCTAAT CCCTGGTGTC                                              20

(2) INFORMATION FOR SEQ ID NO: 438:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 438:

ATATCTAATC CCTGGTGTCT                                              20

(2) INFORMATION FOR SEQ ID NO: 439:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 439:

TATCTAATCC CTGGTGTCTC                                                           20

(2) INFORMATION FOR SEQ ID NO: 440:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 440:

ATCTAATCCC TGGTGTCTCA                                                           20

(2) INFORMATION FOR SEQ ID NO: 441:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 441:

TCTAATCCCT GGTGTCTCAT                                                           20

(2) INFORMATION FOR SEQ ID NO: 442:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 442:

CTAATCCCTG GTGTCTCATT                                                           20

(2) INFORMATION FOR SEQ ID NO: 443:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 443:

TAATCCCTGG TGTCTCATTG                                              20

(2) INFORMATION FOR SEQ ID NO: 444:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 444:

AATCCCTGGT GTCTCATTGT                                              20

(2) INFORMATION FOR SEQ ID NO: 445:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 445:

ATCCCTGGTG TCTCATTGTT                                              20

(2) INFORMATION FOR SEQ ID NO: 446:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 446:

TCCCTGGTGT CTCATTGTTT                                              20

(2) INFORMATION FOR SEQ ID NO: 447:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 447:

CCCTGGTGTC TCATTGTTTA                                         20

(2) INFORMATION FOR SEQ ID NO: 448:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 448:

CCTGGTGTCT CATTGTTTAT                                         20

(2) INFORMATION FOR SEQ ID NO: 449:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 449:

CTGGTGTCTC ATTGTTTATA                                         20

(2) INFORMATION FOR SEQ ID NO: 450:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 450:

TGGTGTCTCA TTGTTTATAC                                         20

(2) INFORMATION FOR SEQ ID NO: 451:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 451:

GGTGTCTCAT TGTTTATACT                                                   20

(2) INFORMATION FOR SEQ ID NO: 452:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 452:

GTGTCTCATT GTTTATACTA                                                   20

(2) INFORMATION FOR SEQ ID NO: 453:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 453:

TGTCTCATTG TTTATACTAG                                                   20

(2) INFORMATION FOR SEQ ID NO: 454:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 454:

GTCTCATTGT TTATACTAGG                                                   20

(2) INFORMATION FOR SEQ ID NO: 455:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 455:

TCTCATTGTT TATACTAGGT                                               20

(2) INFORMATION FOR SEQ ID NO: 456:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 456:

CTCATTGTTT ATACTAGGTA                                               20

(2) INFORMATION FOR SEQ ID NO: 457:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 457:

TCATTGTTTA TACTAGGTAT                                               20

(2) INFORMATION FOR SEQ ID NO: 458:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 458:

CATTGTTTAT ACTAGGTATG                                               20

(2) INFORMATION FOR SEQ ID NO: 459:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 459:

ATTGTTTATA CTAGGTATGG                                               20

(2) INFORMATION FOR SEQ ID NO: 460:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 460:

```
TTGTTTATAC TAGGTATGGT                                             20
```

(2) INFORMATION FOR SEQ ID NO: 461:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 461:

```
TGTTTATACT AGGTATGGTA                                             20
```

(2) INFORMATION FOR SEQ ID NO: 462:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 462:

```
GTTTATACTA GGTATGGTAA                                             20
```

(2) INFORMATION FOR SEQ ID NO: 463:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 463:

```
TTTATACTAG GTATGGTAAA                                             20
```

(2) INFORMATION FOR SEQ ID NO: 464:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 464:

TTATACTAGG TATGGTAAAT                                               20

(2) INFORMATION FOR SEQ ID NO: 465:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 465:

TATACTAGGT ATGGTAAATG                                               20

(2) INFORMATION FOR SEQ ID NO: 466:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 466:

ATACTAGGTA TGGTAAATGC                                               20

(2) INFORMATION FOR SEQ ID NO: 467:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 467:

TACTAGGTAT GGTAAATGCA                                               20

(2) INFORMATION FOR SEQ ID NO: 468:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 468:

ACTAGGTATG GTAAATGCAG                                              20

(2) INFORMATION FOR SEQ ID NO: 469:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 469:

CTAGGTATGG TAAATGCAGT                                              20

(2) INFORMATION FOR SEQ ID NO: 470:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 470:

TAGGTATGGT AAATGCAGTA                                              20

(2) INFORMATION FOR SEQ ID NO: 471:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 471:

AGGTATGGTA AATGCAGTAT                                              20

(2) INFORMATION FOR SEQ ID NO: 472:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 472:

GGTATGGTAA ATGCAGTATA                                                      20

(2) INFORMATION FOR SEQ ID NO: 473:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 473:

GTATGGTAAA TGCAGTATAC                                                      20

(2) INFORMATION FOR SEQ ID NO: 474:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 474:

TATGGTAAAT GCAGTATACT                                                      20

(2) INFORMATION FOR SEQ ID NO: 475:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 475:

ATGGTAAATG CAGTATACTT                                                      20

(2) INFORMATION FOR SEQ ID NO: 476:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 476:

TGGTAAATGC AGTATACTTC                                           20

(2) INFORMATION FOR SEQ ID NO: 477:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 477:

GGTAAATGCA GTATACTTCC                                           20

(2) INFORMATION FOR SEQ ID NO: 478:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 478:

GTAAATGCAG TATACTTCCT                                           20

(2) INFORMATION FOR SEQ ID NO: 479:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 479:

TAAATGCAGT ATACTTCCTG                                           20

(2) INFORMATION FOR SEQ ID NO: 480:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 480:

AAATGCAGTA TACTTCCTGA                                              20

(2) INFORMATION FOR SEQ ID NO: 481:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 481:

AATGCAGTAT ACTTCCTGAA                                              20

(2) INFORMATION FOR SEQ ID NO: 482:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 482:

ATGCAGTATA CTTCCTGAAG                                              20

(2) INFORMATION FOR SEQ ID NO: 483:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 483:

TGCAGTATAC TTCCTGAAGT                                              20

(2) INFORMATION FOR SEQ ID NO: 484:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 484:

GCAGTATACT TCCTGAAGTC                                              20

(2) INFORMATION FOR SEQ ID NO: 485:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 485:

CAGTATACTT CCTGAAGTCT    20

(2) INFORMATION FOR SEQ ID NO: 486:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 486:

AGTATACTTC CTGAAGTCTT    20

(2) INFORMATION FOR SEQ ID NO: 487:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 487:

GTATACTTCC TGAAGTCTTC    20

(2) INFORMATION FOR SEQ ID NO: 488:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 488:

TATACTTCCT GAAGTCTTCA    20

(2) INFORMATION FOR SEQ ID NO: 489:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 489:

ATACTTCCTG AAGTCTTCAT                                                    20

(2) INFORMATION FOR SEQ ID NO: 490:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 490:

TACTTCCTGA AGTCTTCATC                                                    20

(2) INFORMATION FOR SEQ ID NO: 491:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 491:

ACTTCCTGAA GTCTTCATCT                                                    20

(2) INFORMATION FOR SEQ ID NO: 492:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 492:

CTTCCTGAAG TCTTCATCTA                                                    20

(2) INFORMATION FOR SEQ ID NO: 493:

(i) SEQUENCE CHARACTERISTICS:
            (A) LENGTH: 20 base pairs

```
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 493:

TTCCTGAAGT CTTCATCTAA                                                   20

(2) INFORMATION FOR SEQ ID NO: 494:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 494:

TCCTGAAGTC TTCATCTAAG                                                   20

(2) INFORMATION FOR SEQ ID NO: 495:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 495:

CCTGAAGTCT TCATCTAAGG                                                   20

(2) INFORMATION FOR SEQ ID NO: 496:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 496:

CTGAAGTCTT CATCTAAGGG                                                   20

(2) INFORMATION FOR SEQ ID NO: 497:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 497:

TGAAGTCTTC ATCTAAGGGA					20

(2) INFORMATION FOR SEQ ID NO: 498:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 498:

GAAGTCTTCA TCTAAGGGAA					20

(2) INFORMATION FOR SEQ ID NO: 499:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 499:

AAGTCTTCAT CTAAGGGAAC					20

(2) INFORMATION FOR SEQ ID NO: 500:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 500:

AGTCTTCATC TAAGGGAACT					20

(2) INFORMATION FOR SEQ ID NO: 501:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 501:

GTCTTCATCT AAGGGAACTG                                           20

(2) INFORMATION FOR SEQ ID NO: 502:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 502:

TCTTCATCTA AGGGAACTGA                                           20

(2) INFORMATION FOR SEQ ID NO: 503:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 503:

CTTCATCTAA GGGAACTGAA                                           20

(2) INFORMATION FOR SEQ ID NO: 504:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 504:

TTCATCTAAG GAACTGAAA                                            20

(2) INFORMATION FOR SEQ ID NO: 505:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 505:

TCATCTAAGG GAACTGAAAA                                               20

(2) INFORMATION FOR SEQ ID NO: 506:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 506:

CATCTAAGGG AACTGAAAAA                                               20

(2) INFORMATION FOR SEQ ID NO: 507:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 507:

ATCTAAGGGA ACTGAAAAAT                                               20

(2) INFORMATION FOR SEQ ID NO: 508:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 508:

TCTAAGGGAA CTGAAAAATA                                               20

(2) INFORMATION FOR SEQ ID NO: 509:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 509:

```
CTAAGGGAAC TGAAAAATAT                                                    20

(2) INFORMATION FOR SEQ ID NO: 510:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 510:

TAAGGGAACT GAAAAATATG                                                    20

(2) INFORMATION FOR SEQ ID NO: 511:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 511:

AAGGGAACTG AAAAATATGC                                                    20

(2) INFORMATION FOR SEQ ID NO: 512:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 512:

AGGGAACTGA AAAATATGCA                                                    20

(2) INFORMATION FOR SEQ ID NO: 513:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 513:

GGGAACTGAA AAATATGCAT                                                    20
```

(2) INFORMATION FOR SEQ ID NO: 514:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 514:

GGAACTGAAA AATATGCATC                                       20

(2) INFORMATION FOR SEQ ID NO: 515:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 515:

GAACTGAAAA ATATGCATCA                                       20

(2) INFORMATION FOR SEQ ID NO: 516:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 516:

AACTGAAAAA TATGCATCAC                                       20

(2) INFORMATION FOR SEQ ID NO: 517:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 517:

ACTGAAAAAT ATGCATCACC                                       20

(2) INFORMATION FOR SEQ ID NO: 518:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 518:

CTGAAAAATA TGCATCACCC                                               20

(2) INFORMATION FOR SEQ ID NO: 519:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 519:

TGAAAAATAT GCATCACCCA                                               20

(2) INFORMATION FOR SEQ ID NO: 520:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 520:

GAAAAATATG CATCACCCAC                                               20

(2) INFORMATION FOR SEQ ID NO: 521:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 521:

AAAAATATGC ATCACCCACA                                               20

(2) INFORMATION FOR SEQ ID NO: 522:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 522:

AAAATATGCA TCACCCACAT                                               20

(2) INFORMATION FOR SEQ ID NO: 523:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 523:

AAATATGCAT CACCCACATC                                               20

(2) INFORMATION FOR SEQ ID NO: 524:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 524:

AATATGCATC ACCCACATCC                                               20

(2) INFORMATION FOR SEQ ID NO: 525:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 525:

ATATGCATCA CCCACATCCA                                               20

(2) INFORMATION FOR SEQ ID NO: 526:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 526:

TATGCATCAC CCACATCCAG                                                20

(2) INFORMATION FOR SEQ ID NO: 527:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 527:

ATGCATCACC CACATCCAGT                                                20

(2) INFORMATION FOR SEQ ID NO: 528:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 528:

TGCATCACCC ACATCCAGTA                                                20

(2) INFORMATION FOR SEQ ID NO: 529:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 529:

GCATCACCCA CATCCAGTAC                                                20

(2) INFORMATION FOR SEQ ID NO: 530:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 530:

CATCACCCAC ATCCAGTACT                                                    20

(2) INFORMATION FOR SEQ ID NO: 531:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 531:

ATCACCCACA TCCAGTACTG                                                    20

(2) INFORMATION FOR SEQ ID NO: 532:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 532:

TCACCCACAT CCAGTACTGT                                                    20

(2) INFORMATION FOR SEQ ID NO: 533:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 533:

CACCCACATC CAGTACTGTT                                                    20

(2) INFORMATION FOR SEQ ID NO: 534:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 534:

ACCCACATCC AGTACTGTTA                                              20

(2) INFORMATION FOR SEQ ID NO: 535:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 535:

CCCACATCCA GTACTGTTAC                                              20

(2) INFORMATION FOR SEQ ID NO: 536:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 536:

CCACATCCAG TACTGTTACT                                              20

(2) INFORMATION FOR SEQ ID NO: 537:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 537:

CACATCCAGT ACTGTTACTG                                              20

(2) INFORMATION FOR SEQ ID NO: 538:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 538:

ACATCCAGTA CTGTTACTGA                                              20

(2) INFORMATION FOR SEQ ID NO: 539:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 539:

CATCCAGTAC TGTTACTGAT                                          20

(2) INFORMATION FOR SEQ ID NO: 540:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 540:

ATCCAGTACT GTTACTGATT                                          20

(2) INFORMATION FOR SEQ ID NO: 541:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 541:

TCCAGTACTG TTACTGATTT                                          20

(2) INFORMATION FOR SEQ ID NO: 542:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 542:

CCAGTACTGT TACTGATTTT                                          20

(2) INFORMATION FOR SEQ ID NO: 543:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 543:

CAGTACTGTT ACTGATTTTT                                               20

(2) INFORMATION FOR SEQ ID NO: 544:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 544:

AGTACTGTTA CTGATTTTTT                                               20

(2) INFORMATION FOR SEQ ID NO: 545:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 545:

GTACTGTTAC TGATTTTTTC                                               20

(2) INFORMATION FOR SEQ ID NO: 546:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 546:

TACTGTTACT GATTTTTTCT                                               20

(2) INFORMATION FOR SEQ ID NO: 547:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 547:

ACTGTTACTG ATTTTTTCTT                                                      20

(2) INFORMATION FOR SEQ ID NO: 548:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 548:

CTGTTACTGA TTTTTTCTTT                                                      20

(2) INFORMATION FOR SEQ ID NO: 549:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 549:

TGTTACTGAT TTTTTCTTTT                                                      20

(2) INFORMATION FOR SEQ ID NO: 550:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 550:

GTTACTGATT TTTTCTTTTT                                                      20

(2) INFORMATION FOR SEQ ID NO: 551:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 551:

TTACTGATTT TTTCTTTTTT                                                   20

(2) INFORMATION FOR SEQ ID NO: 552:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 552:

TACTGATTTT TTCTTTTTTA                                                   20

(2) INFORMATION FOR SEQ ID NO: 553:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 553:

ACTGATTTTT TCTTTTTTAA                                                   20

(2) INFORMATION FOR SEQ ID NO: 554:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 554:

CTGATTTTTT CTTTTTTAAC                                                   20

(2) INFORMATION FOR SEQ ID NO: 555:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 555:

TGATTTTTTC TTTTTTAACC                                                        20

(2) INFORMATION FOR SEQ ID NO: 556:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 556:

GATTTTTTCT TTTTTAACCC                                                        20

(2) INFORMATION FOR SEQ ID NO: 557:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 557:

ATTTTTTCTT TTTTAACCCT                                                        20

(2) INFORMATION FOR SEQ ID NO: 558:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 558:

TTTTTTCTTT TTTAACCCTG                                                        20

(2) INFORMATION FOR SEQ ID NO: 559:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 559:

TTTTTCTTTT TTAACCCTGC                                           20

(2) INFORMATION FOR SEQ ID NO: 560:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 560:

TTTTCTTTTT TAACCCTGCG                                           20

(2) INFORMATION FOR SEQ ID NO: 561:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 561:

TTTCTTTTTT AACCCTGCGG                                           20

(2) INFORMATION FOR SEQ ID NO: 562:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 562:

TTCTTTTTTA ACCCTGCGGG                                           20

(2) INFORMATION FOR SEQ ID NO: 563:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 563:

TCTTTTTTAA CCCTGCGGGA                                           20

(2) INFORMATION FOR SEQ ID NO: 564:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 564:

CTTTTTTAAC CCTGCGGGAT                                               20

(2) INFORMATION FOR SEQ ID NO: 565:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 565:

TTTTTTAACC CTGCGGGATG                                               20

(2) INFORMATION FOR SEQ ID NO: 566:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 566:

TTTTTAACCC TGCGGGATGT                                               20

(2) INFORMATION FOR SEQ ID NO: 567:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 567:

TTTTAACCCT GCGGGATGTG                                               20

(2) INFORMATION FOR SEQ ID NO: 568:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 568:

TTTAACCCTG CGGGATGTGG                                            20

(2) INFORMATION FOR SEQ ID NO: 569:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 569:

TTAACCCTGC GGGATGTGGT                                            20

(2) INFORMATION FOR SEQ ID NO: 570:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 570:

TAACCCTGCG GGATGTGGTA                                            20

(2) INFORMATION FOR SEQ ID NO: 571:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 571:

AACCCTGCGG GATGTGGTAT                                            20

(2) INFORMATION FOR SEQ ID NO: 572:

(i) SEQUENCE CHARACTERISTICS:
        (A) LENGTH: 20 base pairs
```

(B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 572:

ACCCTGCGGG ATGTGGTATT                                                  20

(2) INFORMATION FOR SEQ ID NO: 573:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 573:

CCCTGCGGGA TGTGGTATTC                                                  20

(2) INFORMATION FOR SEQ ID NO: 574:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 574:

CCTGCGGGAT GTGGTATTCC                                                  20

(2) INFORMATION FOR SEQ ID NO: 575:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 575:

CTGCGGGATG TGGTATTCCT                                                  20

(2) INFORMATION FOR SEQ ID NO: 576:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 576:

TGCGGGATGT GGTATTCCTA                                                    20

(2) INFORMATION FOR SEQ ID NO: 577:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 577:

GCGGGATGTG GTATTCCTAA                                                    20

(2) INFORMATION FOR SEQ ID NO: 578:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 578:

CGGGATGTGG TATTCCTAAT                                                    20

(2) INFORMATION FOR SEQ ID NO: 579:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 579:

GGGATGTGGT ATTCCTAATT                                                    20

(2) INFORMATION FOR SEQ ID NO: 580:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 580:

GGATGTGGTA TTCCTAATTG                                                         20

(2) INFORMATION FOR SEQ ID NO: 581:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 581:

GATGTGGTAT TCCTAATTGA                                                         20

(2) INFORMATION FOR SEQ ID NO: 582:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 582:

ATGTGGTATT CCTAATTGAA                                                         20

(2) INFORMATION FOR SEQ ID NO: 583:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 583:

TGTGGTATTC CTAATTGAAC                                                         20

(2) INFORMATION FOR SEQ ID NO: 584:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 584:

GTGGTATTCC TAATTGAACT                                               20

(2) INFORMATION FOR SEQ ID NO: 585:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 585:

TGGTATTCCT AATTGAACTT                                               20

(2) INFORMATION FOR SEQ ID NO: 586:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 586:

GGTATTCCTA ATTGAACTTC                                               20

(2) INFORMATION FOR SEQ ID NO: 587:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 587:

GTATTCCTAA TTGAACTTCC                                               20

(2) INFORMATION FOR SEQ ID NO: 588:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 588:

```
TATTCCTAAT TGAACTTCCC                                                    20
```

(2) INFORMATION FOR SEQ ID NO: 589:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 589:

```
ATTCCTAATT GAACTTCCCA                                                    20
```

(2) INFORMATION FOR SEQ ID NO: 590:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 590:

```
TTCCTAATTG AACTTCCCAG                                                    20
```

(2) INFORMATION FOR SEQ ID NO: 591:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 591:

```
TCCTAATTGA ACTTCCCAGA                                                    20
```

(2) INFORMATION FOR SEQ ID NO: 592:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 592:

```
CCTAATTGAA CTTCCCAGAA                                                    20
```

(2) INFORMATION FOR SEQ ID NO: 593:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 593:

CTAATTGAAC TTCCCAGAAG                                          20

(2) INFORMATION FOR SEQ ID NO: 594:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 594:

TAATTGAACT TCCCAGAAGT                                          20

(2) INFORMATION FOR SEQ ID NO: 595:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 595:

AATTGAACTT CCCAGAAGTC                                          20

(2) INFORMATION FOR SEQ ID NO: 596:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 596:

ATTGAACTTC CCAGAAGTCT                                          20

(2) INFORMATION FOR SEQ ID NO: 597:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 597:

TTGAACTTCC CAGAAGTCTT                                           20

(2) INFORMATION FOR SEQ ID NO: 598:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 598:

TGAACTTCCC AGAAGTCTTG                                           20

(2) INFORMATION FOR SEQ ID NO: 599:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 599:

GAACTTCCCA GAAGTCTTGA                                           20

(2) INFORMATION FOR SEQ ID NO: 600:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 600:

AACTTCCCAG AAGTCTTGAG                                           20

(2) INFORMATION FOR SEQ ID NO: 601:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 601:

ACTTCCCAGA AGTCTTGAGT                                           20

(2) INFORMATION FOR SEQ ID NO: 602:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 602:

CTTCCCAGAA GTCTTGAGTT                                           20

(2) INFORMATION FOR SEQ ID NO: 603:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 603:

TTCCCAGAAG TCTTGAGTTC                                           20

(2) INFORMATION FOR SEQ ID NO: 604:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 604:

TCCCAGAAGT CTTGAGTTCT                                           20

(2) INFORMATION FOR SEQ ID NO: 605:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 605:

CCCAGAAGTC TTGAGTTCTC                                           20

(2) INFORMATION FOR SEQ ID NO: 606:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 606:

CCAGAAGTCT TGAGTTCTCT                                           20

(2) INFORMATION FOR SEQ ID NO: 607:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 607:

CAGAAGTCTT GAGTTCTCTT                                           20

(2) INFORMATION FOR SEQ ID NO: 608:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 608:

AGAAGTCTTG AGTTCTCTTA                                           20

(2) INFORMATION FOR SEQ ID NO: 609:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 609:

GAAGTCTTGA GTTCTCTTAT                                              20

(2) INFORMATION FOR SEQ ID NO: 610:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 610:

AAGTCTTGAG TTCTCTTATT                                              20

(2) INFORMATION FOR SEQ ID NO: 611:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 611:

AGTCTTGAGT TCTCTTATTA                                              20

(2) INFORMATION FOR SEQ ID NO: 612:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 612:

GTCTTGAGTT CTCTTATTAA                                              20

(2) INFORMATION FOR SEQ ID NO: 613:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 613:

```
TCTTGAGTTC TCTTATTAAG                                                      20

(2) INFORMATION FOR SEQ ID NO: 614:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 614:

CTTGAGTTCT CTTATTAAGT                                                      20

(2) INFORMATION FOR SEQ ID NO: 615:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 615:

TTGAGTTCTC TTATTAAGTT                                                      20

(2) INFORMATION FOR SEQ ID NO: 616:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 616:

TGAGTTCTCT TATTAAGTTC                                                      20

(2) INFORMATION FOR SEQ ID NO: 617:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 617:

GAGTTCTCTT ATTAAGTTCT                                                      20
```

(2) INFORMATION FOR SEQ ID NO: 618:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 618:

AGTTCTCTTA TTAAGTTCTC                                           20

(2) INFORMATION FOR SEQ ID NO: 619:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 619:

GTTCTCTTAT TAAGTTCTCT                                           20

(2) INFORMATION FOR SEQ ID NO: 620:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 620:

TTCTCTTATT AAGTTCTCTG                                           20

(2) INFORMATION FOR SEQ ID NO: 621:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 621:

TCTCTTATTA AGTTCTCTGA                                           20

(2) INFORMATION FOR SEQ ID NO: 622:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 622:

CTCTTATTAA GTTCTCTGAA                                                    20

(2) INFORMATION FOR SEQ ID NO: 623:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 623:

TCTTATTAAG TTCTCTGAAA                                                    20

(2) INFORMATION FOR SEQ ID NO: 624:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 624:

CTTATTAAGT TCTCTGAAAT                                                    20

(2) INFORMATION FOR SEQ ID NO: 625:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 625:

TTATTAAGTT CTCTGAAATC                                                    20

(2) INFORMATION FOR SEQ ID NO: 626:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 626:

TATTAAGTTC TCTGAAATCT                                               20

(2) INFORMATION FOR SEQ ID NO: 627:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 627:

ATTAAGTTCT CTGAAATCTA                                               20

(2) INFORMATION FOR SEQ ID NO: 628:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 628:

TTAAGTTCTC TGAAATCTAC                                               20

(2) INFORMATION FOR SEQ ID NO: 629:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 629:

TAAGTTCTCT GAAATCTACT                                               20

(2) INFORMATION FOR SEQ ID NO: 630:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 630:

AAGTTCTCTG AAATCTACTA                                              20

(2) INFORMATION FOR SEQ ID NO: 631:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 631:

AGTTCTCTGA AATCTACTAA                                              20

(2) INFORMATION FOR SEQ ID NO: 632:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 632:

GTTCTCTGAA ATCTACTAAT                                              20

(2) INFORMATION FOR SEQ ID NO: 633:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 633:

TTCTCTGAAA TCTACTAATT                                              20

(2) INFORMATION FOR SEQ ID NO: 634:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 634:

TCTCTGAAAT CTACTAATTT                                                     20

(2) INFORMATION FOR SEQ ID NO: 635:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 635:

CTCTGAAATC TACTAATTTT                                                     20

(2) INFORMATION FOR SEQ ID NO: 636:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 636:

TCTGAAATCT ACTAATTTTC                                                     20

(2) INFORMATION FOR SEQ ID NO: 637:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 637:

CTGAAATCTA CTAATTTTCT                                                     20

(2) INFORMATION FOR SEQ ID NO: 638:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 638:

TGAAATCTAC TAATTTTCTC                                              20

(2) INFORMATION FOR SEQ ID NO: 639:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 639:

GAAATCTACT AATTTTCTCC                                              20

(2) INFORMATION FOR SEQ ID NO: 640:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 640:

AAATCTACTA ATTTTCTCCA                                              20

(2) INFORMATION FOR SEQ ID NO: 641:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 641:

AATCTACTAA TTTTCTCCAT                                              20

(2) INFORMATION FOR SEQ ID NO: 642:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 642:

ATCTACTAAT TTTCTCCATT                                              20

(2) INFORMATION FOR SEQ ID NO: 643:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 643:

TCTACTAATT TTCTCCATTT                                            20

(2) INFORMATION FOR SEQ ID NO: 644:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 644:

CTACTAATTT TCTCCATTTA                                            20

(2) INFORMATION FOR SEQ ID NO: 645:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 645:

TACTAATTTT CTCCATTTAG                                            20

(2) INFORMATION FOR SEQ ID NO: 646:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 646:

ACTAATTTTC TCCATTTAGT                                            20

(2) INFORMATION FOR SEQ ID NO: 647:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 647:

CTAATTTTCT CCATTTAGTA                                             20

(2) INFORMATION FOR SEQ ID NO: 648:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 648:

TAATTTTCTC CATTTAGTAC                                             20

(2) INFORMATION FOR SEQ ID NO: 649:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 649:

AATTTTCTCC ATTTAGTACT                                             20

(2) INFORMATION FOR SEQ ID NO: 650:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 650:

ATTTTCTCCA TTTAGTACTG                                             20

(2) INFORMATION FOR SEQ ID NO: 651:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 651:

TTTTCTCCAT TTAGTACTGT                                                    20

(2) INFORMATION FOR SEQ ID NO: 652:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 652:

TTTCTCCATT TAGTACTGTC                                                    20

(2) INFORMATION FOR SEQ ID NO: 653:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 653:

TTCTCCATTT AGTACTGTCT                                                    20

(2) INFORMATION FOR SEQ ID NO: 654:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 654:

TCTCCATTTA GTACTGTCTT                                                    20

(2) INFORMATION FOR SEQ ID NO: 655:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        (ii) MOLECULE TYPE: cDNA (iii) HYPOTHETICAL: NO (iv) ANTI-SENSE: NO (xi) SEQUENCE DESCRIPTION: SEQ ID NO: 655:

CTCCATTTAG TACTGTCTTT                                                   20

(2) INFORMATION FOR SEQ ID NO: 656:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 656:

TCCATTTAGT ACTGTCTTTT                                                   20

(2) INFORMATION FOR SEQ ID NO: 657:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 657:

CCATTTAGTA CTGTCTTTTT                                                   20

(2) INFORMATION FOR SEQ ID NO: 658:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 658:

CATTTAGTAC TGTCTTTTTT                                                   20

(2) INFORMATION FOR SEQ ID NO: 659:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 659:

ATTTAGTACT GTCTTTTTTC                                           20

(2) INFORMATION FOR SEQ ID NO: 660:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 660:

TTTAGTACTG TCTTTTTTCT                                           20

(2) INFORMATION FOR SEQ ID NO: 661:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 661:

TTAGTACTGT CTTTTTTCTT                                           20

(2) INFORMATION FOR SEQ ID NO: 662:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 662:

TAGTACTGTC TTTTTTCTTT                                           20

(2) INFORMATION FOR SEQ ID NO: 663:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 663:

AGTACTGTCT TTTTTCTTTA                                           20

(2) INFORMATION FOR SEQ ID NO: 664:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 664:

GTACTGTCTT TTTTCTTTAT                                           20

(2) INFORMATION FOR SEQ ID NO: 665:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 665:

TACTGTCTTT TTTCTTTATG                                           20

(2) INFORMATION FOR SEQ ID NO: 666:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 666:

ACTGTCTTTT TTCTTTATGG                                           20

(2) INFORMATION FOR SEQ ID NO: 667:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 667:

```
CTGTCTTTTT TCTTTATGGC                                              20
```

(2) INFORMATION FOR SEQ ID NO: 668:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 668:

```
TGTCTTTTTT CTTTATGGCA                                              20
```

(2) INFORMATION FOR SEQ ID NO: 669:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 669:

```
GTCTTTTTTC TTTATGGCAA                                              20
```

(2) INFORMATION FOR SEQ ID NO: 670:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 670:

```
TCTTTTTTCT TTATGGCAAA                                              20
```

(2) INFORMATION FOR SEQ ID NO: 671:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 671:

```
CTTTTTTCTT TATGGCAAAT                                              20
```

(2) INFORMATION FOR SEQ ID NO: 672:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 672:

TTTTTTCTTT ATGGCAAATA                                             20

(2) INFORMATION FOR SEQ ID NO: 673:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 673:

TTTTTCTTTA TGGCAAATAC                                             20

(2) INFORMATION FOR SEQ ID NO: 674:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 674:

TTTTCTTTAT GGCAAATACT                                             20

(2) INFORMATION FOR SEQ ID NO: 675:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 675:

TTTCTTTATG GCAAATACTG                                             20

(2) INFORMATION FOR SEQ ID NO: 676:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 676:

TTCTTTATGG CAAATACTGG                                              20

(2) INFORMATION FOR SEQ ID NO: 677:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 677:

TCTTTATGGC AAATACTGGA                                              20

(2) INFORMATION FOR SEQ ID NO: 678:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 678:

CTTTATGGCA AATACTGGAG                                              20

(2) INFORMATION FOR SEQ ID NO: 679:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 679:

TTTATGGCAA ATACTGGAGT                                              20

(2) INFORMATION FOR SEQ ID NO: 680:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 680:

TTATGGCAAA TACTGGAGTA                                                        20

(2) INFORMATION FOR SEQ ID NO: 681:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 681:

TATGGCAAAT ACTGGAGTAT                                                        20

(2) INFORMATION FOR SEQ ID NO: 682:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 682:

ATGGCAAATA CTGGAGTATT                                                        20

(2) INFORMATION FOR SEQ ID NO: 683:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 683:

TGGCAAATAC TGGAGTATTG                                                        20

(2) INFORMATION FOR SEQ ID NO: 684:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 684:

GGCAAATACT GGAGTATTGT                                               20

(2) INFORMATION FOR SEQ ID NO: 685:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 685:

GCAAATACTG GAGTATTGTA                                               20

(2) INFORMATION FOR SEQ ID NO: 686:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 686:

CAAATACTGG AGTATTGTAT                                               20

(2) INFORMATION FOR SEQ ID NO: 687:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 687:

AAATACTGGA GTATTGTATG                                               20

(2) INFORMATION FOR SEQ ID NO: 688:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 688:

AATACTGGAG TATTGTATGG                                              20

(2) INFORMATION FOR SEQ ID NO: 689:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 689:

ATACTGGAGT ATTGTATGGA                                              20

(2) INFORMATION FOR SEQ ID NO: 690:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 690:

TACTGGAGTA TTGTATGGAT                                              20

(2) INFORMATION FOR SEQ ID NO: 691:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 691:

ACTGGAGTAT TGTATGGATT                                              20

(2) INFORMATION FOR SEQ ID NO: 692:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 692:

CTGGAGTATT GTATGGATTC                                    20

(2) INFORMATION FOR SEQ ID NO: 693:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 693:

TGGAGTATTG TATGGATTCT                                    20

(2) INFORMATION FOR SEQ ID NO: 694:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 694:

GGAGTATTGT ATGGATTCTC                                    20

(2) INFORMATION FOR SEQ ID NO: 695:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 695:

GAGTATTGTA TGGATTCTCA                                    20

(2) INFORMATION FOR SEQ ID NO: 696:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 696:

AGTATTGTAT GGATTCTCAG                                    20

(2) INFORMATION FOR SEQ ID NO: 697:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 697:

GTATTGTATG GATTCTCAGG                                          20

(2) INFORMATION FOR SEQ ID NO: 698:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 698:

TATTGTATGG ATTCTCAGGC                                          20

(2) INFORMATION FOR SEQ ID NO: 699:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 699:

ATTGTATGGA TTCTCAGGCC                                          20

(2) INFORMATION FOR SEQ ID NO: 700:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 700:

TTGTATGGAT TCTCAGGCCC                                          20

(2) INFORMATION FOR SEQ ID NO: 701:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 701:

TGTATGGATT CTCAGGCCCA                                              20

(2) INFORMATION FOR SEQ ID NO: 702:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 702:

GTATGGATTC TCAGGCCCAA                                              20

(2) INFORMATION FOR SEQ ID NO: 703:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 703:

TATGGATTCT CAGGCCCAAT                                              20

(2) INFORMATION FOR SEQ ID NO: 704:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 704:

ATGGATTCTC AGGCCCAATT                                              20

(2) INFORMATION FOR SEQ ID NO: 705:

(i) SEQUENCE CHARACTERISTICS:
        (A) LENGTH: 20 base pairs
        (B) TYPE: nucleic acid (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 705:

TGGATTCTCA GGCCCAATTT                                                     20

(2) INFORMATION FOR SEQ ID NO: 706:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 706:

GGATTCTCAG GCCCAATTTT                                                     20

(2) INFORMATION FOR SEQ ID NO: 707:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 707:

GATTCTCAGG CCCAATTTTT                                                     20

(2) INFORMATION FOR SEQ ID NO: 708:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 708:

ATTCTCAGGC CCAATTTTTG                                                     20

(2) INFORMATION FOR SEQ ID NO: 709:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 709:

TTCTCAGGCC CAATTTTTGA                                                    20

(2) INFORMATION FOR SEQ ID NO: 710:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 710:

TCTCAGGCCC AATTTTTGAA                                                    20

(2) INFORMATION FOR SEQ ID NO: 711:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 711:

CTCAGGCCCA ATTTTTGAAA                                                    20

(2) INFORMATION FOR SEQ ID NO: 712:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 712:

TCAGGCCCAA TTTTTGAAAT                                                    20

(2) INFORMATION FOR SEQ ID NO: 713:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 713:

CAGGCCCAAT TTTTGAAATT                                                    20

(2) INFORMATION FOR SEQ ID NO: 714:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 714:

AGGCCCAATT TTTGAAATTT                                                    20

(2) INFORMATION FOR SEQ ID NO: 715:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 715:

GGCCCAATTT TTGAAATTTT                                                    20

(2) INFORMATION FOR SEQ ID NO: 716:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 716:

GCCCAATTTT TGAAATTTTC                                                    20

(2) INFORMATION FOR SEQ ID NO: 717:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 717:

CCCAATTTTT GAAATTTTCC                                    20

(2) INFORMATION FOR SEQ ID NO: 718:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 718:

CCAATTTTTG AAATTTTCCC                                    20

(2) INFORMATION FOR SEQ ID NO: 719:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 719:

CAATTTTTGA AATTTTCCCT                                    20

(2) INFORMATION FOR SEQ ID NO: 720:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 720:

AATTTTTGAA ATTTTCCCTT                                    20

(2) INFORMATION FOR SEQ ID NO: 721:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 721:

ATTTTTGAAA TTTTCCCTTC                                    20

(2) INFORMATION FOR SEQ ID NO: 722:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 722:

TTTTTGAAAT TTTCCCTTCC                                  20

(2) INFORMATION FOR SEQ ID NO: 723:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 723:

TTTTGAAATT TTCCCTTCCT                                  20

(2) INFORMATION FOR SEQ ID NO: 724:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 724:

TTTGAAATTT TCCCTTCCTT                                  20

(2) INFORMATION FOR SEQ ID NO: 725:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 725:

TTGAAATTTT CCCTTCCTTT                                  20

(2) INFORMATION FOR SEQ ID NO: 726:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 726:

TGAAATTTTC CCTTCCTTTT                                                    20

(2) INFORMATION FOR SEQ ID NO: 727:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 727:

GAAATTTTCC CTTCCTTTTC                                                    20

(2) INFORMATION FOR SEQ ID NO: 728:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 728:

AAATTTTCCC TTCCTTTTCC                                                    20

(2) INFORMATION FOR SEQ ID NO: 729:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 729:

AATTTTCCCT TCCTTTTCCA                                                    20

(2) INFORMATION FOR SEQ ID NO: 730:

(i) SEQUENCE CHARACTERISTICS:
            (A) LENGTH: 20 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 730:

ATTTTCCCTT CCTTTTCCAT                                                    20

(2) INFORMATION FOR SEQ ID NO: 731:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 731:

TTTTCCCTTC CTTTTCCATT                                                    20

(2) INFORMATION FOR SEQ ID NO: 732:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 732:

TTTCCCTTCC TTTTCCATTT                                                    20

(2) INFORMATION FOR SEQ ID NO: 733:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 733:

TTCCCTTCCT TTTCCATTTC                                                    20

(2) INFORMATION FOR SEQ ID NO: 734:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 734:

TCCCTTCCTT TTCCATTTCT                                                            20

(2) INFORMATION FOR SEQ ID NO: 735:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 735:

CCCTTCCTTT TCCATTTCTG                                                            20

(2) INFORMATION FOR SEQ ID NO: 736:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 736:

CCTTCCTTTT CCATTTCTGT                                                            20

(2) INFORMATION FOR SEQ ID NO: 737:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 737:

CTTCCTTTTC CATTTCTGTA                                                            20

(2) INFORMATION FOR SEQ ID NO: 738:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA -continued (iii) HYPOTHETICAL: NO (iv) ANTI-SENSE: NO (xi) SEQUENCE DESCRIPTION: SEQ ID NO: 738:

TTCCTTTTCC ATTTCTGTAC                                                       20

(2) INFORMATION FOR SEQ ID NO: 739:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 739:

TCCTTTTCCA TTTCTGTACA                                                       20

(2) INFORMATION FOR SEQ ID NO: 740:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 740:

CCTTTTCCAT TTCTGTACAA                                                       20

(2) INFORMATION FOR SEQ ID NO: 741:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 741:

CTTTTCCATT TCTGTACAAA                                                     20

(2) INFORMATION FOR SEQ ID NO: 742:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO

```
    (xi) SEQUENCE DESCRIPTION: SEQ ID NO: 742:

TTTTCCATTT CTGTACAAAT                                                        20

(2) INFORMATION FOR SEQ ID NO: 743:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 743:

TTTCCATTTC TGTACAAATT                                                        20

(2) INFORMATION FOR SEQ ID NO: 744:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 744:

TTCCATTTCT GTACAAATTT                                                        20

(2) INFORMATION FOR SEQ ID NO: 745:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 745:

TCCATTTCTG TACAAATTTC                                                        20

(2) INFORMATION FOR SEQ ID NO: 746:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 746:
```

CCATTTCTGT ACAAATTTCT                    20

(2) INFORMATION FOR SEQ ID NO: 747:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 747:

CATTTCTGTA CAAATTTCTA                    20

(2) INFORMATION FOR SEQ ID NO: 748:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 748:

ATTTCTGTAC AAATTTCTAC                    20

(2) INFORMATION FOR SEQ ID NO: 749:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 749:

TTTCTGTACA AATTTCTACT                    20

(2) INFORMATION FOR SEQ ID NO: 750:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 750:

TTCTGTACAA ATTTCTACTA                    20

```
(2) INFORMATION FOR SEQ ID NO: 751:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 751:

TCTGTACAAA TTTCTACTAA                                              20

(2) INFORMATION FOR SEQ ID NO: 752:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 752:

CTGTACAAAT TTCTACTAAT                                              20

(2) INFORMATION FOR SEQ ID NO: 753:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 753:

TGTACAAATT TCTACTAATG                                              20

(2) INFORMATION FOR SEQ ID NO: 754:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 754:

GTACAAATTT CTACTAATGC                                              20

(2) INFORMATION FOR SEQ ID NO: 755:

(i) SEQUENCE CHARACTERISTICS:
```

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 755:

TACAAATTTC TACTAATGCT                                          20

(2) INFORMATION FOR SEQ ID NO: 756:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 756:

ACAAATTTCT ACTAATGCTT                                          20

(2) INFORMATION FOR SEQ ID NO: 757:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 757:

CAAATTTCTA CTAATGCTTT                                          20

(2) INFORMATION FOR SEQ ID NO: 758:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 758:

AAATTTCTAC TAATGCTTTT                                          20

(2) INFORMATION FOR SEQ ID NO: 759:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 759:

AATTTCTACT AATGCTTTTA                                              20

(2) INFORMATION FOR SEQ ID NO: 760:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 760:

ATTTCTACTA ATGCTTTTAT                                              20

(2) INFORMATION FOR SEQ ID NO: 761:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 761:

TTTCTACTAA TGCTTTTATT                                              20

(2) INFORMATION FOR SEQ ID NO: 762:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 762:

TTCTACTAAT GCTTTTATTT                                              20

(2) INFORMATION FOR SEQ ID NO: 763:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 763:

TCTACTAATG CTTTTATTTT                                                   20

(2) INFORMATION FOR SEQ ID NO: 764:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 764:

CTACTAATGC TTTTATTTTT                                                   20

(2) INFORMATION FOR SEQ ID NO: 765:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 765:

TACTAATGCT TTTATTTTTT                                                   20

(2) INFORMATION FOR SEQ ID NO: 766:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 766:

ACTAATGCTT TTATTTTTTC                                                   20

(2) INFORMATION FOR SEQ ID NO: 767:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 767:

CTAATGCTTT TATTTTTTCT                                                    20

(2) INFORMATION FOR SEQ ID NO: 768:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 768:

TAATGCTTTT ATTTTTTCTT                                                    20

(2) INFORMATION FOR SEQ ID NO: 769:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 769:

AATGCTTTTA TTTTTTCTTC                                                    20

(2) INFORMATION FOR SEQ ID NO: 770:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 770:

ATGCTTTTAT TTTTCTTCT                                                     20

(2) INFORMATION FOR SEQ ID NO: 771:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 771:

```
TGCTTTTATT TTTTCTTCTG                                          20

(2) INFORMATION FOR SEQ ID NO: 772:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 772:

GCTTTTATTT TTTCTTCTGT                                          20

(2) INFORMATION FOR SEQ ID NO: 773:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 773:

CTTTTATTTT TTCTTCTGTC                                          20

(2) INFORMATION FOR SEQ ID NO: 774:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 774:

TTTTATTTTT TCTTCTGTCA                                          20

(2) INFORMATION FOR SEQ ID NO: 775:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 775:

TTTATTTTTT CTTCTGTCAA                                          20
```

(2) INFORMATION FOR SEQ ID NO: 776:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 776:

TTATTTTTTC TTCTGTCAAT    20

(2) INFORMATION FOR SEQ ID NO: 777:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 777:

TATTTTTTCT TCTGTCAATG    20

(2) INFORMATION FOR SEQ ID NO: 778:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 778:

ATTTTTTCTT CTGTCAATGG    20

(2) INFORMATION FOR SEQ ID NO: 779:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 779:

TTTTTTCTTC TGTCAATGGC    20

(2) INFORMATION FOR SEQ ID NO: 780:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 780:

TTTTTCTTCT GTCAATGGCC                                                  20

(2) INFORMATION FOR SEQ ID NO: 781:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 781:

TTTTCTTCTG TCAATGGCCA                                                  20

(2) INFORMATION FOR SEQ ID NO: 782:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 782:

TTTCTTCTGT CAATGGCCAT                                                  20

(2) INFORMATION FOR SEQ ID NO: 783:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 783:

TTCTTCTGTC AATGGCCATT                                                  20

(2) INFORMATION FOR SEQ ID NO: 784:

(i) SEQUENCE CHARACTERISTICS:
        (A) LENGTH: 20 base pairs
        (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 784:

TCTTCTGTCA ATGGCCATTG                                              20

(2) INFORMATION FOR SEQ ID NO: 785:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 785:

CTTCTGTCAA TGGCCATTGT                                              20

(2) INFORMATION FOR SEQ ID NO: 786:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 786:

TTCTGTCAAT GGCCATTGTT                                              20

(2) INFORMATION FOR SEQ ID NO: 787:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 787:

TCTGTCAATG GCCATTGTTT                                              20

(2) INFORMATION FOR SEQ ID NO: 788:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 788:

CTGTCAATGG CCATTGTTTA                                              20

(2) INFORMATION FOR SEQ ID NO: 789:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 789:

TGTCAATGGC CATTGTTTAA                                              20

(2) INFORMATION FOR SEQ ID NO: 790:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 790:

GTCAATGGCC ATTGTTTAAC                                              20

(2) INFORMATION FOR SEQ ID NO: 791:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 791:

TCAATGGCCA TTGTTTAACT                                              20

(2) INFORMATION FOR SEQ ID NO: 792:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 792:

CAATGGCCAT TGTTTAACTT                                                        20

(2) INFORMATION FOR SEQ ID NO: 793:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 793:

AATGGCCATT GTTTAACTTT                                                        20

(2) INFORMATION FOR SEQ ID NO: 794:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 794:

ATGGCCATTG TTTAACTTTT                                                        20

(2) INFORMATION FOR SEQ ID NO: 795:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 795:

TGGCCATTGT TTAACTTTTG                                                        20

(2) INFORMATION FOR SEQ ID NO: 796:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 796:

GGCCATTGTT TAACTTTTGG                                               20

(2) INFORMATION FOR SEQ ID NO: 797:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 797:

GCCATTGTTT AACTTTTGGG                                               20

(2) INFORMATION FOR SEQ ID NO: 798:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 798:

CCATTGTTTA ACTTTTGGGC                                               20

(2) INFORMATION FOR SEQ ID NO: 799:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 799:

CATTGTTTAA CTTTTGGGCC                                               20

(2) INFORMATION FOR SEQ ID NO: 800:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 800:

ATTGTTTAAC TTTTGGGCCA                                               20

(2) INFORMATION FOR SEQ ID NO: 801:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 801:

TTGTTTAACT TTTGGGCCAT                                           20

(2) INFORMATION FOR SEQ ID NO: 802:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 802:

TGTTTAACTT TTGGGCCATC                                           20

(2) INFORMATION FOR SEQ ID NO: 803:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 803:

GTTTAACTTT TGGGCCATCC                                           20

(2) INFORMATION FOR SEQ ID NO: 804:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 804:

TTTAACTTTT GGGCCATCCA                                           20

(2) INFORMATION FOR SEQ ID NO: 805:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 805:

TTAACTTTTG GGCCATCCAT                                            20

(2) INFORMATION FOR SEQ ID NO: 806:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 806:

TAACTTTTGG GCCATCCATT                                            20

(2) INFORMATION FOR SEQ ID NO: 807:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 807:

AACTTTTGGG CCATCCATTC                                            20

(2) INFORMATION FOR SEQ ID NO: 808:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 808:

ACTTTTGGGC CATCCATTCC                                            20

(2) INFORMATION FOR SEQ ID NO: 809:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 809:

CTTTTGGGCC ATCCATTCCT                                                       20

(2) INFORMATION FOR SEQ ID NO: 810:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 810:

TTTTGGGCCA TCCATTCCTG                                                       20

(2) INFORMATION FOR SEQ ID NO: 811:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 811:

TTTGGGCCAT CCATTCCTGG                                                       20

(2) INFORMATION FOR SEQ ID NO: 812:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 812:

TTGGGCCATC CATTCCTGGC                                                       20

(2) INFORMATION FOR SEQ ID NO: 813:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 813:

TGGGCCATCC ATTCCTGGCT                                                   20

(2) INFORMATION FOR SEQ ID NO: 814:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 814:

GGGCCATCCA TTCCTGGCTT                                                   20

(2) INFORMATION FOR SEQ ID NO: 815:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 815:

GGCCATCCAT TCCTGGCTTT                                                   20

(2) INFORMATION FOR SEQ ID NO: 816:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 816:

GCCATCCATT CCTGGCTTTA                                                   20

(2) INFORMATION FOR SEQ ID NO: 817:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 817:

CCATCCATTC CTGGCTTTAA                                                   20

(2) INFORMATION FOR SEQ ID NO: 818:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 818:

CATCCATTCC TGGCTTTAAT                                                   20

(2) INFORMATION FOR SEQ ID NO: 819:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 819:

ATCCATTCCT GGCTTTAATT                                                   20

(2) INFORMATION FOR SEQ ID NO: 820:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 820:

TCCATTCCTG GCTTTAATTT                                                   20

(2) INFORMATION FOR SEQ ID NO: 821:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 821:

CCATTCCTGG CTTTAATTTT                                          20

(2) INFORMATION FOR SEQ ID NO: 822:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 822:

CATTCCTGGC TTTAATTTTA                                          20

(2) INFORMATION FOR SEQ ID NO: 823:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 823:

ATTCCTGGCT TTAATTTTAC                                          20

(2) INFORMATION FOR SEQ ID NO: 824:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 824:

TTCCTGGCTT TAATTTTACT                                          20

(2) INFORMATION FOR SEQ ID NO: 825:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 825:

TCCTGGCTTT AATTTTACTG                    20

(2) INFORMATION FOR SEQ ID NO: 826:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 826:

CCTGGCTTTA ATTTTACTGG                    20

(2) INFORMATION FOR SEQ ID NO: 827:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 827:

CTGGCTTTAA TTTTACTGGT                    20

(2) INFORMATION FOR SEQ ID NO: 828:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 828:

TGGCTTTAAT TTTACTGGTA                    20

(2) INFORMATION FOR SEQ ID NO: 829:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 829:

GGCTTTAATT TTACTGGTAC                    20

(2) INFORMATION FOR SEQ ID NO: 830:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 830:

GCTTTAATTT TACTGGTACA        20

(2) INFORMATION FOR SEQ ID NO: 831:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 831:

CTTTAATTTT ACTGGTACAG        20

(2) INFORMATION FOR SEQ ID NO: 832:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 832:

TTTAATTTTA CTGGTACAGT        20

(2) INFORMATION FOR SEQ ID NO: 833:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 833:

TTAATTTTAC TGGTACAGTC        20

(2) INFORMATION FOR SEQ ID NO: 834:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 834:

TAATTTTACT GGTACAGTCT                                               20

(2) INFORMATION FOR SEQ ID NO: 835:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 835:

AATTTTACTG GTACAGTCTC                                               20

(2) INFORMATION FOR SEQ ID NO: 836:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 836:

ATTTTACTGG TACAGTCTCA                                               20

(2) INFORMATION FOR SEQ ID NO: 837:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 837:

TTTTACTGGT ACAGTCTCAA                                               20

(2) INFORMATION FOR SEQ ID NO: 838:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 838:

TTTACTGGTA CAGTCTCAAT                                                    20

(2) INFORMATION FOR SEQ ID NO: 839:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 839:

TTACTGGTAC AGTCTCAATA                                                    20

(2) INFORMATION FOR SEQ ID NO: 840:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 840:

TACTGGTACA GTCTCAATAG                                                    20

(2) INFORMATION FOR SEQ ID NO: 841:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 841:

ACTGGTACAG TCTCAATAGG                                                    20

(2) INFORMATION FOR SEQ ID NO: 842:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 842:

CTGGTACAGT CTCAATAGGG                                                  20

(2) INFORMATION FOR SEQ ID NO: 843:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 843:

TGGTACAGTC TCAATAGGGC                                                  20

(2) INFORMATION FOR SEQ ID NO: 844:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 844:

GGTACAGTCT CAATAGGGCT                                                  20

(2) INFORMATION FOR SEQ ID NO: 845:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 845:

GTACAGTCTC AATAGGGCTA                                                  20

(2) INFORMATION FOR SEQ ID NO: 846:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 846:

TACAGTCTCA ATAGGGCTAA                                                    20

(2) INFORMATION FOR SEQ ID NO: 847:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 847:

ACAGTCTCAA TAGGGCTAAT                                                    20

(2) INFORMATION FOR SEQ ID NO: 848:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 848:

CAGTCTCAAT AGGGCTAATG                                                    20

(2) INFORMATION FOR SEQ ID NO: 849:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 849:

AGTCTCAATA GGGCTAATGG                                                    20

(2) INFORMATION FOR SEQ ID NO: 850:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 850:

```
GTCTCAATAG GGCTAATGGG                                              20

(2) INFORMATION FOR SEQ ID NO: 851:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 851:

TCTCAATAGG GCTAATGGGA                                              20

(2) INFORMATION FOR SEQ ID NO: 852:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 852:

CTCAATAGGG CTAATGGGAA                                              20

(2) INFORMATION FOR SEQ ID NO: 853:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 853:

TCAATAGGGC TAATGGGAAA                                              20

(2) INFORMATION FOR SEQ ID NO: 854:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 854:

CAATAGGGCT AATGGGAAAA                                              20
```

(2) INFORMATION FOR SEQ ID NO: 855:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 855:

AATAGGGCTA ATGGGAAAAT                                  20

(2) INFORMATION FOR SEQ ID NO: 856:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 856:

ATAGGGCTAA TGGGAAAATT                                  20

(2) INFORMATION FOR SEQ ID NO: 857:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 857:

TAGGGCTAAT GGGAAAATTT                                  20

(2) INFORMATION FOR SEQ ID NO: 858:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 858:

AGGGCTAATG GGAAAATTTA                                  20

(2) INFORMATION FOR SEQ ID NO: 859:

```
       (i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 859:

GGGCTAATGG GAAAATTTAA                                                   20

(2) INFORMATION FOR SEQ ID NO: 860:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 860:

GGCTAATGGG AAAATTTAAA                                                   20

(2) INFORMATION FOR SEQ ID NO: 861:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 861:

GCTAATGGGA AAATTTAAAG                                                   20

(2) INFORMATION FOR SEQ ID NO: 862:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 862:

CTAATGGGAA AATTTAAAGT                                                   20

(2) INFORMATION FOR SEQ ID NO: 863:

(i) SEQUENCE CHARACTERISTICS:
           (A) LENGTH: 20 base pairs
           (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 863:

TAATGGGAAA ATTTAAAGTG                                               20

(2) INFORMATION FOR SEQ ID NO: 864:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 864:

AATGGGAAAA TTTAAAGTGC                                               20

(2) INFORMATION FOR SEQ ID NO: 865:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 865:

ATGGGAAAAT TTAAAGTGCA                                               20

(2) INFORMATION FOR SEQ ID NO: 866:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 866:

TGGGAAAATT TAAAGTGCAA                                               20

(2) INFORMATION FOR SEQ ID NO: 867:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

```
        (ii) MOLECULE TYPE: cDNA (iii) HYPOTHETICAL: NO (iv) ANTI-SENSE: NO (xi) SEQUENCE DESCRIPTION: SEQ ID NO: 867:

GGGAAAATTT AAAGTGCAAC                                              20

(2) INFORMATION FOR SEQ ID NO: 868:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 868:

GGAAAATTTA AAGTGCAACC                                              20

(2) INFORMATION FOR SEQ ID NO: 869:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 869:

GAAAATTTAA AGTGCAACCA                                              20

(2) INFORMATION FOR SEQ ID NO: 870:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 870:

AAAATTTAAA GTGCAACCAA                                              20

(2) INFORMATION FOR SEQ ID NO: 871:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO
```

(iv) ANTI-SENSE: NO (xi) SEQUENCE DESCRIPTION: SEQ ID NO: 871:

AAATTTAAAG TGCAACCAAT                                         20

(2) INFORMATION FOR SEQ ID NO: 872:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 872:

AATTTAAAGT GCAACCAATC                                         20

(2) INFORMATION FOR SEQ ID NO: 873:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 873:

ATTTAAAGTG CAACCAATCT                                         20

(2) INFORMATION FOR SEQ ID NO: 874:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 874:

TTTAAAGTGC AACCAATCTG                                         20

(2) INFORMATION FOR SEQ ID NO: 875:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 875:

TTAAAGTGCA ACCAATCTGA                                              20

(2) INFORMATION FOR SEQ ID NO: 876:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 876:

TAAAGTGCAA CCAATCTGAG                                              20

(2) INFORMATION FOR SEQ ID NO: 877:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 877:

AAAGTGCAAC CAATCTGAGT                                              20

(2) INFORMATION FOR SEQ ID NO: 878:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 878:

AAGTGCAACC AATCTGAGTC                                              20

(2) INFORMATION FOR SEQ ID NO: 879:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 879:

AGTGCAACCA ATCTGAGTCA                                              20

(2) INFORMATION FOR SEQ ID NO: 880:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 880:

GTGCAACCAA TCTGAGTCAA                                           20

(2) INFORMATION FOR SEQ ID NO: 881:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 881:

TGCAACCAAT CTGAGTCAAC                                           20

(2) INFORMATION FOR SEQ ID NO: 882:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 882:

GCAACCAATC TGAGTCAACA                                           20

(2) INFORMATION FOR SEQ ID NO: 883:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 883:

CAACCAATCT GAGTCAACAG                                           20

(2) INFORMATION FOR SEQ ID NO: 884:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 884:

AACCAATCTG AGTCAACAGA                                                      20

(2) INFORMATION FOR SEQ ID NO: 885:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 885:

ACCAATCTGA GTCAACAGAT                                                      20

(2) INFORMATION FOR SEQ ID NO: 886:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 886:

CCAATCTGAG TCAACAGATT                                                      20

(2) INFORMATION FOR SEQ ID NO: 887:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 887:

CAATCTGAGT CAACAGATTT                                                      20

(2) INFORMATION FOR SEQ ID NO: 888:

(i) SEQUENCE CHARACTERISTICS:
            (A) LENGTH: 20 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 888:

AATCTGAGTC AACAGATTTC                                               20

(2) INFORMATION FOR SEQ ID NO: 889:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 889:

ATCTGAGTCA ACAGATTTCT                                               20

(2) INFORMATION FOR SEQ ID NO: 890:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 890:

TCTGAGTCAA CAGATTTCTT                                               20

(2) INFORMATION FOR SEQ ID NO: 891:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 891:

CTGAGTCAAC AGATTTCTTC                                               20

(2) INFORMATION FOR SEQ ID NO: 892:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 892:

TGAGTCAACA GATTTCTTCC                                                    20

(2) INFORMATION FOR SEQ ID NO: 893:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 893:

GAGTCAACAG ATTTCTTCCA                                                    20

(2) INFORMATION FOR SEQ ID NO: 894:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 894:

AGTCAACAGA TTTCTTCCAA                                                    20

(2) INFORMATION FOR SEQ ID NO: 895:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 895:

GTCAACAGAT TTCTTCCAAT                                                    20

(2) INFORMATION FOR SEQ ID NO: 896:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 896:

TCAACAGATT TCTTCCAATT                                               20

(2) INFORMATION FOR SEQ ID NO: 897:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 897:

CAACAGATTT CTTCCAATTA                                               20

(2) INFORMATION FOR SEQ ID NO: 898:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 898:

AACAGATTTC TTCCAATTAT                                               20

(2) INFORMATION FOR SEQ ID NO: 899:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 899:

ACAGATTTCT TCCAATTATG                                               20

(2) INFORMATION FOR SEQ ID NO: 900:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 900:

CAGATTTCTT CCAATTATGT                                                        20

(2) INFORMATION FOR SEQ ID NO: 901:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 901:

AGATTTCTTC CAATTATGTT                                                        20

(2) INFORMATION FOR SEQ ID NO: 902:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 902:

GATTTCTTCC AATTATGTTG                                                        20

(2) INFORMATION FOR SEQ ID NO: 903:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 903:

ATTTCTTCCA ATTATGTTGA                                                        20

(2) INFORMATION FOR SEQ ID NO: 904:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 904:

```
TTTCTTCCAA TTATGTTGAC                                                    20
```

(2) INFORMATION FOR SEQ ID NO: 905:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 905:

```
TTCTTCCAAT TATGTTGACA                                                    20
```

(2) INFORMATION FOR SEQ ID NO: 906:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 906:

```
TCTTCCAATT ATGTTGACAG                                                    20
```

(2) INFORMATION FOR SEQ ID NO: 907:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 907:

```
CTTCCAATTA TGTTGACAGG                                                    20
```

(2) INFORMATION FOR SEQ ID NO: 908:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 908:

```
TTCCAATTAT GTTGACAGGT                                                    20
```

(2) INFORMATION FOR SEQ ID NO: 909:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 909:

TCCAATTATG TTGACAGGTG    20

(2) INFORMATION FOR SEQ ID NO: 910:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 910:

CCAATTATGT TGACAGGTGT    20

(2) INFORMATION FOR SEQ ID NO: 911:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 911:

CAATTATGTT GACAGGTGTA    20

(2) INFORMATION FOR SEQ ID NO: 912:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 912:

AATTATGTTG ACAGGTGTAG    20

(2) INFORMATION FOR SEQ ID NO: 913:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 913:

ATTATGTTGA CAGGTGTAGG                                            20

(2) INFORMATION FOR SEQ ID NO: 914:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 914:

TTATGTTGAC AGGTGTAGGT                                            20

(2) INFORMATION FOR SEQ ID NO: 915:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 915:

TATGTTGACA GGTGTAGGTC                                            20

(2) INFORMATION FOR SEQ ID NO: 916:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 916:

ATGTTGACAG GTGTAGGTCC                                            20

(2) INFORMATION FOR SEQ ID NO: 917:

(i) SEQUENCE CHARACTERISTICS:
            (A) LENGTH: 20 base pairs
            (B) TYPE: nucleic acid
            (C) STRANDEDNESS: single

```
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 917:

TGTTGACAGG TGTAGGTCCT                                           20

(2) INFORMATION FOR SEQ ID NO: 918:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 918:

GTTGACAGGT GTAGGTCCTA                                           20

(2) INFORMATION FOR SEQ ID NO: 919:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 919:

TTGACAGGTG TAGGTCCTAC                                           20

(2) INFORMATION FOR SEQ ID NO: 920:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 920:

TGACAGGTGT AGGTCCTACT                                           20

(2) INFORMATION FOR SEQ ID NO: 921:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 921:

GACAGGTGTA GGTCCTACTA                                                                    20

(2) INFORMATION FOR SEQ ID NO: 922:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 922:

ACAGGTGTAG GTCCTACTAA                                                                    20

(2) INFORMATION FOR SEQ ID NO: 923:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 923:

CAGGTGTAGG TCCTACTAAT                                                                    20

(2) INFORMATION FOR SEQ ID NO: 924:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 924:

AGGTGTAGGT CCTACTAATA                                                                    20

(2) INFORMATION FOR SEQ ID NO: 925:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 925:

GGTGTAGGTC CTACTAATAC                                                         20

(2) INFORMATION FOR SEQ ID NO: 926:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 926:

GTGTAGGTCC TACTAATACT                                                         20

(2) INFORMATION FOR SEQ ID NO: 927:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 927:

TGTAGGTCCT ACTAATACTG                                                         20

(2) INFORMATION FOR SEQ ID NO: 928:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 928:

GTAGGTCCTA CTAATACTGT                                                         20

(2) INFORMATION FOR SEQ ID NO: 929:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 929:

TAGGTCCTAC TAATACTGTA                                                     20

(2) INFORMATION FOR SEQ ID NO: 930:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 930:

AGGTCCTACT AATACTGTAC                                                     20

(2) INFORMATION FOR SEQ ID NO: 931:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 931:

GGTCCTACTA ATACTGTACC                                                     20

(2) INFORMATION FOR SEQ ID NO: 932:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 932:

GTCCTACTAA TACTGTACCT                                                     20

(2) INFORMATION FOR SEQ ID NO: 933:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 933:

TCCTACTAAT ACTGTACCTA                                                     20

(2) INFORMATION FOR SEQ ID NO: 934:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 934:

CCTACTAATA CTGTACCTAT                                             20

(2) INFORMATION FOR SEQ ID NO: 935:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 935:

CTACTAATAC TGTACCTATA                                             20

(2) INFORMATION FOR SEQ ID NO: 936:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 936:

TACTAATACT GTACCTATAG                                             20

(2) INFORMATION FOR SEQ ID NO: 937:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 937:

ACTAATACTG TACCTATAGC                                           20

(2) INFORMATION FOR SEQ ID NO: 938:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 938:

CTAATACTGT ACCTATAGCT                                            20

(2) INFORMATION FOR SEQ ID NO: 939:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 939:

TAATACTGTA CCTATAGCTT                                            20

(2) INFORMATION FOR SEQ ID NO: 940:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 940:

AATACTGTAC CTATAGCTTT                                            20

(2) INFORMATION FOR SEQ ID NO: 941:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 941:

ATACTGTACC TATAGCTTTA                                            20

(2) INFORMATION FOR SEQ ID NO: 942:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 942:
```

TACTGTACCT ATAGCTTTAT                                                     20

```
(2) INFORMATION FOR SEQ ID NO: 943:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 943:
```

ACTGTACCTA TAGCTTTATG                                                     20

```
(2) INFORMATION FOR SEQ ID NO: 944:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 944:
```

CTGTACCTAT AGCTTTATGT                                                     20

```
(2) INFORMATION FOR SEQ ID NO: 945:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 945:
```

TGTACCTATA GCTTTATGTC                                                     20

```
(2) INFORMATION FOR SEQ ID NO: 946:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 946:

GTACCTATAG CTTTATGTCC                                                      20

(2) INFORMATION FOR SEQ ID NO: 947:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 947:

TACCTATAGC TTTATGTCCA                                                      20

(2) INFORMATION FOR SEQ ID NO: 948:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 948:

ACCTATAGCT TTATGTCCAC                                                      20

(2) INFORMATION FOR SEQ ID NO: 949:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 949:

CCTATAGCTT TATGTCCACA                                                      20

(2) INFORMATION FOR SEQ ID NO: 950:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 950:

CTATAGCTTT ATGTCCACAG                                                   20

(2) INFORMATION FOR SEQ ID NO: 951:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 951:

TATAGCTTTA TGTCCACAGA                                                   20

(2) INFORMATION FOR SEQ ID NO: 952:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 952:

ATAGCTTTAT GTCCACAGAT                                                   20

(2) INFORMATION FOR SEQ ID NO: 953:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 953:

TAGCTTTATG TCCACAGATT                                                   20

(2) INFORMATION FOR SEQ ID NO: 954:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 954:

AGCTTTATGT CCACAGATTT                                         20

(2) INFORMATION FOR SEQ ID NO: 955:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 955:

GCTTTATGTC CACAGATTTC                                         20

(2) INFORMATION FOR SEQ ID NO: 956:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 956:

CTTTATGTCC ACAGATTTCT                                         20

(2) INFORMATION FOR SEQ ID NO: 957:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 957:

TTTATGTCCA CAGATTTCTA                                         20

(2) INFORMATION FOR SEQ ID NO: 958:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 958:

TTATGTCCAC AGATTTCTAT                                         20

(2) INFORMATION FOR SEQ ID NO: 959:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 959:

TATGTCCACA GATTTCTATG                                      20

(2) INFORMATION FOR SEQ ID NO: 960:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 960:

ATGTCCACAG ATTTCTATGA                                      20

(2) INFORMATION FOR SEQ ID NO: 961:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 961:

TGTCCACAGA TTTCTATGAG                                      20

(2) INFORMATION FOR SEQ ID NO: 962:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 962:

GTCCACAGAT TTCTATGAGT                                      20

(2) INFORMATION FOR SEQ ID NO: 963:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 963:

TCCACAGATT TCTATGAGTA                                                     20

(2) INFORMATION FOR SEQ ID NO: 964:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 964:

CCACAGATTT CTATGAGTAT                                                     20

(2) INFORMATION FOR SEQ ID NO: 965:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 965:

CACAGATTTC TATGAGTATC                                                     20

(2) INFORMATION FOR SEQ ID NO: 966:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 966:

ACAGATTTCT ATGAGTATCT                                                     20

(2) INFORMATION FOR SEQ ID NO: 967:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 967:

CAGATTTCTA TGAGTATCTG                                                   20

(2) INFORMATION FOR SEQ ID NO: 968:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 968:

AGATTTCTAT GAGTATCTGA                                                   20

(2) INFORMATION FOR SEQ ID NO: 969:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 969:

GATTTCTATG AGTATCTGAT                                                   20

(2) INFORMATION FOR SEQ ID NO: 970:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 970:

ATTTCTATGA GTATCTGATC                                                   20

(2) INFORMATION FOR SEQ ID NO: 971:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 971:

TTTCTATGAG TATCTGATCA                                                     20

(2) INFORMATION FOR SEQ ID NO: 972:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 972:

TTCTATGAGT ATCTGATCAT                                                     20

(2) INFORMATION FOR SEQ ID NO: 973:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 973:

TCTATGAGTA TCTGATCATA                                                     20

(2) INFORMATION FOR SEQ ID NO: 974:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 974:

CTATGAGTAT CTGATCATAC                                                     20

(2) INFORMATION FOR SEQ ID NO: 975:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 975:

TATGAGTATC TGATCATACT                                                        20

(2) INFORMATION FOR SEQ ID NO: 976:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 976:

ATGAGTATCT GATCATACTG                                                        20

(2) INFORMATION FOR SEQ ID NO: 977:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 977:

TGAGTATCTG ATCATACTGT                                                        20

(2) INFORMATION FOR SEQ ID NO: 978:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 978:

GAGTATCTGA TCATACTGTC                                                        20

(2) INFORMATION FOR SEQ ID NO: 979:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 979:

AGTATCTGAT CATACTGTCT                                                          20

(2) INFORMATION FOR SEQ ID NO: 980:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 980:

GTATCTGATC ATACTGTCTT                                                          20

(2) INFORMATION FOR SEQ ID NO: 981:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 981:

TATCTGATCA TACTGTCTTA                                                          20

(2) INFORMATION FOR SEQ ID NO: 982:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 982:

ATCTGATCAT ACTGTCTTAC                                                          20

(2) INFORMATION FOR SEQ ID NO: 983:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 983:

```
TCTGATCATA CTGTCTTACT                                                    20

(2) INFORMATION FOR SEQ ID NO: 984:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 984:

CTGATCATAC TGTCTTACTT                                                    20

(2) INFORMATION FOR SEQ ID NO: 985:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 985:

TGATCATACT GTCTTACTTT                                                    20

(2) INFORMATION FOR SEQ ID NO: 986:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 986:

GATCATACTG TCTTACTTTG                                                    20

(2) INFORMATION FOR SEQ ID NO: 987:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 987:

ATCATACTGT CTTACTTTGA                                                    20
```

(2) INFORMATION FOR SEQ ID NO: 988:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 988:

TCATACTGTC TTACTTTGAT                                           20

(2) INFORMATION FOR SEQ ID NO: 989:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 989:

CATACTGTCT TACTTTGATA                                           20

(2) INFORMATION FOR SEQ ID NO: 990:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 990:

ATACTGTCTT ACTTTGATAA                                           20

(2) INFORMATION FOR SEQ ID NO: 991:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 991:

TACTGTCTTA CTTTGATAAA                                           20

(2) INFORMATION FOR SEQ ID NO: 992:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 992:

ACTGTCTTAC TTTGATAAAA                                               20

(2) INFORMATION FOR SEQ ID NO: 993:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 993:

CTGTCTTACT TTGATAAAAC                                               20

(2) INFORMATION FOR SEQ ID NO: 994:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 994:

TGTCTTACTT TGATAAAACC                                               20

(2) INFORMATION FOR SEQ ID NO: 995:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 995:

GTCTTACTTT GATAAAACCT                                               20

(2) INFORMATION FOR SEQ ID NO: 996:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 996:

TCTTACTTTG ATAAAACCTC                                               20

(2) INFORMATION FOR SEQ ID NO: 997:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 997:

CTTACTTTGA TAAAACCTCC                                               20

(2) INFORMATION FOR SEQ ID NO: 998:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 998:

TTACTTTGAT AAAACCTCCA                                               20

(2) INFORMATION FOR SEQ ID NO: 999:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 999:

TACTTTGATA AAACCTCCAA                                               20

(2) INFORMATION FOR SEQ ID NO: 1000:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1000:

ACTTTGATAA AACCTCCAAT                                                        20

(2) INFORMATION FOR SEQ ID NO: 1001:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1001:

CTTTGATAAA ACCTCCAATT                                                        20

(2) INFORMATION FOR SEQ ID NO: 1002:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1002:

TTTGATAAAA CCTCCAATTC                                                        20

(2) INFORMATION FOR SEQ ID NO: 1003:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1003:

TTGATAAAAC CTCCAATTCC                                                        20

(2) INFORMATION FOR SEQ ID NO: 1004:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1004:

TGATAAAACC TCCAATTCCC                                                    20

(2) INFORMATION FOR SEQ ID NO: 1005:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1005:

GATAAAACCT CCAATTCCCC                                                    20

(2) INFORMATION FOR SEQ ID NO: 1006:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1006:

ATAAAACCTC CAATTCCCCC                                                    20

(2) INFORMATION FOR SEQ ID NO: 1007:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1007:

TAAAACCTCC AATTCCCCCT                                                    20

(2) INFORMATION FOR SEQ ID NO: 1008:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1008:

AAAACCTCCA ATTCCCCCTA                                                    20

(2) INFORMATION FOR SEQ ID NO: 1009:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1009:

AAACCTCCAA TTCCCCCTAT                                                    20

(2) INFORMATION FOR SEQ ID NO: 1010:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1010:

AACCTCCAAT TCCCCCTATC                                                    20

(2) INFORMATION FOR SEQ ID NO: 1011:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1011:

ACCTCCAATT CCCCCTATCA                                                    20

(2) INFORMATION FOR SEQ ID NO: 1012:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1012:

CCTCCAATTC CCCCTATCAT                                                    20

(2) INFORMATION FOR SEQ ID NO: 1013:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1013:

CTCCAATTCC CCCTATCATT                                        20

(2) INFORMATION FOR SEQ ID NO: 1014:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1014:

TCCAATTCCC CCTATCATTT                                        20

(2) INFORMATION FOR SEQ ID NO: 1015:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1015:

CCAATTCCCC CTATCATTTT                                        20

(2) INFORMATION FOR SEQ ID NO: 1016:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1016:

CAATTCCCCC TATCATTTTT                                        20

(2) INFORMATION FOR SEQ ID NO: 1017:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1017:

AATTCCCCCT ATCATTTTTG                                        20

(2) INFORMATION FOR SEQ ID NO: 1018:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1018:

ATTCCCCCTA TCATTTTTGG                                        20

(2) INFORMATION FOR SEQ ID NO: 1019:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1019:

TTCCCCCTAT CATTTTTGGT                                        20

(2) INFORMATION FOR SEQ ID NO: 1020:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1020:

TCCCCCTATC ATTTTTGGTT                                        20

(2) INFORMATION FOR SEQ ID NO: 1021:

(i) SEQUENCE CHARACTERISTICS:
        (A) LENGTH: 20 base pairs
        (B) TYPE: nucleic acid (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1021:

CCCCCTATCA TTTTTGGTTT                                           20

(2) INFORMATION FOR SEQ ID NO: 1022:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1022:

CCCCTATCAT TTTTGGTTTC                                           20

(2) INFORMATION FOR SEQ ID NO: 1023:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1023:

CCCTATCATT TTTGGTTTCC                                           20

(2) INFORMATION FOR SEQ ID NO: 1024:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1024:

CCTATCATTT TTGGTTTCCA                                           20

(2) INFORMATION FOR SEQ ID NO: 1025:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1025:

CTATCATTTT TGGTTTCCAT                                                  20

(2) INFORMATION FOR SEQ ID NO: 1026:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1026:

TATCATTTTT GGTTTCCATC                                                  20

(2) INFORMATION FOR SEQ ID NO: 1027:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1027:

ATCATTTTTG GTTTCCATCT                                                  20

(2) INFORMATION FOR SEQ ID NO: 1028:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1028:

TCATTTTTGG TTTCCATCTT                                                  20

(2) INFORMATION FOR SEQ ID NO: 1029:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1029:

CATTTTTGGT TTCCATCTTC 20

(2) INFORMATION FOR SEQ ID NO: 1030:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1030:

ATTTTTGGTT TCCATCTTCC 20

(2) INFORMATION FOR SEQ ID NO: 1031:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1031:

TTTTTGGTTT CCATCTTCCT 20

(2) INFORMATION FOR SEQ ID NO: 1032:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1032:

TTTTGGTTTC CATCTTCCTG 20

(2) INFORMATION FOR SEQ ID NO: 1033:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1033:

TTTGGTTTCC ATCTTCCTGG                                                           20

(2) INFORMATION FOR SEQ ID NO: 1034:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1034:

TTGGTTTCCA TCTTCCTGGC                                                           20

(2) INFORMATION FOR SEQ ID NO: 1035:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1035:

TGGTTTCCAT CTTCCTGGCA                                                           20

(2) INFORMATION FOR SEQ ID NO: 1036:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1036:

GGTTTCCATC TTCCTGGCAA                                                           20

(2) INFORMATION FOR SEQ ID NO: 1037:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1037:

GTTTCCATCT TCCTGGCAAA                                                           20

(2) INFORMATION FOR SEQ ID NO: 1038:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1038:

TTTCCATCTT CCTGGCAAAC                                              20

(2) INFORMATION FOR SEQ ID NO: 1039:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1039:

TTCCATCTTC CTGGCAAACT                                              20

(2) INFORMATION FOR SEQ ID NO: 1040:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1040:

TCCATCTTCC TGGCAAACTC                                              20

(2) INFORMATION FOR SEQ ID NO: 1041:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1041:

CCATCTTCCT GGCAAACTCA                                              20

(2) INFORMATION FOR SEQ ID NO: 1042:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1042:

CATCTTCCTG GCAAACTCAT                                                    20

(2) INFORMATION FOR SEQ ID NO: 1043:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1043:

ATCTTCCTGG CAAACTCATT                                                    20

(2) INFORMATION FOR SEQ ID NO: 1044:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1044:

TCTTCCTGGC AAACTCATTT                                                    20

(2) INFORMATION FOR SEQ ID NO: 1045:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1045:

CTTCCTGGCA AACTCATTTC                                                    20

(2) INFORMATION FOR SEQ ID NO: 1046:

(i) SEQUENCE CHARACTERISTICS:
        (A) LENGTH: 20 base pairs
```

(B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1046:

TTCCTGGCAA ACTCATTTCT                                              20

(2) INFORMATION FOR SEQ ID NO: 1047:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1047:

TCCTGGCAAA CTCATTTCTT                                              20

(2) INFORMATION FOR SEQ ID NO: 1048:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1048:

CCTGGCAAAC TCATTTCTTC                                              20

(2) INFORMATION FOR SEQ ID NO: 1049:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1049:

CTGGCAAACT CATTTCTTCT                                              20

(2) INFORMATION FOR SEQ ID NO: 1050:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1050:

TGGCAAACTC ATTTCTTCTA                                            20

(2) INFORMATION FOR SEQ ID NO: 1051:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1051:

GGCAAACTCA TTTCTTCTAA                                            20

(2) INFORMATION FOR SEQ ID NO: 1052:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1052:

GCAAACTCAT TTCTTCTAAT                                            20

(2) INFORMATION FOR SEQ ID NO: 1053:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1053:

CAAACTCATT TCTTCTAATA                                            20

(2) INFORMATION FOR SEQ ID NO: 1054:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1054:

AAACTCATTT CTTCTAATAC                                           20

(2) INFORMATION FOR SEQ ID NO: 1055:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1055:

AACTCATTTC TTCTAATACT                                           20

(2) INFORMATION FOR SEQ ID NO: 1056:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1056:

ACTCATTTCT TCTAATACTG                                           20

(2) INFORMATION FOR SEQ ID NO: 1057:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1057:

CTCATTTCTT CTAATACTGT                                           20

(2) INFORMATION FOR SEQ ID NO: 1058:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1058:

TCATTTCTTC TAATACTGTA                                                           20

(2) INFORMATION FOR SEQ ID NO: 1059:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1059:

CATTTCTTCT AATACTGTAT                                                           20

(2) INFORMATION FOR SEQ ID NO: 1060:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1060:

ATTTCTTCTA ATACTGTATC                                                           20

(2) INFORMATION FOR SEQ ID NO: 1061:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1061:

TTTCTTCTAA TACTGTATCA                                                           20

(2) INFORMATION FOR SEQ ID NO: 1062:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1062:

```
TTCTTCTAAT ACTGTATCAT                                               20

(2) INFORMATION FOR SEQ ID NO: 1063:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1063:

TCTTCTAATA CTGTATCATC                                               20

(2) INFORMATION FOR SEQ ID NO: 1064:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1064:

CTTCTAATAC TGTATCATCT                                               20

(2) INFORMATION FOR SEQ ID NO: 1065:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1065:

TTCTAATACT GTATCATCTG                                               20

(2) INFORMATION FOR SEQ ID NO: 1066:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1066:

TCTAATACTG TATCATCTGC                                               20
```

(2) INFORMATION FOR SEQ ID NO: 1067:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1067:

CTAATACTGT ATCATCTGCT                                              20

(2) INFORMATION FOR SEQ ID NO: 1068:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1068:

TAATACTGTA TCATCTGCTC                                              20

(2) INFORMATION FOR SEQ ID NO: 1069:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1069:

AATACTGTAT CATCTGCTCC                                              20

(2) INFORMATION FOR SEQ ID NO: 1070:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1070:

ATACTGTATC ATCTGCTCCT                                              20

(2) INFORMATION FOR SEQ ID NO: 1071:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1071:

TACTGTATCA TCTGCTCCTG                                               20

(2) INFORMATION FOR SEQ ID NO: 1072:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1072:

ACTGTATCAT CTGCTCCTGT                                               20

(2) INFORMATION FOR SEQ ID NO: 1073:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1073:

CTGTATCATC TGCTCCTGTA                                               20

(2) INFORMATION FOR SEQ ID NO: 1074:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1074:

TGTATCATCT GCTCCTGTAT                                               20

(2) INFORMATION FOR SEQ ID NO: 1075:

(i) SEQUENCE CHARACTERISTICS:
        (A) LENGTH: 20 base pairs
        (B) TYPE: nucleic acid
        (C) STRANDEDNESS: single

```
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1075:

GTATCATCTG CTCCTGTATC                                           20

(2) INFORMATION FOR SEQ ID NO: 1076:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1076:

TATCATCTGC TCCTGTATCT                                           20

(2) INFORMATION FOR SEQ ID NO: 1077:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1077:

ATCATCTGCT CCTGTATCTA                                           20

(2) INFORMATION FOR SEQ ID NO: 1078:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1078:

TCATCTGCTC CTGTATCTAA                                           20

(2) INFORMATION FOR SEQ ID NO: 1079:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 1079:

CATCTGCTCC TGTATCTAAT                                                           20

(2) INFORMATION FOR SEQ ID NO: 1080:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1080:

ATCTGCTCCT GTATCTAATA                                                           20

(2) INFORMATION FOR SEQ ID NO: 1081:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1081:

TCTGCTCCTG TATCTAATAG                                                           20

(2) INFORMATION FOR SEQ ID NO: 1082:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1082:

CTGCTCCTGT ATCTAATAGA                                                           20

(2) INFORMATION FOR SEQ ID NO: 1083:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1083:

TGCTCCTGTA TCTAATAGAG                                                    20

(2) INFORMATION FOR SEQ ID NO: 1084:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1084:

GCTCCTGTAT CTAATAGAGC                                                    20

(2) INFORMATION FOR SEQ ID NO: 1085:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1085:

CTCCTGTATC TAATAGAGCT                                                    20

(2) INFORMATION FOR SEQ ID NO: 1086:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1086:

TCCTGTATCT AATAGAGCTT                                                    20

(2) INFORMATION FOR SEQ ID NO: 1087:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1087:

CCTGTATCTA ATAGAGCTTC                                        20

(2) INFORMATION FOR SEQ ID NO: 1088:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1088:

CTGTATCTAA TAGAGCTTCC                                        20

(2) INFORMATION FOR SEQ ID NO: 1089:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1089:

TGTATCTAAT AGAGCTTCCT                                        20

(2) INFORMATION FOR SEQ ID NO: 1090:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1090:

GTATCTAATA GAGCTTCCTT                                        20

(2) INFORMATION FOR SEQ ID NO: 1091:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1091:

TATCTAATAG AGCTTCCTTT                                        20

-continued

```
(2) INFORMATION FOR SEQ ID NO: 1092:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1092:

ATCTAATAGA GCTTCCTTTA                                          20

(2) INFORMATION FOR SEQ ID NO: 1093:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1093:

TCTAATAGAG CTTCCTTTAG                                          20

(2) INFORMATION FOR SEQ ID NO: 1094:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1094:

CTAATAGAGC TTCCTTTAGT                                          20

(2) INFORMATION FOR SEQ ID NO: 1095:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1095:

TAATAGAGCT TCCTTTAGTT                                          20

(2) INFORMATION FOR SEQ ID NO: 1096:
```

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1096:

AATAGAGCTT CCTTTAGTTG                                                 20

(2) INFORMATION FOR SEQ ID NO: 1097:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1097:

ATAGAGCTTC CTTTAGTTGC                                                 20

(2) INFORMATION FOR SEQ ID NO: 1098:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1098:

TAGAGCTTCC TTTAGTTGCC                                                 20

(2) INFORMATION FOR SEQ ID NO: 1099:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1099:

AGAGCTTCCT TTAGTTGCCC                                                 20

(2) INFORMATION FOR SEQ ID NO: 1100:

(i) SEQUENCE CHARACTERISTICS:
        (A) LENGTH: 20 base pairs
        (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1100:

GAGCTTCCTT TAGTTGCCCC                                           20

(2) INFORMATION FOR SEQ ID NO: 1101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1101:

AGCTTCCTTT AGTTGCCCCC                                           20

(2) INFORMATION FOR SEQ ID NO: 1102:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1102:

GCTTCCTTTA GTTGCCCCCC                                           20

(2) INFORMATION FOR SEQ ID NO: 1103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1103:

CTTCCTTTAG TTGCCCCCCT                                           20

(2) INFORMATION FOR SEQ ID NO: 1104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

```
        (ii) MOLECULE TYPE: cDNA (iii) HYPOTHETICAL: NO (iv) ANTI-SENSE: NO (xi) SEQUENCE DESCRIPTION: SEQ ID NO: 1104:

TTCCTTTAGT TGCCCCCCTA                                                  20

(2) INFORMATION FOR SEQ ID NO: 1105:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1105:

TCCTTTAGTT GCCCCCCTAT                                                  20

(2) INFORMATION FOR SEQ ID NO: 1106:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1106:

CCTTTAGTTG CCCCCCTATC                                                  20

(2) INFORMATION FOR SEQ ID NO: 1107:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1107:

CTTTAGTTGC CCCCCTATCT                                                  20

(2) INFORMATION FOR SEQ ID NO: 1108:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO
```

(iv) ANTI-SENSE: NO (xi) SEQUENCE DESCRIPTION: SEQ ID NO: 1108:

TTTAGTTGCC CCCCTATCTT                                              20

(2) INFORMATION FOR SEQ ID NO: 1109:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1109:

TTAGTTGCCC CCCTATCTTT                                              20

(2) INFORMATION FOR SEQ ID NO: 1110:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1110:

TAGTTGCCCC CCTATCTTTA                                              20

(2) INFORMATION FOR SEQ ID NO: 1111:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1111:

AGTTGCCCCC CTATCTTTAT                                              20

(2) INFORMATION FOR SEQ ID NO: 1112:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1112:

GTTGCCCCCC TATCTTTATT                                           20

(2) INFORMATION FOR SEQ ID NO: 1113:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1113:

TTGCCCCCCT ATCTTTATTG                                           20

(2) INFORMATION FOR SEQ ID NO: 1114:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1114:

TGCCCCCCTA TCTTTATTGT                                           20

(2) INFORMATION FOR SEQ ID NO: 1115:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1115:

GCCCCCCTAT CTTTATTGTG                                           20

(2) INFORMATION FOR SEQ ID NO: 1116:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1116:

CCCCCCTATC TTTATTGTGA                                           20

(2) INFORMATION FOR SEQ ID NO: 1117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1117:

CCCCCTATCT TTATTGTGAC                                       20

(2) INFORMATION FOR SEQ ID NO: 1118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1118:

CCCCTATCTT TATTGTGACG                                       20

(2) INFORMATION FOR SEQ ID NO: 1119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1119:

CCCTATCTTT ATTGTGACGA                                       20

(2) INFORMATION FOR SEQ ID NO: 1120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1120:

CCTATCTTTA TTGTGACGAG                                       20

(2) INFORMATION FOR SEQ ID NO: 1121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1121:

CTATCTTTAT TGTGACGAGG                                               20

(2) INFORMATION FOR SEQ ID NO: 1122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1122:

TATCTTTATT GTGACGAGGG                                               20

(2) INFORMATION FOR SEQ ID NO: 1123:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1123:

ATCTTTATTG TGACGAGGGG                                               20

(2) INFORMATION FOR SEQ ID NO: 1124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1124:

TCTTTATTGT GACGAGGGGT                                               20

(2) INFORMATION FOR SEQ ID NO: 1125:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1125:

CTTTATTGTG ACGAGGGGTC                                           20

(2) INFORMATION FOR SEQ ID NO: 1126:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1126:

TTTATTGTGA CGAGGGGTCG                                           20

(2) INFORMATION FOR SEQ ID NO: 1127:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1127:

TTATTGTGAC GAGGGGTCGT                                           20

(2) INFORMATION FOR SEQ ID NO: 1128:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1128:

TATTGTGACG AGGGGTCGTT                                           20

(2) INFORMATION FOR SEQ ID NO: 1129:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1129:

ATTGTGACGA GGGGTCGTTG                                                          20

(2) INFORMATION FOR SEQ ID NO: 1130:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1130:

TTGTGACGAG GGGTCGTTGC                                                          20

(2) INFORMATION FOR SEQ ID NO: 1131:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1131:

TGTGACGAGG GGTCGTTGCC                                                          20

(2) INFORMATION FOR SEQ ID NO: 1132:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1132:

GTGACGAGGG GTCGTTGCCA                                                          20

(2) INFORMATION FOR SEQ ID NO: 1133:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1133:

TGACGAGGGG TCGTTGCCAA                                                    20

(2) INFORMATION FOR SEQ ID NO: 1134:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1134:

GACGAGGGGT CGTTGCCAAA                                                    20

(2) INFORMATION FOR SEQ ID NO: 1135:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1135:

ACGAGGGGTC GTTGCCAAAG                                                    20

(2) INFORMATION FOR SEQ ID NO: 1136:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1136:

CGAGGGGTCG TTGCCAAAGA                                                    20

(2) INFORMATION FOR SEQ ID NO: 1137:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1137:

GAGGGGTCGT TGCCAAAGAG                                                       20

(2) INFORMATION FOR SEQ ID NO: 1138:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1138:

AGGGGTCGTT GCCAAAGAGT                                                       20

(2) INFORMATION FOR SEQ ID NO: 1139:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1139:

GGGGTCGTTG CCAAAGAGTG                                                       20

(2) INFORMATION FOR SEQ ID NO: 1140:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1140:

GGGTCGTTGC CAAAGAGTGA                                                       20

(2) INFORMATION FOR SEQ ID NO: 1141:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1141:

```
GGTCGTTGCC AAAGAGTGAT                                                    20

(2) INFORMATION FOR SEQ ID NO: 1142:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1142:

GTCGTTGCCA AAGAGTGATC                                                    20

(2) INFORMATION FOR SEQ ID NO: 1143:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1143:

TCGTTGCCAA AGAGTGATCT                                                    20

(2) INFORMATION FOR SEQ ID NO: 1144:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1144:

CGTTGCCAAA GAGTGATCTG                                                    20

(2) INFORMATION FOR SEQ ID NO: 1145:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1145:

GTTGCCAAAG AGTGATCTGA                                                    20
```

(2) INFORMATION FOR SEQ ID NO: 1146:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1146:

TTGCCAAAGA GTGATCTGAG                                                    20

(2) INFORMATION FOR SEQ ID NO: 1147:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1147:

TGCCAAAGAG TGATCTGAGG                                                    20

(2) INFORMATION FOR SEQ ID NO: 1148:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1148:

GCCAAAGAGT GATCTGAGGG                                                    20

(2) INFORMATION FOR SEQ ID NO: 1149:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1149:

CCAAAGAGTG ATCTGAGGGA                                                    20

(2) INFORMATION FOR SEQ ID NO: 1150:

(i) SEQUENCE CHARACTERISTICS:

(A) LENGTH: 20 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1150:

CAAAGAGTGA TCTGAGGGAA                                                   20

(2) INFORMATION FOR SEQ ID NO: 1151:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1151:

AAAGAGTGAT CTGAGGGAAG                                                   20

(2) INFORMATION FOR SEQ ID NO: 1152:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1152:

AAGAGTGATC TGAGGGAAGT                                                   20

(2) INFORMATION FOR SEQ ID NO: 1153:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1153:

AGAGTGATCT GAGGGAAGTT                                                   20

(2) INFORMATION FOR SEQ ID NO: 1154:

(i) SEQUENCE CHARACTERISTICS:
                    (A) LENGTH: 20 base pairs
                    (B) TYPE: nucleic acid
                    (C) STRANDEDNESS: single

```
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1154:

GAGTGATCTG AGGGAAGTTA                                           20

(2) INFORMATION FOR SEQ ID NO: 1155:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1155:

AGTGATCTGA GGGAAGTTAA                                           20

(2) INFORMATION FOR SEQ ID NO: 1156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1156:

GTGATCTGAG GGAAGTTAAA                                           20

(2) INFORMATION FOR SEQ ID NO: 1157:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1157:

TGATCTGAGG GAAGTTAAAG                                           20

(2) INFORMATION FOR SEQ ID NO: 1158:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 1158:

GATCTGAGGG AAGTTAAAGG                                                       20

(2) INFORMATION FOR SEQ ID NO: 1159:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1159:

ATCTGAGGGA AGTTAAAGGA                                                       20

(2) INFORMATION FOR SEQ ID NO: 1160:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1160:

TCTGAGGGAA GTTAAAGGAT                                                       20

(2) INFORMATION FOR SEQ ID NO: 1161:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1161:

CTGAGGGAAG TTAAAGGATA                                                       20

(2) INFORMATION FOR SEQ ID NO: 1162:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1162:

TGAGGGAAGT TAAAGGATAC                                                      20

(2) INFORMATION FOR SEQ ID NO: 1163:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1163:

GAGGGAAGTT AAAGGATACA                                                      20

(2) INFORMATION FOR SEQ ID NO: 1164:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1164:

AGGGAAGTTA AAGGATACAG                                                      20

(2) INFORMATION FOR SEQ ID NO: 1165:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1165:

GGGAAGTTAA AGGATACAGT                                                      20